(12) United States Patent
Evers et al.

(10) Patent No.: US 7,396,846 B2
(45) Date of Patent: *Jul. 8, 2008

(54) GROWTH HORMONE SECRETAGOGUES

(75) Inventors: Britta Evers, Hamburg (DE); Ruehter Gerd, Hamburg (DE); Eva Maria Martin De La Nava, Madrid (ES); Mark Joseph Tebbe, Hamburg (DE)

(73) Assignee: Eli Lilly and Company, Indianapolis, IN (US)

( * ) Notice: Subject to any disclaimer, the term of this patent is extended or adjusted under 35 U.S.C. 154(b) by 112 days.

This patent is subject to a terminal disclaimer.

(21) Appl. No.: 10/510,393

(22) PCT Filed: Mar. 31, 2003

(86) PCT No.: PCT/US03/08821

§ 371 (c)(1),
(2), (4) Date: Oct. 5, 2004

(87) PCT Pub. No.: WO03/087070

PCT Pub. Date: Oct. 23, 2003

(65) Prior Publication Data

US 2005/0240001 A1    Oct. 27, 2005

Related U.S. Application Data

(60) Provisional application No. 60/371,271, filed on Apr. 9, 2002, provisional application No. 60/371,270, filed on Apr. 9, 2002, provisional application No. 60/371,278, filed on Apr. 9, 2002, provisional application No. 60/371,275, filed on Apr. 9, 2002, provisional application No. 60/371,277, filed on Apr. 9, 2002.

(30) Foreign Application Priority Data

| Apr. 9, 2002 | (GB) | ................. | 0208116.4 |
| Apr. 9, 2002 | (GB) | ................. | 0208117.2 |
| Apr. 9, 2002 | (GB) | ................. | 0208118.0 |
| Apr. 9, 2002 | (GB) | ................. | 0208119.8 |
| Apr. 9, 2002 | (GB) | ................. | 0208120.6 |

(51) Int. Cl.
*A61K 31/40* (2006.01)
*A61K 31/425* (2006.01)
*C07D 275/02* (2006.01)
*C07D 207/18* (2006.01)

(52) U.S. Cl. ............... 514/372; 514/409; 514/424; 548/214; 548/408; 548/550

(58) Field of Classification Search ............ 548/214, 548/550, 408; 514/372, 409, 424
See application file for complete search history.

(56) References Cited

U.S. PATENT DOCUMENTS

| 3,711,495 A | 1/1973 | Kulsa et al. |
| 3,984,426 A | 10/1976 | Winkelmann et al. |
| 5,206,235 A | 4/1993 | Fisher et al. |
| 5,242,903 A | 9/1993 | Bender et al. |
| 5,380,866 A | 1/1995 | Barnett et al. |
| 5,401,851 A | 3/1995 | Boyd et al. |
| 5,459,156 A | 10/1995 | Muller-Gliemann et al. |
| 5,492,916 A | 2/1996 | Marriello et al. |
| 5,492,920 A | 2/1996 | Chen et al. |
| 5,494,919 A | 2/1996 | Marriello et al. |
| 5,559,128 A | 9/1996 | Chakravarty et al. |
| 5,574,167 A | 11/1996 | Jaber |
| 5,578,593 A | 11/1996 | Chen et al. |
| 5,583,130 A | 12/1996 | Bochis et al. |
| 5,652,235 A | 7/1997 | Chen et al. |
| 5,661,161 A | 8/1997 | Anthony et al. |
| 5,663,146 A | 9/1997 | Bowers et al. |
| 5,663,171 A | 9/1997 | Chen et al. |
| 5,700,827 A | 12/1997 | Schnorrenberg et al. |
| 5,721,250 A | 2/1998 | Morriello et al. |
| 5,756,528 A | 5/1998 | Anthony et al. |
| 5,773,441 A | 6/1998 | Hipskind et al. |
| 5,798,337 A | 8/1998 | Somers et al. |
| 5,830,855 A | 11/1998 | Takemoto |
| 6,046,333 A | 4/2000 | Dorziotis et al. |
| 6,329,342 B1 | 12/2001 | Kauffman et al. |
| 6,639,076 B1 | 10/2003 | Hauser et al. |

FOREIGN PATENT DOCUMENTS

| EP | 0 662 481 B1 | 8/1993 |
| EP | 0 615 977 A1 | 9/1994 |
| EP | 0 761 219 A1 | 8/1996 |
| EP | 0 761 220 A1 | 12/1997 |
| WO | WO 94/13696 | 6/1994 |
| WO | WO 94/13696 A1 | 6/1994 |
| WO | WO 95/11029 A1 | 4/1995 |
| WO | WO 96/15148 | 5/1996 |
| WO | WO 96/35713 A1 | 11/1996 |
| WO | WO 96/38471 A1 | 12/1996 |
| WO | WO 97/15573 A1 | 5/1997 |
| WO | WO 97/24369 | 7/1997 |
| WO | WO 97/24369 A1 | 7/1997 |

(Continued)

OTHER PUBLICATIONS

Paterson et al., Arch Dis Child, Apr. 2003, 88(4), pp. 283-285.*

(Continued)

*Primary Examiner*—Laura L. Stockton
(74) *Attorney, Agent, or Firm*—James B. Myers

(57) ABSTRACT

This invention relates to novel compounds which are useful in the modulation of endogenous growth hormone levels in a mammal. The invention further relates to novel intermediates for use in the synthesis of said compounds, as well as novel processes employed in these syntheses. Also included are methods of treating a mammal which include the administration of said compounds.

22 Claims, No Drawings

FOREIGN PATENT DOCUMENTS

| WO | WO 97/34604 A1 | 9/1997 |
| WO | WO 97/41878 A1 | 11/1997 |
| WO | WO 98/16527 A1 | 4/1998 |
| WO | WO 98/18815 | 5/1998 |
| WO | 0 761 219 A1 | 12/1998 |
| WO | WO 98/58948 A1 | 12/1998 |
| WO | WO 99 08697 A1 | 2/1999 |
| WO | WO 99/08699 A1 | 2/1999 |
| WO | WO 00/12047 A2 | 3/2000 |
| WO | WO 00/49037 | 8/2000 |
| WO | WO 00/49037 A1 | 8/2000 |
| WO | WO-02/32888 A1 * | 4/2002 |

OTHER PUBLICATIONS

Burman et al. (Endocrine Reviews, 2001, 22(6), pp. 787-799.*

*Synthesis of 4-Nitroimidazoles with 1-Substituents Containing Acid, Ester or Phenol Functions, and Radiosensitizing Efficiency of Some of These Compounds*, Suwinski, et al., Arch. Pharm., vol. 325, pp. 317-324 (1992).

*Synthetic Approaches to the 'Azole' Peptide Mimetics*, Gordon, et al., Tetrahedron Letters, vol. 34, No. 12, pp. 1901-1904 (1993).

Chem. Abst. No. 130:209977, Kaufffman, et al., *Treatment of Congestive Heart Failure with Growth Hormone Secretagogues*, Kauffman, et al. application of WO 99/08697, Aug. 19, 1998.

Chem. Abst. No. 130:182769, Dodge, et al., *Preparation of Heterocyclic Peptide Derivatives as Growth Hormone Secretagogues*, application of WO 9908699, |Aug. 19, 1998.

*New Highly Potent Dipeptide Growth Hormone Secretagogues with Low Molecular Weight*: Eur. J. Med. Chem. 35, pp. 599-618 (2000).

*Growth Hormone Secretagogues Derived from NN703 with Hydrazides as C-terminal*: Eur. J. Med. Chem. 35, pp. 487-497 (2000).

Chem. Abst. No. 119:261758, Uzunov, et al., *Some Aspects of the Enantiorecognition of Derivatized Primary Amines on a Pirkle-Type Chiral Stationary Phase Utilizing Tocainide and Mexiletine as Model Compounds*, (1993).

Chem. Abst. No. 138:221510, Kim et al., *Synthesis and Antiinflammatory-Analgesic Activity of Monovalent and Bivalent Aminoantipyrines* (2002).

* cited by examiner

GROWTH HORMONE SECRETAGOGUES

This is the national phase application, under 35 USC 371, for PCT/US03/08821, filed 31 Mar. 2004 which, claims the benefit, under 35 USC 119(e), of U.S. provisional application 60/371,271, filed 09 Apr. 2002, 60/371,270, filed 09 Apr. 2002, 60/371,278 filed 09 Apr. 2002, 60/371,275 filed 09 Apr. 2002, 60/371,277 filed 09 Apr. 2002, and EP provisional application 0208116.4 filed 09 Apr. 2002, 0208117.2 filed 09 Apr. 2002, 0208118.0 filed 09 Apr. 2002, 0208119.8 filed 09 Apr. 2002, and 0208120.6 filed 09 Apr. 2002.

Growth hormone, which is secreted by the pituitary gland, has wide-ranging developmental effects on the organism. Artificial manipulation of growth hormone levels has been demonstrated to have significant therapeutic utility. Human growth hormone supplementation has been shown to be an effective treatment for growth hormone deficiencies and their related disease states in humans. Apart from this application, studies have uncovered new and significant properties of growth hormone which lend further importance to the ability to control growth hormone levels. For example, clinical studies have indicated that growth hormone supplementation may be useful in combating the maladies of ageing in humans. Elevated growth hormone levels in animals have been shown to result in increased lean muscle mass. One application of this latter observation could result in higher production of leaner meat products or in the production of larger and/or stronger animals.

While growth hormone is naturally produced by the pituitary gland, the secretion of growth hormone into the bloodstream is controlled by a second protein, Growth Hormone Releasing Factor (GRF). This hormone is also commonly known in the art as somatocrinin, Growth Hormone Releasing Hormone (GHRH), and Growth Releasing Hormone (GRH).

There are two ways to approach the problem of increasing circulating levels of growth hormone: (1) increase the level of human growth hormone in the organism directly or (2) increase the organism's natural tendency to produce growth hormone. The latter strategy may be achieved via supplementation with GRF. GRF has been demonstrated to increase the circulatory levels of growth hormone in vivo. (Rivier, et al., Nature (London), 300:276 (1982). The effect of GRF, including structural analogs thereof, on growth hormone production has been widely studied. A primary obstacle to the use of GRF as a direct supplement is its short lifespan in vivo. L. A. Frohman, et al., Journal of Clinical Investigation, 78:906 (1986). More potent and/or longer lasting GRF molecules are therefore desirable for the development of effective human therapeutic or animal husbandry agents.

The structure of GRF has been modified in numerous ways resulting in longer lasting and/or more potent GRF analogs. It has been demonstrated that the first 29 amino acids from the N-terminus are sufficient to retain full GRF activity. Speiss, et al., Biochemistry, 21:6037 (1982). One strategy has been the incorporation of novel D-amino acid residues in various regions of the GRF molecule. V. A. Lance, et al., Biochemical and Biophysical Research Communications, 119:265 (1984); D. H. Coy, et al., Peptides, 8(suppl. 1):49 (1986). Another strategy has modified the peptide backbone of GRF by the incorporation of peptide bond isosteres in the N-terminal region. D. Tourwe, Janssen. Chim. Acta, 3:3 (1985); S. J. Hocart, et al., Journal of Medicinal Chemistry, 33:1954-58 (1990). A series of very active analogs of GHRH is described in European Patent Publication 511,003, published Oct. 28, 1992.

In addition to the actions of GHRH there are various ways known to release growth hormone. For example, chemicals such as arginine, L-3,4-dihydroxyphenylalanine (L-DOPA), glucagon, vasopressin, and insulin-induced hypoglycemia, as well as activities such as sleep and exercise, indirectly cause growth hormone to be released from the pituitary by acting in some fashion on the hypothalamus, perhaps either to decrease somatostatin secretion or to increase the secretion of GHRH.

In cases where increased levels of growth hormone are desired, the problem has generally been solved by providing exogenous growth hormone or by administering GHRH, or a related peptidyl compound which stimulates growth hormone production or release. In either instance the peptidyl nature of the compound has necessitated that it be administered by injection.

Other compounds have been developed which stimulate the release of endogenous growth hormone, such as analogous peptidyl compounds related to GHRH. These peptides, while considerably smaller than growth hormones are still susceptible to metabolic instability.

Administration of the hexapeptide growth hormone releasing peptide-6 (GHRP-6) results in the secretion of growth hormone in many species, including humans. This peptide is one of a series of synthetic peptides, the structures of which were based on the pentapeptide Met-enkephalin. It has been shown that GHRP binds specifically to the pituitary, although the binding does not involve the opioid, GHRH, or the somatostatin receptors.

In recent years significant efforts have been taken to develop nonpeptidyl analogs of this series of compounds. Such compounds, termed growth hormone secretagogues, should be orally bioavailable, induce the production or release of growth hormone, and act in concert, or synergistically with GHRH. These compounds are non-peptidyl in nature and are, therefore, more metabolically stable than growth hormone, growth hormone releasing hormone, or analogs of either of these proteins.

The compounds of this invention are especially desired due to the enhanced in vivo pharmaceutical activity of the compounds.

The present invention relates to compounds of Formula I

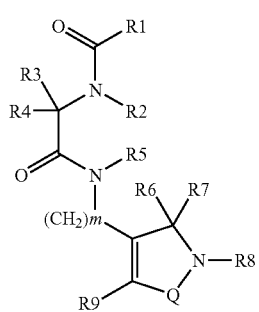

Formula I wherein:

R1 is NHR10, (substituted or unsubstituted $C_1$-$C_6$alkyl) NHR10 or (unsubstituted or substituted $C_3$-$C_8$ cycloalkyl) NHR10;

R10 is hydrogen, $C_1$-$C_6$alkyl, $C_1$-$C_6$alkyl(OH), $C_1$-$C_6$alkylidenyl(OH)R11, or an amino protecting group;

R11 is $C_1$-$C_6$alkyl, $C_2$-$C_6$alkenyl, $C_1$-$C_6$alkyl(O)$C_1$-$C_6$alkyl, C(O)O—$C_1$-$C_6$alkyl, aryl, or $C_1$-$C_6$alkylaryl;

R2 is hydrogen, $C_1$-$C_6$alkyl, aryl, or $C_1$-$C_6$alkylaryl;

R4 is hydrogen, $C_1$-$C_6$alkyl, aryl, $C_1$-$C_6$alkylaryl, or $C_2$-$C_6$alkenyl;

R5 is hydrogen, aryl, $C_1$-$C_6$alkylaryl, hydroxy, $C_1$-$C_6$alkoxy, unsubstituted or substituted $C_1$-$C_6$alkyl;

R6 and R7 are independently hydrogen, unsubstituted or substituted $C_1$-$C_6$alkyl, unsubstituted or substituted $C_2$-$C_6$alkenyl, or R6 and R7 together with the carbon atom to which they are attached form a carbocyclic ring of up to 8 atoms which is optionally partly unsaturated or a substituted $C_3$-$C_8$ cycloalkyl group which is optionally partly unsaturated;

R8 is hydrogen, unsubstituted or substituted $C_1$-$C_6$alkyl, unsubstituted or substituted aryl, unsubstituted or substituted ($C_1$-$C_6$alkyl)$C_3$-$C_8$cycloalkyl, or unsubstituted or substituted $C_1$-$C_6$alkylaryl;

Q is —S(O)$_2$— or —C(O)—;

m is a number selected from 1 or 2;

R3 is substituted $C_1$-$C_6$alkylaryl, substituted $C_1$-$C_6$alkyl (O)—$C_1$-$C_6$alkylaryl, substituted $C_3$-$C_8$ cycloalkyl, substituted ($C_1$-$C_6$ alkyl)$C_3$-$C_8$ cycloalkyl, or aryl substituted by at least one —SO$_2$CF$_3$ group; and R9 is hydrogen, $C_1$-$C_6$alkyl, $C_2$-$C_6$alkenyl, $C_2$-$C_6$alkynyl, $C_3$-$C_8$cycloalkyl, $C_3$-$C_8$cycloalkenyl, cyano, optionally substituted aryl, optionally substituted —O-aryl, optionally substituted —N-aryl, optionally substituted —S-aryl, -aryl-aryl(K1)(K2), —O-aryl-aryl(K1)(K2), —N-aryl-aryl(K1)(K2), S-aryl-aryl (K1)(K2), —O—$C_1$-$C_6$alkyl, or $C_1$-$C_6$alkylaryl, wherein K1 is halo or —CF$_3$, and K2 is hydrogen, halo or —CF$_3$ or K1 and K2 together form a methylenedioxy group; or R3 is optionally substituted aryl, $C_1$-$C_6$alkylaryl, $C_1$-$C_6$alkyl(O)—$C_1$-$C_6$alkylaryl, $C_3$-$C_8$ cycloalkyl, ($C_1$-$C_6$ alkyl)$C_3$-$C_8$ cycloalkyl; and R9 is aryl substituted by at least one —SO$_2$CF$_3$ group, —O-aryl substituted by at least one —SO$_2$CF$_3$ group, —N-aryl substituted by at least one —SO$_2$CF$_3$ group, or —S-aryl substituted by at least one —SO$_2$CF$_3$ group;

or a pharmaceutically acceptable salt or solvate thereof.

The present invention further relates to pharmaceutical formulations containing compounds of formula I, alone or in combination with other growth hormone secretagogue compounds, and/or in combination with suitable bone-antiresorptive agents, and the use of said compounds and/or formulations at least for the increase in endogenous levels of growth hormone in a mammal.

The present invention yet further relates to methods for the treatment or prevention of a physiological condition which may be modulated by an increase in endogenous growth hormone, which method comprises administering to an animal in need of said treatment an effective amount of a compound of formula I.

A preferred embodiment of the invention is a compound of Formula II

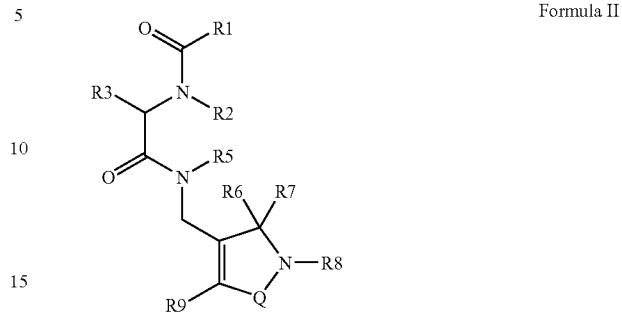

Formula II wherein

R1, R2, R3, R5, R6, R7, R8, R9 and Q are as defined for formula I above or a pharmaceutically acceptable salt or solvate thereof.

A further preferred embodiment of the invention is a compound of Formula III

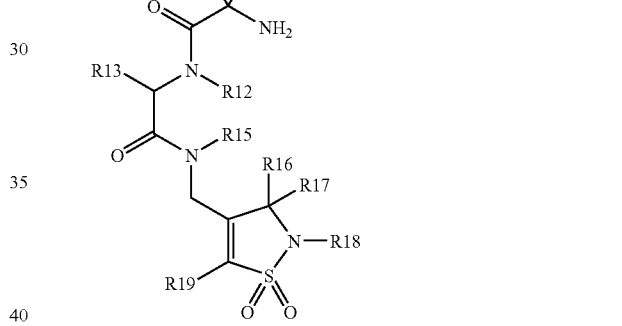

Formula III or a pharmaceutically acceptable salt or solvate thereof, wherein:

R12 is hydrogen, methyl or ethyl;

R13 is substituted 3-arylpropyl, substituted 2-arylethyl, substituted arylmethoxymethyl, substituted 3-indolylmethyl, or substituted cyclohexylmethyl;

R15 is hydrogen, methyl, ethyl, n-propyl, isopropyl, hydroxy, methoxy, 2-hydroxyethyl, 2-fluoroethyl, or 2,2,2-trifluoroethyl;

R16 and R17 are hydrogen, methyl, ethyl, fluoromethyl, trifluoromethyl, 2-fluoroethyl, or 2,2,2-trifluoroethyl or together with the carbon atom to which they are attached form a cyclopentane, cyclohexane, fluorocyclohexane or difluorocyclohexane ring;

R18 is hydrogen, methyl, ethyl, propyl, isopropyl, butyl, isobutyl, cyclopropylmethyl, pentyl, arylmethyl, 1-arylethyl, 2-methoxyethyl, 2-hydroxyethyl, 2-fluoroethyl, 4,4,4-trifluorobutyl, 3,3,3-trifluoropropyl, 2,2-difluoroethyl, 3-fluoropropyl, 4-fluorobutyl, 2,2,2-trifluoroethyl, —CH$_2$CONH$_2$, or —CH$_2$CON(CH$_3$)$_2$;

R19 is thienyl, naphthyl, thiazolyl, oxazolyl, pyridyl, O-phenyl, or phenyl, which are optionally substituted with one or more substituents independently selected from the group consisting of $C_1$-$C_6$ alkyl, $C_1$-$C_6$ alkoxy, CONH$_2$, CONH($C_1$-$C_6$ alkyl), NHCO($C_1$-$C_6$ alkyl), SO$_2$NH$_2$, SO$_2$NH ($C_1$-$C_6$ alkyl), $NHSO_2$($C_1$-$C_6$ alkyl), COOH, COO($C_1$-$C_6$ alkyl), hydroxy, nitro, halo, $SO_2$($C_{1-6}$ alkyl), $SO_2CF_3$, $OCF_3$, $CF_3$ and cyano.

The present invention additionally relates to compounds of formula IV and pharmaceutically acceptable salts or solvates thereof in which R12 to R19 have the same definition as in Formula III:

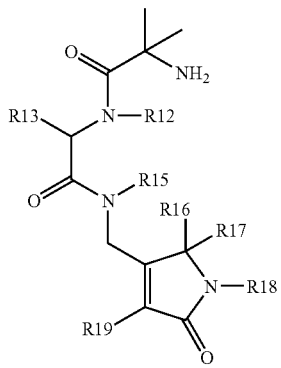

Formula IV

The present invention still further relates to processes for the preparation of compounds of formula I.

The terms and abbreviations used herein have their normal meanings unless otherwise designated. For example "° C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "FDMS" refers to field desorption mass spectrometry; "IS" refers to ion spray ionisation; "EI" refers to electron impact ionisation; "UV" refers to ultraviolet spectroscopy; "IR" refers to infrared spectroscopy; and "NMR" refers to nuclear magnetic resonance spectroscopy.

"TBTU" refers to O-(1H-benzotriazol-1-yl)-N,N,N',N'-pentamethylene-uronium tetrafluoroborate.

As used herein, the term "$C_1$-$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$-$C_6$ alkyl" includes within its definition the term "$C_1$-$C_4$ alkyl".

The term "substituted $C_1$-$C_6$ alkyl" means a $C_1$-$C_6$ alkyl group as defined above which has been substituted by one or more, preferably from one to three groups selected from halo (preferably chloro or fluoro), hydroxy, —$OC_1$-$C_6$ alkyl, cyano, $SO_2$($C_1$-$C_6$ alkyl), $OCF_3$, $CF_3$, $CONH_2$, $CON(CH_3)_2$, or $NO_2$.

As used herein, the term "$C_2$-$C_6$ alkenyl" refers to straight or branched, monovalent, unsaturated aliphatic chains of 2 to 6 carbon atoms including at least one carbon-carbon double bond and includes, but is not limited to, ethenyl, propenyl, isopropenyl, butenyl, isobutenyl, pentenyl, isopentenyl, and hexenyl. The term "$C_2$-$C_6$ alkenyl" includes within its definition the term "$C_2$-$C_4$ alkenyl".

As used herein, the term "$C_2$-$C_6$ alkynyl" refers to straight or branched, monovalent, unsaturated aliphatic chains of 2 to 6 carbon atoms including at least one carbon-carbon triple bond and includes, but is not limited to, ethynyl, propynyl, butynyl, isobutynyl, pentynyl, isopentynyl, and hexynyl. The term "$C_2$-$C_6$ alkynyl" includes within its definition the term "$C_2$-$C_4$ alkynyl".

The term "substituted $C_2$-$C_6$ alkenyl" means a $C_2$-$C_6$ alkenyl group as defined above which has been substituted by one or more, preferably from one to three groups selected from halo (preferably chloro or fluoro), hydroxy, —$OC_1$-$C_6$ alkyl, cyano, $SO_2$($C_1$-$C_6$ alkyl), $OCF_3$, $CF_3$, $CONH_2$, $CON(CH_3)_2$, or $NO_2$.

As used herein, the term "cycloalkyl" refers to cyclized chains of 3 to 8 carbon atoms and includes, but is not limited to, cyclopropyl, cyclobutyl, cyclopentyl, and cyclohexyl.

The term "substituted $C_3$-$C_8$ cycloalkyl" means a $C_3$-$C_8$ cycloalkyl group as defined above which has been substituted by one or more, preferably from one to three groups selected from halo (preferably chloro or fluoro), —$OC_1$-$C_6$ alkyl, cyano, $SO_2$($C_1$-$C_6$ alkyl), $OCF_3$, $CF_3$, $CONH_2$, $CON(CH_3)_2$, or $NO_2$.

The term "halo" means chloro, fluoro, bromo or iodo. Halo may most preferably be fluoro or chloro.

"$C_1$-$C_6$ alkoxy" represents a straight or branched alkyl chain having from one to six carbon atoms attached to an oxygen atom. Typical $C_1$-$C_6$ alkoxy groups include methoxy, ethoxy, propoxy, isopropoxy, butoxy, t-butoxy, pentoxy and the like. The term "$C_1$-$C_6$ alkoxy" includes within its definition the term "$C_1$-$C_4$ alkoxy".

"$C_2$-$C_6$ alkanoyl" represents a straight or branched alkyl chain having from one to five carbon atoms attached through a carbonyl moiety. Typical $C_2$-$C_6$ alkanoyl groups include ethanoyl (also referred to as acetyl), propanoyl, isopropanoyl, butanoyl, t-butanoyl, pentanoyl, hexanoyl, and the like.

"$C_1$-$C_6$ alkylidenyl" refers to a straight or branched, divalent, saturated aliphatic chain of one to six carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like.

The term "aryl" represents an aromatic ring or rings and aromatic residues of 5 to 7-membered mono- or bicyclic rings with 1 to 4 heteroatoms (a "heteroaryl") including but not limited to such groups as phenyl, naphthyl, biphenyl, thiophenyl (also known as thienyl), benzothiophenyl, furanyl, benzofuranyl, oxazolyl, indolyl, pyridyl, thiazolyl, isoxazolyl, isothiazolyl and the like.

The term "substituted aryl", "substituted N-aryl", and "substituted S-aryl" means that each of the respective aryl groups (which aryl group may contain heteroatoms as described above), is optionally substituted, at any available position, with from one to four substituents, independently selected from the group consisting of $C_1$-$C_6$ alkyl, —$OC_1$-$C_6$ alkyl, —$OCF_3$, amide, aryl, aryloxy, $SO_2$($C_{1-6}$ alkyl), $SO_2CF_3$, NHamide, carboxamide, sulfonamide, NHsulfonamide, imide, hydroxy, carboxy, nitro, halo, tri(chloro or fluoro)methyl, and cyano. The aromatic ring may be attached at any carbon atom or heteroatom which affords a stable structure. The group, 3,4-methylenedioxyphenyl is embraced by this definition.

The term "unsubstituted $C_1$-$C_6$ alkylaryl" means an unsubstituted $C_1$-$C_6$ alkyl group, as defined above, bonded to an unsubstituted aryl group as defined above. In preferred unsubstituted $C_1$-$C_6$ alkylaryl groups the unsubstituted $C_1$-$C_6$ alkyl moiety has from 1 to 3 carbon atoms. Also, and independently, in preferred unsubstituted $C_1$-$C_6$ alkylaryl groups the aryl group is selected from phenyl, thiazolyl, pyridyl, naphthyl, thienyl, isoxazolyl, oxazolyl and indolyl.

The term "substituted $C_1$-$C_6$ alkylaryl" means either an unsubstituted or substituted $C_1$-$C_6$ alkyl group, as defined above, bonded to a substituted aryl group as defined above or a substituted $C_1$-$C_6$ alkyl group as defined above bonded to an unsubstituted aryl group as defined above. In preferred compounds of the invention substituted $C_1$-$C_6$ alkylaryl denotes an $C_1$-$C_6$ alkyl group as defined above, bonded to a substituted aryl group as defined above. In more preferred substituted $C_1$-$C_6$ alkylaryl groups the unsubstituted $C_1$-$C_6$ alkyl moiety has from 1 to 3 carbon atoms. Also, and independently, in more preferred substituted $C_1$-$C_6$ alkylaryl groups the substituted aryl group is a selected from phenyl, thiazolyl, pyridyl, naphthyl, thienyl, oxazolyl, isoxazolyl or indolyl substituted, at any available position, by from one to four, preferably one, two or three, substituents independently selected from halo (preferably chloro or fluoro), $C_1$-$C_6$ alkyl, —$OC_1$-$C_6$ alkyl, cyano, $SO_2(C_1$-$C_6$ alkyl), $OCF_3$, $CF_3$, $CONH_2$, $NO_2$, phenyl, phenoxy, thienyl, pyridyl, thiazolyl, oxazolyl, furanyl, benzothiophenyl, benzofuranyl.

The term "unsubstituted $C_1$-$C_6$ alkyl(O)—$C_1$-$C_6$ alkyl aryl" means an unsubstituted $C_1$-$C_6$ alkyl(O)—$C_1$-$C_6$ alkyl group, as defined above, bonded to an unsubstituted aryl group as defined above. In preferred unsubstituted $C_1$-$C_6$ alkyl(O)—$C_1$-$C_6$ alkylaryl groups the unsubstituted $C_1$-$C_6$ alkyl(O)—$C_1$-$C_6$ alkyl moiety is —$CH_2$—O—$CH_2$—, —$CH_2$—O—$CH_2CH_2$—, or —$CH_2CH_2$—O—$CH_2$—, most preferably —$CH_2$—O—$CH_2$—. Also, and independently, in preferred unsubstituted $C_1$-$C_6$ alkyl(O)—$C_1$-$C_6$ alkylaryl groups the aryl group is a selected from phenyl, thiazolyl, pyridyl, naphthyl, thienyl, oxazolyl, isoxazolyl and indolyl.

The term "substituted $C_1$-$C_6$ alkyl(O)—$C_1$-$C_6$ alkyl aryl" means either an unsubstituted or substituted $C_1$-$C_6$ alkyl (O)—$C_1$-$C_6$ alkyl group, as defined above, bonded to a substituted aryl group as defined above or a substituted $C_1$-$C_6$ alkyl(O)—$C_1$-$C_6$ alkyl group as defined above bonded to an unsubstituted aryl group as defined above. In preferred compounds of the invention substituted $C_1$-$C_6$ alkyl(O)—$C_1$-$C_6$ alkylaryl denotes an $C_1$-$C_6$ alkyl(O)—$C_1$-$C_6$ alkyl group as defined above, bonded to a substituted aryl group as defined above. In more preferred substituted $C_1$-$C_6$ alkyl(O)—$C_1$-$C_6$ alkylaryl groups the unsubstituted $C_1$-$C_6$ alkyl(O)—$C_1$-$C_6$ alkyl moiety is —$CH_2$—O—$CH_2$—, —$CH_2$—O—$CH_2CH_2$—, or —$CH_2CH_2$—O—$CH_2$—, most preferably —$CH_2$—O—$CH_2$—. Also, and independently, in more preferred substituted $C_1$-$C_6$ alkyl(O)—$C_1$-$C_6$ alkylaryl groups the substituted aryl group is selected from phenyl, thiazolyl, pyridyl, naphthyl, thienyl, oxazolyl, isooxazolyl and indolyl substituted, at any available position, by from one to four, preferably one, two or three, substituents independently selected from halo (preferably chloro or fluoro), $C_1$-$C_6$ alkyl, —$OC_1$-$C_6$ alkyl, cyano, $SO_2(C_1$-$C_6$ alkyl), $OCF_3$, $CF_3$, $CONH_2$, $NO_2$, phenyl, phenoxy, thienyl, pyridyl, thiazolyl, oxazolyl, furanyl, benzothiophenyl, benzofuranyl.

The term "unsubstituted ($C_1$-$C_6$ alkyl)$C_3$-$C_8$ cycloalkyl" means an unsubstituted $C_1$-$C_6$ alkyl group, as defined above, bonded to an unsubstituted $C_3$-$C_8$ cycloalkyl group as defined above. In preferred unsubstituted ($C_1$-$C_6$ alkyl)$C_3$-$C_8$ cycloalkyl groups the unsubstituted $C_1$-$C_6$ alkyl moiety has from 1 to 3 carbon atoms. Also, and independently, in more preferred unsubstituted ($C_1$-$C_6$ alkyl)$C_3$-$C_8$ cycloalkyl groups the $C_3$-$C_8$ cycloalkyl group is cyclopropyl, cyclopentyl or cyclohexyl.

The term "substituted ($C_1$-$C_6$ alkyl)$C_3$-$C_8$ cycloalkyl" means either an unsubstituted or substituted $C_1$-$C_6$ alkyl group, as defined above, bonded to a substituted $C_3$-$C_8$ cycloalkyl group as defined above or a substituted $C_1$-$C_6$ alkyl group as defined above bonded to an unsubstituted $C_3$-$C_8$ cycloalkyl group as defined above. In preferred compounds of the invention substituted ($C_1$-$C_6$ alkyl)$C_3$-$C_8$ cycloalkyl denotes a $C_1$-$C_6$ alkyl group as defined above, bonded to a substituted $C_3$-$C_8$ cycloalkyl group as defined above. In more preferred substituted ($C_1$-$C_6$ alkyl)$C_3$-$C_8$ cycloalkyl groups the unsubstituted $C_1$-$C_6$ alkyl moiety has from 1 to 3 carbon atoms. Also, and independently, in more preferred substituted ($C_1$-$C_6$ alkyl)$C_3$-$C_8$ cycloalkyl groups the substituted $C_3$-$C_8$ cycloalkyl group is cyclopropyl, cyclopentyl or cyclohexyl substituted, at any available position, by at least one and preferably from one to four substituents independently selected from halo (preferably chloro or fluoro), $C_1$-$C_6$ alkyl, —$OC_1$-$C_6$ alkyl, cyano, $SO_2(C_1$-$C_6$ alkyl), $OCF_3$, $CF_3$, $CONH_2$, $CON(CH_3)_2$, $NO_2$, phenyl, phenoxy, thienyl, pyridyl, thiazolyl, oxazolyl, furanyl, benzothiophenyl, benzofuranyl.

The term "—O-aryl" means an aryloxy substituent which is bonded to the parent molecule through the 0 group. The term "optionally substituted —O-aryl" means that the aryl group of the —O-aryl substituent is optionally substituted with from one to four substituents independently selected from the group consisting of $C_1$-$C_6$ alkyl, —$OC_1$-$C_6$ alkyl, —$OCF_3$, amide, aryl, aryloxy, $SO_2(C_{1-6}$ alkyl), NHamide, $SO_2CF_3$, carboxamide, sulfonamide, NHsulfonamide, imide, hydroxy, carboxy, nitro, halo, tri(chloro or fluoro)methyl, and cyano.

The term "-aryl-aryl(K1)(K2)" refers to an aryl group substituted with an additional aryl group said additional aryl group being disubstituted with K1 and K2. K1 is defined to include halo and —$CF_3$, and K2 is defined to include hydrogen, halo, and —$CF_3$. Alternatively K1 and K2 together may form a methylenedioxy group. Similarly, the terms "—O-aryl-aryl(K1)(K2)", "—N-aryl-aryl(K1)(K2)", and "—S-aryl-aryl(K1)(K2)" are likewise defined. For example, the term "—O-aryl-aryl(K1)(K2)" means an aryloxy substituent as defined above which is substituted with an additional aryl group, said additional aryl group being disubstituted with K1 and K2. K1 and K2 are as defined immediately above.

The term "carboxy-protecting group" as used herein refers to substituents of the carboxy group commonly employed to block or protect the carboxy functionality while reacting other functional groups on the compound. Examples of such protecting groups include methyl, ethyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxy-benzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and the like.

A preferred carboxy-protecting group for the practice of the present invention is methyl or ethyl. Further examples of these groups may be found in E. Haslam, supra, at Chapter 5, and T. W. Greene, et al., supra, at Chapter 5.

The term "amino-protecting group" as used herein refers to substituents of the amino group commonly employed to block or protect the amino functionality while reacting other functional groups on the compound. Examples of such amino-protecting groups can be found at T. W. Greene, et al., supra.

Examples of such amino-protecting groups include, but are not limited to, formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, n-butoxycarbonyl, (NBoc) t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl) ethoxycarbonyl, 2-(triphenylphosphino)-ethoxycarbonyl, fluorenylmethoxy-carbonyl (FMOC), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, and the like; benzoylmethylsulfonyl group, 2-nitrophenylsulfenyl, diphenylphosphine oxide and like amino-protecting groups.

The amino-protecting group employed is usually not critical so long as the derivatized amino group is stable to the condition of subsequent reactions on other positions of the intermediate molecule, and may be selectively removed at the appropriate point without disrupting the remainder of the molecule including any other amino-protecting groups. A preferred amino-protecting group for the practice of the present invention is t-butoxycarbonyl(NBoc). Further examples of groups referred to by the above terms are described by E. Haslam, Protective Groups in Organic Chemistry, (J. G. W. McOmie, ed., 1973), at Chapter 2; and T. W. Greene and P. G. M. Wuts, Protective Groups in Organic Synthesis (1991), at Chapter 7.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, azido, chloro, bromo, fluoro or —O—CO—($C_4$-$C_7$ alkyl).

In the more preferred compounds of formula I, R1 is $C_1$-$C_6$alkylNHR10 where in R10 is selected from hydrogen and $C_1$-$C_6$ alkyl. In the most preferred compounds of the invention R1 is a group of formula —C($CH_3$)$_2$$NH_2$.

In an alternative group of more preferred compounds of formula I wherein R1 is (substituted $C_1$-$C_6$alkyl)NHR10, R10 is selected from hydrogen and $C_1$-$C_6$ alkyl and the substituted $C_1$-$C_6$ alkyl group is a $C_1$-$C_5$ alkyl group, which is more preferably branched, and which is substituted by from 1 to 3 halo atoms, most preferably fluoro atoms. Examples of more preferred R1 groups include —C($CH_2F$)$_2$$NH_2$, —C($CH_2F$)($CH_2CH_2F$)$NH_2$, —C($CF_3$)($CH_3$)$NH_2$, —C($CH_2CH_2F$)$_2$$NH_2$ and —C($CH_2CH_3$)($CH_2CF_3$)$NH_2$. In the most preferred compounds of the invention R1 is a group of formula —C($CH_2F$)$_2$$NH_2$.

In another alternative group of more preferred compounds of formula I wherein R1 is (substituted $C_1$-$C_6$alkyl)NHR10, R1 is —C($CH_3$)($CH_2OH$)$NH_2$.

In a further alternative group of more preferred compounds of formula I wherein R1 is (unsubstituted or substituted $C_3$-$C_8$ cycloalkyl)NHR10, R10 is selected from hydrogen and $C_1$-$C_6$ alkyl and the $C_3$-$C_8$ cycloalkyl group is unsubstituted. Still more preferably the $C_3$-$C_8$ cycloalkyl group is such that the carbonyl and the —NHR10 groups are connected at the same carbon atom. Examples of more preferred R1 groups of this type include

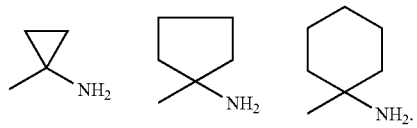

In the more preferred compounds of formula I, R2 is hydrogen or $C_1$-$C_6$ alkyl, preferably methyl. In the most preferred compounds of the invention R2 is hydrogen.

In the more preferred compounds of formula I, R3 is a substituted $C_1$-$C_6$ alkylaryl group or a substituted $C_1$-$C_6$alkyl(O)—$C_1$-$C_6$alkyl aryl group wherein:

the $C_1$-$C_6$alkyl moiety within the substituted $C_1$-$C_6$ alkylaryl group is methyl, ethyl or propyl;

the substituted $C_1$-$C_6$alkyl(O)—$C_1$-$C_6$alkyl moiety within the substituted $C_1$-$C_6$alkyl(O)—$C_1$-$C_6$alkyl aryl group is a moiety of formula —$CH_2OCH_2$—;

the aryl moiety within said groups is selected from phenyl, thiazolyl, pyridyl, naphthyl, thienyl, oxazolyl, isoxazolyl and indolyl which is substituted by from one to three groups independently selected from halo (preferably chloro or fluoro), methyl, methoxy, cyano, $SO_2$Me, trifluoromethyl, and trifluoromethoxy. Most preferably the substituted aryl moiety in said groups is 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,4,6-trifluorophenyl, 2,3,4-trifluorophenyl, 2,4,5-trifluorophenyl, 2,3,6-trifluorophenyl, 2,3,5-trifluorophenyl, 2-chlorophenyl, 3-chlorophenyl, 4-chlorophenyl, 2,6-dichlorophenyl, 2,3-dichlorophenyl, 2,4-dichlorophenyl, 2,5-dichlorophenyl, 2-chloro-4-fluorophenyl, 2-methylphenyl, 2,6-difluoro-3-methylphenyl, 3,6-difluoro-2-chlorophenyl, 2-fluoro-6-chlorophenyl, 2-fluoro-3-chlorophenyl, 2-fluoro-4-chlorophenyl, 2,6-difluoro-3-chlorophenyl, 4-trifluoromethylphenyl, 3-trifluoromethylphenyl, 2-trifluoromethylphenyl, 2-fluoro-5-trifluoromethylphenyl, 2-fluoro-3-trifluoromethylphenyl, 2-fluoro-6-trifluoromethylphenyl, 2-chloro-3-trifluoromethylphenyl, 4-trifluoromethoxyphenyl, 3-trifluoromethoxyphenyl, 2-trifluoromethoxyphenyl, 2-cyanophenyl, 3-cyanophenyl, 4-cyanophenyl, 4-methanesulphonylphenyl, and 2-methyl thiazolyl.

In the more preferred compounds of formula I R4 is hydrogen or $C_1$-$C_6$ alkyl. In the most preferred compounds of the invention R4 is hydrogen or methyl.

In the more preferred compounds of formula I R5 is hydrogen, $C_1$-$C_6$ alkyl, hydroxy, $C_1$-$C_6$alkoxy, $C_1$-$C_6$alkyl which is substituted by hydroxy or $C_1$-$C_6$alkyl which is substituted by one, two, or three halo atoms, preferably fluoro or chloro. In the most preferred compounds of the invention R5 is hydrogen, methyl, ethyl, i-propyl, n-propyl, 2-fluoroethyl, 2-hydroxyethyl, 2,2,2-trifluoroethyl, hydroxy or methoxy.

In the more preferred compounds of formula I R6 and R7 are independently $C_1$-$C_6$ alkyl groups; or R6 and R7 are independently $C_1$-$C_6$alkyl or $C_2$-$C_6$alkenyl, in which one or both groups are substituted by one, two, or three halo atoms; or R6 is hydrogen and R7 is $C_1$-$C_6$alkyl or $C_2$-$C_6$alkenyl which is substituted by one, two, or three halo atoms; or R6 and R7 together form a carbocyclic ring of up to 8 atoms or R6 and R7 together with the carbon atom to which they are attached may form a $C_3$-$C_8$cycloalkyl group which is optionally partly unsaturated and which is substituted by one, two, or three halo atoms. In the most preferred compounds of the invention R6 and R7 are both methyl, ethyl, fluoromethyl, trifluoromethyl, 2-fluoroethyl, or 2,2,2-trifluoroethyl; or R6 is hydrogen and R7 is trifluoromethyl, 2,2,2-trifluoroethyl, or 3,3,3-trifluoropropyl; or R6 and R7 together form a cyclohexane, cyclopentane, fluorocyclohexane or difluorocyclohexane ring.

In the more preferred compounds of formula I, R8 is hydrogen, $C_1$-$C_6$alkyl, $(C_1$-$C_6$alkyl)$C_3$-$C_8$cycloalkyl, benzyl, 1-phenylethyl, $C_1$-$C_6$alkyl which is substituted by hydroxy, methoxy, $CONH_2$, or $CON(CH_3)_2$, or $C_1$-$C_6$alkyl which is substituted by one, two, or three halo atoms, phenyl substituted by one, two, or three halo atoms or benzyl substituted by one, two, or three halo atoms. The Halo atoms are preferably fluoro or chloro. In the most preferred compounds of the invention R8 is hydrogen, methyl, ethyl, propyl, isopropyl, isobutyl, pentyl, cyclopropylmethyl, 1-phenylethyl, benzyl, 2-hydroxyethyl, 2-methoxyethyl, 2-fluoroethyl, 2,2,2-trifluoroethyl, 4,4,4-trifluorobutyl, 3,3,3-trifluoropropyl, $CH_2CONH_2$, $CH_2CON(CH_3)_2$.

In the more preferred compounds of formula I, R9 is $C_1$-$C_6$ alkyl, $C_3$-$C_8$ cycloalkyl, optionally substituted aryl, optionally substituted-O-aryl, or -aryl-aryl(K1)(K2) wherein K1 is halo or —$CF_3$ and K2 is hydrogen, halo or $CF_3$ or K1 and K2 together form a methylenedioxy group. In preferred compounds of the invention wherein R9 is a C1-C6 alkyl group, R9 is most preferably methyl or isopropyl. In preferred compounds of the invention wherein R9 is a C3-C8 cycloalkyl group, R9 is most preferably cyclohexyl. In preferred compounds of the invention wherein R9 is an -aryl-aryl(K1)(K2) group, R9 is a -phenyl-phenyl(K1) (K2), or -phenyl-thienyl (K1)(K2) group, and most preferably is -phenyl-fluorophenyl, -phenyl-chlorophenyl, -phenyl-trifluoromethylphenyl-phenyl-(3,4-methylenedioxyphenyl) or -phenyl-chlorothienyl.

In preferred compounds of the invention wherein R9 is an optionally substituted aryl or optionally substituted-O-aryl group, said optionally substituted aryl moiety is phenyl, naphthyl, pyridyl, thienyl, thiazolyl or oxazolyl, most preferably phenyl. Preferred optional substituents are halo (preferably chloro, fluoro or bromo), methyl, ethyl, propyl, t-butyl, trifluoromethyl, trifluoromethoxy, methoxy, ethoxy, cyano, methylsulphonyl, phenyl, phenoxy, thienyl, pyridyl, thiazolyl, oxazolyl, nitro, $CONH_2$, furanyl, benzothiophenyl and benzofuranyl. In the most preferred compounds of the invention wherein R9 is an optionally substituted aryl or optionally substituted-O-aryl group, R9 is selected from phenyl, 4-methylsulphonylphenyl, 3-methylsulphonylphenyl, 4-fluorophenyl, 2-fluorophenyl, 3-fluorophenyl, 3-chlorophenyl, 2-chlorophenyl, 4-chlorophenyl, 4-t-butylphenyl, 4-trifluoromethylphenyl, 3-trifluoromethylphenyl, 4-nitrophenyl, 3-nitrophenyl, 4-bromophenyl, 3-bromophenyl, 2-bromophenyl, 4-methylphenyl, 3-methylphenyl, 4-phenylphenyl, 3-phenylphenyl, 4-phenoxyphenyl, 3-phenoxyphenyl, 4-cyanophenyl, 3-cyanophenyl, 4-carbamoylphenyl, 4-methoxyphenyl, 3-methoxyphenyl, thienyl, thiazolyl, pyridyl, phenoxy, 4-chlorophenoxy, 2,3-dichlorophenyl, 3,4-dichlorophenyl, naphthyl, oxazolyl, 2,4-difluorophenyl, 3,4-difluorophenyl, 3,5-difluorophenyl, 2,3-difluorophenyl, 2,6-difluorophenyl, 2,5-difluorophenyl, 2-fluoro-3-chlorophenyl, 4-ethylphenyl, 4-ethoxyphenyl, 3,4,5-trifluoromethylphenyl, 3-fluoro-4-chlorophenyl and 4-carbamoylphenyl.

It will be understood that the preferred definitions given above in respect of R2, R3, R5, R6, R7, R8 and R9 in formula I and II apply to the substituents within the definitions at the corresponding positions in formulae III and IV i.e. positions R12, R13, R15, R16, R17, R18 and R19 respectively.

Particularly preferred compounds of the invention are those set out in the following tables I to XXIII and the pharmaceutically acceptable salts and solvates thereof:

TABLE I

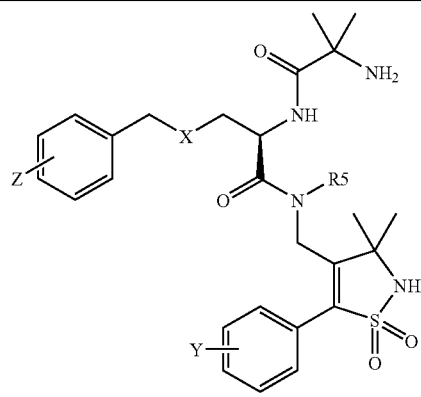

| X | Y | Z | R5 |
|---|---|---|---|
| $CH_2$ | 4-Cl | 2-F | Me |
| O | 4-Cl | 2-F | Me |
| bond | 4-Cl | 2-F | Me |
| $CH_2$ | 4-Cl | 2-F | Et |
| O | 4-Cl | 2-F | Et |
| bond | 4-Cl | 2-F | Et |
| $CH_2$ | 4-Cl | 3-F | Me |
| O | 4-Cl | 3-F | Me |
| bond | 4-Cl | 3-F | Me |
| $CH_2$ | 4-Cl | 3-F | Et |
| O | 4-Cl | 3-F | Et |
| bond | 4-Cl | 3-F | Et |
| $CH_2$ | 4-Cl | 4-F | Me |
| O | 4-Cl | 4-F | Me |
| bond | 4-Cl | 4-F | Me |
| $CH_2$ | 4-Cl | 4-F | Et |
| O | 4-Cl | 4-F | Et |
| bond | 4-Cl | 4-F | Et |
| $CH_2$ | 4-Cl | 2,3-$F_2$ | Me |
| O | 4-Cl | 2,3-$F_2$ | Me |
| bond | 4-Cl | 2,3-$F_2$ | Me |
| $CH_2$ | 4-Cl | 2,3-$F_2$ | Et |
| O | 4-Cl | 2,3-$F_2$ | Et |
| bond | 4-Cl | 2,3-$F_2$ | Et |
| $CH_2$ | 4-Cl | 2,4-$F_2$ | Me |
| O | 4-Cl | 2,4-$F_2$ | Me |
| bond | 4-Cl | 2,4-$F_2$ | Me |
| $CH_2$ | 4-Cl | 2,4-$F_2$ | Et |
| O | 4-Cl | 2,4-$F_2$ | Et |
| bond | 4-Cl | 2,4-$F_2$ | Et |
| $CH_2$ | 4-Cl | 2,5-$F_2$ | Me |
| O | 4-Cl | 2,5-$F_2$ | Me |
| bond | 4-Cl | 2,5-$F_2$ | Me |
| $CH_2$ | 4-Cl | 2,5-$F_2$ | Et |
| O | 4-Cl | 2,5-$F_2$ | Et |
| bond | 4-Cl | 2,5-$F_2$ | Et |
| $CH_2$ | 4-Cl | 2,6-$F_2$ | Me |
| O | 4-Cl | 2,6-$F_2$ | Me |
| bond | 4-Cl | 2,6-$F_2$ | Me |
| $CH_2$ | 4-Cl | 2,6-$F_2$ | Et |
| O | 4-Cl | 2,6-$F_2$ | Et |
| bond | 4-Cl | 2,6-$F_2$ | Et |
| $CH_2$ | 4-Cl | 3,4-$F_2$ | Me |
| O | 4-Cl | 3,4-$F_2$ | Me |
| bond | 4-Cl | 3,4-$F_2$ | Me |
| $CH_2$ | 4-Cl | 3,4-$F_2$ | Et |
| O | 4-Cl | 3,4-$F_2$ | Et |
| bond | 4-Cl | 3,4-$F_2$ | Et |
| $CH_2$ | 4-Cl | 3,5-$F_2$ | Me |
| O | 4-Cl | 3,5-$F_2$ | Me |
| bond | 4-Cl | 3,5-$F_2$ | Me |
| $CH_2$ | 4-Cl | 3,5-$F_2$ | Et |
| O | 4-Cl | 3,5-$F_2$ | Et |
| bond | 4-Cl | 3,5-$F_2$ | Et |
| $CH_2$ | 4-Cl | 2,4,6-$F_3$ | Me |
| O | 4-Cl | 2,4,6-$F_3$ | Me |
| bond | 4-Cl | 2,4,6-$F_3$ | Me |

TABLE I-continued

| X | Y | Z | R5 |
|---|---|---|----|
| CH₂ | 4-Cl | 2,4,6-F₃ | Et |
| O | 4-Cl | 2,4,6-F₃ | Et |
| bond | 4-Cl | 2,4,6-F₃ | Et |
| CH₂ | 4-Cl | 2,4,5-F₃ | Me |
| O | 4-Cl | 2,4,5-F₃ | Me |
| bond | 4-Cl | 2,4,5-F₃ | Me |
| CH₂ | 4-Cl | 2,4,5-F₃ | Et |
| O | 4-Cl | 2,4,5-F₃ | Et |
| bond | 4-Cl | 2,4,5-F₃ | Et |
| CH₂ | 4-Cl | 2,3,6-F₃ | Me |
| O | 4-Cl | 2,3,6-F₃ | Me |
| bond | 4-Cl | 2,3,6-F₃ | Me |
| CH₂ | 4-Cl | 2,3,6-F₃ | Et |
| O | 4-Cl | 2,3,6-F₃ | Et |
| bond | 4-Cl | 2,3,6-F₃ | Et |
| CH₂ | 4-Cl | 2,3,5-F₃ | Me |
| O | 4-Cl | 2,3,5-F₃ | Me |
| bond | 4-Cl | 2,3,5-F₃ | Me |
| CH₂ | 4-Cl | 2,3,5-F₃ | Et |
| O | 4-Cl | 2,3,5-F₃ | Et |
| bond | 4-Cl | 2,3,5-F₃ | Et |
| CH₂ | 4-Cl | 2-Cl | Me |
| O | 4-Cl | 2-Cl | Me |
| bond | 4-Cl | 2-Cl | Me |
| CH₂ | 4-Cl | 2-Cl | Et |
| O | 4-Cl | 2-Cl | Et |
| bond | 4-Cl | 2-Cl | Et |
| CH₂ | 4-Cl | 3-Cl | Me |
| O | 4-Cl | 3-Cl | Me |
| bond | 4-Cl | 3-Cl | Me |
| CH₂ | 4-Cl | 3-Cl | Et |
| O | 4-Cl | 3-Cl | Et |
| bond | 4-Cl | 3-Cl | Et |
| CH₂ | 4-Cl | 4-Cl | Me |
| O | 4-Cl | 4-Cl | Me |
| bond | 4-Cl | 4-Cl | Me |
| CH₂ | 4-Cl | 4-Cl | Et |
| O | 4-Cl | 4-Cl | Et |
| bond | 4-Cl | 4-Cl | Et |
| CH₂ | 4-Cl | 2,6-Cl₂ | Me |
| O | 4-Cl | 2,6-Cl₂ | Me |
| bond | 4-Cl | 2,6-Cl₂ | Me |
| CH₂ | 4-Cl | 2,6-Cl₂ | Et |
| O | 4-Cl | 2,6-Cl₂ | Et |
| bond | 4-Cl | 2,6-Cl₂ | Et |
| CH₂ | 4-Cl | 2-F-6-Cl | Me |
| O | 4-Cl | 2-F-6-Cl | Me |
| bond | 4-Cl | 2-F-6-Cl | Me |
| CH₂ | 4-Cl | 2-F-6-Cl | Et |
| O | 4-Cl | 2-F-6-Cl | Et |
| bond | 4-Cl | 2-F-6-Cl | Et |
| CH₂ | 4-Cl | 2-F-3-Cl | Me |
| O | 4-Cl | 2-F-3-Cl | Me |
| bond | 4-Cl | 2-F-3-Cl | Me |
| CH₂ | 4-Cl | 2-F-3-Cl | Et |
| O | 4-Cl | 2-F-3-Cl | Et |
| bond | 4-Cl | 2-F-3-Cl | Et |
| CH₂ | 4-Cl | 2-F-4-Cl | Me |
| O | 4-Cl | 2-F-4-Cl | Me |
| bond | 4-Cl | 2-F-4-Cl | Me |
| CH₂ | 4-Cl | 2-F-4-Cl | Et |
| O | 4-Cl | 2-F-4-Cl | Et |
| bond | 4-Cl | 2-F-4-Cl | Et |
| CH₂ | 4-Cl | 3-F-4-Cl | Me |
| O | 4-Cl | 3-F-4-Cl | Me |
| bond | 4-Cl | 3-F-4-Cl | Me |
| CH₂ | 4-Cl | 3-F-4-Cl | Et |
| O | 4-Cl | 3-F-4-Cl | Et |
| bond | 4-Cl | 3-F-4-Cl | Et |
| CH₂ | 4-Cl | 2,6-F₂-3-Cl | Me |
| O | 4-Cl | 2,6-F₂-3-Cl | Me |
| bond | 4-Cl | 2,6-F₂-3-Cl | Me |
| CH₂ | 4-Cl | 2,6-F₂-3-Cl | Et |
| O | 4-Cl | 2,6-F₂-3-Cl | Et |
| bond | 4-Cl | 2,6-F₂-3-Cl | Et |
| CH₂ | 4-Cl | 2-Cl-3,6-F₂ | Me |
| O | 4-Cl | 2-Cl-3,6-F₂ | Me |
| bond | 4-Cl | 2-Cl-3,6-F₂ | Me |
| CH₂ | 4-Cl | 2-Cl-3,6-F₂ | Et |
| O | 4-Cl | 2-Cl-3,6-F₂ | Et |
| bond | 4-Cl | 2-Cl-3,6-F₂ | Et |
| CH₂ | 4-Cl | 2,3-Cl₂ | Me |
| O | 4-Cl | 2,3-Cl₂ | Me |
| bond | 4-Cl | 2,3-Cl₂ | Me |
| CH₂ | 4-Cl | 2,3-Cl₂ | Et |
| O | 4-Cl | 2,3-Cl₂ | Et |
| bond | 4-Cl | 2,3-Cl₂ | Et |
| CH₂ | 4-Cl | 4-F-2-Cl | Me |
| O | 4-Cl | 4-F-2-Cl | Me |
| bond | 4-Cl | 4-F-2-Cl | Me |
| CH₂ | 4-Cl | 4-F-2-Cl | Et |
| O | 4-Cl | 4-F-2-Cl | Et |
| bond | 4-Cl | 4-F-2-Cl | Et |
| CH₂ | 4-Cl | 4-CF₃ | Me |
| O | 4-Cl | 4-CF₃ | Me |
| bond | 4-Cl | 4-CF₃ | Me |
| CH₂ | 4-Cl | 4-CF₃ | Et |
| O | 4-Cl | 4-CF₃ | Et |
| bond | 4-Cl | 4-CF₃ | Et |
| CH₂ | 4-Cl | 3-CF₃ | Me |
| O | 4-Cl | 3-CF₃ | Me |
| bond | 4-Cl | 3-CF₃ | Me |
| CH₂ | 4-Cl | 3-CF₃ | Et |
| O | 4-Cl | 3-CF₃ | Et |
| bond | 4-Cl | 3-CF₃ | Et |
| CH₂ | 4-Cl | 2-CF₃ | Me |
| O | 4-Cl | 2-CF₃ | Me |
| bond | 4-Cl | 2-CF₃ | Me |
| CH₂ | 4-Cl | 2-CF₃ | Et |
| O | 4-Cl | 2-CF₃ | Et |
| bond | 4-Cl | 2-CF₃ | Et |
| CH₂ | 4-Cl | 2-F-5-CF₃ | Me |
| O | 4-Cl | 2-F-5-CF₃ | Me |
| bond | 4-Cl | 2-F-5-CF₃ | Me |

TABLE I-continued

| X | Y | Z | R5 |
|---|---|---|---|
| CH₂ | 4-Cl | 2-F-5-CF₃ | Et |
| O | 4-Cl | 2-F-5-CF₃ | Et |
| bond | 4-Cl | 2-F-5-CF₃ | Et |
| CH₂ | 4-Cl | 4-OCF₃ | Me |
| O | 4-Cl | 4-OCF₃ | Me |
| bond | 4-Cl | 4-OCF₃ | Me |
| CH₂ | 4-Cl | 4-OCF₃ | Et |
| O | 4-Cl | 4-OCF₃ | Et |
| bond | 4-Cl | 4-OCF₃ | Et |
| CH₂ | 4-Cl | 3-OCF₃ | Me |
| O | 4-Cl | 3-OCF₃ | Me |
| bond | 4-Cl | 3-OCF₃ | Me |
| CH₂ | 4-Cl | 3-OCF₃ | Et |
| O | 4-Cl | 3-OCF₃ | Et |
| bond | 4-Cl | 3-OCF₃ | Et |
| CH₂ | 4-Cl | 2-OCF₃ | Me |
| O | 4-Cl | 2-OCF₃ | Me |
| bond | 4-Cl | 2-OCF₃ | Me |
| CH₂ | 4-Cl | 2-OCF₃ | Et |
| O | 4-Cl | 2-OCF₃ | Et |
| bond | 4-Cl | 2-OCF₃ | Et |
| CH₂ | 4-Cl | 2-CN | Me |
| O | 4-Cl | 2-CN | Me |
| bond | 4-Cl | 2-CN | Me |
| CH₂ | 4-Cl | 2-CN | Et |
| O | 4-Cl | 2-CN | Et |
| bond | 4-Cl | 2-CN | Et |
| CH₂ | 4-Cl | 3-CN | Me |
| O | 4-Cl | 3-CN | Me |
| bond | 4-Cl | 3-CN | Me |
| CH₂ | 4-Cl | 3-CN | Et |
| O | 4-Cl | 3-CN | Et |
| bond | 4-Cl | 3-CN | Et |
| CH₂ | 4-Cl | 4-CN | Me |
| O | 4-Cl | 4-CN | Me |
| bond | 4-Cl | 4-CN | Me |
| CH₂ | 4-Cl | 4-CN | Et |
| O | 4-Cl | 4-CN | Et |
| bond | 4-Cl | 4-CN | Et |
| CH₂ | 4-Cl | 4-SO₂CH₃ | Me |
| O | 4-Cl | 4-SO₂CH₃ | Me |
| bond | 4-Cl | 4-SO₂CH₃ | Me |
| CH₂ | 4-Cl | 4-SO₂CH₃ | Et |
| O | 4-Cl | 4-SO₂CH₃ | Et |
| bond | 4-Cl | 4-SO₂CH₃ | Et |
| CH₂ | 4-F | 2-F | Me |
| O | 4-F | 2-F | Me |
| bond | 4-F | 2-F | Me |
| CH₂ | 4-F | 2-F | Et |
| O | 4-F | 2-F | Et |
| bond | 4-F | 2-F | Et |
| CH₂ | 4-F | 3-F | Me |
| O | 4-F | 3-F | Me |
| bond | 4-F | 3-F | Me |
| CH₂ | 4-F | 3-F | Et |
| O | 4-F | 3-F | Et |
| bond | 4-F | 3-F | Et |
| CH₂ | 4-F | 4-F | Me |
| O | 4-F | 4-F | Me |
| bond | 4-F | 4-F | Me |
| CH₂ | 4-F | 4-F | Et |
| O | 4-F | 4-F | Et |
| bond | 4-F | 4-F | Et |
| CH₂ | 4-F | 2,3-F₂ | Me |
| O | 4-F | 2,3-F₂ | Me |
| bond | 4-F | 2,3-F₂ | Me |
| CH₂ | 4-F | 2,3-F₂ | Et |
| O | 4-F | 2,3-F₂ | Et |
| bond | 4-F | 2,3-F₂ | Et |
| CH₂ | 4-F | 2,4-F₂ | Me |
| O | 4-F | 2,4-F₂ | Me |
| bond | 4-F | 2,4-F₂ | Me |
| CH₂ | 4-F | 2,4-F₂ | Et |
| O | 4-F | 2,4-F₂ | Et |
| bond | 4-F | 2,4-F₂ | Et |
| CH₂ | 4-F | 2,5-F₂ | Me |
| O | 4-F | 2,5-F₂ | Me |
| bond | 4-F | 2,5-F₂ | Me |
| CH₂ | 4-F | 2,5-F₂ | Et |
| O | 4-F | 2,5-F₂ | Et |
| bond | 4-F | 2,5-F₂ | Et |
| CH₂ | 4-F | 2,6-F₂ | Me |
| O | 4-F | 2,6-F₂ | Me |
| bond | 4-F | 2,6-F₂ | Me |
| CH₂ | 4-F | 2,6-F₂ | Et |
| O | 4-F | 2,6-F₂ | Et |
| bond | 4-F | 2,6-F₂ | Et |
| CH₂ | 4-F | 3,4-F₂ | Me |
| O | 4-F | 3,4-F₂ | Me |
| bond | 4-F | 3,4-F₂ | Me |
| CH₂ | 4-F | 3,4-F₂ | Et |
| O | 4-F | 3,4-F₂ | Et |
| bond | 4-F | 3,4-F₂ | Et |
| CH₂ | 4-F | 3,5-F₂ | Me |
| O | 4-F | 3,5-F₂ | Me |
| bond | 4-F | 3,5-F₂ | Me |
| CH₂ | 4-F | 3,5-F₂ | Et |
| O | 4-F | 3,5-F₂ | Et |
| bond | 4-F | 3,5-F₂ | Et |
| CH₂ | 4-F | 2,4,6-F₃ | Me |
| O | 4-F | 2,4,6-F₃ | Me |
| bond | 4-F | 2,4,6-F₃ | Me |
| CH₂ | 4-F | 2,4,6-F₃ | Et |
| O | 4-F | 2,4,6-F₃ | Et |
| bond | 4-F | 2,4,6-F₃ | Et |
| CH₂ | 4-F | 2,4,5-F₃ | Me |
| O | 4-F | 2,4,5-F₃ | Me |
| bond | 4-F | 2,4,5-F₃ | Me |
| CH₂ | 4-F | 2,4,5-F₃ | Et |
| O | 4-F | 2,4,5-F₃ | Et |
| bond | 4-F | 2,4,5-F₃ | Et |
| CH₂ | 4-F | 2,3,6-F₃ | Me |
| O | 4-F | 2,3,6-F₃ | Me |
| bond | 4-F | 2,3,6-F₃ | Me |

TABLE I-continued

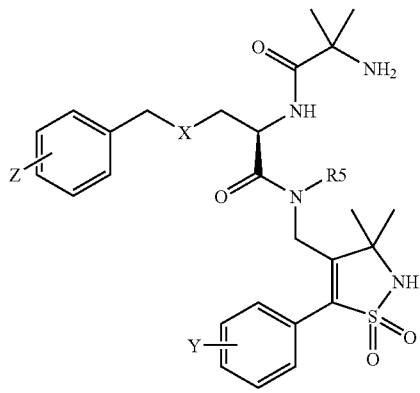

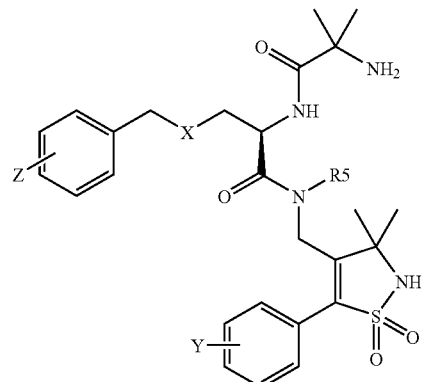

| X | Y | Z | R5 |
|---|---|---|---|
| CH₂ | 4-F | 2,3,6-F₃ | Et |
| O | 4-F | 2,3,6-F₃ | Et |
| bond | 4-F | 2,3,6-F₃ | Et |
| CH₂ | 4-F | 2,3,5-F₃ | Me |
| O | 4-F | 2,3,5-F₃ | Me |
| bond | 4-F | 2,3,5-F₃ | Me |
| CH₂ | 4-F | 2,3,5-F₃ | Et |
| O | 4-F | 2,3,5-F₃ | Et |
| bond | 4-F | 2,3,5-F₃ | Et |
| CH₂ | 4-F | 2-Cl | Me |
| O | 4-F | 2-Cl | Me |
| bond | 4-F | 2-Cl | Me |
| CH₂ | 4-F | 2-Cl | Et |
| O | 4-F | 2-Cl | Et |
| bond | 4-F | 2-Cl | Et |
| CH₂ | 4-F | 3-Cl | Me |
| O | 4-F | 3-Cl | Me |
| bond | 4-F | 3-Cl | Me |
| CH₂ | 4-F | 3-Cl | Et |
| O | 4-F | 3-Cl | Et |
| bond | 4-F | 3-Cl | Et |
| CH₂ | 4-F | 4-Cl | Me |
| O | 4-F | 4-Cl | Me |
| bond | 4-F | 4-Cl | Me |
| CH₂ | 4-F | 4-Cl | Et |
| O | 4-F | 4-Cl | Et |
| bond | 4-F | 4-Cl | Et |
| CH₂ | 4-F | 2,6-Cl₂ | Me |
| O | 4-F | 2,6-Cl₂ | Me |
| bond | 4-F | 2,6-Cl₂ | Me |
| CH₂ | 4-F | 2,6-Cl₂ | Et |
| O | 4-F | 2,6-Cl₂ | Et |
| bond | 4-F | 2,6-Cl₂ | Et |
| CH₂ | 4-F | 2-F-6-Cl | Me |
| O | 4-F | 2-F-6-Cl | Me |
| bond | 4-F | 2-F-6-Cl | Me |
| CH₂ | 4-F | 2-F-6-Cl | Et |
| O | 4-F | 2-F-6-Cl | Et |
| bond | 4-F | 2-F-6-Cl | Et |
| CH₂ | 4-F | 2-F-3-Cl | Me |
| O | 4-F | 2-F-3-Cl | Me |
| bond | 4-F | 2-F-3-Cl | Me |
| CH₂ | 4-F | 2-F-3-Cl | Et |
| O | 4-F | 2-F-3-Cl | Et |
| bond | 4-F | 2-F-3-Cl | Et |
| CH₂ | 4-F | 2-F-4-Cl | Me |
| O | 4-F | 2-F-4-Cl | Me |
| bond | 4-F | 2-F-4-Cl | Me |
| CH₂ | 4-F | 2-F-4-Cl | Et |
| O | 4-F | 2-F-4-Cl | Et |
| bond | 4-F | 2-F-4-Cl | Et |
| CH₂ | 4-F | 3-F-4-Cl | Me |
| O | 4-F | 3-F-4-Cl | Me |
| bond | 4-F | 3-F-4-Cl | Me |
| CH₂ | 4-F | 3-F-4-Cl | Et |
| O | 4-F | 3-F-4-Cl | Et |
| bond | 4-F | 3-F-4-Cl | Et |
| CH₂ | 4-F | 2,6-F₂-3-Cl | Me |
| O | 4-F | 2,6-F₂-3-Cl | Me |
| bond | 4-F | 2,6-F₂-3-Cl | Me |
| CH₂ | 4-F | 2,6-F₂-3-Cl | Et |
| O | 4-F | 2,6-F₂-3-Cl | Et |
| bond | 4-F | 2,6-F₂-3-Cl | Et |
| CH₂ | 4-F | 2-Cl-3,6-F₂ | Me |
| O | 4-F | 2-Cl-3,6-F₂ | Me |
| bond | 4-F | 2-Cl-3,6-F₂ | Me |
| CH₂ | 4-F | 2-Cl-3,6-F₂ | Et |
| O | 4-F | 2-Cl-3,6-F₂ | Et |
| bond | 4-F | 2-Cl-3,6-F₂ | Et |
| CH₂ | 4-F | 2,3-Cl₂ | Me |
| O | 4-F | 2,3-Cl₂ | Me |
| bond | 4-F | 2,3-Cl₂ | Me |
| CH₂ | 4-F | 2,3-Cl₂ | Et |
| O | 4-F | 2,3-Cl₂ | Et |
| bond | 4-F | 2,3-Cl₂ | Et |
| CH₂ | 4-F | 4-F-2-Cl | Me |
| O | 4-F | 4-F-2-Cl | Me |
| bond | 4-F | 4-F-2-Cl | Me |
| CH₂ | 4-F | 4-F-2-Cl | Et |
| O | 4-F | 4-F-2-Cl | Et |
| bond | 4-F | 4-F-2-Cl | Et |
| CH₂ | 4-F | 4-CF₃ | Me |
| O | 4-F | 4-CF₃ | Me |
| bond | 4-F | 4-CF₃ | Me |
| CH₂ | 4-F | 4-CF₃ | Et |
| O | 4-F | 4-CF₃ | Et |
| bond | 4-F | 4-CF₃ | Et |
| CH₂ | 4-F | 3-CF₃ | Me |
| O | 4-F | 3-CF₃ | Me |
| bond | 4-F | 3-CF₃ | Me |
| CH₂ | 4-F | 3-CF₃ | Et |
| O | 4-F | 3-CF₃ | Et |
| bond | 4-F | 3-CF₃ | Et |
| CH₂ | 4-F | 2-CF₃ | Me |
| O | 4-F | 2-CF₃ | Me |
| bond | 4-F | 2-CF₃ | Me |
| CH₂ | 4-F | 2-CF₃ | Et |
| O | 4-F | 2-CF₃ | Et |
| bond | 4-F | 2-CF₃ | Et |
| CH₂ | 4-F | 2-F-5-CF₃ | Me |
| O | 4-F | 2-F-5-CF₃ | Me |
| bond | 4-F | 2-F-5-CF₃ | Me |
| CH₂ | 4-F | 2-F-5-CF₃ | Et |
| O | 4-F | 2-F-5-CF₃ | Et |
| bond | 4-F | 2-F-5-CF₃ | Et |
| CH₂ | 4-F | 4-OCF₃ | Me |
| O | 4-F | 4-OCF₃ | Me |
| bond | 4-F | 4-OCF₃ | Me |
| CH₂ | 4-F | 4-OCF₃ | Et |
| O | 4-F | 4-OCF₃ | Et |
| bond | 4-F | 4-OCF₃ | Et |
| CH₂ | 4-F | 3-OCF₃ | Me |
| O | 4-F | 3-OCF₃ | Me |
| bond | 4-F | 3-OCF₃ | Me |

TABLE I-continued

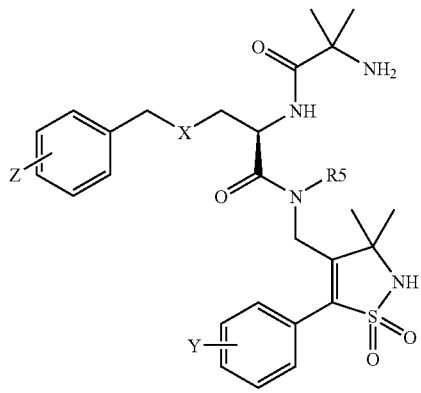

| X | Y | Z | R5 |
|---|---|---|---|
| CH₂ | 4-F | 3-OCF₃ | Et |
| O | 4-F | 3-OCF₃ | Et |
| bond | 4-F | 3-OCF₃ | Et |
| CH₂ | 4-F | 2-OCF₃ | Me |
| O | 4-F | 2-OCF₃ | Me |
| bond | 4-F | 2-OCF₃ | Me |
| CH₂ | 4-F | 2-OCF₃ | Et |
| O | 4-F | 2-OCF₃ | Et |
| bond | 4-F | 2-OCF₃ | Et |
| CH₂ | 4-F | 2-CN | Me |
| O | 4-F | 2-CN | Me |
| bond | 4-F | 2-CN | Me |
| CH₂ | 4-F | 2-CN | Et |
| O | 4-F | 2-CN | Et |
| bond | 4-F | 2-CN | Et |
| CH₂ | 4-F | 3-CN | Me |
| O | 4-F | 3-CN | Me |
| bond | 4-F | 3-CN | Me |
| CH₂ | 4-F | 3-CN | Et |
| O | 4-F | 3-CN | Et |
| bond | 4-F | 3-CN | Et |
| CH₂ | 4-F | 4-CN | Me |
| O | 4-F | 4-CN | Me |
| bond | 4-F | 4-CN | Me |
| CH₂ | 4-F | 4-CN | Et |
| O | 4-F | 4-CN | Et |
| bond | 4-F | 4-CN | Et |
| CH₂ | 4-F | 4-SO₂CH₃ | Me |
| O | 4-F | 4-SO₂CH₃ | Me |
| bond | 4-F | 4-SO₂CH₃ | Me |
| CH₂ | 4-F | 4-SO₂CH₃ | Et |
| O | 4-F | 4-SO₂CH₃ | Et |
| bond | 4-F | 4-SO₂CH₃ | Et |
| O | 4-Cl | 2-F | CH₂CH₂F |
| O | 4-Cl | 3-F | CH₂CH₂F |
| O | 4-Cl | 4-F | CH₂CH₂F |
| O | 4-Cl | 4-Cl | CH₂CH₂F |
| O | 4-Cl | 2,5-F₂ | CH₂CH₂F |
| O | 4-Cl | 2,4-F₂ | CH₂CH₂F |
| O | 4-Cl | 2-Cl | CH₂CH₂F |
| O | 4-Cl | 2,6-F₂ | CH₂CH₂F |
| O | 4-Cl | 3,5-F₂ | CH₂CH₂F |
| O | 4-Cl | 2,3-F₂ | CH₂CH₂F |
| O | 4-Cl | 3,4-F₂ | CH₂CH₂F |
| O | 4-Cl | 2,3,5-F₃ | CH₂CH₂F |
| O | 4-Cl | 2,3,6-F₃ | CH₂CH₂F |
| O | 4-Cl | 2,4,5-F₃ | CH₂CH₂F |
| O | 4-Cl | 2,6-Cl₂ | CH₂CH₂F |
| O | 4-Cl | 2-F-6-Cl | CH₂CH₂F |
| O | 4-Cl | 2-F-3-Cl | CH₂CH₂F |
| O | 4-Cl | 2-F-4-Cl | CH₂CH₂F |
| O | 4-Cl | 4-F-2-Cl | CH₂CH₂F |
| O | 4-Cl | 2,3-Cl₂ | CH₂CH₂F |
| O | 4-Cl | 2-Cl-3,6-F₂ | CH₂CH₂F |
| O | 4-F | 2-F | CH₂CH₂F |
| O | 4-F | 3-F | CH₂CH₂F |
| O | 4-F | 4-F | CH₂CH₂F |

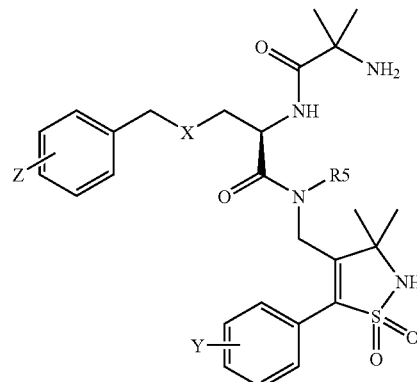

| X | Y | Z | R5 |
|---|---|---|---|
| O | 4-F | 4-Cl | CH₂CH₂F |
| O | 4-F | 2,5-F₂ | CH₂CH₂F |
| O | 4-F | 2,4-F₂ | CH₂CH₂F |
| O | 4-F | 2-Cl | CH₂CH₂F |
| O | 4-F | 2,6-F₂ | CH₂CH₂F |
| O | 4-F | 3,5-F₂ | CH₂CH₂F |
| O | 4-F | 2,3-F₂ | CH₂CH₂F |
| O | 4-F | 3,4-F₂ | CH₂CH₂F |
| O | 4-F | 2,3,5-F₃ | CH₂CH₂F |
| O | 4-F | 2,3,6-F₃ | CH₂CH₂F |
| O | 4-F | 2,4,5-F₃ | CH₂CH₂F |
| O | 4-F | 2,6-Cl₂ | CH₂CH₂F |
| O | 4-F | 2-F-6-Cl | CH₂CH₂F |
| O | 4-F | 2-F-3-Cl | CH₂CH₂F |
| CH₂ | 4-Cl | 3,5-F₂ | CH₂CH₂F |
| CH₂ | 4-Cl | 4-F | CH₂CH₂F |
| CH₂ | 4-Cl | 2,6-F₂ | CH₂CH₂F |
| CH₂ | 4-F | 3,5-F₂ | CH₂CH₂F |
| CH₂ | 4-F | 4-F | CH₂CH₂F |
| CH₂ | 4-F | 2,6-F₂ | CH₂CH₂F |
| O | 4-F | 2-F-4-Cl | CH₂CH₂F |
| O | 4-F | 4-F-2-Cl | CH₂CH₂F |
| O | 4-F | 2,3-Cl₂ | CH₂CH₂F |
| O | 4-F | 2-Cl-3,6-F₂ | CH₂CH₂F |
| O | 3-Cl | 3,5-F₂ | CH₂CH₂F |
| O | 3-Cl | 4-F | CH₂CH₂F |
| O | 3-Cl | 2,6-F₂ | CH₂CH₂F |
| O | 3-Cl | 2,5-F₂ | CH₂CH₂F |
| O | 3-F | 3,5-F₂ | CH₂CH₂F |
| O | 3-F | 4-F | CH₂CH₂F |
| O | 3-F | 2,6-F₂ | CH₂CH₂F |
| O | 3-F | 2,5-F₂ | CH₂CH₂F |
| O | 4-CN | 3,5-F₂ | CH₂CH₂F |
| O | 4-CN | 4-F | CH₂CH₂F |
| O | 4-CN | 2,6-F₂ | CH₂CH₂F |
| O | 4-CN | 2,5-F₂ | CH₂CH₂F |
| O | 2,5-F₂ | 3,5-F₂ | CH₂CH₂F |
| O | 2,5-F₂ | 4-F | CH₂CH₂F |
| O | 2,5-F₂ | 2,6-F₂ | CH₂CH₂F |
| O | 2,5-F₂ | 2,5-F₂ | CH₂CH₂F |
| O | 3,5-F₂ | 3,5-F₂ | CH₂CH₂F |
| O | 3,5-F₂ | 4-F | CH₂CH₂F |
| O | 3,5-F₂ | 2,6-F₂ | CH₂CH₂F |
| O | 3,5-F₂ | 2,5-F₂ | CH₂CH₂F |
| O | 3,4-F₂ | 3,5-F₂ | CH₂CH₂F |
| O | 3,4-F₂ | 4-F | CH₂CH₂F |
| O | 3,4-F₂ | 2,6-F₂ | CH₂CH₂F |
| O | 3,4-F₂ | 2,5-F₂ | CH₂CH₂F |
| O | 4-CF₃ | 3,5-F₂ | CH₂CH₂F |
| O | 4-CF₃ | 4-F | CH₂CH₂F |
| O | 4-CF₃ | 2,6-F₂ | CH₂CH₂F |
| O | 4-CF₃ | 2,5-F₂ | CH₂CH₂F |
| O | 4-Cl | 2-F | CH₂CH₂OH |
| O | 4-Cl | 3-F | CH₂CH₂OH |
| O | 4-Cl | 4-F | CH₂CH₂OH |
| O | 4-Cl | 4-Cl | CH₂CH₂OH |
| O | 4-Cl | 2,5-F₂ | CH₂CH₂OH |

TABLE I-continued

| X | Y | Z | R5 |
|---|---|---|---|
| O | 4-Cl | 2,4-F$_2$ | CH$_2$CH$_2$OH |
| O | 4-Cl | 2-Cl | CH$_2$CH$_2$OH |
| O | 4-Cl | 2,6-F$_2$ | CH$_2$CH$_2$OH |
| O | 4-Cl | 3,5-F$_2$ | CH$_2$CH$_2$OH |
| O | 4-Cl | 2,3-F$_2$ | CH$_2$CH$_2$OH |
| O | 4-Cl | 3,4-F$_2$ | CH$_2$CH$_2$OH |
| O | 4-Cl | 2,3,5-F$_3$ | CH$_2$CH$_2$OH |
| O | 4-Cl | 2,3,6-F$_3$ | CH$_2$CH$_2$OH |
| O | 4-Cl | 2,4,5-F$_3$ | CH$_2$CH$_2$OH |
| O | 4-Cl | 2,6-Cl$_2$ | CH$_2$CH$_2$OH |
| O | 4-Cl | 2-F-6-Cl | CH$_2$CH$_2$OH |
| O | 4-Cl | 2-F-3-Cl | CH$_2$CH$_2$OH |
| O | 4-Cl | 2-F-4-Cl | CH$_2$CH$_2$OH |
| O | 4-Cl | 4-F-2-Cl | CH$_2$CH$_2$OH |
| O | 4-Cl | 2,3-Cl$_2$ | CH$_2$CH$_2$OH |
| O | 4-Cl | 2-Cl-3,6-F$_2$ | CH$_2$CH$_2$OH |
| O | 4-F | 2-F | CH$_2$CH$_2$OH |
| O | 4-F | 3-F | CH$_2$CH$_2$OH |
| O | 4-F | 4-F | CH$_2$CH$_2$OH |
| O | 4-F | 4-Cl | CH$_2$CH$_2$OH |
| O | 4-F | 2,5-F$_2$ | CH$_2$CH$_2$OH |
| O | 4-F | 2,4-F$_2$ | CH$_2$CH$_2$OH |
| O | 4-F | 2-Cl | CH$_2$CH$_2$OH |
| O | 4-F | 2,6-F$_2$ | CH$_2$CH$_2$OH |
| O | 4-F | 3,5-F$_2$ | CH$_2$CH$_2$OH |
| O | 4-F | 2,3-F$_2$ | CH$_2$CH$_2$OH |
| O | 4-F | 3,4-F$_2$ | CH$_2$CH$_2$OH |
| O | 4-F | 2,3,5-F$_3$ | CH$_2$CH$_2$OH |
| O | 4-F | 2,3,6-F$_3$ | CH$_2$CH$_2$OH |
| O | 4-F | 2,4,5-F$_3$ | CH$_2$CH$_2$OH |
| O | 4-F | 2,6-Cl$_2$ | CH$_2$CH$_2$OH |
| O | 4-F | 2-F-6-Cl | CH$_2$CH$_2$OH |
| O | 4-F | 2-F-3-Cl | CH$_2$CH$_2$OH |
| O | 4-F | 2-F-4-Cl | CH$_2$CH$_2$OH |
| O | 4-F | 4-F-2-Cl | CH$_2$CH$_2$OH |
| O | 4-F | 2,3-Cl$_2$ | CH$_2$CH$_2$OH |
| O | 4-F | 2-Cl-3,6-F$_2$ | CH$_2$CH$_2$OH |
| CH$_2$ | 4-Cl | 3,5-F$_2$ | CH$_2$CH$_2$OH |
| CH$_2$ | 4-Cl | 4-F | CH$_2$CH$_2$OH |
| CH$_2$ | 4-Cl | 2,6-F$_2$ | CH$_2$CH$_2$OH |
| CH$_2$ | 4-F | 3,5-F$_2$ | CH$_2$CH$_2$OH |
| CH$_2$ | 4-F | 4-F | CH$_2$CH$_2$OH |
| CH$_2$ | 4-F | 2,6-F$_2$ | CH$_2$CH$_2$OH |
| O | 3-F | 3,5-F$_2$ | CH$_2$CH$_2$OH |
| O | 3-F | 4-F | CH$_2$CH$_2$OH |
| O | 3-F | 2,6-F$_2$ | CH$_2$CH$_2$OH |
| O | 3-F | 2,5-F$_2$ | CH$_2$CH$_2$OH |
| O | 2,5-F$_2$ | 3,5-F$_2$ | CH$_2$CH$_2$OH |
| O | 2,5-F$_2$ | 4-F | CH$_2$CH$_2$OH |
| O | 2,5-F$_2$ | 2,6-F$_2$ | CH$_2$CH$_2$OH |
| O | 2,5-F$_2$ | 2,5-F$_2$ | CH$_2$CH$_2$OH |
| O | 3,5-F$_2$ | 3,5-F$_2$ | CH$_2$CH$_2$OH |
| O | 3,5-F$_2$ | 4-F | CH$_2$CH$_2$OH |
| O | 3,5-F$_2$ | 2,6-F$_2$ | CH$_2$CH$_2$OH |
| O | 3,5-F$_2$ | 2,5-F$_2$ | CH$_2$CH$_2$OH |
| O | 3,4-F$_2$ | 3,5-F$_2$ | CH$_2$CH$_2$OH |
| O | 3,4-F$_2$ | 4-F | CH$_2$CH$_2$OH |
| O | 3,4-F$_2$ | 2,6-F$_2$ | CH$_2$CH$_2$OH |
| O | 3,4-F$_2$ | 2,5-F$_2$ | CH$_2$CH$_2$OH |
| O | 4-CF$_3$ | 3,5-F$_2$ | CH$_2$CH$_2$OH |
| O | 4-CF$_3$ | 4-F | CH$_2$CH$_2$OH |
| O | 4-CF$_3$ | 2,6-F$_2$ | CH$_2$CH$_2$OH |
| O | 4-CF$_3$ | 2,5-F$_2$ | CH$_2$CH$_2$OH |

TABLE II

| X | Y | Ar | R5 |
|---|---|---|---|
| CH$_2$ | 4-Cl | 2-methyl-4-thiazolyl | Me |
| O | 4-Cl | 2-methyl-4-thiazolyl | Me |
| bond | 4-Cl | 2-methyl-4-thiazolyl | Me |
| CH$_2$ | 4-Cl | 2-methyl-4-thiazolyl | Et |
| O | 4-Cl | 2-methyl-4-thiazolyl | Et |
| bond | 4-Cl | 2-methyl-4-thiazolyl | Et |
| CH$_2$ | 4-F | 2-methyl-4-thiazolyl | Me |
| O | 4-F | 2-methyl-4-thiazolyl | Me |
| bond | 4-F | 2-methyl-4-thiazolyl | Me |
| CH$_2$ | 4-F | 2-methyl-4-thiazolyl | Et |
| O | 4-F | 2-methyl-4-thiazolyl | Et |
| bond | 4-F | 2-methyl-4-thiazolyl | Et |

TABLE III

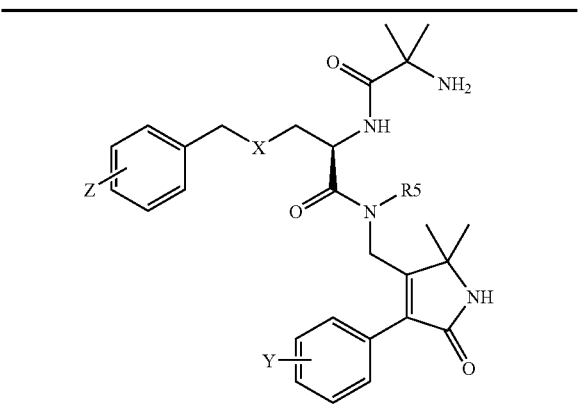

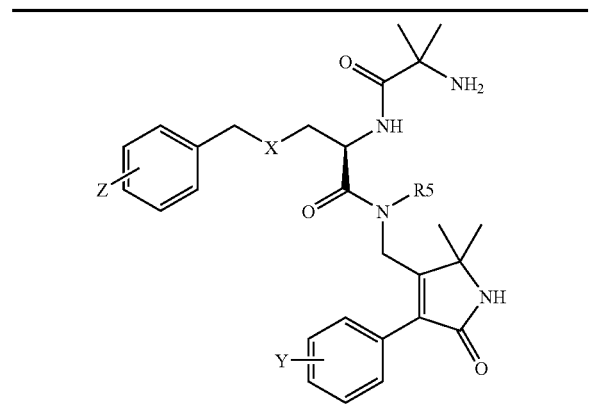

| X | Y | Z | R5 |
|---|---|---|----|
| CH₂ | 4-Cl | 2-F | Me |
| O | 4-Cl | 2-F | Me |
| bond | 4-Cl | 2-F | Me |
| CH₂ | 4-Cl | 2-F | Et |
| O | 4-Cl | 2-F | Et |
| bond | 4-Cl | 2-F | Et |
| CH₂ | 4-Cl | 3-F | Me |
| O | 4-Cl | 3-F | Me |
| bond | 4-Cl | 3-F | Me |
| CH₂ | 4-Cl | 3-F | Et |
| O | 4-Cl | 3-F | Et |
| bond | 4-Cl | 3-F | Et |
| CH₂ | 4-Cl | 4-F | Me |
| O | 4-Cl | 4-F | Me |
| bond | 4-Cl | 4-F | Me |
| CH₂ | 4-Cl | 4-F | Et |
| O | 4-Cl | 4-F | Et |
| bond | 4-Cl | 4-F | Et |
| CH₂ | 4-Cl | 2,3-F₂ | Me |
| O | 4-Cl | 2,3-F₂ | Me |
| bond | 4-Cl | 2,3-F₂ | Me |
| CH₂ | 4-Cl | 2,3-F₂ | Et |
| O | 4-Cl | 2,3-F₂ | Et |
| bond | 4-Cl | 2,3-F₂ | Et |
| CH₂ | 4-Cl | 2,4-F₂ | Me |
| O | 4-Cl | 2,4-F₂ | Me |
| bond | 4-Cl | 2,4-F₂ | Me |
| CH₂ | 4-Cl | 2,4-F₂ | Et |
| O | 4-Cl | 2,4-F₂ | Et |
| bond | 4-Cl | 2,4-F₂ | Et |
| CH₂ | 4-Cl | 2,5-F₂ | Me |
| O | 4-Cl | 2,5-F₂ | Me |
| bond | 4-Cl | 2,5-F₂ | Me |
| CH₂ | 4-Cl | 2,5-F₂ | Et |
| O | 4-Cl | 2,5-F₂ | Et |
| bond | 4-Cl | 2,5-F₂ | Et |
| CH₂ | 4-Cl | 2,6-F₂ | Me |
| O | 4-Cl | 2,6-F₂ | Me |
| bond | 4-Cl | 2,6-F₂ | Me |
| CH₂ | 4-Cl | 2,6-F₂ | Et |
| O | 4-Cl | 2,6-F₂ | Et |
| bond | 4-Cl | 2,6-F₂ | Et |
| CH₂ | 4-Cl | 3,4-F₂ | Me |
| O | 4-Cl | 3,4-F₂ | Me |
| bond | 4-Cl | 3,4-F₂ | Me |
| CH₂ | 4-Cl | 3,4-F₂ | Et |
| O | 4-Cl | 3,4-F₂ | Et |
| bond | 4-Cl | 3,4-F₂ | Et |
| CH₂ | 4-Cl | 3,5-F₂ | Me |
| O | 4-Cl | 3,5-F₂ | Me |
| bond | 4-Cl | 3,5-F₂ | Me |
| CH₂ | 4-Cl | 3,5-F₂ | Et |
| O | 4-Cl | 3,5-F₂ | Et |
| bond | 4-Cl | 3,5-F₂ | Et |
| CH₂ | 4-Cl | 2,4,6-F₃ | Me |
| O | 4-Cl | 2,4,6-F₃ | Me |
| bond | 4-Cl | 2,4,6-F₃ | Me |
| CH₂ | 4-Cl | 2,4,6-F₃ | Et |
| O | 4-Cl | 2,4,6-F₃ | Et |
| bond | 4-Cl | 2,4,6-F₃ | Et |
| CH₂ | 4-Cl | 2,4,5-F₃ | Me |
| O | 4-Cl | 2,4,5-F₃ | Me |
| bond | 4-Cl | 2,4,5-F₃ | Me |
| CH₂ | 4-Cl | 2,4,5-F₃ | Et |
| O | 4-Cl | 2,4,5-F₃ | Et |
| bond | 4-Cl | 2,4,5-F₃ | Et |
| CH₂ | 4-Cl | 2,3,6-F₃ | Me |
| O | 4-Cl | 2,3,6-F₃ | Me |
| bond | 4-Cl | 2,3,6-F₃ | Me |
| CH₂ | 4-Cl | 2,3,6-F₃ | Et |
| O | 4-Cl | 2,3,6-F₃ | Et |
| bond | 4-Cl | 2,3,6-F₃ | Et |
| CH₂ | 4-Cl | 2,3,5-F₃ | Me |
| O | 4-Cl | 2,3,5-F₃ | Me |
| bond | 4-Cl | 2,3,5-F₃ | Me |
| CH₂ | 4-Cl | 2,3,5-F₃ | Et |
| O | 4-Cl | 2,3,5-F₃ | Et |
| bond | 4-Cl | 2,3,5-F₃ | Et |
| CH₂ | 4-Cl | 2-Cl | Me |
| O | 4-Cl | 2-Cl | Me |
| bond | 4-Cl | 2-Cl | Me |
| CH₂ | 4-Cl | 2-Cl | Et |
| O | 4-Cl | 2-Cl | Et |
| bond | 4-Cl | 2-Cl | Et |
| CH₂ | 4-Cl | 3-Cl | Me |
| O | 4-Cl | 3-Cl | Me |
| bond | 4-Cl | 3-Cl | Me |
| CH₂ | 4-Cl | 3-Cl | Et |
| O | 4-Cl | 3-Cl | Et |
| bond | 4-Cl | 3-Cl | Et |
| CH₂ | 4-Cl | 4-Cl | Me |
| O | 4-Cl | 4-Cl | Me |
| bond | 4-Cl | 4-Cl | Me |
| CH₂ | 4-Cl | 4-Cl | Et |
| O | 4-Cl | 4-Cl | Et |
| bond | 4-Cl | 4-Cl | Et |
| CH₂ | 4-Cl | 2,6-Cl₂ | Me |
| O | 4-Cl | 2,6-Cl₂ | Me |
| bond | 4-Cl | 2,6-Cl₂ | Me |
| CH₂ | 4-Cl | 2,6-Cl₂ | Et |
| O | 4-Cl | 2,6-Cl₂ | Et |
| bond | 4-Cl | 2,6-Cl₂ | Et |
| CH₂ | 4-Cl | 2-F-6-Cl | Me |
| O | 4-Cl | 2-F-6-Cl | Me |
| bond | 4-Cl | 2-F-6-Cl | Me |
| CH₂ | 4-Cl | 2-F-6-Cl | Et |
| O | 4-Cl | 2-F-6-Cl | Et |
| bond | 4-Cl | 2-F-6-Cl | Et |
| CH₂ | 4-Cl | 2-F-3-Cl | Me |
| O | 4-Cl | 2-F-3-Cl | Me |
| bond | 4-Cl | 2-F-3-Cl | Me |
| CH₂ | 4-Cl | 2-F-3-Cl | Et |
| O | 4-Cl | 2-F-3-Cl | Et |
| bond | 4-Cl | 2-F-3-Cl | Et |

TABLE III-continued

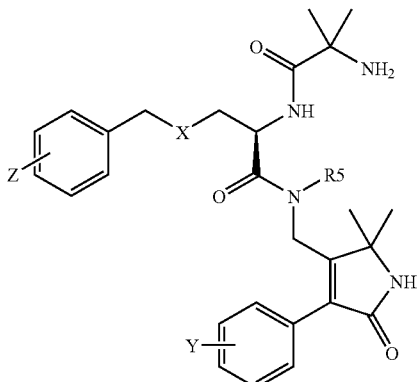

| X | Y | Z | R5 |
|---|---|---|---|
| CH₂ | 4-Cl | 2-F-4-Cl | Me |
| O | 4-Cl | 2-F-4-Cl | Me |
| bond | 4-Cl | 2-F-4-Cl | Me |
| CH₂ | 4-Cl | 2-F-4-Cl | Et |
| O | 4-Cl | 2-F-4-Cl | Et |
| bond | 4-Cl | 2-F-4-Cl | Et |
| CH₂ | 4-Cl | 3-F-4-Cl | Me |
| O | 4-Cl | 3-F-4-Cl | Me |
| bond | 4-Cl | 3-F-4-Cl | Me |
| CH₂ | 4-Cl | 3-F-4-Cl | Et |
| O | 4-Cl | 3-F-4-Cl | Et |
| bond | 4-Cl | 3-F-4-Cl | Et |
| CH₂ | 4-Cl | 2,6-F₂-3-Cl | Me |
| O | 4-Cl | 2,6-F₂-3-Cl | Me |
| bond | 4-Cl | 2,6-F₂-3-Cl | Me |
| CH₂ | 4-Cl | 2,6-F₂-3-Cl | Et |
| O | 4-Cl | 2,6-F₂-3-Cl | Et |
| bond | 4-Cl | 2,6-F₂-3-Cl | Et |
| CH₂ | 4-Cl | 4-CF₃ | Me |
| O | 4-Cl | 4-CF₃ | Me |
| bond | 4-Cl | 4-CF₃ | Me |
| CH₂ | 4-Cl | 4-CF₃ | Et |
| O | 4-Cl | 4-CF₃ | Et |
| bond | 4-Cl | 4-CF₃ | Et |
| CH₂ | 4-Cl | 3-CF₃ | Me |
| O | 4-Cl | 3-CF₃ | Me |
| bond | 4-Cl | 3-CF₃ | Me |
| CH₂ | 4-Cl | 3-CF₃ | Et |
| O | 4-Cl | 3-CF₃ | Et |
| bond | 4-Cl | 3-CF₃ | Et |
| CH₂ | 4-Cl | 2-CF₃ | Me |
| O | 4-Cl | 2-CF₃ | Me |
| bond | 4-Cl | 2-CF₃ | Me |
| CH₂ | 4-Cl | 2-CF₃ | Et |
| O | 4-Cl | 2-CF₃ | Et |
| bond | 4-Cl | 2-CF₃ | Et |
| CH₂ | 4-Cl | 2-F-5-CF₃ | Me |
| O | 4-Cl | 2-F-5-CF₃ | Me |
| bond | 4-Cl | 2-F-5-CF₃ | Me |
| CH₂ | 4-Cl | 2-F-5-CF₃ | Et |
| O | 4-Cl | 2-F-5-CF₃ | Et |
| bond | 4-Cl | 2-F-5-CF₃ | Et |
| CH₂ | 4-Cl | 4-OCF₃ | Me |
| O | 4-Cl | 4-OCF₃ | Me |
| bond | 4-Cl | 4-OCF₃ | Me |
| CH₂ | 4-Cl | 4-OCF₃ | Et |
| O | 4-Cl | 4-OCF₃ | Et |
| bond | 4-Cl | 4-OCF₃ | Et |
| CH₂ | 4-Cl | 3-OCF₃ | Me |
| O | 4-Cl | 3-OCF₃ | Me |
| bond | 4-Cl | 3-OCF₃ | Me |
| CH₂ | 4-Cl | 3-OCF₃ | Et |
| O | 4-Cl | 3-OCF₃ | Et |
| bond | 4-Cl | 3-OCF₃ | Et |
| CH₂ | 4-Cl | 2-OCF₃ | Me |
| O | 4-Cl | 2-OCF₃ | Me |
| bond | 4-Cl | 2-OCF₃ | Me |

TABLE III-continued

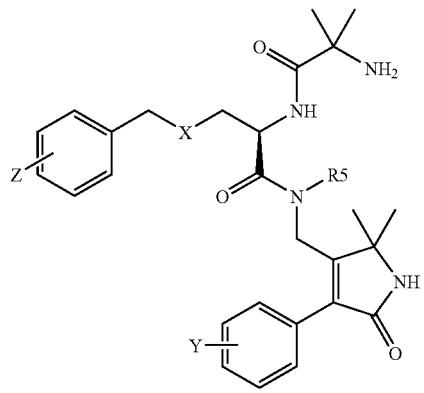

| X | Y | Z | R5 |
|---|---|---|---|
| CH₂ | 4-Cl | 2-OCF₃ | Et |
| O | 4-Cl | 2-OCF₃ | Et |
| bond | 4-Cl | 2-OCF₃ | Et |
| CH₂ | 4-Cl | 2-CN | Me |
| O | 4-Cl | 2-CN | Me |
| bond | 4-Cl | 2-CN | Me |
| CH₂ | 4-Cl | 2-CN | Et |
| O | 4-Cl | 2-CN | Et |
| bond | 4-Cl | 2-CN | Et |
| CH₂ | 4-Cl | 3-CN | Me |
| O | 4-Cl | 3-CN | Me |
| bond | 4-Cl | 3-CN | Me |
| CH₂ | 4-Cl | 3-CN | Et |
| O | 4-Cl | 3-CN | Et |
| bond | 4-Cl | 3-CN | Et |
| CH₂ | 4-Cl | 4-CN | Me |
| O | 4-Cl | 4-CN | Me |
| bond | 4-Cl | 4-CN | Me |
| CH₂ | 4-Cl | 4-CN | Et |
| O | 4-Cl | 4-CN | Et |
| bond | 4-Cl | 4-CN | Et |
| CH₂ | 4-Cl | 4-SO₂CH₃ | Me |
| O | 4-Cl | 4-SO₂CH₃ | Me |
| bond | 4-Cl | 4-SO₂CH₃ | Me |
| CH₂ | 4-Cl | 4-SO₂CH₃ | Et |
| O | 4-Cl | 4-SO₂CH₃ | Et |
| bond | 4-Cl | 4-SO₂CH₃ | Et |
| CH₂ | 4-F | 2-F | Me |
| O | 4-F | 2-F | Me |
| bond | 4-F | 2-F | Me |
| CH₂ | 4-F | 2-F | Et |
| O | 4-F | 2-F | Et |
| bond | 4-F | 2-F | Et |
| CH₂ | 4-F | 3-F | Me |
| O | 4-F | 3-F | Me |
| bond | 4-F | 3-F | Me |
| CH₂ | 4-F | 3-F | Et |
| O | 4-F | 3-F | Et |
| bond | 4-F | 3-F | Et |
| CH₂ | 4-F | 4-F | Me |
| O | 4-F | 4-F | Me |
| bond | 4-F | 4-F | Me |
| CH₂ | 4-F | 4-F | Et |
| O | 4-F | 4-F | Et |
| bond | 4-F | 4-F | Et |
| CH₂ | 4-F | 2,3-F₂ | Me |
| O | 4-F | 2,3-F₂ | Me |
| bond | 4-F | 2,3-F₂ | Me |
| CH₂ | 4-F | 2,3-F₂ | Et |
| O | 4-F | 2,3-F₂ | Et |
| bond | 4-F | 2,3-F₂ | Et |
| CH₂ | 4-F | 2,4-F₂ | Me |
| O | 4-F | 2,4-F₂ | Me |
| bond | 4-F | 2,4-F₂ | Me |
| CH₂ | 4-F | 2,4-F₂ | Et |
| O | 4-F | 2,4-F₂ | Et |
| bond | 4-F | 2,4-F₂ | Et |

TABLE III-continued

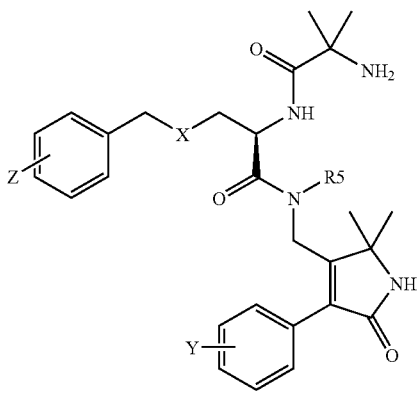

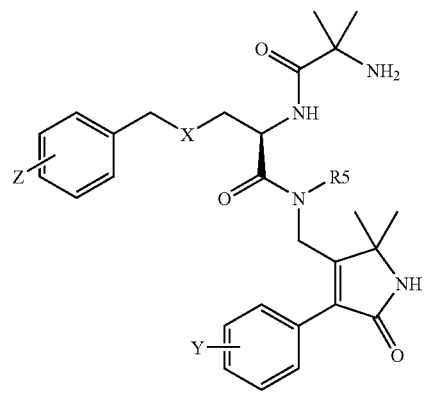

| X | Y | Z | R5 |
|---|---|---|---|
| CH₂ | 4-F | 2,5-F₂ | Me |
| O | 4-F | 2,5-F₂ | Me |
| bond | 4-F | 2,5-F₂ | Me |
| CH₂ | 4-F | 2,5-F₂ | Et |
| O | 4-F | 2,5-F₂ | Et |
| bond | 4-F | 2,5-F₂ | Et |
| CH₂ | 4-F | 2,6-F₂ | Me |
| O | 4-F | 2,6-F₂ | Me |
| bond | 4-F | 2,6-F₂ | Me |
| CH₂ | 4-F | 2,6-F₂ | Et |
| O | 4-F | 2,6-F₂ | Et |
| bond | 4-F | 2,6-F₂ | Et |
| CH₂ | 4-F | 3,4-F₂ | Me |
| O | 4-F | 3,4-F₂ | Me |
| bond | 4-F | 3,4-F₂ | Me |
| CH₂ | 4-F | 3,4-F₂ | Et |
| O | 4-F | 3,4-F₂ | Et |
| bond | 4-F | 3,4-F₂ | Et |
| CH₂ | 4-F | 3,5-F₂ | Me |
| O | 4-F | 3,5-F₂ | Me |
| bond | 4-F | 3,5-F₂ | Me |
| CH₂ | 4-F | 3,5-F₂ | Et |
| O | 4-F | 3,5-F₂ | Et |
| bond | 4-F | 3,5-F₂ | Et |
| CH₂ | 4-F | 2,4,6-F₃ | Me |
| O | 4-F | 2,4,6-F₃ | Me |
| bond | 4-F | 2,4,6-F₃ | Me |
| CH₂ | 4-F | 2,4,6-F₃ | Et |
| O | 4-F | 2,4,6-F₃ | Et |
| bond | 4-F | 2,4,6-F₃ | Et |
| CH₂ | 4-F | 2,4,5-F₃ | Me |
| O | 4-F | 2,4,5-F₃ | Me |
| bond | 4-F | 2,4,5-F₃ | Me |
| CH₂ | 4-F | 2,4,5-F₃ | Et |
| O | 4-F | 2,4,5-F₃ | Et |
| bond | 4-F | 2,4,5-F₃ | Et |
| CH₂ | 4-F | 2,3,6-F₃ | Me |
| O | 4-F | 2,3,6-F₃ | Me |
| bond | 4-F | 2,3,6-F₃ | Me |
| CH₂ | 4-F | 2,3,6-F₃ | Et |
| O | 4-F | 2,3,6-F₃ | Et |
| bond | 4-F | 2,3,6-F₃ | Et |
| CH₂ | 4-F | 2,3,5-F₃ | Me |
| O | 4-F | 2,3,5-F₃ | Me |
| bond | 4-F | 2,3,5-F₃ | Me |
| CH₂ | 4-F | 2,3,5-F₃ | Et |
| O | 4-F | 2,3,5-F₃ | Et |
| bond | 4-F | 2,3,5-F₃ | Et |
| CH₂ | 4-F | 2-Cl | Me |
| O | 4-F | 2-Cl | Me |
| bond | 4-F | 2-Cl | Me |
| CH₂ | 4-F | 2-Cl | Et |
| O | 4-F | 2-Cl | Et |
| bond | 4-F | 2-Cl | Et |
| CH₂ | 4-F | 3-Cl | Me |
| O | 4-F | 3-Cl | Me |
| bond | 4-F | 3-Cl | Me |
| CH₂ | 4-F | 3-Cl | Et |
| O | 4-F | 3-Cl | Et |
| bond | 4-F | 3-Cl | Et |
| CH₂ | 4-F | 4-Cl | Me |
| O | 4-F | 4-Cl | Me |
| bond | 4-F | 4-Cl | Me |
| CH₂ | 4-F | 4-Cl | Et |
| O | 4-F | 4-Cl | Et |
| bond | 4-F | 4-Cl | Et |
| CH₂ | 4-F | 2,6-Cl₂ | Me |
| O | 4-F | 2,6-Cl₂ | Me |
| bond | 4-F | 2,6-Cl₂ | Me |
| CH₂ | 4-F | 2,6-Cl₂ | Et |
| O | 4-F | 2,6-Cl₂ | Et |
| bond | 4-F | 2,6-Cl₂ | Et |
| CH₂ | 4-F | 2-F-6-Cl | Me |
| O | 4-F | 2-F-6-Cl | Me |
| bond | 4-F | 2-F-6-Cl | Me |
| CH₂ | 4-F | 2-F-6-Cl | Et |
| O | 4-F | 2-F-6-Cl | Et |
| bond | 4-F | 2-F-6-Cl | Et |
| CH₂ | 4-F | 2-F-3-Cl | Me |
| O | 4-F | 2-F-3-Cl | Me |
| bond | 4-F | 2-F-3-Cl | Me |
| CH₂ | 4-F | 2-F-3-Cl | Et |
| O | 4-F | 2-F-3-Cl | Et |
| bond | 4-F | 2-F-3-Cl | Et |
| CH₂ | 4-F | 2-F-4-Cl | Me |
| O | 4-F | 2-F-4-Cl | Me |
| bond | 4-F | 2-F-4-Cl | Me |
| CH₂ | 4-F | 2-F-4-Cl | Et |
| O | 4-F | 2-F-4-Cl | Et |
| bond | 4-F | 2-F-4-Cl | Et |
| CH₂ | 4-F | 3-F-4-Cl | Me |
| O | 4-F | 3-F-4-Cl | Me |
| bond | 4-F | 3-F-4-Cl | Me |
| CH₂ | 4-F | 3-F-4-Cl | Et |
| O | 4-F | 3-F-4-Cl | Et |
| bond | 4-F | 3-F-4-Cl | Et |
| CH₂ | 4-F | 2,6-F₂-3-Cl | Me |
| O | 4-F | 2,6-F₂-3-Cl | Me |
| bond | 4-F | 2,6-F₂-3-Cl | Me |
| CH₂ | 4-F | 2,6-F₂-3-Cl | Et |
| O | 4-F | 2,6-F₂-3-Cl | Et |
| bond | 4-F | 2,6-F₂-3-Cl | Et |
| CH₂ | 4-F | 4-CF₃ | Me |
| O | 4-F | 4-CF₃ | Me |
| bond | 4-F | 4-CF₃ | Me |
| CH₂ | 4-F | 4-CF₃ | Et |
| O | 4-F | 4-CF₃ | Et |
| bond | 4-F | 4-CF₃ | Et |
| CH₂ | 4-F | 3-CF₃ | Me |
| O | 4-F | 3-CF₃ | Me |
| bond | 4-F | 3-CF₃ | Me |
| CH₂ | 4-F | 3-CF₃ | Et |
| O | 4-F | 3-CF₃ | Et |
| bond | 4-F | 3-CF₃ | Et |

TABLE III-continued

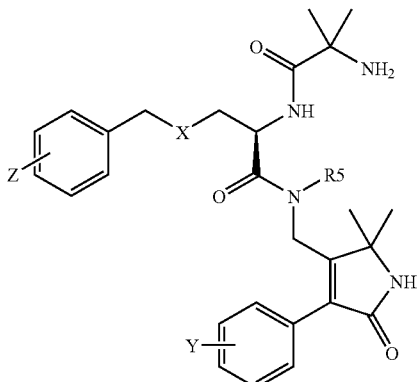

| X | Y | Z | R5 |
|---|---|---|---|
| CH₂ | 4-F | 2-CF₃ | Me |
| O | 4-F | 2-CF₃ | Me |
| bond | 4-F | 2-CF₃ | Me |
| CH₂ | 4-F | 2-CF₃ | Et |
| O | 4-F | 2-CF₃ | Et |
| bond | 4-F | 2-CF₃ | Et |
| CH₂ | 4-F | 2-F-5-CF₃ | Me |
| O | 4-F | 2-F-5-CF₃ | Me |
| bond | 4-F | 2-F-5-CF₃ | Me |
| CH₂ | 4-F | 2-F-5-CF₃ | Et |
| O | 4-F | 2-F-5-CF₃ | Et |
| bond | 4-F | 2-F-5-CF₃ | Et |
| CH₂ | 4-F | 4-OCF₃ | Me |
| O | 4-F | 4-OCF₃ | Me |
| bond | 4-F | 4-OCF₃ | Me |
| CH₂ | 4-F | 4-OCF₃ | Et |
| O | 4-F | 4-OCF₃ | Et |
| bond | 4-F | 4-OCF₃ | Et |
| CH₂ | 4-F | 3-OCF₃ | Me |
| O | 4-F | 3-OCF₃ | Me |
| bond | 4-F | 3-OCF₃ | Me |
| CH₂ | 4-F | 3-OCF₃ | Et |
| O | 4-F | 3-OCF₃ | Et |
| bond | 4-F | 3-OCF₃ | Et |
| CH₂ | 4-F | 2-OCF₃ | Me |
| O | 4-F | 2-OCF₃ | Me |
| bond | 4-F | 2-OCF₃ | Me |
| CH₂ | 4-F | 2-OCF₃ | Et |
| O | 4-F | 2-OCF₃ | Et |
| bond | 4-F | 2-OCF₃ | Et |
| CH₂ | 4-F | 2-CN | Me |
| O | 4-F | 2-CN | Me |
| bond | 4-F | 2-CN | Me |
| CH₂ | 4-F | 2-CN | Et |
| O | 4-F | 2-CN | Et |
| bond | 4-F | 2-CN | Et |
| CH₂ | 4-F | 3-CN | Me |
| O | 4-F | 3-CN | Me |
| bond | 4-F | 3-CN | Me |
| CH₂ | 4-F | 3-CN | Et |
| O | 4-F | 3-CN | Et |
| bond | 4-F | 3-CN | Et |
| CH₂ | 4-F | 4-CN | Me |
| O | 4-F | 4-CN | Me |
| bond | 4-F | 4-CN | Me |
| CH₂ | 4-F | 4-CN | Et |
| O | 4-F | 4-CN | Et |
| bond | 4-F | 4-CN | Et |
| CH₂ | 4-F | 4-SO₂CH₃ | Me |
| O | 4-F | 4-SO₂CH₃ | Me |
| bond | 4-F | 4-SO₂CH₃ | Me |
| CH₂ | 4-F | 4-SO₂CH₃ | Et |
| O | 4-F | 4-SO₂CH₃ | Et |
| bond | 4-F | 4-SO₂CH₃ | Et |
| O | 4-Cl | 2-F | CH₂CH₂F |
| O | 4-Cl | 3-F | CH₂CH₂F |
| O | 4-Cl | 4-F | CH₂CH₂F |

TABLE III-continued

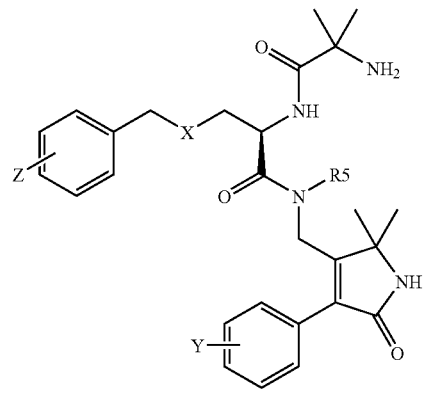

| X | Y | Z | R5 |
|---|---|---|---|
| O | 4-Cl | 4-Cl | CH₂CH₂F |
| O | 4-Cl | 2,5-F₂ | CH₂CH₂F |
| O | 4-Cl | 2,4-F₂ | CH₂CH₂F |
| O | 4-Cl | 2-Cl | CH₂CH₂F |
| O | 4-Cl | 2,6-F₂ | CH₂CH₂F |
| O | 4-Cl | 3,5-F₂ | CH₂CH₂F |
| O | 4-Cl | 2,3-F₂ | CH₂CH₂F |
| O | 4-Cl | 3,4-F₂ | CH₂CH₂F |
| O | 4-Cl | 2,3,5-F₃ | CH₂CH₂F |
| O | 4-Cl | 2,3,6-F₃ | CH₂CH₂F |
| O | 4-Cl | 2,4,5-F₃ | CH₂CH₂F |
| O | 4-Cl | 2,6-Cl₂ | CH₂CH₂F |
| O | 4-Cl | 2-F-6-Cl | CH₂CH₂F |
| O | 4-Cl | 2-F-3-Cl | CH₂CH₂F |
| O | 4-F | 2-F | CH₂CH₂F |
| O | 4-F | 3-F | CH₂CH₂F |
| O | 4-F | 4-F | CH₂CH₂F |
| O | 4-F | 4-Cl | CH₂CH₂F |
| O | 4-F | 2,5-F₂ | CH₂CH₂F |
| O | 4-F | 2,4-F₂ | CH₂CH₂F |
| O | 4-F | 2-Cl | CH₂CH₂F |
| O | 4-F | 2,6-F₂ | CH₂CH₂F |
| O | 4-F | 3,5-F₂ | CH₂CH₂F |
| O | 4-F | 2,3-F₂ | CH₂CH₂F |
| O | 4-F | 3,4-F₂ | CH₂CH₂F |
| O | 4-F | 2,3,5-F₃ | CH₂CH₂F |
| O | 4-F | 2,3,6-F₃ | CH₂CH₂F |
| O | 4-F | 2,4,5-F₃ | CH₂CH₂F |
| O | 4-F | 2,6-Cl₂ | CH₂CH₂F |
| O | 4-F | 2-F-6-Cl | CH₂CH₂F |
| O | 4-F | 2-F-3-Cl | CH₂CH₂F |
| CH₂ | 4-Cl | 3,5-F₂ | CH₂CH₂F |
| CH₂ | 4-Cl | 4-F | CH₂CH₂F |
| CH₂ | 4-Cl | 2,6-F₂ | CH₂CH₂F |
| CH₂ | 4-F | 3,5-F₂ | CH₂CH₂F |
| CH₂ | 4-F | 4-F | CH₂CH₂F |
| CH₂ | 4-F | 2,6-F₂ | CH₂CH₂F |
| O | 3-Cl | 3,5-F₂ | CH₂CH₂F |
| O | 3-Cl | 4-F | CH₂CH₂F |
| O | 3-Cl | 2,6-F₂ | CH₂CH₂F |
| O | 3-Cl | 2,5-F₂ | CH₂CH₂F |
| O | 3-F | 3,5-F₂ | CH₂CH₂F |
| O | 3-F | 4-F | CH₂CH₂F |
| O | 3-F | 2,6-F₂ | CH₂CH₂F |
| O | 3-F | 2,5-F₂ | CH₂CH₂F |
| O | 4-CN | 3,5-F₂ | CH₂CH₂F |
| O | 4-CN | 4-F | CH₂CH₂F |
| O | 4-CN | 2,6-F₂ | CH₂CH₂F |
| O | 4-CN | 2,5-F₂ | CH₂CH₂F |
| O | 2,5-F₂ | 3,5-F₂ | CH₂CH₂F |
| O | 2,5-F₂ | 4-F | CH₂CH₂F |
| O | 2,5-F₂ | 2,6-F₂ | CH₂CH₂F |
| O | 2,5-F₂ | 2,5-F₂ | CH₂CH₂F |
| O | 3,5-F₂ | 3,5-F₂ | CH₂CH₂F |
| O | 3,5-F₂ | 4-F | CH₂CH₂F |
| O | 3,5-F₂ | 2,6-F₂ | CH₂CH₂F |
| O | 3,5-F₂ | 2,5-F₂ | CH₂CH₂F |

TABLE III-continued

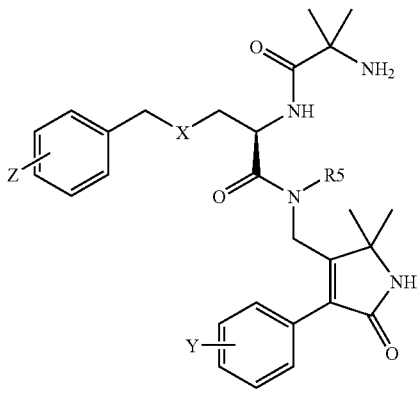

| X | Y | Z | R5 |
|---|---|---|---|
| O | 3,4-F$_2$ | 3,5-F$_2$ | CH$_2$CH$_2$F |
| O | 3,4-F$_2$ | 4-F | CH$_2$CH$_2$F |
| O | 3,4-F$_2$ | 2,6-F$_2$ | CH$_2$CH$_2$F |
| O | 3,4-F$_2$ | 2,5-F$_2$ | CH$_2$CH$_2$F |
| O | 4-CF$_3$ | 3,5-F$_2$ | CH$_2$CH$_2$F |
| O | 4-CF$_3$ | 4-F | CH$_2$CH$_2$F |
| O | 4-CF$_3$ | 2,6-F$_2$ | CH$_2$CH$_2$F |
| O | 4-CF$_3$ | 2,5-F$_2$ | CH$_2$CH$_2$F |
| O | 4-Cl | 2-F | CH$_2$CH$_2$OH |
| O | 4-Cl | 3-F | CH$_2$CH$_2$OH |
| O | 4-Cl | 4-F | CH$_2$CH$_2$OH |
| O | 4-Cl | 4-Cl | CH$_2$CH$_2$OH |
| O | 4-Cl | 2,5-F$_2$ | CH$_2$CH$_2$OH |
| O | 4-Cl | 2,4-F$_2$ | CH$_2$CH$_2$OH |
| O | 4-Cl | 2-Cl | CH$_2$CH$_2$OH |
| O | 4-Cl | 2,6-F$_2$ | CH$_2$CH$_2$OH |
| O | 4-Cl | 3,5-F$_2$ | CH$_2$CH$_2$OH |
| O | 4-Cl | 2,3-F$_2$ | CH$_2$CH$_2$OH |
| O | 4-Cl | 3,4-F$_2$ | CH$_2$CH$_2$OH |
| O | 4-Cl | 2,3,5-F$_3$ | CH$_2$CH$_2$OH |
| O | 4-Cl | 2,3,6-F$_3$ | CH$_2$CH$_2$OH |
| O | 4-Cl | 2,4,5-F$_3$ | CH$_2$CH$_2$OH |
| O | 4-Cl | 2,6-Cl$_2$ | CH$_2$CH$_2$OH |
| O | 4-Cl | 2-F-6-Cl | CH$_2$CH$_2$OH |
| O | 4-Cl | 2-F-3-Cl | CH$_2$CH$_2$OH |
| O | 4-F | 2-F | CH$_2$CH$_2$OH |
| O | 4-F | 3-F | CH$_2$CH$_2$OH |
| O | 4-F | 4-F | CH$_2$CH$_2$OH |
| O | 4-F | 4-Cl | CH$_2$CH$_2$OH |
| O | 4-F | 2,5-F$_2$ | CH$_2$CH$_2$OH |
| O | 4-F | 2,4-F$_2$ | CH$_2$CH$_2$OH |
| O | 4-F | 2-Cl | CH$_2$CH$_2$OH |
| O | 4-F | 2,6-F$_2$ | CH$_2$CH$_2$OH |
| O | 4-F | 3,5-F$_2$ | CH$_2$CH$_2$OH |
| O | 4-F | 2,3-F$_2$ | CH$_2$CH$_2$OH |
| O | 4-F | 3,4-F$_2$ | CH$_2$CH$_2$OH |
| O | 4-F | 2,3,5-F$_3$ | CH$_2$CH$_2$OH |
| O | 4-F | 2,3,6-F$_3$ | CH$_2$CH$_2$OH |
| O | 4-F | 2,4,5-F$_3$ | CH$_2$CH$_2$OH |
| O | 4-F | 2,6-Cl$_2$ | CH$_2$CH$_2$OH |
| O | 4-F | 2-F-6-Cl | CH$_2$CH$_2$OH |
| O | 4-F | 2-F-3-Cl | CH$_2$CH$_2$OH |
| CH$_2$ | 4-Cl | 3,5-F$_2$ | CH$_2$CH$_2$OH |
| CH$_2$ | 4-Cl | 4-F | CH$_2$CH$_2$OH |
| CH$_2$ | 4-Cl | 2,6-F$_2$ | CH$_2$CH$_2$OH |
| CH$_2$ | 4-F | 3,5-F$_2$ | CH$_2$CH$_2$OH |
| CH$_2$ | 4-F | 4-F | CH$_2$CH$_2$OH |
| CH$_2$ | 4-F | 2,6-F$_2$ | CH$_2$CH$_2$OH |
| O | 3-F | 3,5-F$_2$ | CH$_2$CH$_2$OH |
| O | 3-F | 4-F | CH$_2$CH$_2$OH |
| O | 3-F | 2,6-F$_2$ | CH$_2$CH$_2$OH |
| O | 3-F | 2,5-F$_2$ | CH$_2$CH$_2$OH |
| O | 2,5-F$_2$ | 3,5-F$_2$ | CH$_2$CH$_2$OH |
| O | 2,5-F$_2$ | 4-F | CH$_2$CH$_2$OH |
| O | 2,5-F$_2$ | 2,6-F$_2$ | CH$_2$CH$_2$OH |
| O | 2,5-F$_2$ | 2,5-F$_2$ | CH$_2$CH$_2$OH |
| O | 3,5-F$_2$ | 3,5-F$_2$ | CH$_2$CH$_2$OH |

TABLE III-continued

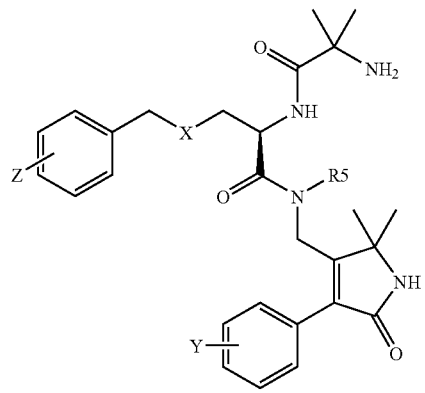

| X | Y | Z | R5 |
|---|---|---|---|
| O | 3,5-F$_2$ | 4-F | CH$_2$CH$_2$OH |
| O | 3,5-F$_2$ | 2,6-F$_2$ | CH$_2$CH$_2$OH |
| O | 3,5-F$_2$ | 2,5-F$_2$ | CH$_2$CH$_2$OH |
| O | 3,4-F$_2$ | 3,5-F$_2$ | CH$_2$CH$_2$OH |
| O | 3,4-F$_2$ | 4-F | CH$_2$CH$_2$OH |
| O | 3,4-F$_2$ | 2,6-F$_2$ | CH$_2$CH$_2$OH |
| O | 3,4-F$_2$ | 2,5-F$_2$ | CH$_2$CH$_2$OH |
| O | 4-CF$_3$ | 3,5-F$_2$ | CH$_2$CH$_2$OH |
| O | 4-CF$_3$ | 4-F | CH$_2$CH$_2$OH |
| O | 4-CF$_3$ | 2,6-F$_2$ | CH$_2$CH$_2$OH |
| O | 4-CF$_3$ | 2,5-F$_2$ | CH$_2$CH$_2$OH |

TABLE IV

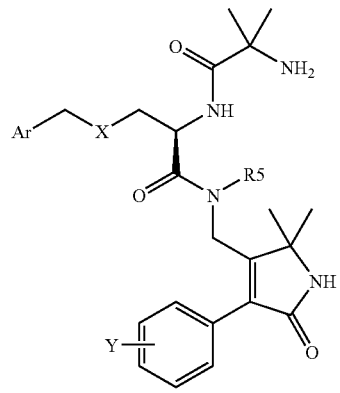

| X | Y | Ar | R5 |
|---|---|---|---|
| CH$_2$ | 4-Cl | 2-methyl-4-thiazolyl | Me |
| O | 4-Cl | 2-methyl-4-thiazolyl | Me |
| bond | 4-Cl | 2-methyl-4-thiazolyl | Me |
| CH$_2$ | 4-Cl | 2-methyl-4-thiazolyl | Et |
| O | 4-Cl | 2-methyl-4-thiazolyl | Et |
| bond | 4-Cl | 2-methyl-4-thiazolyl | Et |
| CH$_2$ | 4-F | 2-methyl-4-thiazolyl | Me |
| O | 4-F | 2-methyl-4-thiazolyl | Me |
| bond | 4-F | 2-methyl-4-thiazolyl | Me |
| CH$_2$ | 4-F | 2-methyl-4-thiazolyl | Et |
| O | 4-F | 2-methyl-4-thiazolyl | Et |
| bond | 4-F | 2-methyl-4-thiazolyl | Et |

TABLE V

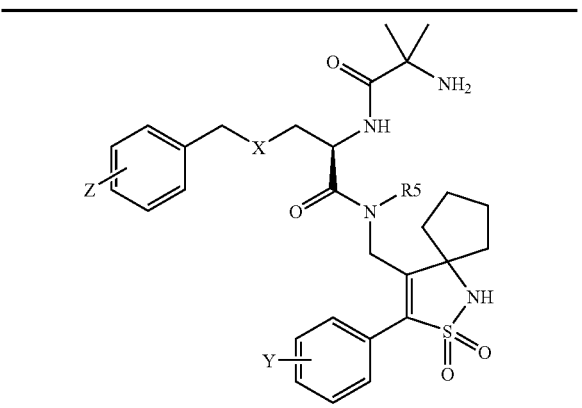

| X | Y | Z | R5 |
|---|---|---|---|
| CH₂ | 4-Cl | 2-F | Me |
| O | 4-Cl | 2-F | Me |
| bond | 4-Cl | 2-F | Me |
| CH₂ | 4-Cl | 2-F | Et |
| O | 4-Cl | 2-F | Et |
| bond | 4-Cl | 2-F | Et |
| CH₂ | 4-Cl | 3-F | Me |
| O | 4-Cl | 3-F | Me |
| bond | 4-Cl | 3-F | Me |
| CH₂ | 4-Cl | 3-F | Et |
| O | 4-Cl | 3-F | Et |
| bond | 4-Cl | 3-F | Et |
| CH₂ | 4-Cl | 4-F | Me |
| O | 4-Cl | 4-F | Me |
| bond | 4-Cl | 4-F | Me |
| CH₂ | 4-Cl | 4-F | Et |
| O | 4-Cl | 4-F | Et |
| bond | 4-Cl | 4-F | Et |
| CH₂ | 4-Cl | 2,3-F₂ | Me |
| O | 4-Cl | 2,3-F₂ | Me |
| bond | 4-Cl | 2,3-F₂ | Me |
| CH₂ | 4-Cl | 2,3-F₂ | Et |
| O | 4-Cl | 2,3-F₂ | Et |
| bond | 4-Cl | 2,3-F₂ | Et |
| CH₂ | 4-Cl | 2,4-F₂ | Me |
| O | 4-Cl | 2,4-F₂ | Me |
| bond | 4-Cl | 2,4-F₂ | Me |
| CH₂ | 4-Cl | 2,4-F₂ | Et |
| O | 4-Cl | 2,4-F₂ | Et |
| bond | 4-Cl | 2,4-F₂ | Et |
| CH₂ | 4-Cl | 2,5-F₂ | Me |
| O | 4-Cl | 2,5-F₂ | Me |
| bond | 4-Cl | 2,5-F₂ | Me |
| CH₂ | 4-Cl | 2,5-F₂ | Et |
| O | 4-Cl | 2,5-F₂ | Et |
| bond | 4-Cl | 2,5-F₂ | Et |
| CH₂ | 4-Cl | 2,6-F₂ | Me |
| O | 4-Cl | 2,6-F₂ | Me |
| bond | 4-Cl | 2,6-F₂ | Me |
| CH₂ | 4-Cl | 2,6-F₂ | Et |
| O | 4-Cl | 2,6-F₂ | Et |
| bond | 4-Cl | 2,6-F₂ | Et |
| CH₂ | 4-Cl | 3,4-F₂ | Me |
| O | 4-Cl | 3,4-F₂ | Me |
| bond | 4-Cl | 3,4-F₂ | Me |
| CH₂ | 4-Cl | 3,4-F₂ | Et |
| O | 4-Cl | 3,4-F₂ | Et |
| bond | 4-Cl | 3,4-F₂ | Et |
| CH₂ | 4-Cl | 3,5-F₂ | Me |
| O | 4-Cl | 3,5-F₂ | Me |
| bond | 4-Cl | 3,5-F₂ | Me |
| CH₂ | 4-Cl | 3,5-F₂ | Et |
| O | 4-Cl | 3,5-F₂ | Et |
| bond | 4-Cl | 3,5-F₂ | Et |
| CH₂ | 4-Cl | 2,4,6-F₃ | Me |
| O | 4-Cl | 2,4,6-F₃ | Me |
| bond | 4-Cl | 2,4,6-F₃ | Me |

TABLE V-continued

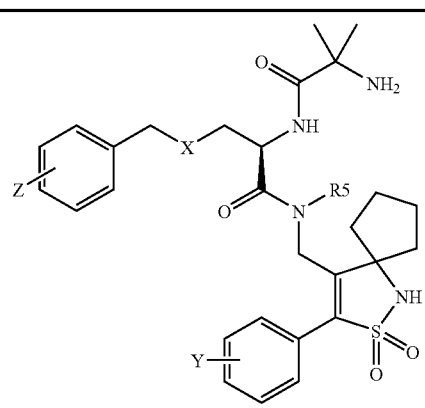

| X | Y | Z | R5 |
|---|---|---|---|
| CH₂ | 4-Cl | 2,4,6-F₃ | Et |
| O | 4-Cl | 2,4,6-F₃ | Et |
| bond | 4-Cl | 2,4,6-F₃ | Et |
| CH₂ | 4-Cl | 2,4,5-F₃ | Me |
| O | 4-Cl | 2,4,5-F₃ | Me |
| bond | 4-Cl | 2,4,5-F₃ | Me |
| CH₂ | 4-Cl | 2,4,5-F₃ | Et |
| O | 4-Cl | 2,4,5-F₃ | Et |
| bond | 4-Cl | 2,4,5-F₃ | Et |
| CH₂ | 4-Cl | 2,3,6-F₃ | Me |
| O | 4-Cl | 2,3,6-F₃ | Me |
| bond | 4-Cl | 2,3,6-F₃ | Me |
| CH₂ | 4-Cl | 2,3,6-F₃ | Et |
| O | 4-Cl | 2,3,6-F₃ | Et |
| bond | 4-Cl | 2,3,6-F₃ | Et |
| CH₂ | 4-Cl | 2,3,5-F₃ | Me |
| O | 4-Cl | 2,3,5-F₃ | Me |
| bond | 4-Cl | 2,3,5-F₃ | Me |
| CH₂ | 4-Cl | 2,3,5-F₃ | Et |
| O | 4-Cl | 2,3,5-F₃ | Et |
| bond | 4-Cl | 2,3,5-F₃ | Et |
| CH₂ | 4-Cl | 2-Cl | Me |
| O | 4-Cl | 2-Cl | Me |
| bond | 4-Cl | 2-Cl | Me |
| CH₂ | 4-Cl | 2-Cl | Et |
| O | 4-Cl | 2-Cl | Et |
| bond | 4-Cl | 2-Cl | Et |
| CH₂ | 4-Cl | 3-Cl | Me |
| O | 4-Cl | 3-Cl | Me |
| bond | 4-Cl | 3-Cl | Me |
| CH₂ | 4-Cl | 3-Cl | Et |
| O | 4-Cl | 3-Cl | Et |
| bond | 4-Cl | 3-Cl | Et |
| CH₂ | 4-Cl | 4-Cl | Me |
| O | 4-Cl | 4-Cl | Me |
| bond | 4-Cl | 4-Cl | Me |
| CH₂ | 4-Cl | 4-Cl | Et |
| O | 4-Cl | 4-Cl | Et |
| bond | 4-Cl | 4-Cl | Et |
| CH₂ | 4-Cl | 2,6-Cl₂ | Me |
| O | 4-Cl | 2,6-Cl₂ | Me |
| bond | 4-Cl | 2,6-Cl₂ | Me |
| CH₂ | 4-Cl | 2,6-Cl₂ | Et |
| O | 4-Cl | 2,6-Cl₂ | Et |
| bond | 4-Cl | 2,6-Cl₂ | Et |
| CH₂ | 4-Cl | 2-F-6-Cl | Me |
| O | 4-Cl | 2-F-6-Cl | Me |
| bond | 4-Cl | 2-F-6-Cl | Me |
| CH₂ | 4-Cl | 2-F-6-Cl | Et |
| O | 4-Cl | 2-F-6-Cl | Et |
| bond | 4-Cl | 2-F-6-Cl | Et |
| CH₂ | 4-Cl | 2-F-3-Cl | Me |
| O | 4-Cl | 2-F-3-Cl | Me |
| bond | 4-Cl | 2-F-3-Cl | Me |
| CH₂ | 4-Cl | 2-F-3-Cl | Et |
| O | 4-Cl | 2-F-3-Cl | Et |
| bond | 4-Cl | 2-F-3-Cl | Et |

TABLE V-continued

| X | Y | Z | R5 |
|---|---|---|---|
| CH₂ | 4-Cl | 2-F-4-Cl | Me |
| O | 4-Cl | 2-F-4-Cl | Me |
| bond | 4-Cl | 2-F-4-Cl | Me |
| CH₂ | 4-Cl | 2-F-4-Cl | Et |
| O | 4-Cl | 2-F-4-Cl | Et |
| bond | 4-Cl | 2-F-4-Cl | Et |
| CH₂ | 4-Cl | 3-F-4-Cl | Me |
| O | 4-Cl | 3-F-4-Cl | Me |
| bond | 4-Cl | 3-F-4-Cl | Me |
| CH₂ | 4-Cl | 3-F-4-Cl | Et |
| O | 4-Cl | 3-F-4-Cl | Et |
| bond | 4-Cl | 3-F-4-Cl | Et |
| CH₂ | 4-Cl | 2,6-F₂-3-Cl | Me |
| O | 4-Cl | 2,6-F₂-3-Cl | Me |
| bond | 4-Cl | 2,6-F₂-3-Cl | Me |
| CH₂ | 4-Cl | 2,6-F₂-3-Cl | Et |
| O | 4-Cl | 2,6-F₂-3-Cl | Et |
| bond | 4-Cl | 2,6-F₂-3-Cl | Et |
| CH₂ | 4-Cl | 2-Cl-3,6-F₂ | Me |
| O | 4-Cl | 2-Cl-3,6-F₂ | Me |
| bond | 4-Cl | 2-Cl-3,6-F₂ | Me |
| CH₂ | 4-Cl | 2-Cl-3,6-F₂ | Et |
| O | 4-Cl | 2-Cl-3,6-F₂ | Et |
| bond | 4-Cl | 2-Cl-3,6-F₂ | Et |
| CH₂ | 4-Cl | 2,3-Cl₂ | Me |
| O | 4-Cl | 2,3-Cl₂ | Me |
| bond | 4-Cl | 2,3-Cl₂ | Me |
| CH₂ | 4-Cl | 2,3-Cl₂ | Et |
| O | 4-Cl | 2,3-Cl₂ | Et |
| bond | 4-Cl | 2,3-Cl₂ | Et |
| CH₂ | 4-Cl | 4-F-2-Cl | Me |
| O | 4-Cl | 4-F-2-Cl | Me |
| bond | 4-Cl | 4-F-2-Cl | Me |
| CH₂ | 4-Cl | 4-F-2-Cl | Et |
| O | 4-Cl | 4-F-2-Cl | Et |
| bond | 4-Cl | 4-F-2-Cl | Et |
| CH₂ | 4-Cl | 4-CF₃ | Me |
| O | 4-Cl | 4-CF₃ | Me |
| bond | 4-Cl | 4-CF₃ | Me |
| CH₂ | 4-Cl | 4-CF₃ | Et |
| O | 4-Cl | 4-CF₃ | Et |
| bond | 4-Cl | 4-CF₃ | Et |
| CH₂ | 4-Cl | 3-CF₃ | Me |
| O | 4-Cl | 3-CF₃ | Me |
| bond | 4-Cl | 3-CF₃ | Me |
| CH₂ | 4-Cl | 3-CF₃ | Et |
| O | 4-Cl | 3-CF₃ | Et |
| bond | 4-Cl | 3-CF₃ | Et |
| CH₂ | 4-Cl | 2-CF₃ | Me |
| O | 4-Cl | 2-CF₃ | Me |
| bond | 4-Cl | 2-CF₃ | Me |
| CH₂ | 4-Cl | 2-CF₃ | Et |
| O | 4-Cl | 2-CF₃ | Et |
| bond | 4-Cl | 2-CF₃ | Et |
| CH₂ | 4-Cl | 2-F-5-CF₃ | Me |
| O | 4-Cl | 2-F-5-CF₃ | Me |
| bond | 4-Cl | 2-F-5-CF₃ | Me |
| CH₂ | 4-Cl | 2-F-5-CF₃ | Et |
| O | 4-Cl | 2-F-5-CF₃ | Et |
| bond | 4-Cl | 2-F-5-CF₃ | Et |
| CH₂ | 4-Cl | 4-OCF₃ | Me |
| O | 4-Cl | 4-OCF₃ | Me |
| bond | 4-Cl | 4-OCF₃ | Me |
| CH₂ | 4-Cl | 4-OCF₃ | Et |
| O | 4-Cl | 4-OCF₃ | Et |
| bond | 4-Cl | 4-OCF₃ | Et |
| CH₂ | 4-Cl | 3-OCF₃ | Me |
| O | 4-Cl | 3-OCF₃ | Me |
| bond | 4-Cl | 3-OCF₃ | Me |
| CH₂ | 4-Cl | 3-OCF₃ | Et |
| O | 4-Cl | 3-OCF₃ | Et |
| bond | 4-Cl | 3-OCF₃ | Et |
| CH₂ | 4-Cl | 2-OCF₃ | Me |
| O | 4-Cl | 2-OCF₃ | Me |
| bond | 4-Cl | 2-OCF₃ | Me |
| CH₂ | 4-Cl | 2-OCF₃ | Et |
| O | 4-Cl | 2-OCF₃ | Et |
| bond | 4-Cl | 2-OCF₃ | Et |
| CH₂ | 4-Cl | 2-CN | Me |
| O | 4-Cl | 2-CN | Me |
| bond | 4-Cl | 2-CN | Me |
| CH₂ | 4-Cl | 2-CN | Et |
| O | 4-Cl | 2-CN | Et |
| bond | 4-Cl | 2-CN | Et |
| CH₂ | 4-Cl | 3-CN | Me |
| O | 4-Cl | 3-CN | Me |
| bond | 4-Cl | 3-CN | Me |
| CH₂ | 4-Cl | 3-CN | Et |
| O | 4-Cl | 3-CN | Et |
| bond | 4-Cl | 3-CN | Et |
| CH₂ | 4-Cl | 4-CN | Me |
| O | 4-Cl | 4-CN | Me |
| bond | 4-Cl | 4-CN | Me |
| CH₂ | 4-Cl | 4-CN | Et |
| O | 4-Cl | 4-CN | Et |
| bond | 4-Cl | 4-CN | Et |
| CH₂ | 4-Cl | 4-SO₂CH₃ | Me |
| O | 4-Cl | 4-SO₂CH₃ | Me |
| bond | 4-Cl | 4-SO₂CH₃ | Me |
| CH₂ | 4-Cl | 4-SO₂CH₃ | Et |
| O | 4-Cl | 4-SO₂CH₃ | Et |
| bond | 4-Cl | 4-SO₂CH₃ | Et |
| CH₂ | 4-F | 2-F | Me |
| O | 4-F | 2-F | Me |
| bond | 4-F | 2-F | Me |
| CH₂ | 4-F | 2-F | Et |
| O | 4-F | 2-F | Et |
| bond | 4-F | 2-F | Et |
| CH₂ | 4-F | 3-F | Me |
| O | 4-F | 3-F | Me |
| bond | 4-F | 3-F | Me |
| CH₂ | 4-F | 3-F | Et |
| O | 4-F | 3-F | Et |
| bond | 4-F | 3-F | Et |

TABLE V-continued

| X | Y | Z | R5 |
|---|---|---|---|
| CH₂ | 4-F | 4-F | Me |
| O | 4-F | 4-F | Me |
| bond | 4-F | 4-F | Me |
| CH₂ | 4-F | 4-F | Et |
| O | 4-F | 4-F | Et |
| bond | 4-F | 4-F | Et |
| CH₂ | 4-F | 2,3-F₂ | Me |
| O | 4-F | 2,3-F₂ | Me |
| bond | 4-F | 2,3-F₂ | Me |
| CH₂ | 4-F | 2,3-F₂ | Et |
| O | 4-F | 2,3-F₂ | Et |
| bond | 4-F | 2,3-F₂ | Et |
| CH₂ | 4-F | 2,4-F₂ | Me |
| O | 4-F | 2,4-F₂ | Me |
| bond | 4-F | 2,4-F₂ | Me |
| CH₂ | 4-F | 2,4-F₂ | Et |
| O | 4-F | 2,4-F₂ | Et |
| bond | 4-F | 2,4-F₂ | Et |
| CH₂ | 4-F | 2,5-F₂ | Me |
| O | 4-F | 2,5-F₂ | Me |
| bond | 4-F | 2,5-F₂ | Me |
| CH₂ | 4-F | 2,5-F₂ | Et |
| O | 4-F | 2,5-F₂ | Et |
| bond | 4-F | 2,5-F₂ | Et |
| CH₂ | 4-F | 2,6-F₂ | Me |
| O | 4-F | 2,6-F₂ | Me |
| bond | 4-F | 2,6-F₂ | Me |
| CH₂ | 4-F | 2,6-F₂ | Et |
| O | 4-F | 2,6-F₂ | Et |
| bond | 4-F | 2,6-F₂ | Et |
| CH₂ | 4-F | 3,4-F₂ | Me |
| O | 4-F | 3,4-F₂ | Me |
| bond | 4-F | 3,4-F₂ | Me |
| CH₂ | 4-F | 3,4-F₂ | Et |
| O | 4-F | 3,4-F₂ | Et |
| bond | 4-F | 3,4-F₂ | Et |
| CH₂ | 4-F | 3,5-F₂ | Me |
| O | 4-F | 3,5-F₂ | Me |
| bond | 4-F | 3,5-F₂ | Me |
| CH₂ | 4-F | 3,5-F₂ | Et |
| O | 4-F | 3,5-F₂ | Et |
| bond | 4-F | 3,5-F₂ | Et |
| CH₂ | 4-F | 2,4,6-F₃ | Me |
| O | 4-F | 2,4,6-F₃ | Me |
| bond | 4-F | 2,4,6-F₃ | Me |
| CH₂ | 4-F | 2,4,6-F₃ | Et |
| O | 4-F | 2,4,6-F₃ | Et |
| bond | 4-F | 2,4,6-F₃ | Et |
| CH₂ | 4-F | 2,4,5-F₃ | Me |
| O | 4-F | 2,4,5-F₃ | Me |
| bond | 4-F | 2,4,5-F₃ | Me |
| CH₂ | 4-F | 2,4,5-F₃ | Et |
| O | 4-F | 2,4,5-F₃ | Et |
| bond | 4-F | 2,4,5-F₃ | Et |
| CH₂ | 4-F | 2,3,6-F₃ | Me |
| O | 4-F | 2,3,6-F₃ | Me |
| bond | 4-F | 2,3,6-F₃ | Me |
| CH₂ | 4-F | 2,3,6-F₃ | Et |
| O | 4-F | 2,3,6-F₃ | Et |
| bond | 4-F | 2,3,6-F₃ | Et |
| CH₂ | 4-F | 2,3,5-F₃ | Me |
| O | 4-F | 2,3,5-F₃ | Me |
| bond | 4-F | 2,3,5-F₃ | Me |
| CH₂ | 4-F | 2,3,5-F₃ | Et |
| O | 4-F | 2,3,5-F₃ | Et |
| bond | 4-F | 2,3,5-F₃ | Et |
| CH₂ | 4-F | 2-Cl | Me |
| O | 4-F | 2-Cl | Me |
| bond | 4-F | 2-Cl | Me |
| CH₂ | 4-F | 2-Cl | Et |
| O | 4-F | 2-Cl | Et |
| bond | 4-F | 2-Cl | Et |
| CH₂ | 4-F | 3-Cl | Me |
| O | 4-F | 3-Cl | Me |
| bond | 4-F | 3-Cl | Me |
| CH₂ | 4-F | 3-Cl | Et |
| O | 4-F | 3-Cl | Et |
| bond | 4-F | 3-Cl | Et |
| CH₂ | 4-F | 4-Cl | Me |
| O | 4-F | 4-Cl | Me |
| bond | 4-F | 4-Cl | Me |
| CH₂ | 4-F | 4-Cl | Et |
| O | 4-F | 4-Cl | Et |
| bond | 4-F | 4-Cl | Et |
| CH₂ | 4-F | 2,6-Cl₂ | Me |
| O | 4-F | 2,6-Cl₂ | Me |
| bond | 4-F | 2,6-Cl₂ | Me |
| CH₂ | 4-F | 2,6-Cl₂ | Et |
| O | 4-F | 2,6-Cl₂ | Et |
| bond | 4-F | 2,6-Cl₂ | Et |
| CH₂ | 4-F | 2-F-6-Cl | Me |
| O | 4-F | 2-F-6-Cl | Me |
| bond | 4-F | 2-F-6-Cl | Me |
| CH₂ | 4-F | 2-F-6-Cl | Et |
| O | 4-F | 2-F-6-Cl | Et |
| bond | 4-F | 2-F-6-Cl | Et |
| CH₂ | 4-F | 2-F-3-Cl | Me |
| O | 4-F | 2-F-3-Cl | Me |
| bond | 4-F | 2-F-3-Cl | Me |
| CH₂ | 4-F | 2-F-3-Cl | Et |
| O | 4-F | 2-F-3-Cl | Et |
| bond | 4-F | 2-F-3-Cl | Et |
| CH₂ | 4-F | 2-F-4-Cl | Me |
| O | 4-F | 2-F-4-Cl | Me |
| bond | 4-F | 2-F-4-Cl | Me |
| CH₂ | 4-F | 2-F-4-Cl | Et |
| O | 4-F | 2-F-4-Cl | Et |
| bond | 4-F | 2-F-4-Cl | Et |
| CH₂ | 4-F | 3-F-4-Cl | Me |
| O | 4-F | 3-F-4-Cl | Me |
| bond | 4-F | 3-F-4-Cl | Me |
| CH₂ | 4-F | 3-F-4-Cl | Et |
| O | 4-F | 3-F-4-Cl | Et |
| bond | 4-F | 3-F-4-Cl | Et |

TABLE V-continued

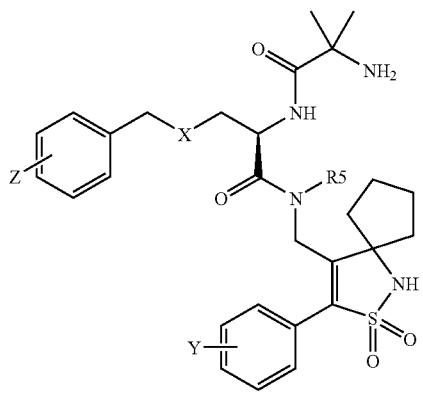

| X | Y | Z | R5 |
|---|---|---|---|
| CH₂ | 4-F | 2,6-F₂-3-Cl | Me |
| O | 4-F | 2,6-F₂-3-Cl | Me |
| bond | 4-F | 2,6-F₂-3-Cl | Me |
| CH₂ | 4-F | 2,6-F₂-3-Cl | Et |
| O | 4-F | 2,6-F₂-3-Cl | Et |
| bond | 4-F | 2,6-F₂-3-Cl | Et |
| CH₂ | 4-F | 2-Cl-3,6-F₂ | Me |
| O | 4-F | 2-Cl-3,6-F₂ | Me |
| bond | 4-F | 2-Cl-3,6-F₂ | Me |
| CH₂ | 4-F | 2-Cl-3,6-F₂ | Et |
| O | 4-F | 2-Cl-3,6-F₂ | Et |
| bond | 4-F | 2-Cl-3,6-F₂ | Et |
| CH₂ | 4-F | 2,3-Cl₂ | Me |
| O | 4-F | 2,3-Cl₂ | Me |
| bond | 4-F | 2,3-Cl₂ | Me |
| CH₂ | 4-F | 2,3-Cl₂ | Et |
| O | 4-F | 2,3-Cl₂ | Et |
| bond | 4-F | 2,3-Cl₂ | Et |
| CH₂ | 4-F | 4-F-2-Cl | Me |
| O | 4-F | 4-F-2-Cl | Me |
| bond | 4-F | 4-F-2-Cl | Me |
| CH₂ | 4-F | 4-F-2-Cl | Et |
| O | 4-F | 4-F-2-Cl | Et |
| bond | 4-F | 4-F-2-Cl | Et |
| CH₂ | 4-F | 4-CF₃ | Me |
| O | 4-F | 4-CF₃ | Me |
| bond | 4-F | 4-CF₃ | Me |
| CH₂ | 4-F | 4-CF₃ | Et |
| O | 4-F | 4-CF₃ | Et |
| bond | 4-F | 4-CF₃ | Et |
| CH₂ | 4-F | 3-CF₃ | Me |
| O | 4-F | 3-CF₃ | Me |
| bond | 4-F | 3-CF₃ | Me |
| CH₂ | 4-F | 3-CF₃ | Et |
| O | 4-F | 3-CF₃ | Et |
| bond | 4-F | 3-CF₃ | Et |
| CH₂ | 4-F | 2-CF₃ | Me |
| O | 4-F | 2-CF₃ | Me |
| bond | 4-F | 2-CF₃ | Me |
| CH₂ | 4-F | 2-CF₃ | Et |
| O | 4-F | 2-CF₃ | Et |
| bond | 4-F | 2-CF₃ | Et |
| CH₂ | 4-F | 2-F-5-CF₃ | Me |
| O | 4-F | 2-F-5-CF₃ | Me |
| bond | 4-F | 2-F-5-CF₃ | Me |
| CH₂ | 4-F | 2-F-5-CF₃ | Et |
| O | 4-F | 2-F-5-CF₃ | Et |
| bond | 4-F | 2-F-5-CF₃ | Et |
| CH₂ | 4-F | 4-OCF₃ | Me |
| O | 4-F | 4-OCF₃ | Me |
| bond | 4-F | 4-OCF₃ | Me |
| CH₂ | 4-F | 4-OCF₃ | Et |
| O | 4-F | 4-OCF₃ | Et |
| bond | 4-F | 4-OCF₃ | Et |
| CH₂ | 4-F | 3-OCF₃ | Me |
| O | 4-F | 3-OCF₃ | Me |
| bond | 4-F | 3-OCF₃ | Me |

TABLE V-continued

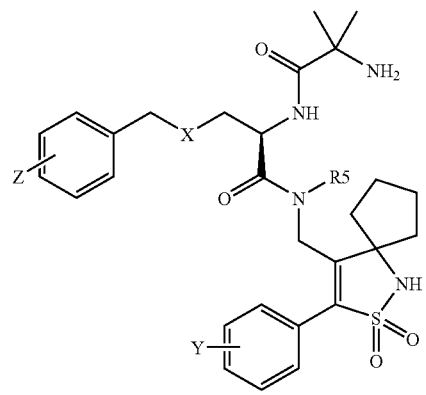

| X | Y | Z | R5 |
|---|---|---|---|
| CH₂ | 4-F | 3-OCF₃ | Et |
| O | 4-F | 3-OCF₃ | Et |
| bond | 4-F | 3-OCF₃ | Et |
| CH₂ | 4-F | 2-OCF₃ | Me |
| O | 4-F | 2-OCF₃ | Me |
| bond | 4-F | 2-OCF₃ | Me |
| CH₂ | 4-F | 2-OCF₃ | Et |
| O | 4-F | 2-OCF₃ | Et |
| bond | 4-F | 2-OCF₃ | Et |
| CH₂ | 4-F | 2-CN | Me |
| O | 4-F | 2-CN | Me |
| bond | 4-F | 2-CN | Me |
| CH₂ | 4-F | 2-CN | Et |
| O | 4-F | 2-CN | Et |
| bond | 4-F | 2-CN | Et |
| CH₂ | 4-F | 3-CN | Me |
| O | 4-F | 3-CN | Me |
| bond | 4-F | 3-CN | Me |
| CH₂ | 4-F | 3-CN | Et |
| O | 4-F | 3-CN | Et |
| bond | 4-F | 3-CN | Et |
| CH₂ | 4-F | 4-CN | Me |
| O | 4-F | 4-CN | Me |
| bond | 4-F | 4-CN | Me |
| CH₂ | 4-F | 4-CN | Et |
| O | 4-F | 4-CN | Et |
| bond | 4-F | 4-CN | Et |
| CH₂ | 4-F | 4-SO₂CH₃ | Me |
| O | 4-F | 4-SO₂CH₃ | Me |
| bond | 4-F | 4-SO₂CH₃ | Me |
| CH₂ | 4-F | 4-SO₂CH₃ | Et |
| O | 4-F | 4-SO₂CH₃ | Et |
| bond | 4-F | 4-SO₂CH₃ | Et |
| O | 4-Cl | 2-F | CH₂CH₂F |
| O | 4-Cl | 3-F | CH₂CH₂F |
| O | 4-Cl | 4-F | CH₂CH₂F |
| O | 4-Cl | 4-Cl | CH₂CH₂F |
| O | 4-Cl | 2,5-F₂ | CH₂CH₂F |
| O | 4-Cl | 2,4-F₂ | CH₂CH₂F |
| O | 4-Cl | 2-Cl | CH₂CH₂F |
| O | 4-Cl | 2,6-F₂ | CH₂CH₂F |
| O | 4-Cl | 3,5-F₂ | CH₂CH₂F |
| O | 4-Cl | 2,3-F₂ | CH₂CH₂F |
| O | 4-Cl | 3,4-F₂ | CH₂CH₂F |
| O | 4-Cl | 2,3,5-F₃ | CH₂CH₂F |
| O | 4-Cl | 2,3,6-F₃ | CH₂CH₂F |
| O | 4-Cl | 2,4,5-F₃ | CH₂CH₂F |
| O | 4-Cl | 2,6-Cl₂ | CH₂CH₂F |
| O | 4-Cl | 2-F-6-Cl | CH₂CH₂F |
| O | 4-Cl | 2-F-3-Cl | CH₂CH₂F |
| O | 4-Cl | 2-F-4-Cl | CH₂CH₂F |
| O | 4-Cl | 4-F-2-Cl | CH₂CH₂F |
| O | 4-Cl | 2,3-Cl₂ | CH₂CH₂F |
| O | 4-Cl | 2-Cl-3,6-F₂ | CH₂CH₂F |
| O | 4-F | 2-F | CH₂CH₂F |
| O | 4-F | 3-F | CH₂CH₂F |
| O | 4-F | 4-F | CH₂CH₂F |

TABLE V-continued

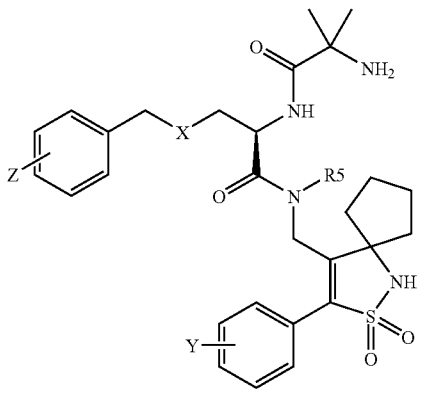

| X | Y | Z | R5 |
|---|---|---|---|
| O | 4-F | 4-Cl | CH₂CH₂F |
| O | 4-F | 2,5-F₂ | CH₂CH₂F |
| O | 4-F | 2,4-F₂ | CH₂CH₂F |
| O | 4-F | 2-Cl | CH₂CH₂F |
| O | 4-F | 2,6-F₂ | CH₂CH₂F |
| O | 4-F | 3,5-F₂ | CH₂CH₂F |
| O | 4-F | 2,3-F₂ | CH₂CH₂F |
| O | 4-F | 3,4-F₂ | CH₂CH₂F |
| O | 4-F | 2,3,5-F₃ | CH₂CH₂F |
| O | 4-F | 2,3,6-F₃ | CH₂CH₂F |
| O | 4-F | 2,4,5-F₃ | CH₂CH₂F |
| O | 4-F | 2,6-Cl₂ | CH₂CH₂F |
| O | 4-F | 2-F-6-Cl | CH₂CH₂F |
| O | 4-F | 2-F-3-Cl | CH₂CH₂F |
| O | 4-F | 2-F-4-Cl | CH₂CH₂F |
| O | 4-F | 4-F-2-Cl | CH₂CH₂F |
| O | 4-F | 2,3-Cl₂ | CH₂CH₂F |
| O | 4-F | 2-Cl-3,6-F₂ | CH₂CH₂F |
| CH₂ | 4-Cl | 3,5-F₂ | CH₂CH₂F |
| CH₂ | 4-Cl | 4-F | CH₂CH₂F |
| CH₂ | 4-Cl | 2,6-F₂ | CH₂CH₂F |
| CH₂ | 4-F | 3,5-F₂ | CH₂CH₂F |
| CH₂ | 4-F | 4-F | CH₂CH₂F |
| CH₂ | 4-F | 2,6-F₂ | CH₂CH₂F |
| O | 3-Cl | 3,5-F₂ | CH₂CH₂F |
| O | 3-Cl | 4-F | CH₂CH₂F |
| O | 3-Cl | 2,6-F₂ | CH₂CH₂F |
| O | 3-Cl | 2,5-F₂ | CH₂CH₂F |
| O | 3-F | 3,5-F₂ | CH₂CH₂F |
| O | 3-F | 4-F | CH₂CH₂F |
| O | 3-F | 2,6-F₂ | CH₂CH₂F |
| O | 3-F | 2,5-F₂ | CH₂CH₂F |
| O | 4-CN | 3,5-F₂ | CH₂CH₂F |
| O | 4-CN | 4-F | CH₂CH₂F |
| O | 4-CN | 2,6-F₂ | CH₂CH₂F |
| O | 4-CN | 2,5-F₂ | CH₂CH₂F |
| O | 2,5-F₂ | 3,5-F₂ | CH₂CH₂F |
| O | 2,5-F₂ | 4-F | CH₂CH₂F |
| O | 2,5-F₂ | 2,6-F₂ | CH₂CH₂F |
| O | 2,5-F₂ | 2,5-F₂ | CH₂CH₂F |
| O | 3,5-F₂ | 3,5-F₂ | CH₂CH₂F |
| O | 3,5-F₂ | 4-F | CH₂CH₂F |
| O | 3,5-F₂ | 2,6-F₂ | CH₂CH₂F |
| O | 3,5-F₂ | 2,5-F₂ | CH₂CH₂F |
| O | 3,4-F₂ | 3,5-F₂ | CH₂CH₂F |
| O | 3,4-F₂ | 4-F | CH₂CH₂F |
| O | 3,4-F₂ | 2,6-F₂ | CH₂CH₂F |
| O | 3,4-F₂ | 2,5-F₂ | CH₂CH₂F |
| O | 4-CF₃ | 3,5-F₂ | CH₂CH₂F |
| O | 4-CF₃ | 4-F | CH₂CH₂F |
| O | 4-CF₃ | 2,6-F₂ | CH₂CH₂F |
| O | 4-CF₃ | 2,5-F₂ | CH₂CH₂F |
| O | 4-Cl | 2-F | CH₂CH₂OH |
| O | 4-Cl | 3-F | CH₂CH₂OH |
| O | 4-Cl | 4-F | CH₂CH₂OH |
| O | 4-Cl | 4-Cl | CH₂CH₂OH |
| O | 4-Cl | 2,5-F₂ | CH₂CH₂OH |

TABLE V-continued

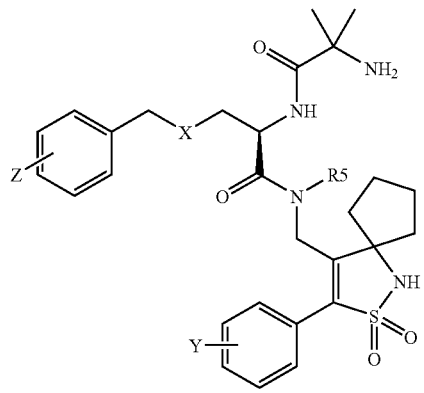

| X | Y | Z | R5 |
|---|---|---|---|
| O | 4-Cl | 2,4-F₂ | CH₂CH₂OH |
| O | 4-Cl | 2-Cl | CH₂CH₂OH |
| O | 4-Cl | 2,6-F₂ | CH₂CH₂OH |
| O | 4-Cl | 3,5-F₂ | CH₂CH₂OH |
| O | 4-Cl | 2,3-F₂ | CH₂CH₂OH |
| O | 4-Cl | 3,4-F₂ | CH₂CH₂OH |
| O | 4-Cl | 2,3,5-F₃ | CH₂CH₂OH |
| O | 4-Cl | 2,3,6-F₃ | CH₂CH₂OH |
| O | 4-Cl | 2,4,5-F₃ | CH₂CH₂OH |
| O | 4-Cl | 2,6-Cl₂ | CH₂CH₂OH |
| O | 4-Cl | 2-F-6-Cl | CH₂CH₂OH |
| O | 4-Cl | 2-F-3-Cl | CH₂CH₂OH |
| O | 4-Cl | 2-F-4-Cl | CH₂CH₂OH |
| O | 4-Cl | 4-F-2-Cl | CH₂CH₂OH |
| O | 4-Cl | 2,3-Cl₂ | CH₂CH₂OH |
| O | 4-Cl | 2-Cl-3,6-F₂ | CH₂CH₂OH |
| O | 4-F | 2-F | CH₂CH₂OH |
| O | 4-F | 3-F | CH₂CH₂OH |
| O | 4-F | 4-F | CH₂CH₂OH |
| O | 4-F | 4-Cl | CH₂CH₂OH |
| O | 4-F | 2,5-F₂ | CH₂CH₂OH |
| O | 4-F | 2,4-F₂ | CH₂CH₂OH |
| O | 4-F | 2-Cl | CH₂CH₂OH |
| O | 4-F | 2,6-F₂ | CH₂CH₂OH |
| O | 4-F | 3,5-F₂ | CH₂CH₂OH |
| O | 4-F | 2,3-F₂ | CH₂CH₂OH |
| O | 4-F | 3,4-F₂ | CH₂CH₂OH |
| O | 4-F | 2,3,5-F₃ | CH₂CH₂OH |
| O | 4-F | 2,3,6-F₃ | CH₂CH₂OH |
| O | 4-F | 2,4,5-F₃ | CH₂CH₂OH |
| O | 4-F | 2,6-Cl₂ | CH₂CH₂OH |
| O | 4-F | 2-F-6-Cl | CH₂CH₂OH |
| O | 4-F | 2-F-3-Cl | CH₂CH₂OH |
| O | 4-F | 2-F-4-Cl | CH₂CH₂OH |
| O | 4-F | 4-F-2-Cl | CH₂CH₂OH |
| O | 4-F | 2,3-Cl₂ | CH₂CH₂OH |
| O | 4-F | 2-Cl-3,6-F | CH₂CH₂OH |
| CH₂ | 4-Cl | 3,5-F₂ | CH₂CH₂OH |
| CH₂ | 4-Cl | 4-F | CH₂CH₂OH |
| CH₂ | 4-Cl | 2,6-F₂ | CH₂CH₂OH |
| CH₂ | 4-F | 3,5-F₂ | CH₂CH₂OH |
| CH₂ | 4-F | 4-F | CH₂CH₂OH |
| CH₂ | 4-F | 2,6-F₂ | CH₂CH₂OH |
| O | 3-F | 3,5-F₂ | CH₂CH₂OH |
| O | 3-F | 4-F | CH₂CH₂OH |
| O | 3-F | 2,6-F₂ | CH₂CH₂OH |
| O | 3-F | 2,5-F₂ | CH₂CH₂OH |
| O | 2,5-F₂ | 3,5-F₂ | CH₂CH₂OH |
| O | 2,5-F₂ | 4-F | CH₂CH₂OH |
| O | 2,5-F₂ | 2,6-F₂ | CH₂CH₂OH |
| O | 2,5-F₂ | 2,5-F₂ | CH₂CH₂OH |
| O | 3,5-F₂ | 3,5-F₂ | CH₂CH₂OH |
| O | 3,5-F₂ | 4-F | CH₂CH₂OH |
| O | 3,5-F₂ | 2,6-F₂ | CH₂CH₂OH |
| O | 3,5-F₂ | 2,5-F₂ | CH₂CH₂OH |
| O | 3,4-F₂ | 3,5-F₂ | CH₂CH₂OH |
| O | 3,4-F₂ | 4-F | CH₂CH₂OH |

TABLE V-continued

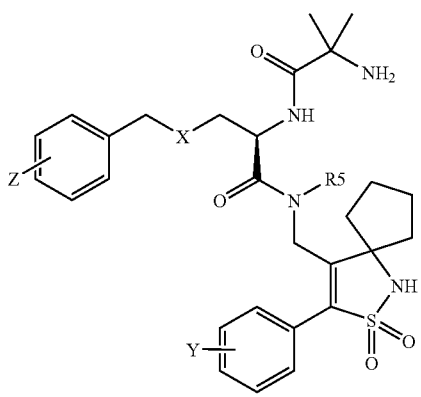

| X | Y | Z | R5 |
|---|---|---|---|
| O | 3,4-F$_2$ | 2,6-F$_2$ | CH$_2$CH$_2$OH |
| O | 3,4-F$_2$ | 2,5-F$_2$ | CH$_2$CH$_2$OH |
| O | 4-CF$_3$ | 3,5-F$_2$ | CH$_2$CH$_2$OH |
| O | 4-CF$_3$ | 4-F | CH$_2$CH$_2$OH |
| O | 4-CF$_3$ | 2,6-F$_2$ | CH$_2$CH$_2$OH |
| O | 4-CF$_3$ | 2,5-F$_2$ | CH$_2$CH$_2$OH |

TABLE VI

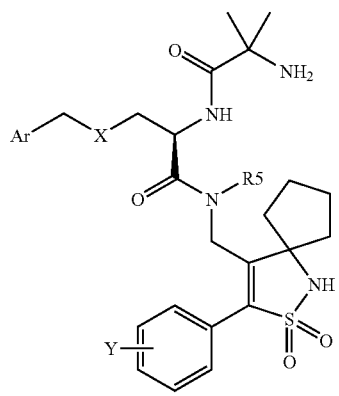

| X | Y | Ar | R5 |
|---|---|---|---|
| CH$_2$ | 4-Cl | 2-methyl-4-thiazolyl | Me |
| O | 4-Cl | 2-methyl-4-thiazolyl | Me |
| bond | 4-Cl | 2-methyl-4-thiazolyl | Me |
| CH$_2$ | 4-Cl | 2-methyl-4-thiazolyl | Et |
| O | 4-Cl | 2-methyl-4-thiazolyl | Et |
| bond | 4-Cl | 2-methyl-4-thiazolyl | Et |
| CH$_2$ | 4-F | 2-methyl-4-thiazolyl | Me |
| O | 4-F | 2-methyl-4-thiazolyl | Me |
| bond | 4-F | 2-methyl-4-thiazolyl | Me |
| CH$_2$ | 4-F | 2-methyl-4-thiazolyl | Et |
| O | 4-F | 2-methyl-4-thiazolyl | Et |
| bond | 4-F | 2-methyl-4-thiazolyl | Et |

TABLE VII

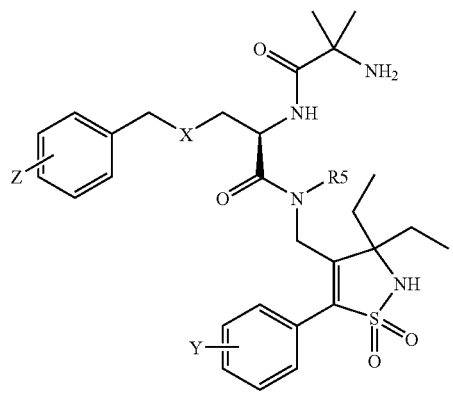

| X | Y | Z | R5 |
|---|---|---|---|
| O | 4-Cl | 2-F | CH$_2$CH$_2$F |
| O | 4-Cl | 3-F | CH$_2$CH$_2$F |
| O | 4-Cl | 4-F | CH$_2$CH$_2$F |
| O | 4-Cl | 4-Cl | CH$_2$CH$_2$F |
| O | 4-Cl | 2,5-F$_2$ | CH$_2$CH$_2$F |
| O | 4-Cl | 2,4-F$_2$ | CH$_2$CH$_2$F |
| O | 4-Cl | 2-Cl | CH$_2$CH$_2$F |
| O | 4-Cl | 2,6-F$_2$ | CH$_2$CH$_2$F |
| O | 4-Cl | 3,5-F$_2$ | CH$_2$CH$_2$F |
| O | 4-Cl | 2,3-F$_2$ | CH$_2$CH$_2$F |
| O | 4-Cl | 3,4-F$_2$ | CH$_2$CH$_2$F |
| O | 4-Cl | 2,3,5-F$_3$ | CH$_2$CH$_2$F |
| O | 4-Cl | 2,3,6-F$_3$ | CH$_2$CH$_2$F |
| O | 4-Cl | 2,4,5-F$_3$ | CH$_2$CH$_2$F |
| O | 4-Cl | 2,6-Cl$_2$ | CH$_2$CH$_2$F |
| O | 4-Cl | 2-F-6-Cl | CH$_2$CH$_2$F |
| O | 4-Cl | 2-F-3-Cl | CH$_2$CH$_2$F |
| O | 4-F | 2-F | CH$_2$CH$_2$F |
| O | 4-F | 3-F | CH$_2$CH$_2$F |
| O | 4-F | 4-F | CH$_2$CH$_2$F |
| O | 4-F | 4-Cl | CH$_2$CH$_2$F |
| O | 4-F | 2,5-F$_2$ | CH$_2$CH$_2$F |
| O | 4-F | 2,4-F$_2$ | CH$_2$CH$_2$F |
| O | 4-F | 2-Cl | CH$_2$CH$_2$F |
| O | 4-F | 2,6-F$_2$ | CH$_2$CH$_2$F |
| O | 4-F | 3,5-F$_2$ | CH$_2$CH$_2$F |
| O | 4-F | 2,3-F$_2$ | CH$_2$CH$_2$F |
| O | 4-F | 3,4-F$_2$ | CH$_2$CH$_2$F |
| O | 4-F | 2,3,5-F$_3$ | CH$_2$CH$_2$F |
| O | 4-F | 2,3,6-F$_3$ | CH$_2$CH$_2$F |
| O | 4-F | 2,4,5-F$_3$ | CH$_2$CH$_2$F |
| O | 4-F | 2,6-Cl$_2$ | CH$_2$CH$_2$F |
| O | 4-F | 2-F-6-Cl | CH$_2$CH$_2$F |
| O | 4-F | 2-F-3-Cl | CH$_2$CH$_2$F |
| CH$_2$ | 4-Cl | 3,5-F$_2$ | CH$_2$CH$_2$F |
| CH$_2$ | 4-Cl | 4-F | CH$_2$CH$_2$F |
| CH$_2$ | 4-Cl | 2,6-F$_2$ | CH$_2$CH$_2$F |
| CH$_2$ | 4-F | 3,5-F$_2$ | CH$_2$CH$_2$F |
| CH$_2$ | 4-F | 4-F | CH$_2$CH$_2$F |
| CH$_2$ | 4-F | 2,6-F$_2$ | CH$_2$CH$_2$F |
| O | 3-Cl | 3,5-F$_2$ | CH$_2$CH$_2$F |
| O | 3-Cl | 4-F | CH$_2$CH$_2$F |
| O | 3-Cl | 2,6-F$_2$ | CH$_2$CH$_2$F |
| O | 3-Cl | 2,5-F$_2$ | CH$_2$CH$_2$F |
| O | 3-F | 3,5-F$_2$ | CH$_2$CH$_2$F |
| O | 3-F | 4-F | CH$_2$CH$_2$F |
| O | 3-F | 2,6-F$_2$ | CH$_2$CH$_2$F |
| O | 3-F | 2,5-F$_2$ | CH$_2$CH$_2$F |
| O | 4-CN | 3,5-F$_2$ | CH$_2$CH$_2$F |
| O | 4-CN | 4-F | CH$_2$CH$_2$F |
| O | 4-CN | 2,6-F$_2$ | CH$_2$CH$_2$F |
| O | 4-CN | 2,5-F$_2$ | CH$_2$CH$_2$F |
| O | 2,5-F$_2$ | 3,5-F$_2$ | CH$_2$CH$_2$F |
| O | 2,5-F$_2$ | 4-F | CH$_2$CH$_2$F |
| O | 2,5-F$_2$ | 2,6-F$_2$ | CH$_2$CH$_2$F |
| O | 2,5-F$_2$ | 2,5-F$_2$ | CH$_2$CH$_2$F |
| O | 3,5-F$_2$ | 3,5-F$_2$ | CH$_2$CH$_2$F |

TABLE VII-continued

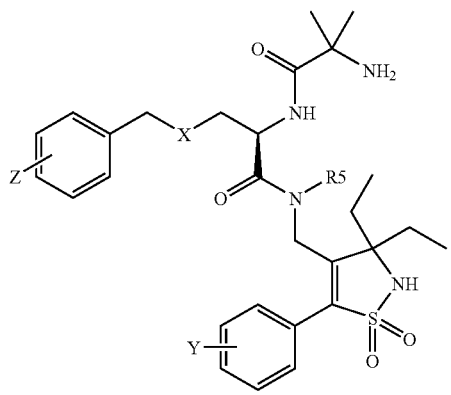

| X | Y | Z | R5 |
|---|---|---|---|
| O | 3,5-F₂ | 4-F | CH₂CH₂F |
| O | 3,5-F₂ | 2,6-F₂ | CH₂CH₂F |
| O | 3,5-F₂ | 2,5-F₂ | CH₂CH₂F |
| O | 3,4-F₂ | 3,5-F₂ | CH₂CH₂F |
| O | 3,4-F₂ | 4-F | CH₂CH₂F |
| O | 3,4-F₂ | 2,6-F₂ | CH₂CH₂F |
| O | 3,4-F₂ | 2,5-F₂ | CH₂CH₂F |
| O | 4-CF₃ | 3,5-F₂ | CH₂CH₂F |
| O | 4-CF₃ | 4-F | CH₂CH₂F |
| O | 4-CF₃ | 2,6-F₂ | CH₂CH₂F |
| O | 4-CF₃ | 2,5-F₂ | CH₂CH₂F |
| O | 4-Cl | 2-F | CH₂CH₂OH |
| O | 4-Cl | 3-F | CH₂CH₂OH |
| O | 4-Cl | 4-F | CH₂CH₂OH |
| O | 4-Cl | 4-Cl | CH₂CH₂OH |
| O | 4-Cl | 2,5-F₂ | CH₂CH₂OH |
| O | 4-Cl | 2,4-F₂ | CH₂CH₂OH |
| O | 4-Cl | 2-Cl | CH₂CH₂OH |
| O | 4-Cl | 2,6-F₂ | CH₂CH₂OH |
| O | 4-Cl | 3,5-F₂ | CH₂CH₂OH |
| O | 4-Cl | 2,3-F₂ | CH₂CH₂OH |
| O | 4-Cl | 3,4-F₂ | CH₂CH₂OH |
| O | 4-Cl | 2,3,5-F₃ | CH₂CH₂OH |
| O | 4-Cl | 2,3,6-F₃ | CH₂CH₂OH |
| O | 4-Cl | 2,4,5-F₃ | CH₂CH₂OH |
| O | 4-Cl | 2,6-Cl₂ | CH₂CH₂OH |
| O | 4-Cl | 2-F-6-Cl | CH₂CH₂OH |
| O | 4-Cl | 2-F-3-Cl | CH₂CH₂OH |
| O | 4-F | 2-F | CH₂CH₂OH |
| O | 4-F | 3-F | CH₂CH₂OH |
| O | 4-F | 4-F | CH₂CH₂OH |
| O | 4-F | 4-Cl | CH₂CH₂OH |
| O | 4-F | 2,5-F₂ | CH₂CH₂OH |
| O | 4-F | 2,4-F₂ | CH₂CH₂OH |
| O | 4-F | 2-Cl | CH₂CH₂OH |
| O | 4-F | 2,6-F₂ | CH₂CH₂OH |
| O | 4-F | 3,5-F₂ | CH₂CH₂OH |
| O | 4-F | 2,3-F₂ | CH₂CH₂OH |
| O | 4-F | 3,4-F₂ | CH₂CH₂OH |
| O | 4-F | 2,3,5-F₃ | CH₂CH₂OH |
| O | 4-F | 2,3,6-F₃ | CH₂CH₂OH |
| O | 4-F | 2,4,5-F₃ | CH₂CH₂OH |
| O | 4-F | 2,6-Cl₂ | CH₂CH₂OH |
| O | 4-F | 2-F-6-Cl | CH₂CH₂OH |
| O | 4-F | 2-F-3-Cl | CH₂CH₂OH |
| CH₂ | 4-Cl | 3,5-F₂ | CH₂CH₂OH |
| CH₂ | 4-Cl | 4-F | CH₂CH₂OH |
| CH₂ | 4-Cl | 2,6-F₂ | CH₂CH₂OH |
| CH₂ | 4-F | 3,5-F₂ | CH₂CH₂OH |
| CH₂ | 4-F | 4-F | CH₂CH₂OH |
| CH₂ | 4-F | 2,6-F₂ | CH₂CH₂OH |
| O | 3-F | 3,5-F₂ | CH₂CH₂OH |
| O | 3-F | 4-F | CH₂CH₂OH |
| O | 3-F | 2,6-F₂ | CH₂CH₂OH |
| O | 3-F | 2,5-F₂ | CH₂CH₂OH |
| O | 2,5-F₂ | 3,5-F₂ | CH₂CH₂OH |
| O | 2,5-F₂ | 4-F | CH₂CH₂OH |

TABLE VII-continued

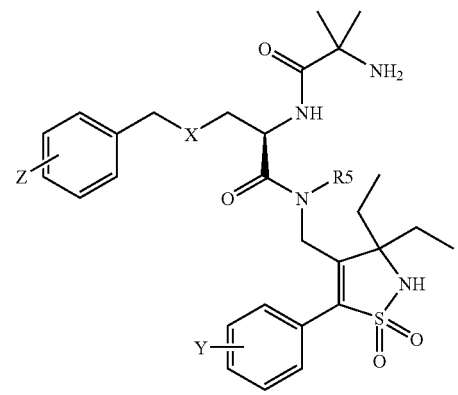

| X | Y | Z | R5 |
|---|---|---|---|
| O | 2,5-F₂ | 2,6-F₂ | CH₂CH₂OH |
| O | 2,5-F₂ | 2,5-F₂ | CH₂CH₂OH |
| O | 3,5-F₂ | 3,5-F₂ | CH₂CH₂OH |
| O | 3,5-F₂ | 4-F | CH₂CH₂OH |
| O | 3,5-F₂ | 2,6-F₂ | CH₂CH₂OH |
| O | 3,5-F₂ | 2,5-F₂ | CH₂CH₂OH |
| O | 3,4-F₂ | 3,5-F₂ | CH₂CH₂OH |
| O | 3,4-F₂ | 4-F | CH₂CH₂OH |
| O | 3,4-F₂ | 2,6-F₂ | CH₂CH₂OH |
| O | 3,4-F₂ | 2,5-F₂ | CH₂CH₂OH |
| O | 4-CF₃ | 3,5-F₂ | CH₂CH₂OH |
| O | 4-CF₃ | 4-F | CH₂CH₂OH |
| O | 4-CF₃ | 2,6-F₂ | CH₂CH₂OH |
| O | 4-CF₃ | 2,5-F₂ | CH₂CH₂OH |

TABLE VIII

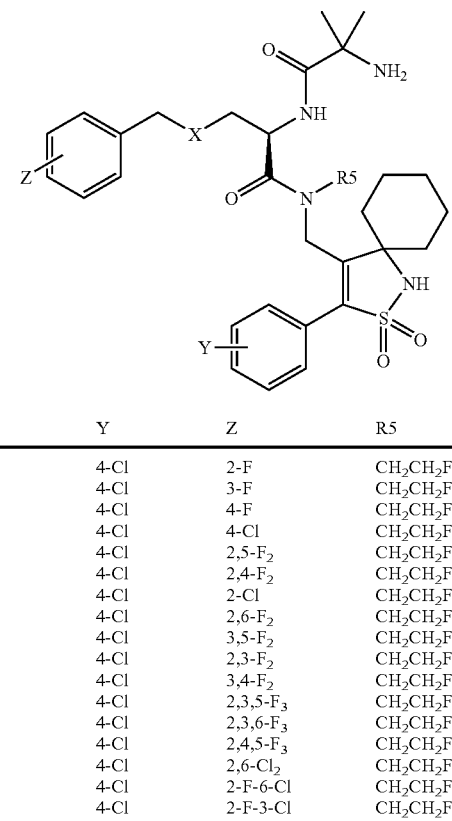

| X | Y | Z | R5 |
|---|---|---|---|
| O | 4-Cl | 2-F | CH₂CH₂F |
| O | 4-Cl | 3-F | CH₂CH₂F |
| O | 4-Cl | 4-F | CH₂CH₂F |
| O | 4-Cl | 4-Cl | CH₂CH₂F |
| O | 4-Cl | 2,5-F₂ | CH₂CH₂F |
| O | 4-Cl | 2,4-F₂ | CH₂CH₂F |
| O | 4-Cl | 2-Cl | CH₂CH₂F |
| O | 4-Cl | 2,6-F₂ | CH₂CH₂F |
| O | 4-Cl | 3,5-F₂ | CH₂CH₂F |
| O | 4-Cl | 2,3-F₂ | CH₂CH₂F |
| O | 4-Cl | 3,4-F₂ | CH₂CH₂F |
| O | 4-Cl | 2,3,5-F₃ | CH₂CH₂F |
| O | 4-Cl | 2,3,6-F₃ | CH₂CH₂F |
| O | 4-Cl | 2,4,5-F₃ | CH₂CH₂F |
| O | 4-Cl | 2,6-Cl₂ | CH₂CH₂F |
| O | 4-Cl | 2-F-6-Cl | CH₂CH₂F |
| O | 4-Cl | 2-F-3-Cl | CH₂CH₂F |

TABLE VIII-continued

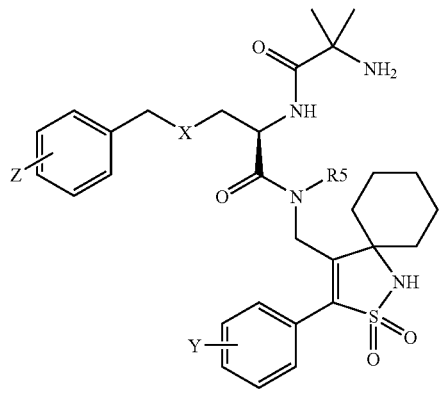

| X | Y | Z | R5 |
|---|---|---|---|
| O | 4-F | 2-F | CH₂CH₂F |
| O | 4-F | 3-F | CH₂CH₂F |
| O | 4-F | 4-F | CH₂CH₂F |
| O | 4-F | 4-Cl | CH₂CH₂F |
| O | 4-F | 2,5-F₂ | CH₂CH₂F |
| O | 4-F | 2,4-F₂ | CH₂CH₂F |
| O | 4-F | 2-Cl | CH₂CH₂F |
| O | 4-F | 2,6-F₂ | CH₂CH₂F |
| O | 4-F | 3,5-F₂ | CH₂CH₂F |
| O | 4-F | 2,3-F₂ | CH₂CH₂F |
| O | 4-F | 3,4-F₂ | CH₂CH₂F |
| O | 4-F | 2,3,5-F₃ | CH₂CH₂F |
| O | 4-F | 2,3,6-F₃ | CH₂CH₂F |
| O | 4-F | 2,4,5-F₃ | CH₂CH₂F |
| O | 4-F | 2,6-Cl₂ | CH₂CH₂F |
| O | 4-F | 2-F-6-Cl | CH₂CH₂F |
| O | 4-F | 2-F-3-Cl | CH₂CH₂F |
| CH₂ | 4-Cl | 3,5-F₂ | CH₂CH₂F |
| CH₂ | 4-Cl | 4-F | CH₂CH₂F |
| CH₂ | 4-Cl | 2,6-F₂ | CH₂CH₂F |
| CH₂ | 4-F | 3,5-F₂ | CH₂CH₂F |
| CH₂ | 4-F | 4-F | CH₂CH₂F |
| CH₂ | 4-F | 2,6-F₂ | CH₂CH₂F |
| O | 3-Cl | 3,5-F₂ | CH₂CH₂F |
| O | 3-Cl | 4-F | CH₂CH₂F |
| O | 3-Cl | 2,6-F₂ | CH₂CH₂F |
| O | 3-Cl | 2,5-F₂ | CH₂CH₂F |
| O | 3-F | 3,5-F₂ | CH₂CH₂F |
| O | 3-F | 4-F | CH₂CH₂F |
| O | 3-F | 2,6-F₂ | CH₂CH₂F |
| O | 3-F | 2,5-F₂ | CH₂CH₂F |
| O | 4-CN | 3,5-F₂ | CH₂CH₂F |
| O | 4-CN | 4-F | CH₂CH₂F |
| O | 4-CN | 2,6-F₂ | CH₂CH₂F |
| O | 4-CN | 2,5-F₂ | CH₂CH₂F |
| O | 2,5-F₂ | 3,5-F₂ | CH₂CH₂F |
| O | 2,5-F₂ | 4-F | CH₂CH₂F |
| O | 2,5-F₂ | 2,6-F₂ | CH₂CH₂F |
| O | 2,5-F₂ | 2,5-F₂ | CH₂CH₂F |
| O | 3,5-F₂ | 3,5-F₂ | CH₂CH₂F |
| O | 3,5-F₂ | 4-F | CH₂CH₂F |
| O | 3,5-F₂ | 2,6-F₂ | CH₂CH₂F |
| O | 3,5-F₂ | 2,5-F₂ | CH₂CH₂F |
| O | 3,4-F₂ | 3,5-F₂ | CH₂CH₂F |
| O | 3,4-F₂ | 4-F | CH₂CH₂F |
| O | 3,4-F₂ | 2,6-F₂ | CH₂CH₂F |
| O | 3,4-F₂ | 2,5-F₂ | CH₂CH₂F |
| O | 4-CF₃ | 3,5-F₂ | CH₂CH₂F |
| O | 4-CF₃ | 4-F | CH₂CH₂F |
| O | 4-CF₃ | 2,6-F₂ | CH₂CH₂F |
| O | 4-CF₃ | 2,5-F₂ | CH₂CH₂F |
| O | 4-Cl | 2-F | CH₂CH₂OH |
| O | 4-Cl | 3-F | CH₂CH₂OH |
| O | 4-Cl | 4-F | CH₂CH₂OH |
| O | 4-Cl | 4-Cl | CH₂CH₂OH |
| O | 4-Cl | 2,5-F₂ | CH₂CH₂OH |
| O | 4-Cl | 2,4-F₂ | CH₂CH₂OH |

TABLE VIII-continued

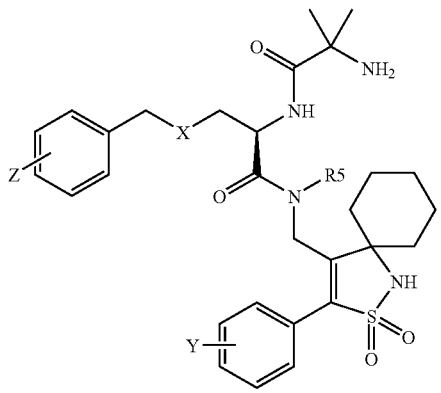

| X | Y | Z | R5 |
|---|---|---|---|
| O | 4-Cl | 2-Cl | CH₂CH₂OH |
| O | 4-Cl | 2,6-F₂ | CH₂CH₂OH |
| O | 4-Cl | 3,5-F₂ | CH₂CH₂OH |
| O | 4-Cl | 2,3-F₂ | CH₂CH₂OH |
| O | 4-Cl | 3,4-F₂ | CH₂CH₂OH |
| O | 4-Cl | 2,3,5-F₃ | CH₂CH₂OH |
| O | 4-Cl | 2,3,6-F₃ | CH₂CH₂OH |
| O | 4-Cl | 2,4,5-F₃ | CH₂CH₂OH |
| O | 4-Cl | 2,6-Cl₂ | CH₂CH₂OH |
| O | 4-Cl | 2-F-6-Cl | CH₂CH₂OH |
| O | 4-Cl | 2-F-3-Cl | CH₂CH₂OH |
| O | 4-F | 2-F | CH₂CH₂OH |
| O | 4-F | 3-F | CH₂CH₂OH |
| O | 4-F | 4-F | CH₂CH₂OH |
| O | 4-F | 4-Cl | CH₂CH₂OH |
| O | 4-F | 2,5-F₂ | CH₂CH₂OH |
| O | 4-F | 2,4-F₂ | CH₂CH₂OH |
| O | 4-F | 2-Cl | CH₂CH₂OH |
| O | 4-F | 2,6-F₂ | CH₂CH₂OH |
| O | 4-F | 3,5-F₂ | CH₂CH₂OH |
| O | 4-F | 2,3-F₂ | CH₂CH₂OH |
| O | 4-F | 3,4-F₂ | CH₂CH₂OH |
| O | 4-F | 2,3,5-F₃ | CH₂CH₂OH |
| O | 4-F | 2,3,6-F₃ | CH₂CH₂OH |
| O | 4-F | 2,4,5-F₃ | CH₂CH₂OH |
| O | 4-F | 2,6-Cl₂ | CH₂CH₂OH |
| O | 4-F | 2-F-6-Cl | CH₂CH₂OH |
| O | 4-F | 2-F-3-Cl | CH₂CH₂OH |
| CH₂ | 4-Cl | 3,5-F₂ | CH₂CH₂OH |
| CH₂ | 4-Cl | 4-F | CH₂CH₂OH |
| CH₂ | 4-Cl | 2,6-F₂ | CH₂CH₂OH |
| CH₂ | 4-F | 3,5-F₂ | CH₂CH₂OH |
| CH₂ | 4-F | 4-F | CH₂CH₂OH |
| CH₂ | 4-F | 2,6-F₂ | CH₂CH₂OH |
| O | 3-F | 3,5-F₂ | CH₂CH₂OH |
| O | 3-F | 4-F | CH₂CH₂OH |
| O | 3-F | 2,6-F₂ | CH₂CH₂OH |
| O | 3-F | 2,5-F₂ | CH₂CH₂OH |
| O | 2,5-F | 3,5-F₂ | CH₂CH₂OH |
| O | 2,5-F₂ | 4-F | CH₂CH₂OH |
| O | 2,5-F₂ | 2,6-F₂ | CH₂CH₂OH |
| O | 2,5-F₂ | 2,5-F₂ | CH₂CH₂OH |
| O | 3,5-F₂ | 3,5-F₂ | CH₂CH₂OH |
| O | 3,5-F₂ | 4-F | CH₂CH₂OH |
| O | 3,5-F₂ | 2,6-F₂ | CH₂CH₂OH |
| O | 3,5-F₂ | 2,5-F₂ | CH₂CH₂OH |
| O | 3,4-F₂ | 3,5-F₂ | CH₂CH₂OH |
| O | 3,4-F₂ | 4-F | CH₂CH₂OH |
| O | 3,4-F₂ | 2,6-F₂ | CH₂CH₂OH |
| O | 3,4-F₂ | 2,5-F₂ | CH₂CH₂OH |
| O | 4-CF₃ | 3,5-F₂ | CH₂CH₂OH |
| O | 4-CF₃ | 4-F | CH₂CH₂OH |
| O | 4-CF₃ | 2,6-F₂ | CH₂CH₂OH |
| O | 4-CF₃ | 2,5-F₂ | CH₂CH₂OH |

TABLE IX

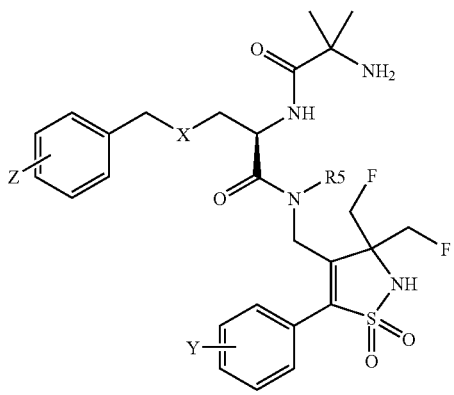

| X | Y | Z | R5 |
|---|---|---|---|
| O | 4-Cl | 2-F | CH₂CH₃ |
| O | 4-Cl | 3-F | CH₂CH₃ |
| O | 4-Cl | 4-F | CH₂CH₃ |
| O | 4-Cl | 4-Cl | CH₂CH₃ |
| O | 4-Cl | 2,5-F₂ | CH₂CH₃ |
| O | 4-Cl | 2,4-F₂ | CH₂CH₃ |
| O | 4-Cl | 2-Cl | CH₂CH₃ |
| O | 4-Cl | 2,6-F₂ | CH₂CH₃ |
| O | 4-Cl | 3,5-F₂ | CH₂CH₃ |
| O | 4-Cl | 2,3-F₂ | CH₂CH₃ |
| O | 4-Cl | 3,4-F₂ | CH₂CH₃ |
| O | 4-Cl | 2,3,5-F₃ | CH₂CH₃ |
| O | 4-Cl | 2,3,6-F₃ | CH₂CH₃ |
| O | 4-Cl | 2,4,5-F₃ | CH₂CH₃ |
| O | 4-Cl | 2,6-Cl₂ | CH₂CH₃ |
| O | 4-Cl | 2-F-3-Cl | CH₂CH₃ |
| O | 4-Cl | 2-F-6-Cl | CH₂CH₃ |
| O | 4-F | 2-F | CH₂CH₃ |
| O | 4-F | 3-F | CH₂CH₃ |
| O | 4-F | 4-F | CH₂CH₃ |
| O | 4-F | 4-Cl | CH₂CH₃ |
| O | 4-F | 2,5-F₂ | CH₂CH₃ |
| O | 4-F | 2,4-F₂ | CH₂CH₃ |
| O | 4-F | 2-Cl | CH₂CH₃ |
| O | 4-F | 2,6-F₂ | CH₂CH₃ |
| O | 4-F | 3,5-F₂ | CH₂CH₃ |
| O | 4-F | 2,3-F₂ | CH₂CH₃ |
| O | 4-F | 3,4-F₂ | CH₂CH₃ |
| O | 4-F | 2,3,5-F₃ | CH₂CH₃ |
| O | 4-F | 2,3,6-F₃ | CH₂CH₃ |
| O | 4-F | 2,4,5-F₃ | CH₂CH₃ |
| O | 4-F | 2,6-Cl₂ | CH₂CH₃ |
| O | 4-F | 2-F-3-Cl | CH₂CH₃ |
| O | 4-F | 2-F-6-Cl | CH₂CH₃ |
| CH₂ | 4-Cl | 3,5-F₂ | CH₂CH₃ |
| CH₂ | 4-Cl | 4-F | CH₂CH₃ |
| CH₂ | 4-Cl | 2,6-F₂ | CH₂CH₃ |
| CH₂ | 4-F | 3,5-F₂ | CH₂CH₃ |
| CH₂ | 4-F | 4-F | CH₂CH₃ |
| CH₂ | 4-F | 2,6-F₂ | CH₂CH₃ |
| O | 3-Cl | 3,5-F₂ | CH₂CH₃ |
| O | 3-Cl | 4-F | CH₂CH₃ |
| O | 3-Cl | 2,6-F₂ | CH₂CH₃ |
| O | 3-Cl | 2,5-F₂ | CH₂CH₃ |
| O | 3-F | 3,5-F₂ | CH₂CH₃ |
| O | 3-F | 4-F | CH₂CH₃ |
| O | 3-F | 2,6-F₂ | CH₂CH₃ |
| O | 3-F | 2,5-F₂ | CH₂CH₃ |
| O | 4-CN | 3,5-F₂ | CH₂CH₃ |
| O | 4-CN | 4-F | CH₂CH₃ |
| O | 4-CN | 2,6-F₂ | CH₂CH₃ |
| O | 4-CN | 2,5-F₂ | CH₂CH₃ |
| O | 2,5-F₂ | 3,5-F₂ | CH₂CH₃ |
| O | 2,5-F₂ | 4-F | CH₂CH₃ |
| O | 2,5-F₂ | 2,6-F₂ | CH₂CH₃ |
| O | 2,5-F₂ | 2,5-F₂ | CH₂CH₃ |
| O | 3,5-F₂ | 3,5-F₂ | CH₂CH₃ |

TABLE IX-continued

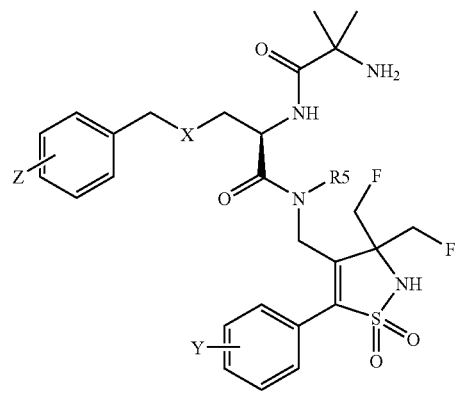

| X | Y | Z | R5 |
|---|---|---|---|
| O | 3,5-F₂ | 4-F | CH₂CH₃ |
| O | 3,5-F₂ | 2,6-F₂ | CH₂CH₃ |
| O | 3,5-F₂ | 2,5-F₂ | CH₂CH₃ |
| O | 3,4-F₂ | 3,5-F₂ | CH₂CH₃ |
| O | 3,4-F₂ | 4-F | CH₂CH₃ |
| O | 3,4-F₂ | 2,6-F₂ | CH₂CH₃ |
| O | 3,4-F₂ | 2,5-F₂ | CH₂CH₃ |
| O | 4-CF₃ | 3,5-F₂ | CH₂CH₃ |
| O | 4-CF₃ | 4-F | CH₂CH₃ |
| O | 4-CF₃ | 2,6-F₂ | CH₂CH₃ |
| O | 4-CF₃ | 2,5-F₂ | CH₂CH₃ |
| O | 4-Cl | 2-F | CH₃ |
| O | 4-Cl | 3-F | CH₃ |
| O | 4-Cl | 4-F | CH₃ |
| O | 4-Cl | 4-Cl | CH₃ |
| O | 4-Cl | 2,5-F₂ | CH₃ |
| O | 4-Cl | 2,4-F₂ | CH₃ |
| O | 4-Cl | 2-Cl | CH₃ |
| O | 4-Cl | 2,6-F₂ | CH₃ |
| O | 4-Cl | 3,5-F₂ | CH₃ |
| O | 4-Cl | 2,3-F₂ | CH₃ |
| O | 4-Cl | 3,4-F₂ | CH₃ |
| O | 4-Cl | 2,3,5-F₃ | CH₃ |
| O | 4-Cl | 2,3,6-F₃ | CH₃ |
| O | 4-Cl | 2,4,5-F₃ | CH₃ |
| O | 4-Cl | 2,6-Cl₂ | CH₃ |
| O | 4-Cl | 2-F-3-Cl | CH₃ |
| O | 4-Cl | 2-F-6-Cl | CH₃ |
| O | 4-F | 2-F | CH₃ |
| O | 4-F | 3-F | CH₃ |
| O | 4-F | 4-F | CH₃ |
| O | 4-F | 4-Cl | CH₃ |
| O | 4-F | 2,5-F₂ | CH₃ |
| O | 4-F | 2,4-F₂ | CH₃ |
| O | 4-F | 2-Cl | CH₃ |
| O | 4-F | 2,6-F₂ | CH₃ |
| O | 4-F | 3,5-F₂ | CH₃ |
| O | 4-F | 2,3-F₂ | CH₃ |
| O | 4-F | 3,4-F₂ | CH₃ |
| O | 4-F | 2,3,5-F₃ | CH₃ |
| O | 4-F | 2,3,6-F₃ | CH₃ |
| O | 4-F | 2,4,5-F₃ | CH₃ |
| O | 4-F | 2,6-Cl₂ | CH₃ |
| O | 4-F | 2-F-3-Cl | CH₃ |
| O | 4-F | 2-F-6-Cl | CH₃ |
| CH₂ | 4-Cl | 3,5-F₂ | CH₃ |
| CH₂ | 4-Cl | 4-F | CH₃ |
| CH₂ | 4-Cl | 2,6-F₂ | CH₃ |
| CH₂ | 4-F | 3,5-F₂ | CH₃ |
| CH₂ | 4-F | 4-F | CH₃ |
| CH₂ | 4-F | 2,6-F₂ | CH₃ |
| O | 3-F | 3,5-F₂ | CH₃ |
| O | 3-F | 4-F | CH₃ |
| O | 3-F | 2,6-F₂ | CH₃ |
| O | 3-F | 2,5-F₂ | CH₃ |
| O | 2,5-F₂ | 3,5-F₂ | CH₃ |
| O | 2,5-F₂ | 4-F | CH₃ |

TABLE IX-continued

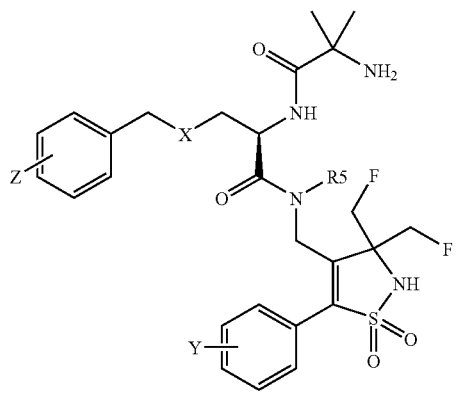

| X | Y | Z | R5 |
|---|---|---|---|
| O | 2,5-F$_2$ | 2,6-F$_2$ | CH$_3$ |
| O | 2,5-F$_2$ | 2,5-F$_2$ | CH$_3$ |
| O | 3,5-F$_2$ | 3,5-F$_2$ | CH$_3$ |
| O | 3,5-F$_2$ | 4-F | CH$_3$ |
| O | 3,5-F$_2$ | 2,6-F$_2$ | CH$_3$ |
| O | 3,5-F$_2$ | 2,5-F$_2$ | CH$_3$ |
| O | 3,4-F$_2$ | 3,5-F$_2$ | CH$_3$ |
| O | 3,4-F$_2$ | 4-F | CH$_3$ |
| O | 3,4-F$_2$ | 2,6-F$_2$ | CH$_3$ |
| O | 3,4-F$_2$ | 2,5-F$_2$ | CH$_3$ |
| O | 4-CF$_3$ | 3,5-F$_2$ | CH$_3$ |
| O | 4-CF$_3$ | 4-F | CH$_3$ |
| O | 4-CF$_3$ | 2,6-F$_2$ | CH$_3$ |
| O | 4-CF$_3$ | 2,5-F$_2$ | CH$_3$ |

TABLE X

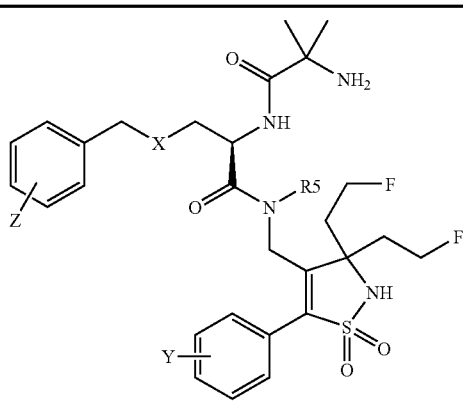

| X | Y | Z | R5 |
|---|---|---|---|
| O | 4-Cl | 2-F | CH$_2$CH$_3$ |
| O | 4-Cl | 3-F | CH$_2$CH$_3$ |
| O | 4-Cl | 4-F | CH$_2$CH$_3$ |
| O | 4-Cl | 4-Cl | CH$_2$CH$_3$ |
| O | 4-Cl | 2,5-F$_2$ | CH$_2$CH$_3$ |
| O | 4-Cl | 2,4-F$_2$ | CH$_2$CH$_3$ |
| O | 4-Cl | 2-Cl | CH$_2$CH$_3$ |
| O | 4-Cl | 2,6-F$_2$ | CH$_2$CH$_3$ |
| O | 4-Cl | 3,5-F$_2$ | CH$_2$CH$_3$ |
| O | 4-Cl | 2,3-F$_2$ | CH$_2$CH$_3$ |
| O | 4-Cl | 3,4-F$_2$ | CH$_2$CH$_3$ |
| O | 4-Cl | 2,3,5-F$_3$ | CH$_2$CH$_3$ |
| O | 4-Cl | 2,3,6-F$_3$ | CH$_2$CH$_3$ |
| O | 4-Cl | 2,4,5-F$_3$ | CH$_2$CH$_3$ |
| O | 4-Cl | 2,6-Cl$_2$ | CH$_2$CH$_3$ |
| O | 4-Cl | 2-F-3-Cl | CH$_2$CH$_3$ |
| O | 4-Cl | 2-F-6-Cl | CH$_2$CH$_3$ |

TABLE X-continued

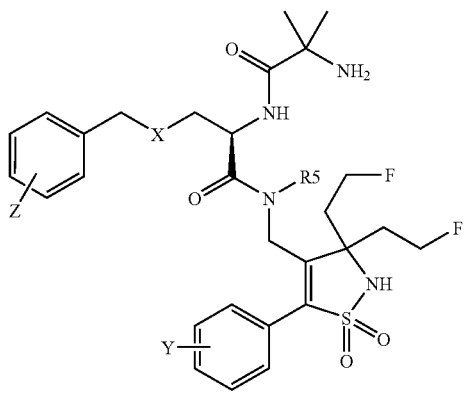

| X | Y | Z | R5 |
|---|---|---|---|
| O | 4-F | 2-F | CH$_2$CH$_3$ |
| O | 4-F | 3-F | CH$_2$CH$_3$ |
| O | 4-F | 4-F | CH$_2$CH$_3$ |
| O | 4-F | 4-Cl | CH$_2$CH$_3$ |
| O | 4-F | 2,5-F$_2$ | CH$_2$CH$_3$ |
| O | 4-F | 2,4-F$_2$ | CH$_2$CH$_3$ |
| O | 4-F | 2-Cl | CH$_2$CH$_3$ |
| O | 4-F | 2,6-F$_2$ | CH$_2$CH$_3$ |
| O | 4-F | 3,5-F$_2$ | CH$_2$CH$_3$ |
| O | 4-F | 2,3-F$_2$ | CH$_2$CH$_3$ |
| O | 4-F | 3,4-F$_2$ | CH$_2$CH$_3$ |
| O | 4-F | 2,3,5-F$_3$ | CH$_2$CH$_3$ |
| O | 4-F | 2,4,5-F$_3$ | CH$_2$CH$_3$ |
| O | 4-F | 2,6-Cl$_2$ | CH$_2$CH$_3$ |
| O | 4-F | 2-F-3-Cl | CH$_2$CH$_3$ |
| O | 4-F | 2-F-6-Cl | CH$_2$CH$_3$ |
| CH$_2$ | 4-Cl | 3,5-F$_2$ | CH$_2$CH$_3$ |
| CH$_2$ | 4-Cl | 4-F | CH$_2$CH$_3$ |
| CH$_2$ | 4-Cl | 2,6-F$_2$ | CH$_2$CH$_3$ |
| CH$_2$ | 4-F | 3,5-F$_2$ | CH$_2$CH$_3$ |
| CH$_2$ | 4-F | 4-F | CH$_2$CH$_3$ |
| CH$_2$ | 4-F | 2,6-F$_2$ | CH$_2$CH$_3$ |
| O | 3-Cl | 3,5-F$_2$ | CH$_2$CH$_3$ |
| O | 3-Cl | 4-F | CH$_2$CH$_3$ |
| O | 3-Cl | 2,6-F$_2$ | CH$_2$CH$_3$ |
| O | 3-Cl | 2,5-F$_2$ | CH$_2$CH$_3$ |
| O | 3-F | 3,5-F$_2$ | CH$_2$CH$_3$ |
| O | 3-F | 4-F | CH$_2$CH$_3$ |
| O | 3-F | 2,6-F$_2$ | CH$_2$CH$_3$ |
| O | 3-F | 2,5-F$_2$ | CH$_2$CH$_3$ |
| O | 4-CN | 3,5-F$_2$ | CH$_2$CH$_3$ |
| O | 4-CN | 4-F | CH$_2$CH$_3$ |
| O | 4-CN | 2,6-F$_2$ | CH$_2$CH$_3$ |
| O | 4-CN | 2,5-F$_2$ | CH$_2$CH$_3$ |
| O | 2,5-F$_2$ | 3,5-F$_2$ | CH$_2$CH$_3$ |
| O | 2,5-F$_2$ | 4-F | CH$_2$CH$_3$ |
| O | 2,5-F$_2$ | 2,6-F$_2$ | CH$_2$CH$_3$ |
| O | 2,5-F$_2$ | 2,5-F$_2$ | CH$_2$CH$_3$ |
| O | 3,5-F$_2$ | 3,5-F$_2$ | CH$_2$CH$_3$ |
| O | 3,5-F$_2$ | 4-F | CH$_2$CH$_3$ |
| O | 3,5-F$_2$ | 2,6-F$_2$ | CH$_2$CH$_3$ |
| O | 3,5-F$_2$ | 2,5-F$_2$ | CH$_2$CH$_3$ |
| O | 3,4-F$_2$ | 3,5-F$_2$ | CH$_2$CH$_3$ |
| O | 3,4-F$_2$ | 4-F | CH$_2$CH$_3$ |
| O | 3,4-F$_2$ | 2,6-F$_2$ | CH$_2$CH$_3$ |
| O | 3,4-F$_2$ | 2,5-F$_2$ | CH$_2$CH$_3$ |
| O | 4-CF$_3$ | 3,5-F$_2$ | CH$_2$CH$_3$ |
| O | 4-CF$_3$ | 4-F | CH$_2$CH$_3$ |
| O | 4-CF$_3$ | 2,6-F$_2$ | CH$_2$CH$_3$ |
| O | 4-CF$_3$ | 2,5-F$_2$ | CH$_2$CH$_3$ |
| O | 4-Cl | 2-F | CH$_3$ |
| O | 4-Cl | 3-F | CH$_3$ |
| O | 4-Cl | 4-F | CH$_3$ |
| O | 4-Cl | 4-Cl | CH$_3$ |
| O | 4-Cl | 2,5-F$_2$ | CH$_3$ |
| O | 4-Cl | 2,4-F$_2$ | CH$_3$ |

TABLE X-continued

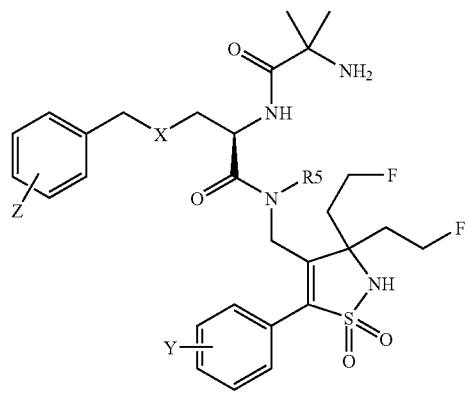

| X | Y | Z | R5 |
|---|---|---|---|
| O | 4-Cl | 2-Cl | CH₃ |
| O | 4-Cl | 2,6-F₂ | CH₃ |
| O | 4-Cl | 3,5-F₂ | CH₃ |
| O | 4-Cl | 2,3-F₂ | CH₃ |
| O | 4-Cl | 3,4-F₂ | CH₃ |
| O | 4-Cl | 2,3,5-F₃ | CH₃ |
| O | 4-Cl | 2,3,6-F₃ | CH₃ |
| O | 4-Cl | 2,4,5-F₃ | CH₃ |
| O | 4-Cl | 2,6-Cl₂ | CH₃ |
| O | 4-Cl | 2-F-3-Cl | CH₃ |
| O | 4-Cl | 2-F-6-Cl | CH₃ |
| O | 4-F | 2-F | CH₃ |
| O | 4-F | 3-F | CH₃ |
| O | 4-F | 4-F | CH₃ |
| O | 4-F | 4-Cl | CH₃ |
| O | 4-F | 2,5-F₂ | CH₃ |
| O | 4-F | 2,4-F₂ | CH₃ |
| O | 4-F | 2-Cl | CH₃ |
| O | 4-F | 2,6-F₂ | CH₃ |
| O | 4-F | 3,5-F₂ | CH₃ |
| O | 4-F | 2,3-F₂ | CH₃ |
| O | 4-F | 3,4-F₂ | CH₃ |
| O | 4-F | 2,3,5-F₃ | CH₃ |
| O | 4-F | 2,3,6-F₃ | CH₃ |
| O | 4-F | 2,4,5-F₃ | CH₃ |
| O | 4-F | 2,6-Cl₂ | CH₃ |
| O | 4-F | 2-F-3-Cl | CH₃ |
| O | 4-F | 2-F-6-Cl | CH₃ |
| CH₂ | 4-Cl | 3,5-F₂ | CH₃ |
| CH₂ | 4-Cl | 4-F | CH₃ |
| CH₂ | 4-Cl | 2,6-F₂ | CH₃ |
| CH₂ | 4-F | 3,5-F₂ | CH₃ |
| CH₂ | 4-F | 4-F | CH₃ |
| CH₂ | 4-F | 2,6-F₂ | CH₃ |
| O | 3-F | 3,5-F₂ | CH₃ |
| O | 3-F | 4-F | CH₃ |
| O | 3-F | 2,6-F₂ | CH₃ |
| O | 3-F | 2,5-F₂ | CH₃ |
| O | 2,5-F₂ | 3,5-F₂ | CH₃ |
| O | 2,5-F₂ | 4-F | CH₃ |
| O | 2,5-F₂ | 2,6-F₂ | CH₃ |
| O | 2,5-F₂ | 2,5-F₂ | CH₃ |
| O | 3,5-F₂ | 3,5-F₂ | CH₃ |
| O | 3,5-F₂ | 4-F | CH₃ |
| O | 3,5-F₂ | 2,6-F₂ | CH₃ |
| O | 3,5-F₂ | 2,5-F₂ | CH₃ |
| O | 3,4-F₂ | 3,5-F₂ | CH₃ |
| O | 3,4-F₂ | 4-F | CH₃ |
| O | 3,4-F₂ | 2,6-F₂ | CH₃ |
| O | 3,4-F₂ | 2,5-F₂ | CH₃ |
| O | 4-CF₃ | 3,5-F₂ | CH₃ |
| O | 4-CF₃ | 4-F | CH₃ |
| O | 4-CF₃ | 2,6-F₂ | CH₃ |
| O | 4-CF₃ | 2,5-F₂ | CH₃ |

TABLE XI

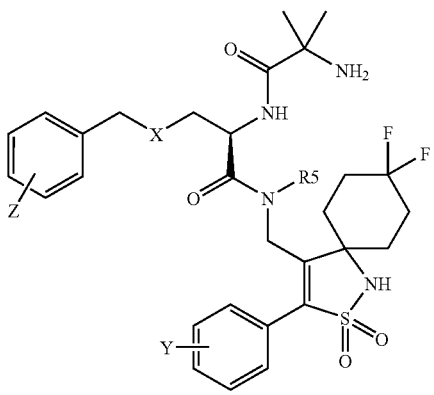

| X | Y | Z | R5 |
|---|---|---|---|
| O | 4-Cl | 2-F | CH₂CH₃ |
| O | 4-Cl | 3-F | CH₂CH₃ |
| O | 4-Cl | 4-F | CH₂CH₃ |
| O | 4-Cl | 4-Cl | CH₂CH₃ |
| O | 4-Cl | 2,5-F₂ | CH₂CH₃ |
| O | 4-Cl | 2,4-F₂ | CH₂CH₃ |
| O | 4-Cl | 2-Cl | CH₂CH₃ |
| O | 4-Cl | 2,6-F₂ | CH₂CH₃ |
| O | 4-Cl | 3,5-F₂ | CH₂CH₃ |
| O | 4-Cl | 2,3-F₂ | CH₂CH₃ |
| O | 4-Cl | 3,4-F₂ | CH₂CH₃ |
| O | 4-Cl | 2,3,5-F₃ | CH₂CH₃ |
| O | 4-Cl | 2,3,6-F₃ | CH₂CH₃ |
| O | 4-Cl | 2,4,5-F₃ | CH₂CH₃ |
| O | 4-Cl | 2,6-Cl₂ | CH₂CH₃ |
| O | 4-Cl | 2-F-3-Cl | CH₂CH₃ |
| O | 4-Cl | 2-F-6-Cl | CH₂CH₃ |
| O | 4-F | 2-F | CH₂CH₃ |
| O | 4-F | 3-F | CH₂CH₃ |
| O | 4-F | 4-F | CH₂CH₃ |
| O | 4-F | 4-Cl | CH₂CH₃ |
| O | 4-F | 2,5-F₂ | CH₂CH₃ |
| O | 4-F | 2,4-F₂ | CH₂CH₃ |
| O | 4-F | 2-Cl | CH₂CH₃ |
| O | 4-F | 2,6-F₂ | CH₂CH₃ |
| O | 4-F | 3,5-F₂ | CH₂CH₃ |
| O | 4-F | 2,3-F₂ | CH₂CH₃ |
| O | 4-F | 3,4-F₂ | CH₂CH₃ |
| O | 4-F | 2,3,5-F₃ | CH₂CH₃ |
| O | 4-F | 2,3,6-F₃ | CH₂CH₃ |
| O | 4-F | 2,4,5-F₃ | CH₂CH₃ |
| O | 4-F | 2,6-Cl₂ | CH₂CH₃ |
| O | 4-F | 2-F-3-Cl | CH₂CH₃ |
| O | 4-F | 2-F-6-Cl | CH₂CH₃ |
| CH₂ | 4-Cl | 3,5-F₂ | CH₂CH₃ |
| CH₂ | 4-Cl | 4-F | CH₂CH₃ |
| CH₂ | 4-Cl | 2,6-F₂ | CH₂CH₃ |
| CH₂ | 4-F | 3,5-F₂ | CH₂CH₃ |
| CH₂ | 4-F | 4-F | CH₂CH₃ |
| CH₂ | 4-F | 2,6-F₂ | CH₂CH₃ |
| O | 3-Cl | 3,5-F₂ | CH₂CH₃ |
| O | 3-Cl | 4-F | CH₂CH₃ |
| O | 3-Cl | 2,6-F₂ | CH₂CH₃ |
| O | 3-Cl | 2,5-F₂ | CH₂CH₃ |
| O | 3-F | 3,5-F₂ | CH₂CH₃ |
| O | 3-F | 4-F | CH₂CH₃ |
| O | 3-F | 2,6-F₂ | CH₂CH₃ |
| O | 3-F | 2,5-F₂ | CH₂CH₃ |
| O | 4-CN | 3,5-F₂ | CH₂CH₃ |
| O | 4-CN | 4-F | CH₂CH₃ |
| O | 4-CN | 2,6-F₂ | CH₂CH₃ |
| O | 4-CN | 2,5-F₂ | CH₂CH₃ |
| O | 2,5-F₂ | 3,5-F₂ | CH₂CH₃ |
| O | 2,5-F₂ | 4-F | CH₂CH₃ |
| O | 2,5-F₂ | 2,6-F₂ | CH₂CH₃ |
| O | 2,5-F₂ | 2,5-F₂ | CH₂CH₃ |
| O | 3,5-F₂ | 3,5-F₂ | CH₂CH₃ |

TABLE XI-continued

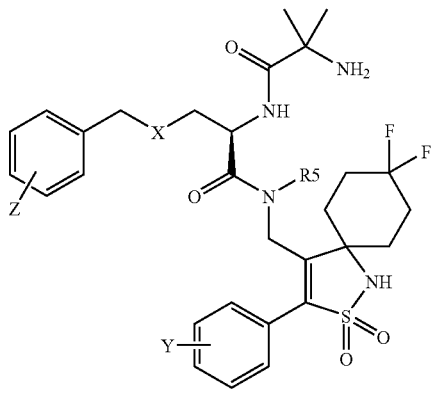

| X | Y | Z | R5 |
|---|---|---|---|
| O | 3,5-F$_2$ | 4-F | CH$_2$CH$_3$ |
| O | 3,5-F$_2$ | 2,6-F$_2$ | CH$_2$CH$_3$ |
| O | 3,5-F$_2$ | 2,5-F$_2$ | CH$_2$CH$_3$ |
| O | 3,4-F$_2$ | 3,5-F$_2$ | CH$_2$CH$_3$ |
| O | 3,4-F$_2$ | 4-F | CH$_2$CH$_3$ |
| O | 3,4-F$_2$ | 2,6-F$_2$ | CH$_2$CH$_3$ |
| O | 3,4-F$_2$ | 2,5-F$_2$ | CH$_2$CH$_3$ |
| O | 4-CF$_3$ | 3,5-F$_2$ | CH$_2$CH$_3$ |
| O | 4-CF$_3$ | 4-F | CH$_2$CH$_3$ |
| O | 4-CF$_3$ | 2,6-F$_2$ | CH$_2$CH$_3$ |
| O | 4-CF$_3$ | 2,5-F$_2$ | CH$_2$CH$_3$ |
| O | 4-Cl | 2-F | CH$_3$ |
| O | 4-Cl | 3-F | CH$_3$ |
| O | 4-Cl | 4-F | CH$_3$ |
| O | 4-Cl | 4-Cl | CH$_3$ |
| O | 4-Cl | 2,5-F$_2$ | CH$_3$ |
| O | 4-Cl | 2,4-F$_2$ | CH$_3$ |
| O | 4-Cl | 2-Cl | CH$_3$ |
| O | 4-Cl | 2,6-F$_2$ | CH$_3$ |
| O | 4-Cl | 3,5-F$_2$ | CH$_3$ |
| O | 4-Cl | 2,3-F$_2$ | CH$_3$ |
| O | 4-Cl | 3,4-F$_2$ | CH$_3$ |
| O | 4-Cl | 2,3,5-F$_3$ | CH$_3$ |
| O | 4-Cl | 2,3,6-F$_3$ | CH$_3$ |
| O | 4-Cl | 2,4,5-F$_3$ | CH$_3$ |
| O | 4-Cl | 2,6-Cl$_2$ | CH$_3$ |
| O | 4-Cl | 2-F-3-Cl | CH$_3$ |
| O | 4-Cl | 2-F-6-Cl | CH$_3$ |
| O | 4-F | 2-F | CH$_3$ |
| O | 4-F | 3-F | CH$_3$ |
| O | 4-F | 4-F | CH$_3$ |
| O | 4-F | 4-Cl | CH$_3$ |
| O | 4-F | 2,5-F$_2$ | CH$_3$ |
| O | 4-F | 2,4-F$_2$ | CH$_3$ |
| O | 4-F | 2-Cl | CH$_3$ |
| O | 4-F | 2,6-F$_2$ | CH$_3$ |
| O | 4-F | 3,5-F$_2$ | CH$_3$ |
| O | 4-F | 2,3-F$_2$ | CH$_3$ |
| O | 4-F | 3,4-F$_2$ | CH$_3$ |
| O | 4-F | 2,3,5-F$_3$ | CH$_3$ |
| O | 4-F | 2,3,6-F$_3$ | CH$_3$ |
| O | 4-F | 2,4,5-F$_3$ | CH$_3$ |
| O | 4-F | 2,6-Cl$_2$ | CH$_3$ |
| O | 4-F | 2-F-3-Cl | CH$_3$ |
| O | 4-F | 2-F-6-Cl | CH$_3$ |
| CH$_2$ | 4-Cl | 3,5-F$_2$ | CH$_3$ |
| CH$_2$ | 4-Cl | 4-F | CH$_3$ |
| CH$_2$ | 4-Cl | 2,6-F$_2$ | CH$_3$ |
| CH$_2$ | 4-F | 3,5-F$_2$ | CH$_3$ |
| CH$_2$ | 4-F | 4-F | CH$_3$ |
| CH$_2$ | 4-F | 2,6-F$_2$ | CH$_3$ |
| O | 3-F | 3,5-F$_2$ | CH$_3$ |
| O | 3-F | 4-F | CH$_3$ |
| O | 3-F | 2,6-F$_2$ | CH$_3$ |
| O | 3-F | 2,5-F$_2$ | CH$_3$ |
| O | 2,5-F$_2$ | 3,5-F$_2$ | CH$_3$ |
| O | 2,5-F$_2$ | 4-F | CH$_3$ |

TABLE XI-continued

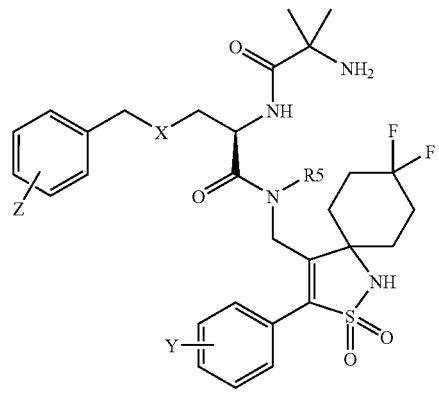

| X | Y | Z | R5 |
|---|---|---|---|
| O | 2,5-F$_2$ | 2,6-F$_2$ | CH$_3$ |
| O | 2,5-F$_2$ | 2,5-F$_2$ | CH$_3$ |
| O | 3,5-F$_2$ | 3,5-F$_2$ | CH$_3$ |
| O | 3,5-F$_2$ | 4-F | CH$_3$ |
| O | 3,5-F$_2$ | 2,6-F$_2$ | CH$_3$ |
| O | 3,5-F$_2$ | 2,5-F$_2$ | CH$_3$ |
| O | 3,4-F$_2$ | 3,5-F$_2$ | CH$_3$ |
| O | 3,4-F$_2$ | 4-F | CH$_3$ |
| O | 3,4-F$_2$ | 2,6-F$_2$ | CH$_3$ |
| O | 3,4-F$_2$ | 2,5-F$_2$ | CH$_3$ |
| O | 4-CF$_3$ | 3,5-F$_2$ | CH$_3$ |
| O | 4-CF$_3$ | 4-F | CH$_3$ |
| O | 4-CF$_3$ | 2,6-F$_2$ | CH$_3$ |
| O | 4-CF$_3$ | 2,5-F$_2$ | CH$_3$ |

TABLE XII

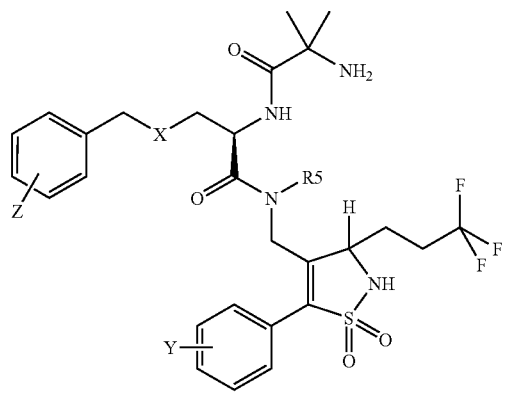

| X | Y | Z | R5 |
|---|---|---|---|
| O | 4-Cl | 2-F | CH$_2$CH$_3$ |
| O | 4-Cl | 3-F | CH$_2$CH$_3$ |
| O | 4-Cl | 4-F | CH$_2$CH$_3$ |
| O | 4-Cl | 4-Cl | CH$_2$CH$_3$ |
| O | 4-Cl | 2,5-F$_2$ | CH$_2$CH$_3$ |
| O | 4-Cl | 2,4-F$_2$ | CH$_2$CH$_3$ |
| O | 4-Cl | 2-Cl | CH$_2$CH$_3$ |
| O | 4-Cl | 2,6-F$_2$ | CH$_2$CH$_3$ |
| O | 4-Cl | 3,5-F$_2$ | CH$_2$CH$_3$ |
| O | 4-Cl | 2,3-F$_2$ | CH$_2$CH$_3$ |
| O | 4-Cl | 3,4-F$_2$ | CH$_2$CH$_3$ |
| O | 4-Cl | 2,3,5-F$_3$ | CH$_2$CH$_3$ |
| O | 4-Cl | 2,3,6-F$_3$ | CH$_2$CH$_3$ |
| O | 4-Cl | 2,4,5-F$_3$ | CH$_2$CH$_3$ |
| O | 4-Cl | 2,6-Cl$_2$ | CH$_2$CH$_3$ |
| O | 4-Cl | 2-F-3-Cl | CH$_2$CH$_3$ |
| O | 4-Cl | 2-F-6-Cl | CH$_2$CH$_3$ |

TABLE XII-continued

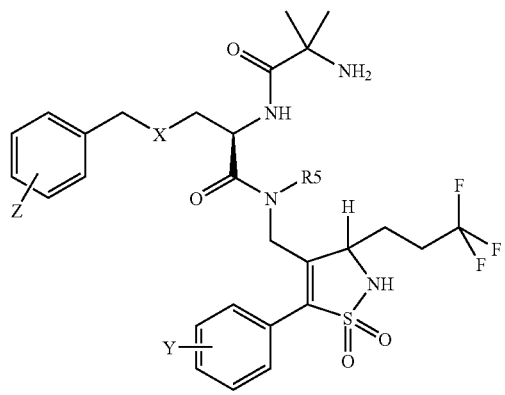

| X | Y | Z | R5 |
|---|---|---|---|
| O | 4-F | 2-F | CH₂CH₃ |
| O | 4-F | 3-F | CH₂CH₃ |
| O | 4-F | 4-F | CH₂CH₃ |
| O | 4-F | 4-Cl | CH₂CH₃ |
| O | 4-F | 2,5-F₂ | CH₂CH₃ |
| O | 4-F | 2,4-F₂ | CH₂CH₃ |
| O | 4-F | 2-Cl | CH₂CH₃ |
| O | 4-F | 2,6-F₂ | CH₂CH₃ |
| O | 4-F | 3,5-F₂ | CH₂CH₃ |
| O | 4-F | 2,3-F₂ | CH₂CH₃ |
| O | 4-F | 3,4-F₂ | CH₂CH₃ |
| O | 4-F | 2,3,5-F₃ | CH₂CH₃ |
| O | 4-F | 2,3,6-F₃ | CH₂CH₃ |
| O | 4-F | 2,4,5-F₃ | CH₂CH₃ |
| O | 4-F | 2,6-Cl₂ | CH₂CH₃ |
| O | 4-F | 2-F-3-Cl | CH₂CH₃ |
| O | 4-F | 2-F-6-Cl | CH₂CH₃ |
| CH₂ | 4-Cl | 3,5-F₂ | CH₂CH₃ |
| CH₂ | 4-Cl | 4-F | CH₂CH₃ |
| CH₂ | 4-Cl | 2,6-F₂ | CH₂CH₃ |
| CH₂ | 4-F | 3,5-F₂ | CH₂CH₃ |
| CH₂ | 4-F | 4-F | CH₂CH₃ |
| CH₂ | 4-F | 2,6-F₂ | CH₂CH₃ |
| O | 3-Cl | 3,5-F₂ | CH₂CH₃ |
| O | 3-Cl | 4-F | CH₂CH₃ |
| O | 3-Cl | 2,6-F₂ | CH₂CH₃ |
| O | 3-Cl | 2,5-F₂ | CH₂CH₃ |
| O | 3-F | 3,5-F₂ | CH₂CH₃ |
| O | 3-F | 4-F | CH₂CH₃ |
| O | 3-F | 2,6-F₂ | CH₂CH₃ |
| O | 3-F | 2,5-F₂ | CH₂CH₃ |
| O | 4-CN | 3,5-F₂ | CH₂CH₃ |
| O | 4-CN | 4-F | CH₂CH₃ |
| O | 4-CN | 2,6-F₂ | CH₂CH₃ |
| O | 4-CN | 2,5-F₂ | CH₂CH₃ |
| O | 2,5-F₂ | 3,5-F₂ | CH₂CH₃ |
| O | 2,5-F₂ | 4-F | CH₂CH₃ |
| O | 2,5-F₂ | 2,6-F₂ | CH₂CH₃ |
| O | 2,5-F₂ | 2,5-F₂ | CH₂CH₃ |
| O | 3,5-F₂ | 3,5-F₂ | CH₂CH₃ |
| O | 3,5-F₂ | 4-F | CH₂CH₃ |
| O | 3,5-F₂ | 2,6-F₂ | CH₂CH₃ |
| O | 3,5-F₂ | 2,5-F₂ | CH₂CH₃ |
| O | 3,4-F₂ | 3,5-F₂ | CH₂CH₃ |
| O | 3,4-F₂ | 4-F | CH₂CH₃ |
| O | 3,4-F₂ | 2,6-F₂ | CH₂CH₃ |
| O | 3,4-F₂ | 2,5-F₂ | CH₂CH₃ |
| O | 4-CF₃ | 3,5-F₂ | CH₂CH₃ |
| O | 4-CF₃ | 4-F | CH₂CH₃ |
| O | 4-CF₃ | 2,6-F₂ | CH₂CH₃ |
| O | 4-CF₃ | 2,5-F₂ | CH₂CH₃ |
| O | 4-Cl | 2-F | CH₃ |
| O | 4-Cl | 3-F | CH₃ |
| O | 4-Cl | 4-F | CH₃ |
| O | 4-Cl | 4-Cl | CH₃ |
| O | 4-Cl | 2,5-F₂ | CH₃ |
| O | 4-Cl | 2,4-F₂ | CH₃ |

TABLE XII-continued

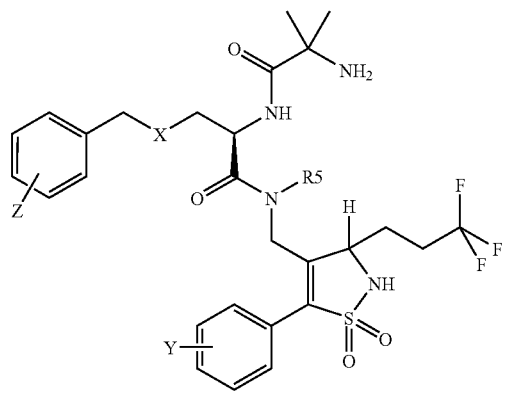

| X | Y | Z | R5 |
|---|---|---|---|
| O | 4-Cl | 2-Cl | CH₃ |
| O | 4-Cl | 2,6-F₂ | CH₃ |
| O | 4-Cl | 3,5-F₂ | CH₃ |
| O | 4-Cl | 2,3-F₂ | CH₃ |
| O | 4-Cl | 3,4-F₂ | CH₃ |
| O | 4-Cl | 2,3,5-F₃ | CH₃ |
| O | 4-Cl | 2,3,6-F₃ | CH₃ |
| O | 4-Cl | 2,4,5-F₃ | CH₃ |
| O | 4-Cl | 2,6-Cl₂ | CH₃ |
| O | 4-Cl | 2-F-3-Cl | CH₃ |
| O | 4-Cl | 2-F-6-Cl | CH₃ |
| O | 4-F | 2-F | CH₃ |
| O | 4-F | 3-F | CH₃ |
| O | 4-F | 4-F | CH₃ |
| O | 4-F | 4-Cl | CH₃ |
| O | 4-F | 2,5-F₂ | CH₃ |
| O | 4-F | 2,4-F₂ | CH₃ |
| O | 4-F | 2-Cl | CH₃ |
| O | 4-F | 2,6-F₂ | CH₃ |
| O | 4-F | 3,5-F₂ | CH₃ |
| O | 4-F | 2,3-F₂ | CH₃ |
| O | 4-F | 3,4-F₂ | CH₃ |
| O | 4-F | 2,3,5-F₃ | CH₃ |
| O | 4-F | 2,3,6-F₃ | CH₃ |
| O | 4-F | 2,4,5-F₃ | CH₃ |
| O | 4-F | 2,6-Cl₂ | CH₃ |
| O | 4-F | 2-F-3-Cl | CH₃ |
| O | 4-F | 2-F-6-Cl | CH₃ |
| CH₂ | 4-Cl | 3,5-F₂ | CH₃ |
| CH₂ | 4-Cl | 4-F | CH₃ |
| CH₂ | 4-Cl | 2,6-F₂ | CH₃ |
| CH₂ | 4-F | 3,5-F₂ | CH₃ |
| CH₂ | 4-F | 4-F | CH₃ |
| CH₂ | 4-F | 2,6-F₂ | CH₃ |
| O | 3-F | 3,5-F₂ | CH₃ |
| O | 3-F | 4-F | CH₃ |
| O | 3-F | 2,6-F₂ | CH₃ |
| O | 3-F | 2,5-F₂ | CH₃ |
| O | 2,5-F₂ | 3,5-F₂ | CH₃ |
| O | 2,5-F₂ | 4-F | CH₃ |
| O | 2,5-F₂ | 2,6-F₂ | CH₃ |
| O | 2,5-F₂ | 2,5-F₂ | CH₃ |
| O | 3,5-F₂ | 3,5-F₂ | CH₃ |
| O | 3,5-F₂ | 4-F | CH₃ |
| O | 3,5-F₂ | 2,6-F₂ | CH₃ |
| O | 3,5-F₂ | 2,5-F₂ | CH₃ |
| O | 3,4-F₂ | 3,5-F₂ | CH₃ |
| O | 3,4-F₂ | 4-F | CH₃ |
| O | 3,4-F₂ | 2,6-F₂ | CH₃ |
| O | 3,4-F₂ | 2,5-F₂ | CH₃ |
| O | 4-CF₃ | 3,5-F₂ | CH₃ |
| O | 4-CF₃ | 4-F | CH₃ |
| O | 4-CF₃ | 2,6-F₂ | CH₃ |
| O | 4-CF₃ | 2,5-F₂ | CH₃ |

TABLE XIII

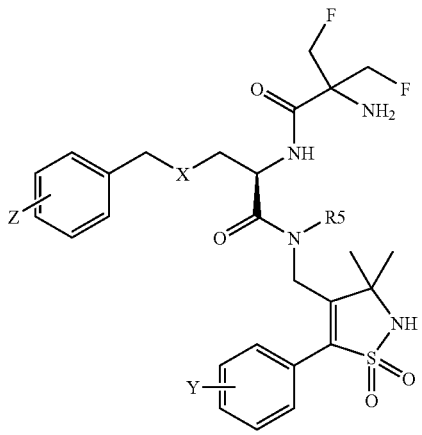

| X | Y | Z | R5 |
|---|---|---|---|
| O | 4-Cl | 2-F | CH₂CH₃ |
| O | 4-Cl | 3-F | CH₂CH₃ |
| O | 4-Cl | 4-F | CH₂CH₃ |
| O | 4-Cl | 4-Cl | CH₂CH₃ |
| O | 4-Cl | 2,5-F₂ | CH₂CH₃ |
| O | 4-Cl | 2,4-F₂ | CH₂CH₃ |
| O | 4-Cl | 2-Cl | CH₂CH₃ |
| O | 4-Cl | 2,6-F₂ | CH₂CH₃ |
| O | 4-Cl | 3,5-F₂ | CH₂CH₃ |
| O | 4-Cl | 2,3-F₂ | CH₂CH₃ |
| O | 4-Cl | 3,4-F₂ | CH₂CH₃ |
| O | 4-Cl | 2,3,5-F₃ | CH₂CH₃ |
| O | 4-Cl | 2,3,6-F₃ | CH₂CH₃ |
| O | 4-Cl | 2,4,5-F₃ | CH₂CH₃ |
| O | 4-Cl | 2,6-Cl₂ | CH₂CH₃ |
| O | 4-Cl | 2-F-3-Cl | CH₂CH₃ |
| O | 4-Cl | 2-F-6-Cl | CH₂CH₃ |
| O | 4-F | 2-F | CH₂CH₃ |
| O | 4-F | 3-F | CH₂CH₃ |
| O | 4-F | 4-F | CH₂CH₃ |
| O | 4-F | 4-Cl | CH₂CH₃ |
| O | 4-F | 2,5-F₂ | CH₂CH₃ |
| O | 4-F | 2,4-F₂ | CH₂CH₃ |
| O | 4-F | 2-Cl | CH₂CH₃ |
| O | 4-F | 2,6-F₂ | CH₂CH₃ |
| O | 4-F | 3,5-F₂ | CH₂CH₃ |
| O | 4-F | 2,3-F₂ | CH₂CH₃ |
| O | 4-F | 3,4-F₂ | CH₂CH₃ |
| O | 4-F | 2,3,5-F₃ | CH₂CH₃ |
| O | 4-F | 2,3,6-F₃ | CH₂CH₃ |
| O | 4-F | 2,4,5-F₃ | CH₂CH₃ |
| O | 4-F | 2,6-Cl₂ | CH₂CH₃ |
| O | 4-F | 2-F-3-Cl | CH₂CH₃ |
| O | 4-F | 2-F-6-Cl | CH₂CH₃ |
| CH₂ | 4-Cl | 3,5-F₂ | CH₂CH₃ |
| CH₂ | 4-Cl | 4-F | CH₂CH₃ |
| CH₂ | 4-Cl | 2,6-F₂ | CH₂CH₃ |
| CH₂ | 4-F | 3,5-F₂ | CH₂CH₃ |
| CH₂ | 4-F | 4-F | CH₂CH₃ |
| CH₂ | 4-F | 2,6-F₂ | CH₂CH₃ |
| O | 3-Cl | 3,5-F₂ | CH₂CH₃ |
| O | 3-Cl | 4-F | CH₂CH₃ |
| O | 3-Cl | 2,6-F₂ | CH₂CH₃ |
| O | 3-Cl | 2,5-F₂ | CH₂CH₃ |
| O | 3-F | 3,5-F₂ | CH₂CH₃ |
| O | 3-F | 4-F | CH₂CH₃ |
| O | 3-F | 2,6-F₂ | CH₂CH₃ |
| O | 3-F | 2,5-F₂ | CH₂CH₃ |
| O | 4-CN | 3,5-F₂ | CH₂CH₃ |
| O | 4-CN | 4-F | CH₂CH₃ |
| O | 4-CN | 2,6-F₂ | CH₂CH₃ |
| O | 4-CN | 2,5-F₂ | CH₂CH₃ |
| O | 2,5-F₂ | 3,5-F₂ | CH₂CH₃ |
| O | 2,5-F₂ | 4-F | CH₂CH₃ |
| O | 2,5-F₂ | 2,6-F₂ | CH₂CH₃ |

TABLE XIII-continued

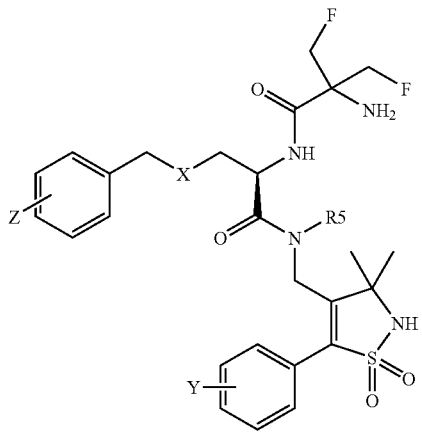

| X | Y | Z | R5 |
|---|---|---|---|
| O | 2,5-F₂ | 2,5-F₂ | CH₂CH₃ |
| O | 3,5-F₂ | 3,5-F₂ | CH₂CH₃ |
| O | 3,5-F₂ | 4-F | CH₂CH₃ |
| O | 3,5-F₂ | 2,6-F₂ | CH₂CH₃ |
| O | 3,5-F₂ | 2,5-F₂ | CH₂CH₃ |
| O | 3,4-F₂ | 3,5-F₂ | CH₂CH₃ |
| O | 3,4-F₂ | 4-F | CH₂CH₃ |
| O | 3,4-F₂ | 2,6-F₂ | CH₂CH₃ |
| O | 3,4-F₂ | 2,5-F₂ | CH₂CH₃ |
| O | 4-CF₃ | 3,5-F₂ | CH₂CH₃ |
| O | 4-CF₃ | 4-F | CH₂CH₃ |
| O | 4-CF₃ | 2,6-F₂ | CH₂CH₃ |
| O | 4-CF₃ | 2,5-F₂ | CH₂CH₃ |
| O | 4-Cl | 2-F | CH₃ |
| O | 4-Cl | 3-F | CH₃ |
| O | 4-Cl | 4-F | CH₃ |
| O | 4-Cl | 4-Cl | CH₃ |
| O | 4-Cl | 2,5-F₂ | CH₃ |
| O | 4-Cl | 2,4-F₂ | CH₃ |
| O | 4-Cl | 2-Cl | CH₃ |
| O | 4-Cl | 2,6-F₂ | CH₃ |
| O | 4-Cl | 3,5-F₂ | CH₃ |
| O | 4-Cl | 2,3-F₂ | CH₃ |
| O | 4-Cl | 3,4-F₂ | CH₃ |
| O | 4-Cl | 2,3,5-F₃ | CH₃ |
| O | 4-Cl | 2,3,6-F₃ | CH₃ |
| O | 4-Cl | 2,4,5-F₃ | CH₃ |
| O | 4-Cl | 2,6-Cl₂ | CH₃ |
| O | 4-Cl | 2-F-3-Cl | CH₃ |
| O | 4-Cl | 2-F-6-Cl | CH₃ |
| O | 4-F | 2-F | CH₃ |
| O | 4-F | 3-F | CH₃ |
| O | 4-F | 4-F | CH₃ |
| O | 4-F | 4-Cl | CH₃ |
| O | 4-F | 2,5-F₂ | CH₃ |
| O | 4-F | 2,4-F₂ | CH₃ |
| O | 4-F | 2-Cl | CH₃ |
| O | 4-F | 2,6-F₂ | CH₃ |
| O | 4-F | 3,5-F₂ | CH₃ |
| O | 4-F | 2,3-F₂ | CH₃ |
| O | 4-F | 3,4-F₂ | CH₃ |
| O | 4-F | 2,3,5-F₃ | CH₃ |
| O | 4-F | 2,3,6-F₃ | CH₃ |
| O | 4-F | 2,4,5-F₃ | CH₃ |
| O | 4-F | 2,6-Cl₂ | CH₃ |
| O | 4-F | 2-F-3-Cl | CH₃ |
| O | 4-F | 2-F-6-Cl | CH₃ |
| CH₂ | 4-Cl | 3,5-F₂ | CH₃ |
| CH₂ | 4-Cl | 4-F | CH₃ |
| CH₂ | 4-Cl | 2,6-F₂ | CH₃ |
| CH₂ | 4-F | 3,5-F₂ | CH₃ |
| CH₂ | 4-F | 4-F | CH₃ |
| CH₂ | 4-F | 2,6-F₂ | CH₃ |
| O | 3-F | 3,5-F₂ | CH₃ |
| O | 3-F | 4-F | CH₃ |

TABLE XIII-continued

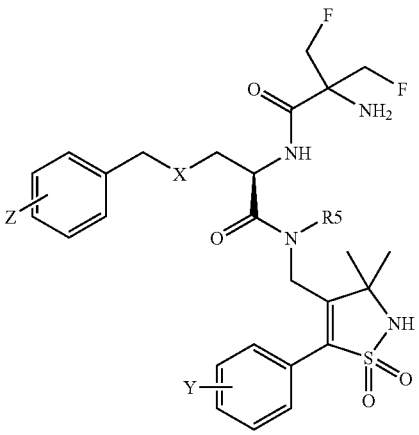

| X | Y | Z | R5 |
|---|---|---|---|
| O | 3-F | 2,6-F$_2$ | CH$_3$ |
| O | 3-F | 2,5-F$_2$ | CH$_3$ |
| O | 2,5-F$_2$ | 3,5-F$_2$ | CH$_3$ |
| O | 2,5-F$_2$ | 4-F | CH$_3$ |
| O | 2,5-F$_2$ | 2,6-F$_2$ | CH$_3$ |
| O | 2,5-F$_2$ | 2,5-F$_2$ | CH$_3$ |
| O | 3,5-F$_2$ | 3,5-F$_2$ | CH$_3$ |
| O | 3,5-F$_2$ | 4-F | CH$_3$ |
| O | 3,5-F$_2$ | 2,6-F$_2$ | CH$_3$ |
| O | 3,5-F$_2$ | 2,5-F$_2$ | CH$_3$ |
| O | 3,4-F$_2$ | 3,5-F$_2$ | CH$_3$ |
| O | 3,4-F$_2$ | 4-F | CH$_3$ |
| O | 3,4-F$_2$ | 2,6-F$_2$ | CH$_3$ |
| O | 3,4-F$_2$ | 2,5-F$_2$ | CH$_3$ |
| O | 4-CF$_3$ | 3,5-F$_2$ | CH$_3$ |
| O | 4-CF$_3$ | 4-F | CH$_3$ |
| O | 4-CF$_3$ | 2,6-F$_2$ | CH$_3$ |
| O | 4-CF$_3$ | 2,5-F$_2$ | CH$_3$ |

TABLE XIV

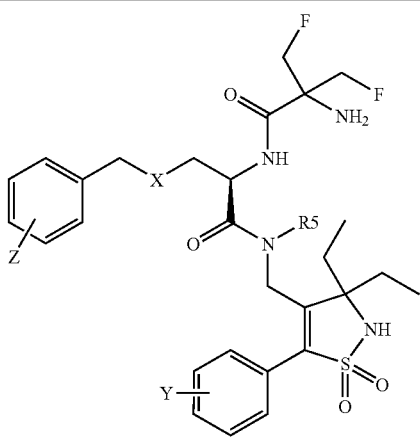

| X | Y | Z | R5 |
|---|---|---|---|
| O | 4-Cl | 2-F | CH$_2$CH$_3$ |
| O | 4-Cl | 3-F | CH$_2$CH$_3$ |
| O | 4-Cl | 4-F | CH$_2$CH$_3$ |
| O | 4-Cl | 4-Cl | CH$_2$CH$_3$ |
| O | 4-Cl | 2,5-F$_2$ | CH$_2$CH$_3$ |
| O | 4-Cl | 2,4-F$_2$ | CH$_2$CH$_3$ |
| O | 4-Cl | 2-Cl | CH$_2$CH$_3$ |
| O | 4-Cl | 2,6-F$_2$ | CH$_2$CH$_3$ |
| O | 4-Cl | 3,5-F$_2$ | CH$_2$CH$_3$ |

TABLE XIV-continued

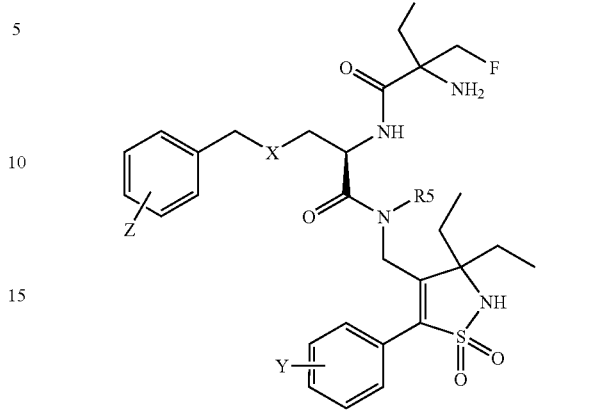

| X | Y | Z | R5 |
|---|---|---|---|
| O | 4-Cl | 2,3-F$_2$ | CH$_2$CH$_3$ |
| O | 4-Cl | 3,4-F$_2$ | CH$_2$CH$_3$ |
| O | 4-Cl | 2,3,5-F$_3$ | CH$_2$CH$_3$ |
| O | 4-Cl | 2,3,6-F$_3$ | CH$_2$CH$_3$ |
| O | 4-Cl | 2,4,5-F$_3$ | CH$_2$CH$_3$ |
| O | 4-Cl | 2,6-Cl$_2$ | CH$_2$CH$_3$ |
| O | 4-Cl | 2-F-3-Cl | CH$_2$CH$_3$ |
| O | 4-Cl | 2-F-6-Cl | CH$_2$CH$_3$ |
| O | 4-F | 2-F | CH$_2$CH$_3$ |
| O | 4-F | 3-F | CH$_2$CH$_3$ |
| O | 4-F | 4-F | CH$_2$CH$_3$ |
| O | 4-F | 4-Cl | CH$_2$CH$_3$ |
| O | 4-F | 2,5-F$_2$ | CH$_2$CH$_3$ |
| O | 4-F | 2,4-F$_2$ | CH$_2$CH$_3$ |
| O | 4-F | 2-Cl | CH$_2$CH$_3$ |
| O | 4-F | 2,6-F$_2$ | CH$_2$CH$_3$ |
| O | 4-F | 3,5-F$_2$ | CH$_2$CH$_3$ |
| O | 4-F | 2,3-F$_2$ | CH$_2$CH$_3$ |
| O | 4-F | 3,4-F$_2$ | CH$_2$CH$_3$ |
| O | 4-F | 2,3,5-F$_3$ | CH$_2$CH$_3$ |
| O | 4-F | 2,3,6-F$_3$ | CH$_2$CH$_3$ |
| O | 4-F | 2,4,5-F$_3$ | CH$_2$CH$_3$ |
| O | 4-F | 2,6-Cl$_2$ | CH$_2$CH$_3$ |
| O | 4-F | 2-F-3-Cl | CH$_2$CH$_3$ |
| O | 4-F | 2-F-6-Cl | CH$_2$CH$_3$ |
| CH$_2$ | 4-Cl | 3,5-F$_2$ | CH$_2$CH$_3$ |
| CH$_2$ | 4-Cl | 4-F | CH$_2$CH$_3$ |
| CH$_2$ | 4-Cl | 2,6-F$_2$ | CH$_2$CH$_3$ |
| CH$_2$ | 4-F | 3,5-F$_2$ | CH$_2$CH$_3$ |
| CH$_2$ | 4-F | 4-F | CH$_2$CH$_3$ |
| CH$_2$ | 4-F | 2,6-F$_2$ | CH$_2$CH$_3$ |
| O | 3-Cl | 3,5-F$_2$ | CH$_2$CH$_3$ |
| O | 3-Cl | 4-F | CH$_2$CH$_3$ |
| O | 3-Cl | 2,6-F$_2$ | CH$_2$CH$_3$ |
| O | 3-Cl | 2,5-F$_2$ | CH$_2$CH$_3$ |
| O | 3-F | 3,5-F$_2$ | CH$_2$CH$_3$ |
| O | 3-F | 4-F | CH$_2$CH$_3$ |
| O | 3-F | 2,6-F$_2$ | CH$_2$CH$_3$ |
| O | 3-F | 2,5-F$_2$ | CH$_2$CH$_3$ |
| O | 4-CN | 3,5-F$_2$ | CH$_2$CH$_3$ |
| O | 4-CN | 4-F | CH$_2$CH$_3$ |
| O | 4-CN | 2,6-F$_2$ | CH$_2$CH$_3$ |
| O | 4-CN | 2,5-F$_2$ | CH$_2$CH$_3$ |
| O | 2,5-F$_2$ | 3,5-F$_2$ | CH$_2$CH$_3$ |
| O | 2,5-F$_2$ | 4-F | CH$_2$CH$_3$ |
| O | 2,5-F$_2$ | 2,6-F$_2$ | CH$_2$CH$_3$ |
| O | 2,5-F$_2$ | 2,5-F$_2$ | CH$_2$CH$_3$ |
| O | 3,5-F$_2$ | 3,5-F$_2$ | CH$_2$CH$_3$ |
| O | 3,5-F$_2$ | 4-F | CH$_2$CH$_3$ |
| O | 3,5-F$_2$ | 2,6-F$_2$ | CH$_2$CH$_3$ |
| O | 3,5-F$_2$ | 2,5-F$_2$ | CH$_2$CH$_3$ |
| O | 3,4-F$_2$ | 3,5-F$_2$ | CH$_2$CH$_3$ |
| O | 3,4-F$_2$ | 4-F | CH$_2$CH$_3$ |
| O | 3,4-F$_2$ | 2,6-F$_2$ | CH$_2$CH$_3$ |
| O | 3,4-F$_2$ | 2,5-F$_2$ | CH$_2$CH$_3$ |

TABLE XIV-continued

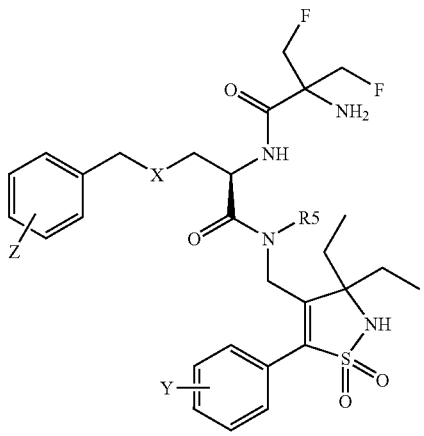

| X | Y | Z | R5 |
|---|---|---|---|
| O | 4-CF$_3$ | 3,5-F$_2$ | CH$_2$CH$_3$ |
| O | 4-CF$_3$ | 4-F | CH$_2$CH$_3$ |
| O | 4-CF$_3$ | 2,6-F$_2$ | CH$_2$CH$_3$ |
| O | 4-CF$_3$ | 2,5-F$_2$ | CH$_2$CH$_3$ |
| O | 4-Cl | 2-F | CH$_3$ |
| O | 4-Cl | 3-F | CH$_3$ |
| O | 4-Cl | 4-F | CH$_3$ |
| O | 4-Cl | 4-Cl | CH$_3$ |
| O | 4-Cl | 2,5-F$_2$ | CH$_3$ |
| O | 4-Cl | 2,4-F$_2$ | CH$_3$ |
| O | 4-Cl | 2-Cl | CH$_3$ |
| O | 4-Cl | 2,6-F$_2$ | CH$_3$ |
| O | 4-Cl | 3,5-F$_2$ | CH$_3$ |
| O | 4-Cl | 2,3-F$_2$ | CH$_3$ |
| O | 4-Cl | 3,4-F$_2$ | CH$_3$ |
| O | 4-Cl | 2,3,5-F$_3$ | CH$_3$ |
| O | 4-Cl | 2,3,6-F$_3$ | CH$_3$ |
| O | 4-Cl | 2,4,5-F$_3$ | CH$_3$ |
| O | 4-Cl | 2,6-Cl$_2$ | CH$_3$ |
| O | 4-Cl | 2-F-3-Cl | CH$_3$ |
| O | 4-Cl | 2-F-6-Cl | CH$_3$ |
| O | 4-F | 2-F | CH$_3$ |
| O | 4-F | 3-F | CH$_3$ |
| O | 4-F | 4-F | CH$_3$ |
| O | 4-F | 4-Cl | CH$_3$ |
| O | 4-F | 2,5-F$_2$ | CH$_3$ |
| O | 4-F | 2,4-F$_2$ | CH$_3$ |
| O | 4-F | 2-Cl | CH$_3$ |
| O | 4-F | 2,6-F$_2$ | CH$_3$ |
| O | 4-F | 3,5-F$_2$ | CH$_3$ |
| O | 4-F | 2,3-F$_2$ | CH$_3$ |
| O | 4-F | 3,4-F$_2$ | CH$_3$ |
| O | 4-F | 2,3,5-F$_3$ | CH$_3$ |
| O | 4-F | 2,3,6-F$_3$ | CH$_3$ |
| O | 4-F | 2,4,5-F$_3$ | CH$_3$ |
| O | 4-F | 2,6-Cl$_2$ | CH$_3$ |
| O | 4-F | 2-F-3-Cl | CH$_3$ |
| O | 4-F | 2-F-6-Cl | CH$_3$ |
| CH$_2$ | 4-Cl | 3,5-F$_2$ | CH$_3$ |
| CH$_2$ | 4-Cl | 4-F | CH$_3$ |
| CH$_2$ | 4-Cl | 2,6-F$_2$ | CH$_3$ |
| CH$_2$ | 4-F | 3,5-F$_2$ | CH$_3$ |
| CH$_2$ | 4-F | 4-F | CH$_3$ |
| CH$_2$ | 4-F | 2,6-F$_2$ | CH$_3$ |
| O | 3-F | 3,5-F$_2$ | CH$_3$ |
| O | 3-F | 4-F | CH$_3$ |
| O | 3-F | 2,6-F$_2$ | CH$_3$ |
| O | 3-F | 2,5-F$_2$ | CH$_3$ |
| O | 2,5-F$_2$ | 3,5-F$_2$ | CH$_3$ |
| O | 2,5-F$_2$ | 4-F | CH$_3$ |
| O | 2,5-F$_2$ | 2,6-F$_2$ | CH$_3$ |
| O | 2,5-F$_2$ | 2,5-F$_2$ | CH$_3$ |
| O | 3,5-F$_2$ | 3,5-F$_2$ | CH$_3$ |
| O | 3,5-F$_2$ | 4-F | CH$_3$ |
| O | 3,5-F$_2$ | 2,6-F$_2$ | CH$_3$ |

TABLE XIV-continued

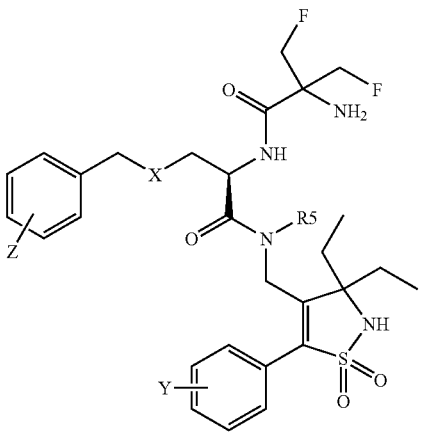

| X | Y | Z | R5 |
|---|---|---|---|
| O | 3,5-F$_2$ | 2,5-F$_2$ | CH$_3$ |
| O | 3,4-F$_2$ | 3,5-F$_2$ | CH$_3$ |
| O | 3,4-F$_2$ | 4-F | CH$_3$ |
| O | 3,4-F$_2$ | 2,6-F$_2$ | CH$_3$ |
| O | 3,4-F$_2$ | 2,5-F$_2$ | CH$_3$ |
| O | 4-CF$_3$ | 3,5-F$_2$ | CH$_3$ |
| O | 4-CF$_3$ | 4-F | CH$_3$ |
| O | 4-CF$_3$ | 2,6-F$_2$ | CH$_3$ |
| O | 4-CF$_3$ | 2,5-F$_2$ | CH$_3$ |

TABLE XV

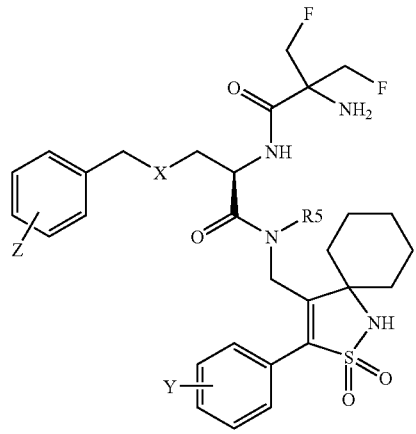

| X | Y | Z | R5 |
|---|---|---|---|
| O | 4-Cl | 2-F | CH$_2$CH$_3$ |
| O | 4-Cl | 3-F | CH$_2$CH$_3$ |
| O | 4-Cl | 4-F | CH$_2$CH$_3$ |
| O | 4-Cl | 4-Cl | CH$_2$CH$_3$ |
| O | 4-Cl | 2,5-F$_2$ | CH$_2$CH$_3$ |
| O | 4-Cl | 2,4-F$_2$ | CH$_2$CH$_3$ |
| O | 4-Cl | 2-Cl | CH$_2$CH$_3$ |
| O | 4-Cl | 2,6-F$_2$ | CH$_2$CH$_3$ |
| O | 4-Cl | 3,5-F$_2$ | CH$_2$CH$_3$ |
| O | 4-Cl | 2,3-F$_2$ | CH$_2$CH$_3$ |
| O | 4-Cl | 3,4-F$_2$ | CH$_2$CH$_3$ |
| O | 4-Cl | 2,3,5-F$_3$ | CH$_2$CH$_3$ |
| O | 4-Cl | 2,3,6-F$_3$ | CH$_2$CH$_3$ |
| O | 4-Cl | 2,4,5-F$_3$ | CH$_2$CH$_3$ |
| O | 4-Cl | 2,6-Cl$_2$ | CH$_2$CH$_3$ |
| O | 4-Cl | 2-F-3-Cl | CH$_2$CH$_3$ |
| O | 4-Cl | 2-F-6-Cl | CH$_2$CH$_3$ |
| O | 4-F | 2-F | CH$_2$CH$_3$ |
| O | 4-F | 3-F | CH$_2$CH$_3$ |

TABLE XV-continued

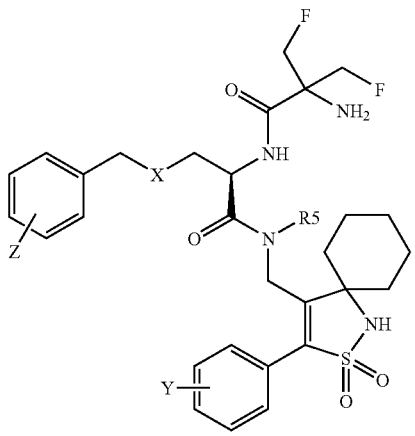

| X | Y | Z | R5 |
|---|---|---|---|
| O | 4-F | 4-F | CH₂CH₃ |
| O | 4-F | 4-Cl | CH₂CH₃ |
| O | 4-F | 2,5-F₂ | CH₂CH₃ |
| O | 4-F | 2,4-F₂ | CH₂CH₃ |
| O | 4-F | 2-Cl | CH₂CH₃ |
| O | 4-F | 2,6-F₂ | CH₂CH₃ |
| O | 4-F | 3,5-F₂ | CH₂CH₃ |
| O | 4-F | 2,3-F₂ | CH₂CH₃ |
| O | 4-F | 3,4-F₂ | CH₂CH₃ |
| O | 4-F | 2,3,5-F₃ | CH₂CH₃ |
| O | 4-F | 2,3,6-F₃ | CH₂CH₃ |
| O | 4-F | 2,4,5-F₃ | CH₂CH₃ |
| O | 4-F | 2,6-Cl₂ | CH₂CH₃ |
| O | 4-F | 2-F-3-Cl | CH₂CH₃ |
| O | 4-F | 2-F-6-Cl | CH₂CH₃ |
| CH₂ | 4-Cl | 3,5-F₂ | CH₂CH₃ |
| CH₂ | 4-Cl | 4-F | CH₂CH₃ |
| CH₂ | 4-Cl | 2,6-F₂ | CH₂CH₃ |
| CH₂ | 4-F | 3,5-F₂ | CH₂CH₃ |
| CH₂ | 4-F | 4-F | CH₂CH₃ |
| CH₂ | 4-F | 2,6-F₂ | CH₂CH₃ |
| O | 3-Cl | 3,5-F₂ | CH₂CH₃ |
| O | 3-Cl | 4-F | CH₂CH₃ |
| O | 3-Cl | 2,6-F₂ | CH₂CH₃ |
| O | 3-Cl | 2,5-F₂ | CH₂CH₃ |
| O | 3-F | 3,5-F₂ | CH₂CH₃ |
| O | 3-F | 4-F | CH₂CH₃ |
| O | 3-F | 2,6-F₂ | CH₂CH₃ |
| O | 3-F | 2,5-F₂ | CH₂CH₃ |
| O | 4-CN | 3,5-F₂ | CH₂CH₃ |
| O | 4-CN | 4-F | CH₂CH₃ |
| O | 4-CN | 2,6-F₂ | CH₂CH₃ |
| O | 4-CN | 2,5-F₂ | CH₂CH₃ |
| O | 2,5-F₂ | 3,5-F₂ | CH₂CH₃ |
| O | 2,5-F₂ | 4-F | CH₂CH₃ |
| O | 2,5-F₂ | 2,6-F₂ | CH₂CH₃ |
| O | 2,5-F₂ | 2,5-F₂ | CH₂CH₃ |
| O | 3,5-F₂ | 3,5-F₂ | CH₂CH₃ |
| O | 3,5-F₂ | 4-F | CH₂CH₃ |
| O | 3,5-F₂ | 2,6-F₂ | CH₂CH₃ |
| O | 3,5-F₂ | 2,5-F₂ | CH₂CH₃ |
| O | 3,4-F₂ | 3,5-F₂ | CH₂CH₃ |
| O | 3,4-F₂ | 4-F | CH₂CH₃ |
| O | 3,4-F₂ | 2,6-F₂ | CH₂CH₃ |
| O | 3,4-F₂ | 2,5-F₂ | CH₂CH₃ |
| O | 4-CF₃ | 3,5-F₂ | CH₂CH₃ |
| O | 4-CF₃ | 4-F | CH₂CH₃ |
| O | 4-CF₃ | 2,6-F₂ | CH₂CH₃ |
| O | 4-CF₃ | 2,5-F₂ | CH₂CH₃ |
| O | 4-Cl | 2-F | CH₃ |
| O | 4-Cl | 3-F | CH₃ |
| O | 4-Cl | 4-F | CH₃ |
| O | 4-Cl | 4-Cl | CH₃ |
| O | 4-Cl | 2,5-F₂ | CH₃ |
| O | 4-Cl | 2,4-F₂ | CH₃ |

TABLE XV-continued

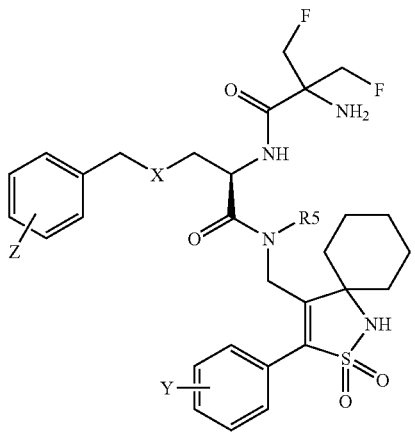

| X | Y | Z | R5 |
|---|---|---|---|
| O | 4-Cl | 2-Cl | CH₃ |
| O | 4-Cl | 2,6-F₂ | CH₃ |
| O | 4-Cl | 3,5-F₂ | CH₃ |
| O | 4-Cl | 2,3-F₂ | CH₃ |
| O | 4-Cl | 3,4-F₂ | CH₃ |
| O | 4-Cl | 2,3,5-F₃ | CH₃ |
| O | 4-Cl | 2,3,6-F₃ | CH₃ |
| O | 4-Cl | 2,4,5-F₃ | CH₃ |
| O | 4-Cl | 2,6-Cl₂ | CH₃ |
| O | 4-Cl | 2-F-3-Cl | CH₃ |
| O | 4-Cl | 2-F-6-Cl | CH₃ |
| O | 4-F | 2-F | CH₃ |
| O | 4-F | 3-F | CH₃ |
| O | 4-F | 4-F | CH₃ |
| O | 4-F | 4-Cl | CH₃ |
| O | 4-F | 2,5-F₂ | CH₃ |
| O | 4-F | 2,4-F₂ | CH₃ |
| O | 4-F | 2-Cl | CH₃ |
| O | 4-F | 2,6-F₂ | CH₃ |
| O | 4-F | 3,5-F₂ | CH₃ |
| O | 4-F | 2,3-F₂ | CH₃ |
| O | 4-F | 3,4-F₂ | CH₃ |
| O | 4-F | 2,3,5-F₃ | CH₃ |
| O | 4-F | 2,3,6-F₃ | CH₃ |
| O | 4-F | 2,4,5-F₃ | CH₃ |
| O | 4-F | 2,6-Cl₂ | CH₃ |
| O | 4-F | 2-F-3-Cl | CH₃ |
| O | 4-F | 2-F-6-Cl | CH₃ |
| CH₂ | 4-Cl | 3,5-F₂ | CH₃ |
| CH₂ | 4-Cl | 4-F | CH₃ |
| CH₂ | 4-Cl | 2,6-F₂ | CH₃ |
| CH₂ | 4-F | 3,5-F₂ | CH₃ |
| CH₂ | 4-F | 4-F | CH₃ |
| CH₂ | 4-F | 2,6-F₂ | CH₃ |
| O | 3-F | 3,5-F₂ | CH₃ |
| O | 3-F | 4-F | CH₃ |
| O | 3-F | 2,6-F₂ | CH₃ |
| O | 3-F | 2,5-F₂ | CH₃ |
| O | 2,5-F₂ | 3,5-F₂ | CH₃ |
| O | 2,5-F₂ | 4-F | CH₃ |
| O | 2,5-F₂ | 2,6-F₂ | CH₃ |
| O | 2,5-F₂ | 2,5-F₂ | CH₃ |
| O | 3,5-F₂ | 3,5-F₂ | CH₃ |
| O | 3,5-F₂ | 4-F | CH₃ |
| O | 3,5-F₂ | 2,6-F₂ | CH₃ |
| O | 3,5-F₂ | 2,5-F₂ | CH₃ |
| O | 3,4-F₂ | 3,5-F₂ | CH₃ |
| O | 3,4-F₂ | 4-F | CH₃ |
| O | 3,4-F₂ | 2,6-F₂ | CH₃ |
| O | 3,4-F₂ | 2,5-F₂ | CH₃ |
| O | 4-CF₃ | 3,5-F₂ | CH₃ |
| O | 4-CF₃ | 4-F | CH₃ |
| O | 4-CF₃ | 2,6-F₂ | CH₃ |
| O | 4-CF₃ | 2,5-F₂ | CH₃ |

TABLE XVI

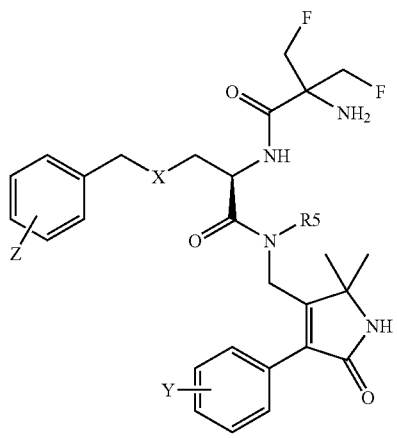

| X | Y | Z | R5 |
|---|---|---|---|
| O | 4-Cl | 2-F | CH₂CH₃ |
| O | 4-Cl | 3-F | CH₂CH₃ |
| O | 4-Cl | 4-F | CH₂CH₃ |
| O | 4-Cl | 4-Cl | CH₂CH₃ |
| O | 4-Cl | 2,5-F₂ | CH₂CH₃ |
| O | 4-Cl | 2,4-F₂ | CH₂CH₃ |
| O | 4-Cl | 2-Cl | CH₂CH₃ |
| O | 4-Cl | 2,6-F₂ | CH₂CH₃ |
| O | 4-Cl | 3,5-F₂ | CH₂CH₃ |
| O | 4-Cl | 2,3-F₂ | CH₂CH₃ |
| O | 4-Cl | 3,4-F₂ | CH₂CH₃ |
| O | 4-Cl | 2,3,5-F₃ | CH₂CH₃ |
| O | 4-Cl | 2,3,6-F₃ | CH₂CH₃ |
| O | 4-Cl | 2,4,5-F₃ | CH₂CH₃ |
| O | 4-Cl | 2,6-Cl₂ | CH₂CH₃ |
| O | 4-Cl | 2-F-3-Cl | CH₂CH₃ |
| O | 4-Cl | 2-F-6-Cl | CH₂CH₃ |
| O | 4-F | 2-F | CH₂CH₃ |
| O | 4-F | 3-F | CH₂CH₃ |
| O | 4-F | 4-F | CH₂CH₃ |
| O | 4-F | 4-Cl | CH₂CH₃ |
| O | 4-F | 2,5-F₂ | CH₂CH₃ |
| O | 4-F | 2,4-F₂ | CH₂CH₃ |
| O | 4-F | 2-Cl | CH₂CH₃ |
| O | 4-F | 2,6-F₂ | CH₂CH₃ |
| O | 4-F | 3,5-F₂ | CH₂CH₃ |
| O | 4-F | 2,3-F₂ | CH₂CH₃ |
| O | 4-F | 3,4-F₂ | CH₂CH₃ |
| O | 4-F | 2,3,5-F₃ | CH₂CH₃ |
| O | 4-F | 2,3,6-F₃ | CH₂CH₃ |
| O | 4-F | 2,4,5-F₃ | CH₂CH₃ |
| O | 4-F | 2,6-Cl₂ | CH₂CH₃ |
| O | 4-F | 2-F-3-Cl | CH₂CH₃ |
| O | 4-F | 2-F-6-Cl | CH₂CH₃ |
| CH₂ | 4-Cl | 3,5-F₂ | CH₂CH₃ |
| CH₂ | 4-Cl | 4-F | CH₂CH₃ |
| CH₂ | 4-Cl | 2,6-F₂ | CH₂CH₃ |
| CH₂ | 4-F | 3,5-F₂ | CH₂CH₃ |
| CH₂ | 4-F | 4-F | CH₂CH₃ |
| CH₂ | 4-F | 2,6-F₂ | CH₂CH₃ |
| O | 3-Cl | 3,5-F₂ | CH₂CH₃ |
| O | 3-Cl | 4-F | CH₂CH₃ |
| O | 3-Cl | 2,6-F₂ | CH₂CH₃ |
| O | 3-Cl | 2,5-F₂ | CH₂CH₃ |
| O | 3-F | 3,5-F₂ | CH₂CH₃ |
| O | 3-F | 4-F | CH₂CH₃ |
| O | 3-F | 2,6-F₂ | CH₂CH₃ |
| O | 3-F | 2,5-F₂ | CH₂CH₃ |
| O | 4-CN | 3,5-F₂ | CH₂CH₃ |
| O | 4-CN | 4-F | CH₂CH₃ |
| O | 4-CN | 2,6-F₂ | CH₂CH₃ |
| O | 4-CN | 2,5-F₂ | CH₂CH₃ |
| O | 2,5-F₂ | 3,5-F₂ | CH₂CH₃ |
| O | 2,5-F₂ | 4-F | CH₂CH₃ |
| O | 2,5-F₂ | 2,6-F₂ | CH₂CH₃ |

TABLE XVI-continued

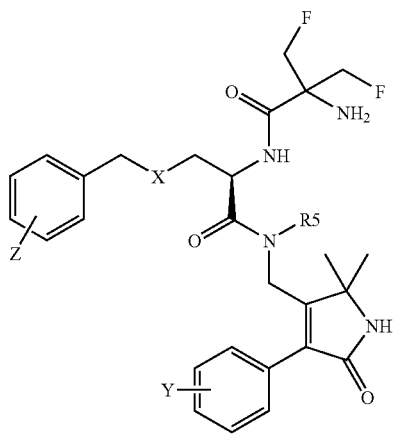

| X | Y | Z | R5 |
|---|---|---|---|
| O | 2,5-F₂ | 2,5-F₂ | CH₂CH₃ |
| O | 3,5-F₂ | 3,5-F₂ | CH₂CH₃ |
| O | 3,5-F₂ | 4-F | CH₂CH₃ |
| O | 3,5-F₂ | 2,6-F₂ | CH₂CH₃ |
| O | 3,5-F₂ | 2,5-F₂ | CH₂CH₃ |
| O | 3,4-F₂ | 3,5-F₂ | CH₂CH₃ |
| O | 3,4-F₂ | 4-F | CH₂CH₃ |
| O | 3,4-F₂ | 2,6-F₂ | CH₂CH₃ |
| O | 3,4-F₂ | 2,5-F₂ | CH₂CH₃ |
| O | 4-CF₃ | 3,5-F₂ | CH₂CH₃ |
| O | 4-CF₃ | 4-F | CH₂CH₃ |
| O | 4-CF₃ | 2,6-F₂ | CH₂CH₃ |
| O | 4-CF₃ | 2,5-F₂ | CH₂CH₃ |
| O | 4-Cl | 2-F | CH₃ |
| O | 4-Cl | 3-F | CH₃ |
| O | 4-Cl | 4-F | CH₃ |
| O | 4-Cl | 4-Cl | CH₃ |
| O | 4-Cl | 2,5-F₂ | CH₃ |
| O | 4-Cl | 2,4-F₂ | CH₃ |
| O | 4-Cl | 2-Cl | CH₃ |
| O | 4-Cl | 2,6-F₂ | CH₃ |
| O | 4-Cl | 3,5-F₂ | CH₃ |
| O | 4-Cl | 2,3-F₂ | CH₃ |
| O | 4-Cl | 3,4-F₂ | CH₃ |
| O | 4-Cl | 2,3,5-F₃ | CH₃ |
| O | 4-Cl | 2,3,6-F₃ | CH₃ |
| O | 4-Cl | 2,4,5-F₃ | CH₃ |
| O | 4-Cl | 2,6-Cl₂ | CH₃ |
| O | 4-Cl | 2-F-3-Cl | CH₃ |
| O | 4-Cl | 2-F-6-Cl | CH₃ |
| O | 4-F | 2-F | CH₃ |
| O | 4-F | 3-F | CH₃ |
| O | 4-F | 4-F | CH₃ |
| O | 4-F | 4-Cl | CH₃ |
| O | 4-F | 2,5-F₂ | CH₃ |
| O | 4-F | 2,4-F₂ | CH₃ |
| O | 4-F | 2-Cl | CH₃ |
| O | 4-F | 2,6-F₂ | CH₃ |
| O | 4-F | 3,5-F₂ | CH₃ |
| O | 4-F | 2,3-F₂ | CH₃ |
| O | 4-F | 3,4-F₂ | CH₃ |
| O | 4-F | 2,3,5-F₃ | CH₃ |
| O | 4-F | 2,3,6-F₃ | CH₃ |
| O | 4-F | 2,4,5-F₃ | CH₃ |
| O | 4-F | 2,6-Cl₂ | CH₃ |
| O | 4-F | 2-F-3-Cl | CH₃ |
| O | 4-F | 2-F-6-Cl | CH₃ |
| CH₂ | 4-Cl | 3,5-F₂ | CH₃ |
| CH₂ | 4-Cl | 4-F | CH₃ |
| CH₂ | 4-Cl | 2,6-F₂ | CH₃ |
| CH₂ | 4-F | H | CH₃ |
| CH₂ | 4-F | 3,5-F₂ | CH₃ |
| CH₂ | 4-F | 4-F | CH₃ |
| CH₂ | 4-F | 2,6-F₂ | CH₃ |
| O | 3-F | 3,5-F₂ | CH₃ |

TABLE XVI-continued

| X | Y | Z | R5 |
|---|---|---|----|
| O | 3-F | 4-F | CH$_3$ |
| O | 3-F | 2,6-F$_2$ | CH$_3$ |
| O | 3-F | 2,5-F$_2$ | CH$_3$ |
| O | 2,5-F$_2$ | 3,5-F$_2$ | CH$_3$ |
| O | 2,5-F$_2$ | 4-F | CH$_3$ |
| O | 2,5-F$_2$ | 2,6-F$_2$ | CH$_3$ |
| O | 2,5-F$_2$ | 2,5-F$_2$ | CH$_3$ |
| O | 3,5-F$_2$ | 3,5-F$_2$ | CH$_3$ |
| O | 3,5-F$_2$ | 4-F | CH$_3$ |
| O | 3,5-F$_2$ | 2,6-F$_2$ | CH$_3$ |
| O | 3,5-F$_2$ | 2,5-F$_2$ | CH$_3$ |
| O | 3,4-F$_2$ | 3,5-F$_2$ | CH$_3$ |
| O | 3,4-F$_2$ | 4-F | CH$_3$ |
| O | 3,4-F$_2$ | 2,6-F$_2$ | CH$_3$ |
| O | 3,4-F$_2$ | 2,5-F$_2$ | CH$_3$ |
| O | 4-CF$_3$ | 3,5-F$_2$ | CH$_3$ |
| O | 4-CF$_3$ | 4-F | CH$_3$ |
| O | 4-CF$_3$ | 2,6-F$_2$ | CH$_3$ |
| O | 4-CF$_3$ | 2,5-F$_2$ | CH$_3$ |

TABLE XVII

| X | Y | Z | R5 |
|---|---|---|----|
| O | 4-Cl | 2-F | CH$_2$CH$_3$ |
| O | 4-Cl | 3-F | CH$_2$CH$_3$ |
| O | 4-Cl | 4-F | CH$_2$CH$_3$ |
| O | 4-Cl | 4-Cl | CH$_2$CH$_3$ |
| O | 4-Cl | 2,5-F$_2$ | CH$_2$CH$_3$ |
| O | 4-Cl | 2,4-F$_2$ | CH$_2$CH$_3$ |
| O | 4-Cl | 2-Cl | CH$_2$CH$_3$ |
| O | 4-Cl | 2,6-F$_2$ | CH$_2$CH$_3$ |

TABLE XVII-continued

| X | Y | Z | R5 |
|---|---|---|----|
| O | 4-Cl | 3,5-F$_2$ | CH$_2$CH$_3$ |
| O | 4-Cl | 2,3-F$_2$ | CH$_2$CH$_3$ |
| O | 4-Cl | 3,4-F$_2$ | CH$_2$CH$_3$ |
| O | 4-Cl | 2,3,5-F$_3$ | CH$_2$CH$_3$ |
| O | 4-Cl | 2,3,6-F$_3$ | CH$_2$CH$_3$ |
| O | 4-Cl | 2,4,5-F$_3$ | CH$_2$CH$_3$ |
| O | 4-Cl | 2,6-Cl$_2$ | CH$_2$CH$_3$ |
| O | 4-Cl | 2-F-3-Cl | CH$_2$CH$_3$ |
| O | 4-Cl | 2-F-6-Cl | CH$_2$CH$_3$ |
| O | 4-F | 2-F | CH$_2$CH$_3$ |
| O | 4-F | 3-F | CH$_2$CH$_3$ |
| O | 4-F | 4-F | CH$_2$CH$_3$ |
| O | 4-F | 4-Cl | CH$_2$CH$_3$ |
| O | 4-F | 2,5-F$_2$ | CH$_2$CH$_3$ |
| O | 4-F | 2,4-F$_2$ | CH$_2$CH$_3$ |
| O | 4-F | 2-Cl | CH$_2$CH$_3$ |
| O | 4-F | 2,6-F$_2$ | CH$_2$CH$_3$ |
| O | 4-F | 3,5-F$_2$ | CH$_2$CH$_3$ |
| O | 4-F | 2,3-F$_2$ | CH$_2$CH$_3$ |
| O | 4-F | 3,4-F$_2$ | CH$_2$CH$_3$ |
| O | 4-F | 2,3,5-F$_3$ | CH$_2$CH$_3$ |
| O | 4-F | 2,3,6-F$_3$ | CH$_2$CH$_3$ |
| O | 4-F | 2,4,5-F$_3$ | CH$_2$CH$_3$ |
| O | 4-F | 2,6-Cl$_2$ | CH$_2$CH$_3$ |
| O | 4-F | 2-F-3-Cl | CH$_2$CH$_3$ |
| O | 4-F | 2-F-6-Cl | CH$_2$CH$_3$ |
| CH$_2$ | 4-Cl | 3,5-F$_2$ | CH$_2$CH$_3$ |
| CH$_2$ | 4-Cl | 4-F | CH$_2$CH$_3$ |
| CH$_2$ | 4-Cl | 2,6-F$_2$ | CH$_2$CH$_3$ |
| CH$_2$ | 4-F | 3,5-F$_2$ | CH$_2$CH$_3$ |
| CH$_2$ | 4-F | 4-F | CH$_2$CH$_3$ |
| CH$_2$ | 4-F | 2,6-F$_2$ | CH$_2$CH$_3$ |
| O | 3-Cl | 3,5-F$_2$ | CH$_2$CH$_3$ |
| O | 3-Cl | 4-F | CH$_2$CH$_3$ |
| O | 3-Cl | 2,6-F$_2$ | CH$_2$CH$_3$ |
| O | 3-Cl | 2,5-F$_2$ | CH$_2$CH$_3$ |
| O | 3-F | 3,5-F$_2$ | CH$_2$CH$_3$ |
| O | 3-F | 4-F | CH$_2$CH$_3$ |
| O | 3-F | 2,6-F$_2$ | CH$_2$CH$_3$ |
| O | 3-F | 2,5-F$_2$ | CH$_2$CH$_3$ |
| O | 4-CN | 3,5-F$_2$ | CH$_2$CH$_3$ |
| O | 4-CN | 4-F | CH$_2$CH$_3$ |
| O | 4-CN | 2,6-F$_2$ | CH$_2$CH$_3$ |
| O | 4-CN | 2,5-F$_2$ | CH$_2$CH$_3$ |
| O | 2,5-F$_2$ | 3,5-F$_2$ | CH$_2$CH$_3$ |
| O | 2,5-F$_2$ | 4-F | CH$_2$CH$_3$ |
| O | 2,5-F$_2$ | 2,6-F$_2$ | CH$_2$CH$_3$ |
| O | 2,5-F$_2$ | 2,5-F$_2$ | CH$_2$CH$_3$ |
| O | 3,5-F$_2$ | 3,5-F$_2$ | CH$_2$CH$_3$ |
| O | 3,5-F$_2$ | 4-F | CH$_2$CH$_3$ |
| O | 3,5-F$_2$ | 2,6-F$_2$ | CH$_2$CH$_3$ |
| O | 3,5-F$_2$ | 2,5-F$_2$ | CH$_2$CH$_3$ |
| O | 3,4-F$_2$ | 3,5-F$_2$ | CH$_2$CH$_3$ |
| O | 3,4-F$_2$ | 4-F | CH$_2$CH$_3$ |
| O | 3,4-F$_2$ | 2,6-F$_2$ | CH$_2$CH$_3$ |

TABLE XVII-continued

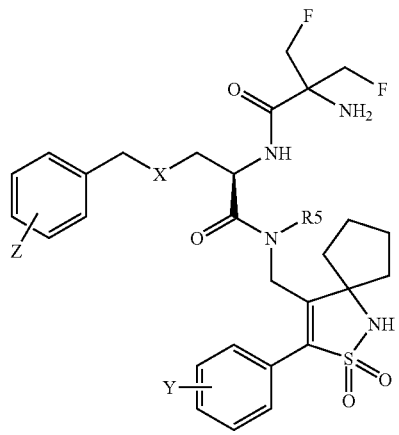

| X | Y | Z | R5 |
|---|---|---|---|
| O | 3,4-F$_2$ | 2,5-F$_2$ | CH$_2$CH$_3$ |
| O | 4-CF$_3$ | 3,5-F$_2$ | CH$_2$CH$_3$ |
| O | 4-CF$_3$ | 4-F | CH$_2$CH$_3$ |
| O | 4-CF$_3$ | 2,6-F$_2$ | CH$_2$CH$_3$ |
| O | 4-CF$_3$ | 2,5-F$_2$ | CH$_2$CH$_3$ |
| O | 4-Cl | 2-F | CH$_3$ |
| O | 4-Cl | 3-F | CH$_3$ |
| O | 4-Cl | 4-F | CH$_3$ |
| O | 4-Cl | 4-Cl | CH$_3$ |
| O | 4-Cl | 2,5-F$_2$ | CH$_3$ |
| O | 4-Cl | 2,4-F$_2$ | CH$_3$ |
| O | 4-Cl | 2-Cl | CH$_3$ |
| O | 4-Cl | 2,6-F$_2$ | CH$_3$ |
| O | 4-Cl | 3,5-F$_2$ | CH$_3$ |
| O | 4-Cl | 2,3-F$_2$ | CH$_3$ |
| O | 4-Cl | 3,4-F$_2$ | CH$_3$ |
| O | 4-Cl | 2,3,5-F$_3$ | CH$_3$ |
| O | 4-Cl | 2,3,6-F$_3$ | CH$_3$ |
| O | 4-Cl | 2,4,5-F$_3$ | CH$_3$ |
| O | 4-Cl | 2,6-Cl$_2$ | CH$_3$ |
| O | 4-Cl | 2-F-3-Cl | CH$_3$ |
| O | 4-Cl | 2-F-6-Cl | CH$_3$ |
| O | 4-F | 2-F | CH$_3$ |
| O | 4-F | 3-F | CH$_3$ |
| O | 4-F | 4-F | CH$_3$ |
| O | 4-F | 4-Cl | CH$_3$ |
| O | 4-F | 2,5-F$_2$ | CH$_3$ |
| O | 4-F | 2,4-F$_2$ | CH$_3$ |
| O | 4-F | 2-Cl | CH$_3$ |
| O | 4-F | 2,6-F$_2$ | CH$_3$ |
| O | 4-F | 3,5-F$_2$ | CH$_3$ |
| O | 4-F | 2,3-F$_2$ | CH$_3$ |
| O | 4-F | 3,4-F$_2$ | CH$_3$ |
| O | 4-F | 2,3,5-F$_3$ | CH$_3$ |
| O | 4-F | 2,3,6-F$_3$ | CH$_3$ |
| O | 4-F | 2,4,5-F$_3$ | CH$_3$ |
| O | 4-F | 2,6-Cl$_2$ | CH$_3$ |
| O | 4-F | 2-F-3-Cl | CH$_3$ |
| O | 4-F | 2-F-6-Cl | CH$_3$ |
| CH$_2$ | 4-Cl | 3,5-F$_2$ | CH$_3$ |
| CH$_2$ | 4-Cl | 4-F | CH$_3$ |
| CH$_2$ | 4-Cl | 2,6-F$_2$ | CH$_3$ |
| CH$_2$ | 4-F | 3,5-F$_2$ | CH$_3$ |
| CH$_2$ | 4-F | 4-F | CH$_3$ |
| CH$_2$ | 4-F | 2,6-F$_2$ | CH$_3$ |
| O | 3-F | 3,5-F$_2$ | CH$_3$ |
| O | 3-F | 4-F | CH$_3$ |
| O | 3-F | 2,6-F$_2$ | CH$_3$ |
| O | 3-F | 2,5-F$_2$ | CH$_3$ |
| O | 2,5-F$_2$ | 3,5-F$_2$ | CH$_3$ |
| O | 2,5-F$_2$ | 4-F | CH$_3$ |
| O | 2,5-F$_2$ | 2,6-F$_2$ | CH$_3$ |
| O | 2,5-F$_2$ | 2,5-F$_2$ | CH$_3$ |
| O | 3,5-F$_2$ | 3,5-F$_2$ | CH$_3$ |
| O | 3,5-F$_2$ | 4-F | CH$_3$ |

TABLE XVII-continued

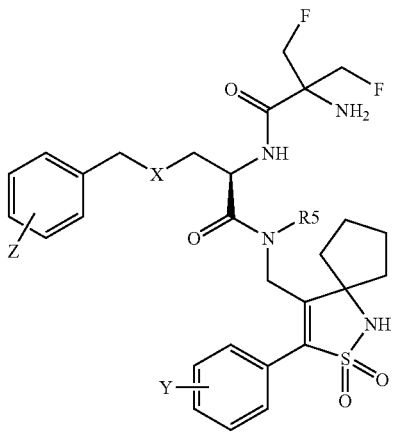

| X | Y | Z | R5 |
|---|---|---|---|
| O | 3,5-F$_2$ | 2,6-F$_2$ | CH$_3$ |
| O | 3,5-F$_2$ | 2,5-F$_2$ | CH$_3$ |
| O | 3,4-F$_2$ | 3,5-F$_2$ | CH$_3$ |
| O | 3,4-F$_2$ | 4-F | CH$_3$ |
| O | 3,4-F$_2$ | 2,6-F$_2$ | CH$_3$ |
| O | 3,4-F$_2$ | 2,5-F$_2$ | CH$_3$ |
| O | 4-CF$_3$ | 3,5-F$_2$ | CH$_3$ |
| O | 4-CF$_3$ | 4-F | CH$_3$ |
| O | 4-CF$_3$ | 2,6-F$_2$ | CH$_3$ |
| O | 4-CF$_3$ | 2,5-F$_2$ | CH$_3$ |

TABLE XVIII

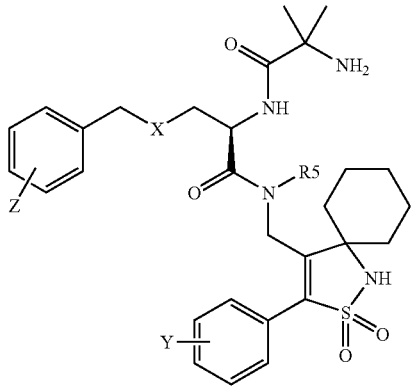

| X | Y | Z | R5 |
|---|---|---|---|
| CH$_2$ | 4-Cl | 2-F | Me |
| O | 4-Cl | 2-F | Me |
| bond | 4-Cl | 2-F | Me |
| CH$_2$ | 4-Cl | 2-F | Et |
| O | 4-Cl | 2-F | Et |
| bond | 4-Cl | 2-F | Et |
| CH$_2$ | 4-Cl | 3-F | Me |
| O | 4-Cl | 3-F | Me |
| bond | 4-Cl | 3-F | Me |
| CH$_2$ | 4-Cl | 3-F | Et |
| O | 4-Cl | 3-F | Et |
| bond | 4-Cl | 3-F | Et |
| CH$_2$ | 4-Cl | 4-F | Me |
| O | 4-Cl | 4-F | Me |
| bond | 4-Cl | 4-F | Me |
| CH$_2$ | 4-Cl | 4-F | Et |
| O | 4-Cl | 4-F | Et |
| bond | 4-Cl | 4-F | Et |
| CH$_2$ | 4-Cl | 2,3-F$_2$ | Me |

TABLE XVIII-continued

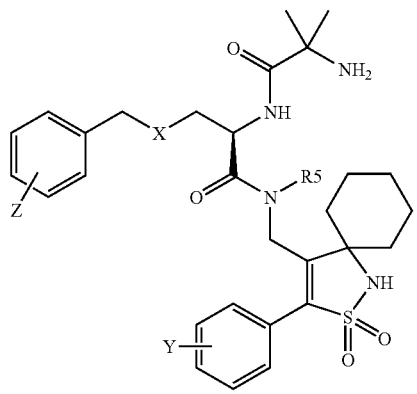

| X | Y | Z | R5 |
|---|---|---|---|
| O | 4-Cl | 2,3-F$_2$ | Me |
| bond | 4-Cl | 2,3-F$_2$ | Me |
| CH$_2$ | 4-Cl | 2,3-F$_2$ | Et |
| O | 4-Cl | 2,3-F$_2$ | Et |
| bond | 4-Cl | 2,3-F$_2$ | Et |
| CH$_2$ | 4-Cl | 2,4-F$_2$ | Me |
| O | 4-Cl | 2,4-F$_2$ | Me |
| bond | 4-Cl | 2,4-F$_2$ | Me |
| CH$_2$ | 4-Cl | 2,4-F$_2$ | Et |
| O | 4-Cl | 2,4-F$_2$ | Et |
| bond | 4-Cl | 2,4-F$_2$ | Et |
| CH$_2$ | 4-Cl | 2,5-F$_2$ | Me |
| O | 4-Cl | 2,5-F$_2$ | Me |
| bond | 4-Cl | 2,5-F$_2$ | Me |
| CH$_2$ | 4-Cl | 2,5-F$_2$ | Et |
| O | 4-Cl | 2,5-F$_2$ | Et |
| bond | 4-Cl | 2,5-F$_2$ | Et |
| CH$_2$ | 4-Cl | 2,6-F$_2$ | Me |
| O | 4-Cl | 2,6-F$_2$ | Me |
| bond | 4-Cl | 2,6-F$_2$ | Me |
| CH$_2$ | 4-Cl | 2,6-F$_2$ | Et |
| O | 4-Cl | 2,6-F$_2$ | Et |
| bond | 4-Cl | 2,6-F$_2$ | Et |
| CH$_2$ | 4-Cl | 3,4-F$_2$ | Me |
| O | 4-Cl | 3,4-F$_2$ | Me |
| bond | 4-Cl | 3,4-F$_2$ | Me |
| CH$_2$ | 4-Cl | 3,4-F$_2$ | Et |
| O | 4-Cl | 3,4-F$_2$ | Et |
| bond | 4-Cl | 3,4-F$_2$ | Et |
| CH$_2$ | 4-Cl | 3,5-F$_2$ | Me |
| O | 4-Cl | 3,5-F$_2$ | Me |
| bond | 4-Cl | 3,5-F$_2$ | Me |
| CH$_2$ | 4-Cl | 3,5-F$_2$ | Et |
| O | 4-Cl | 3,5-F$_2$ | Et |
| bond | 4-Cl | 3,5-F$_2$ | Et |
| CH$_2$ | 4-Cl | 2,4,6-F$_3$ | Me |
| O | 4-Cl | 2,4,6-F$_3$ | Me |
| bond | 4-Cl | 2,4,6-F$_3$ | Me |
| CH$_2$ | 4-Cl | 2,4,6-F$_3$ | Et |
| O | 4-Cl | 2,4,6-F$_3$ | Et |
| bond | 4-Cl | 2,4,6-F$_3$ | Et |
| CH$_2$ | 4-Cl | 2,4,5-F$_3$ | Me |
| O | 4-Cl | 2,4,5-F$_3$ | Me |
| bond | 4-Cl | 2,4,5-F$_3$ | Me |
| CH$_2$ | 4-Cl | 2,4,5-F$_3$ | Et |
| O | 4-Cl | 2,4,5-F$_3$ | Et |
| bond | 4-Cl | 2,4,5-F$_3$ | Et |
| CH$_2$ | 4-Cl | 2,3,6-F$_3$ | Me |
| O | 4-Cl | 2,3,6-F$_3$ | Me |
| bond | 4-Cl | 2,3,6-F$_3$ | Me |
| CH$_2$ | 4-Cl | 2,3,6-F$_3$ | Et |
| O | 4-Cl | 2,3,6-F$_3$ | Et |
| bond | 4-Cl | 2,3,6-F$_3$ | Et |
| CH$_2$ | 4-Cl | 2,3,5-F$_3$ | Me |
| O | 4-Cl | 2,3,5-F$_3$ | Me |
| bond | 4-Cl | 2,3,5-F$_3$ | Me |
| CH$_2$ | 4-Cl | 2,3,5-F$_3$ | Et |

TABLE XVIII-continued

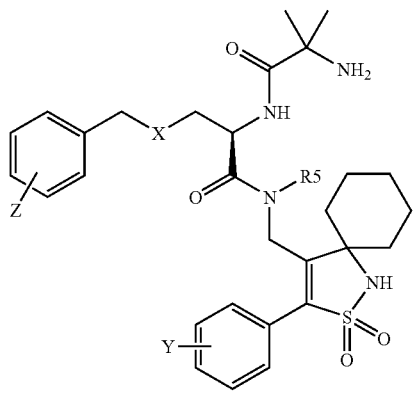

| X | Y | Z | R5 |
|---|---|---|---|
| O | 4-Cl | 2,3,5-F$_3$ | Et |
| bond | 4-Cl | 2,3,5-F$_3$ | Et |
| CH$_2$ | 4-Cl | 2-Cl | Me |
| O | 4-Cl | 2-Cl | Me |
| bond | 4-Cl | 2-Cl | Me |
| CH$_2$ | 4-Cl | 2-Cl | Et |
| O | 4-Cl | 2-Cl | Et |
| bond | 4-Cl | 2-Cl | Et |
| CH$_2$ | 4-Cl | 3-Cl | Me |
| O | 4-Cl | 3-Cl | Me |
| bond | 4-Cl | 3-Cl | Me |
| CH$_2$ | 4-Cl | 3-Cl | Et |
| O | 4-Cl | 3-Cl | Et |
| bond | 4-Cl | 3-Cl | Et |
| CH$_2$ | 4-Cl | 4-Cl | Me |
| O | 4-Cl | 4-Cl | Me |
| bond | 4-Cl | 4-Cl | Me |
| CH$_2$ | 4-Cl | 4-Cl | Et |
| O | 4-Cl | 4-Cl | Et |
| bond | 4-Cl | 4-Cl | Et |
| CH$_2$ | 4-Cl | 2,6-Cl$_2$ | Me |
| O | 4-Cl | 2,6-Cl$_2$ | Me |
| bond | 4-Cl | 2,6-Cl$_2$ | Me |
| CH$_2$ | 4-Cl | 2,6-Cl$_2$ | Et |
| O | 4-Cl | 2,6-Cl$_2$ | Et |
| bond | 4-Cl | 2,6-Cl$_2$ | Et |
| CH$_2$ | 4-Cl | 2-F-6-Cl | Me |
| O | 4-Cl | 2-F-6-Cl | Me |
| bond | 4-Cl | 2-F-6-Cl | Me |
| CH$_2$ | 4-Cl | 2-F-6-Cl | Et |
| O | 4-Cl | 2-F-6-Cl | Et |
| bond | 4-Cl | 2-F-6-Cl | Et |
| CH$_2$ | 4-Cl | 2-F-3-Cl | Me |
| O | 4-Cl | 2-F-3-Cl | Me |
| bond | 4-Cl | 2-F-3-Cl | Me |
| CH$_2$ | 4-Cl | 2-F-3-Cl | Et |
| O | 4-Cl | 2-F-3-Cl | Et |
| bond | 4-Cl | 2-F-3-Cl | Et |
| CH$_2$ | 4-Cl | 2-F-4-Cl | Me |
| O | 4-Cl | 2-F-4-Cl | Me |
| bond | 4-Cl | 2-F-4-Cl | Me |
| CH$_2$ | 4-Cl | 2-F-4-Cl | Et |
| O | 4-Cl | 2-F-4-Cl | Et |
| bond | 4-Cl | 2-F-4-Cl | Et |
| CH$_2$ | 4-Cl | 3-F-4-Cl | Me |
| O | 4-Cl | 3-F-4-Cl | Me |
| bond | 4-Cl | 3-F-4-Cl | Me |
| CH$_2$ | 4-Cl | 3-F-4-Cl | Et |
| O | 4-Cl | 3-F-4-Cl | Et |
| bond | 4-Cl | 3-F-4-Cl | Et |
| CH$_2$ | 4-Cl | 2,6-F$_2$-3-Cl | Me |
| O | 4-Cl | 2,6-F$_2$-3-Cl | Me |
| bond | 4-Cl | 2,6-F$_2$-3-Cl | Me |
| CH$_2$ | 4-Cl | 2,6-F$_2$-3-Cl | Et |
| O | 4-Cl | 2,6-F$_2$-3-Cl | Et |
| bond | 4-Cl | 2,6-F$_2$-3-Cl | Et |
| CH$_2$ | 4-Cl | 2-Cl-3,6-F$_2$ | Me |

TABLE XVIII-continued

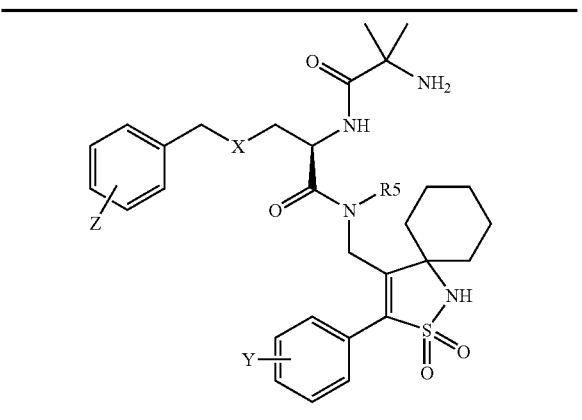

| X | Y | Z | R5 |
|---|---|---|---|
| O | 4-Cl | 2-Cl-3,6-F$_2$ | Me |
| bond | 4-Cl | 2-Cl-3,6-F$_2$ | Me |
| CH$_2$ | 4-Cl | 2-Cl-3,6-F$_2$ | Et |
| O | 4-Cl | 2-Cl-3,6-F$_2$ | Et |
| bond | 4-Cl | 2-Cl-3,6-F$_2$ | Et |
| CH$_2$ | 4-Cl | 2,3-Cl$_2$ | Me |
| O | 4-Cl | 2,3-Cl$_2$ | Me |
| bond | 4-Cl | 2,3-Cl$_2$ | Me |
| CH$_2$ | 4-Cl | 2,3-Cl$_2$ | Et |
| O | 4-Cl | 2,3-Cl$_2$ | Et |
| bond | 4-Cl | 2,3-Cl$_2$ | Et |
| CH$_2$ | 4-Cl | 4-F-2-Cl | Me |
| O | 4-Cl | 4-F-2-Cl | Me |
| bond | 4-Cl | 4-F-2-Cl | Me |
| CH$_2$ | 4-Cl | 4-F-2-Cl | Et |
| O | 4-Cl | 4-F-2-Cl | Et |
| bond | 4-Cl | 4-F-2-Cl | Et |
| CH$_2$ | 4-Cl | 4-CF$_3$ | Me |
| O | 4-Cl | 4-CF$_3$ | Me |
| bond | 4-Cl | 4-CF$_3$ | Me |
| CH$_2$ | 4-Cl | 4-CF$_3$ | Et |
| O | 4-Cl | 4-CF$_3$ | Et |
| bond | 4-Cl | 4-CF$_3$ | Et |
| CH$_2$ | 4-Cl | 3-CF$_3$ | Me |
| O | 4-Cl | 3-CF$_3$ | Me |
| bond | 4-Cl | 3-CF$_3$ | Me |
| CH$_2$ | 4-Cl | 3-CF$_3$ | Et |
| O | 4-Cl | 3-CF$_3$ | Et |
| bond | 4-Cl | 3-CF$_3$ | Et |
| CH$_2$ | 4-Cl | 2-CF$_3$ | Me |
| O | 4-Cl | 2-CF$_3$ | Me |
| bond | 4-Cl | 2-CF$_3$ | Me |
| CH$_2$ | 4-Cl | 2-CF$_3$ | Et |
| O | 4-Cl | 2-CF$_3$ | Et |
| bond | 4-Cl | 2-CF$_3$ | Et |
| CH$_2$ | 4-Cl | 2-F-5-CF$_3$ | Me |
| O | 4-Cl | 2-F-5-CF$_3$ | Me |
| bond | 4-Cl | 2-F-5-CF$_3$ | Me |
| CH$_2$ | 4-Cl | 2-F-5-CF$_3$ | Et |
| O | 4-Cl | 2-F-5-CF$_3$ | Et |
| bond | 4-Cl | 2-F-5-CF$_3$ | Et |
| CH$_2$ | 4-Cl | 4-OCF$_3$ | Me |
| O | 4-Cl | 4-OCF$_3$ | Me |
| bond | 4-Cl | 4-OCF$_3$ | Me |
| CH$_2$ | 4-Cl | 4-OCF$_3$ | Et |
| O | 4-Cl | 4-OCF$_3$ | Et |
| bond | 4-Cl | 4-OCF$_3$ | Et |
| CH$_2$ | 4-Cl | 3-OCF$_3$ | Me |
| O | 4-Cl | 3-OCF$_3$ | Me |
| bond | 4-Cl | 3-OCF$_3$ | Me |
| CH$_2$ | 4-Cl | 3-OCF$_3$ | Et |
| O | 4-Cl | 3-OCF$_3$ | Et |
| bond | 4-Cl | 3-OCF$_3$ | Et |
| CH$_2$ | 4-Cl | 2-OCF$_3$ | Me |
| O | 4-Cl | 2-OCF$_3$ | Me |
| bond | 4-Cl | 2-OCF$_3$ | Me |
| CH$_2$ | 4-Cl | 2-OCF$_3$ | Et |

TABLE XVIII-continued

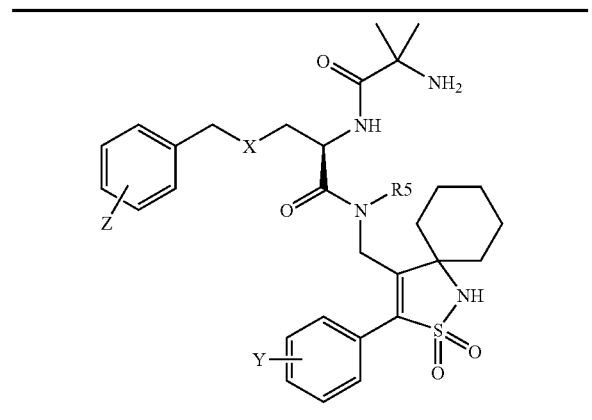

| X | Y | Z | R5 |
|---|---|---|---|
| O | 4-Cl | 2-OCF$_3$ | Et |
| bond | 4-Cl | 2-OCF$_3$ | Et |
| CH$_2$ | 4-Cl | 2-CN | Me |
| O | 4-Cl | 2-CN | Me |
| bond | 4-Cl | 2-CN | Me |
| CH$_2$ | 4-Cl | 2-CN | Et |
| O | 4-Cl | 2-CN | Et |
| bond | 4-Cl | 2-CN | Et |
| CH$_2$ | 4-Cl | 3-CN | Me |
| O | 4-Cl | 3-CN | Me |
| bond | 4-Cl | 3-CN | Me |
| CH$_2$ | 4-Cl | 3-CN | Et |
| O | 4-Cl | 3-CN | Et |
| bond | 4-Cl | 3-CN | Et |
| CH$_2$ | 4-Cl | 4-CN | Me |
| O | 4-Cl | 4-CN | Me |
| bond | 4-Cl | 4-CN | Me |
| CH$_2$ | 4-Cl | 4-CN | Et |
| O | 4-Cl | 4-CN | Et |
| bond | 4-Cl | 4-CN | Et |
| CH$_2$ | 4-Cl | 4-SO$_2$CH$_3$ | Me |
| O | 4-Cl | 4-SO$_2$CH$_3$ | Me |
| bond | 4-Cl | 4-SO$_2$CH$_3$ | Me |
| CH$_2$ | 4-Cl | 4-SO$_2$CH$_3$ | Et |
| O | 4-Cl | 4-SO$_2$CH$_3$ | Et |
| bond | 4-Cl | 4-SO$_2$CH$_3$ | Et |
| CH$_2$ | 4-F | 2-F | Me |
| O | 4-F | 2-F | Me |
| bond | 4-F | 2-F | Me |
| CH$_2$ | 4-F | 2-F | Et |
| O | 4-F | 2-F | Et |
| bond | 4-F | 2-F | Et |
| CH$_2$ | 4-F | 3-F | Me |
| O | 4-F | 3-F | Me |
| bond | 4-F | 3-F | Me |
| CH$_2$ | 4-F | 3-F | Et |
| O | 4-F | 3-F | Et |
| bond | 4-F | 3-F | Et |
| CH$_2$ | 4-F | 4-F | Me |
| O | 4-F | 4-F | Me |
| bond | 4-F | 4-F | Me |
| CH$_2$ | 4-F | 4-F | Et |
| O | 4-F | 4-F | Et |
| bond | 4-F | 4-F | Et |
| CH$_2$ | 4-F | 2,3-F$_2$ | Me |
| O | 4-F | 2,3-F$_2$ | Me |
| bond | 4-F | 2,3-F$_2$ | Me |
| CH$_2$ | 4-F | 2,3-F$_2$ | Et |
| O | 4-F | 2,3-F$_2$ | Et |
| bond | 4-F | 2,3-F$_2$ | Et |
| CH$_2$ | 4-F | 2,4-F$_2$ | Me |
| O | 4-F | 2,4-F$_2$ | Me |
| bond | 4-F | 2,4-F$_2$ | Me |
| CH$_2$ | 4-F | 2,4-F$_2$ | Et |
| O | 4-F | 2,4-F$_2$ | Et |
| bond | 4-F | 2,4-F$_2$ | Et |
| CH$_2$ | 4-F | 2,5-F$_2$ | Me |

TABLE XVIII-continued

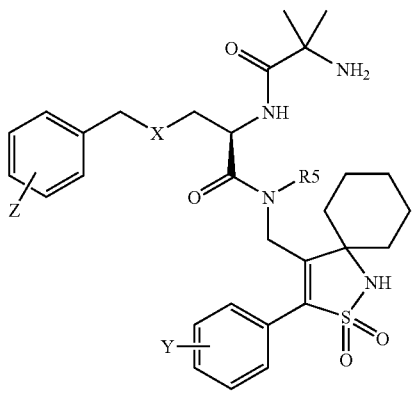

| X | Y | Z | R5 |
|---|---|---|---|
| O | 4-F | 2,5-F$_2$ | Me |
| bond | 4-F | 2,5-F$_2$ | Me |
| CH$_2$ | 4-F | 2,5-F$_2$ | Et |
| O | 4-F | 2,5-F$_2$ | Et |
| bond | 4-F | 2,5-F$_2$ | Et |
| CH$_2$ | 4-F | 2,6-F$_2$ | Me |
| O | 4-F | 2,6-F$_2$ | Me |
| bond | 4-F | 2,6-F$_2$ | Me |
| CH$_2$ | 4-F | 2,6-F$_2$ | Et |
| O | 4-F | 2,6-F$_2$ | Et |
| bond | 4-F | 2,6-F$_2$ | Et |
| CH$_2$ | 4-F | 3,4-F$_2$ | Me |
| O | 4-F | 3,4-F$_2$ | Me |
| bond | 4-F | 3,4-F$_2$ | Me |
| CH$_2$ | 4-F | 3,4-F$_2$ | Et |
| O | 4-F | 3,4-F$_2$ | Et |
| bond | 4-F | 3,4-F$_2$ | Et |
| CH$_2$ | 4-F | 3,5-F$_2$ | Me |
| O | 4-F | 3,5-F$_2$ | Me |
| bond | 4-F | 3,5-F$_2$ | Me |
| CH$_2$ | 4-F | 3,5-F$_2$ | Et |
| O | 4-F | 3,5-F$_2$ | Et |
| bond | 4-F | 3,5-F$_2$ | Et |
| CH$_2$ | 4-F | 2,4,6-F$_3$ | Me |
| O | 4-F | 2,4,6-F$_3$ | Me |
| bond | 4-F | 2,4,6-F$_3$ | Me |
| CH$_2$ | 4-F | 2,4,6-F$_3$ | Et |
| O | 4-F | 2,4,6-F$_3$ | Et |
| bond | 4-F | 2,4,6-F$_3$ | Et |
| CH$_2$ | 4-F | 2,4,5-F$_3$ | Me |
| O | 4-F | 2,4,5-F$_3$ | Me |
| bond | 4-F | 2,4,5-F$_3$ | Me |
| CH$_2$ | 4-F | 2,4,5-F$_3$ | Et |
| O | 4-F | 2,4,5-F$_3$ | Et |
| bond | 4-F | 2,4,5-F$_3$ | Et |
| CH$_2$ | 4-F | 2,3,6-F$_3$ | Me |
| O | 4-F | 2,3,6-F$_3$ | Me |
| bond | 4-F | 2,3,6-F$_3$ | Me |
| CH$_2$ | 4-F | 2,3,6-F$_3$ | Et |
| O | 4-F | 2,3,6-F$_3$ | Et |
| bond | 4-F | 2,3,6-F$_3$ | Et |
| CH$_2$ | 4-F | 2,3,5-F$_3$ | Me |
| O | 4-F | 2,3,5-F$_3$ | Me |
| bond | 4-F | 2,3,5-F$_3$ | Me |
| CH$_2$ | 4-F | 2,3,5-F$_3$ | Et |
| O | 4-F | 2,3,5-F$_3$ | Et |
| bond | 4-F | 2,3,5-F$_3$ | Et |
| CH$_2$ | 4-F | 2-Cl | Me |
| O | 4-F | 2-Cl | Me |
| bond | 4-F | 2-Cl | Me |
| CH$_2$ | 4-F | 2-Cl | Et |
| O | 4-F | 2-Cl | Et |
| bond | 4-F | 2-Cl | Et |
| CH$_2$ | 4-F | 3-Cl | Me |
| O | 4-F | 3-Cl | Me |
| bond | 4-F | 3-Cl | Me |
| CH$_2$ | 4-F | 3-Cl | Et |

TABLE XVIII-continued

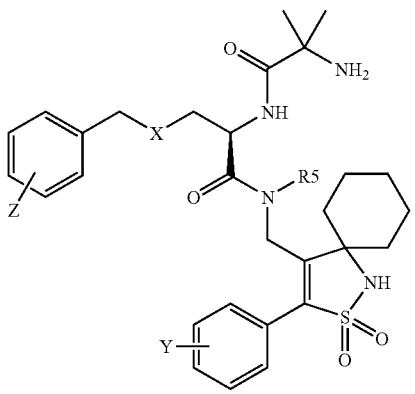

| X | Y | Z | R5 |
|---|---|---|---|
| O | 4-F | 3-Cl | Et |
| bond | 4-F | 3-Cl | Et |
| CH$_2$ | 4-F | 4-Cl | Me |
| O | 4-F | 4-Cl | Me |
| bond | 4-F | 4-Cl | Me |
| CH$_2$ | 4-F | 4-Cl | Et |
| O | 4-F | 4-Cl | Et |
| bond | 4-F | 4-Cl | Et |
| CH$_2$ | 4-F | 2,6-Cl$_2$ | Me |
| O | 4-F | 2,6-Cl$_2$ | Me |
| bond | 4-F | 2,6-Cl$_2$ | Me |
| CH$_2$ | 4-F | 2,6-Cl$_2$ | Et |
| O | 4-F | 2,6-Cl$_2$ | Et |
| bond | 4-F | 2,6-Cl$_2$ | Et |
| CH$_2$ | 4-F | 2-F-6-Cl | Me |
| O | 4-F | 2-F-6-Cl | Me |
| bond | 4-F | 2-F-6-Cl | Me |
| CH$_2$ | 4-F | 2-F-6-Cl | Et |
| O | 4-F | 2-F-6-Cl | Et |
| bond | 4-F | 2-F-6-Cl | Et |
| CH$_2$ | 4-F | 2-F-3-Cl | Me |
| O | 4-F | 2-F-3-Cl | Me |
| bond | 4-F | 2-F-3-Cl | Me |
| CH$_2$ | 4-F | 2-F-3-Cl | Et |
| O | 4-F | 2-F-3-Cl | Et |
| bond | 4-F | 2-F-3-Cl | Et |
| CH$_2$ | 4-F | 2-F-4-Cl | Me |
| O | 4-F | 2-F-4-Cl | Me |
| bond | 4-F | 2-F-4-Cl | Me |
| CH$_2$ | 4-F | 2-F-4-Cl | Et |
| O | 4-F | 2-F-4-Cl | Et |
| bond | 4-F | 2-F-4-Cl | Et |
| CH$_2$ | 4-F | 3-F-4-Cl | Me |
| O | 4-F | 3-F-4-Cl | Me |
| bond | 4-F | 3-F-4-Cl | Me |
| CH$_2$ | 4-F | 3-F-4-Cl | Et |
| O | 4-F | 3-F-4-Cl | Et |
| bond | 4-F | 3-F-4-Cl | Et |
| CH$_2$ | 4-F | 2,6-F$_2$-3-Cl | Me |
| O | 4-F | 2,6-F$_2$-3-Cl | Me |
| bond | 4-F | 2,6-F$_2$-3-Cl | Me |
| CH$_2$ | 4-F | 2,6-F$_2$-3-Cl | Et |
| O | 4-F | 2,6-F$_2$-3-Cl | Et |
| bond | 4-F | 2,6-F$_2$-3-Cl | Et |
| CH$_2$ | 4-F | 2-Cl-3,6-F$_2$ | Me |
| O | 4-F | 2-Cl-3,6-F$_2$ | Me |
| bond | 4-F | 2-Cl-3,6-F$_2$ | Me |
| CH$_2$ | 4-F | 2-Cl-3,6-F$_2$ | Et |
| O | 4-F | 2-Cl-3,6-F$_2$ | Et |
| bond | 4-F | 2-Cl-3,6-F$_2$ | Et |
| CH$_2$ | 4-F | 2,3-Cl$_2$ | Me |
| O | 4-F | 2,3-Cl$_2$ | Me |
| bond | 4-F | 2,3-Cl$_2$ | Me |
| CH$_2$ | 4-F | 2,3-Cl$_2$ | Et |
| O | 4-F | 2,3-Cl$_2$ | Et |
| bond | 4-F | 2,3-Cl$_2$ | Et |
| CH$_2$ | 4-F | 4-F-2-Cl | Me |

TABLE XVIII-continued

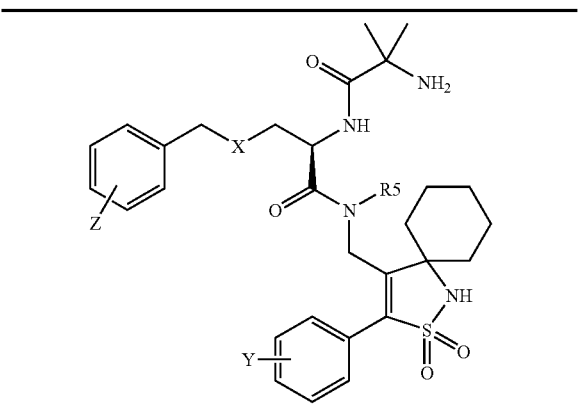

| X | Y | Z | R5 |
|---|---|---|---|
| O | 4-F | 4-F-2-Cl | Me |
| bond | 4-F | 4-F-2-Cl | Me |
| $CH_2$ | 4-F | 4-F-2-Cl | Et |
| O | 4-F | 4-F-2-Cl | Et |
| bond | 4-F | 4-F-2-Cl | Et |
| $CH_2$ | 4-F | 4-$CF_3$ | Me |
| O | 4-F | 4-$CF_3$ | Me |
| bond | 4-F | 4-$CF_3$ | Me |
| $CH_2$ | 4-F | 4-$CF_3$ | Et |
| O | 4-F | 4-$CF_3$ | Et |
| bond | 4-F | 4-$CF_3$ | Et |
| $CH_2$ | 4-F | 3-$CF_3$ | Me |
| O | 4-F | 3-$CF_3$ | Me |
| bond | 4-F | 3-$CF_3$ | Me |
| $CH_2$ | 4-F | 3-$CF_3$ | Et |
| O | 4-F | 3-$CF_3$ | Et |
| bond | 4-F | 3-$CF_3$ | Et |
| $CH_2$ | 4-F | 2-$CF_3$ | Me |
| O | 4-F | 2-$CF_3$ | Me |
| bond | 4-F | 2-$CF_3$ | Me |
| $CH_2$ | 4-F | 2-$CF_3$ | Et |
| O | 4-F | 2-$CF_3$ | Et |
| bond | 4-F | 2-$CF_3$ | Et |
| $CH_2$ | 4-F | 2-F-5-$CF_3$ | Me |
| O | 4-F | 2-F-5-$CF_3$ | Me |
| bond | 4-F | 2-F-5-$CF_3$ | Me |
| $CH_2$ | 4-F | 2-F-5-$CF_3$ | Et |
| O | 4-F | 2-F-5-$CF_3$ | Et |
| bond | 4-F | 2-F-5-$CF_3$ | Et |
| $CH_2$ | 4-F | 4-$OCF_3$ | Me |
| O | 4-F | 4-$OCF_3$ | Me |
| bond | 4-F | 4-$OCF_3$ | Me |
| $CH_2$ | 4-F | 4-$OCF_3$ | Et |
| O | 4-F | 4-$OCF_3$ | Et |
| bond | 4-F | 4-$OCF_3$ | Et |
| $CH_2$ | 4-F | 3-$OCF_3$ | Me |
| O | 4-F | 3-$OCF_3$ | Me |
| bond | 4-F | 3-$OCF_3$ | Me |
| $CH_2$ | 4-F | 3-$OCF_3$ | Et |
| O | 4-F | 3-$OCF_3$ | Et |
| bond | 4-F | 3-$OCF_3$ | Et |
| $CH_2$ | 4-F | 2-$OCF_3$ | Me |
| O | 4-F | 2-$OCF_3$ | Me |
| bond | 4-F | 2-$OCF_3$ | Me |
| $CH_2$ | 4-F | 2-$OCF_3$ | Et |
| O | 4-F | 2-$OCF_3$ | Et |
| bond | 4-F | 2-$OCF_3$ | Et |
| $CH_2$ | 4-F | 2-CN | Me |
| O | 4-F | 2-CN | Me |
| bond | 4-F | 2-CN | Me |
| $CH_2$ | 4-F | 2-CN | Et |
| O | 4-F | 2-CN | Et |
| bond | 4-F | 2-CN | Et |
| $CH_2$ | 4-F | 3-CN | Me |
| O | 4-F | 3-CN | Me |
| bond | 4-F | 3-CN | Me |
| $CH_2$ | 4-F | 3-CN | Et |

TABLE XVIII-continued

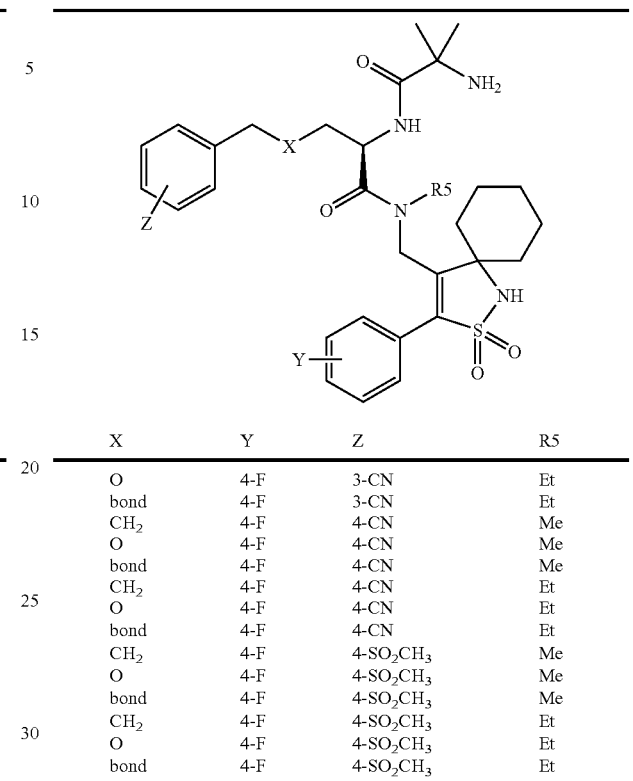

| X | Y | Z | R5 |
|---|---|---|---|
| O | 4-F | 3-CN | Et |
| bond | 4-F | 3-CN | Et |
| $CH_2$ | 4-F | 4-CN | Me |
| O | 4-F | 4-CN | Me |
| bond | 4-F | 4-CN | Me |
| $CH_2$ | 4-F | 4-CN | Et |
| O | 4-F | 4-CN | Et |
| bond | 4-F | 4-CN | Et |
| $CH_2$ | 4-F | 4-$SO_2CH_3$ | Me |
| O | 4-F | 4-$SO_2CH_3$ | Me |
| bond | 4-F | 4-$SO_2CH_3$ | Me |
| $CH_2$ | 4-F | 4-$SO_2CH_3$ | Et |
| O | 4-F | 4-$SO_2CH_3$ | Et |
| bond | 4-F | 4-$SO_2CH_3$ | Et |

TABLE XIX

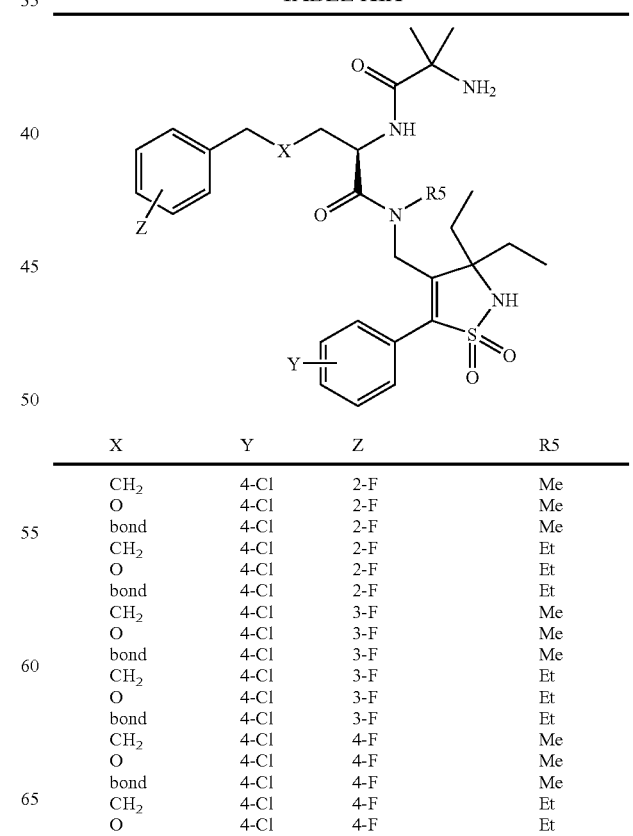

| X | Y | Z | R5 |
|---|---|---|---|
| $CH_2$ | 4-Cl | 2-F | Me |
| O | 4-Cl | 2-F | Me |
| bond | 4-Cl | 2-F | Me |
| $CH_2$ | 4-Cl | 2-F | Et |
| O | 4-Cl | 2-F | Et |
| bond | 4-Cl | 2-F | Et |
| $CH_2$ | 4-Cl | 3-F | Me |
| O | 4-Cl | 3-F | Me |
| bond | 4-Cl | 3-F | Me |
| $CH_2$ | 4-Cl | 3-F | Et |
| O | 4-Cl | 3-F | Et |
| bond | 4-Cl | 3-F | Et |
| $CH_2$ | 4-Cl | 4-F | Me |
| O | 4-Cl | 4-F | Me |
| bond | 4-Cl | 4-F | Me |
| $CH_2$ | 4-Cl | 4-F | Et |
| O | 4-Cl | 4-F | Et |

TABLE XIX-continued

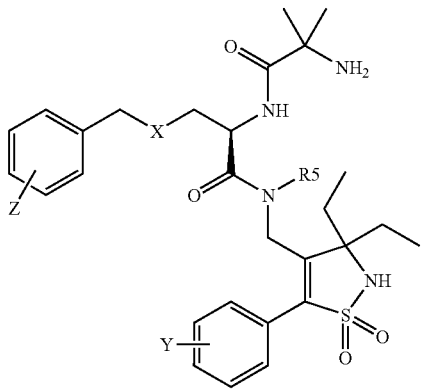

| X | Y | Z | R5 |
|---|---|---|---|
| bond | 4-Cl | 4-F | Et |
| CH₂ | 4-Cl | 2,3-F₂ | Me |
| O | 4-Cl | 2,3-F₂ | Me |
| bond | 4-Cl | 2,3-F₂ | Me |
| CH₂ | 4-Cl | 2,3-F₂ | Et |
| O | 4-Cl | 2,3-F₂ | Et |
| bond | 4-Cl | 2,3-F₂ | Et |
| CH₂ | 4-Cl | 2,4-F₂ | Me |
| O | 4-Cl | 2,4-F₂ | Me |
| bond | 4-Cl | 2,4-F₂ | Me |
| CH₂ | 4-Cl | 2,4-F₂ | Et |
| O | 4-Cl | 2,4-F₂ | Et |
| bond | 4-Cl | 2,4-F₂ | Et |
| CH₂ | 4-Cl | 2,5-F₂ | Me |
| O | 4-Cl | 2,5-F₂ | Me |
| bond | 4-Cl | 2,5-F₂ | Me |
| CH₂ | 4-Cl | 2,5-F₂ | Et |
| O | 4-Cl | 2,5-F₂ | Et |
| bond | 4-Cl | 2,5-F₂ | Et |
| CH₂ | 4-Cl | 2,6-F₂ | Me |
| O | 4-Cl | 2,6-F₂ | Me |
| bond | 4-Cl | 2,6-F₂ | Me |
| CH₂ | 4-Cl | 2,6-F₂ | Et |
| O | 4-Cl | 2,6-F₂ | Et |
| bond | 4-Cl | 2,6-F₂ | Et |
| CH₂ | 4-Cl | 3,4-F₂ | Me |
| O | 4-Cl | 3,4-F₂ | Me |
| bond | 4-Cl | 3,4-F₂ | Me |
| CH₂ | 4-Cl | 3,4-F₂ | Et |
| O | 4-Cl | 3,4-F₂ | Et |
| bond | 4-Cl | 3,4-F₂ | Et |
| CH₂ | 4-Cl | 3,5-F₂ | Me |
| O | 4-Cl | 3,5-F₂ | Me |
| bond | 4-Cl | 3,5-F₂ | Me |
| CH₂ | 4-Cl | 3,5-F₂ | Et |
| O | 4-Cl | 3,5-F₂ | Et |
| bond | 4-Cl | 3,5-F₂ | Et |
| CH₂ | 4-Cl | 2,4,6-F₃ | Me |
| O | 4-Cl | 2,4,6-F₃ | Me |
| bond | 4-Cl | 2,4,6-F₃ | Me |
| CH₂ | 4-Cl | 2,4,6-F₃ | Et |
| O | 4-Cl | 2,4,6-F₃ | Et |
| bond | 4-Cl | 2,4,6-F₃ | Et |
| CH₂ | 4-Cl | 2,4,5-F₃ | Me |
| O | 4-Cl | 2,4,5-F₃ | Me |
| bond | 4-Cl | 2,4,5-F₃ | Me |
| CH₂ | 4-Cl | 2,4,5-F₃ | Et |
| O | 4-Cl | 2,4,5-F₃ | Et |
| bond | 4-Cl | 2,4,5-F₃ | Et |
| CH₂ | 4-Cl | 2,3,6-F₃ | Me |
| O | 4-Cl | 2,3,6-F₃ | Me |
| bond | 4-Cl | 2,3,6-F₃ | Me |
| CH₂ | 4-Cl | 2,3,6-F₃ | Et |
| O | 4-Cl | 2,3,6-F₃ | Et |
| bond | 4-Cl | 2,3,6-F₃ | Et |
| CH₂ | 4-Cl | 2,3,5-F₃ | Me |
| O | 4-Cl | 2,3,5-F₃ | Me |

TABLE XIX-continued

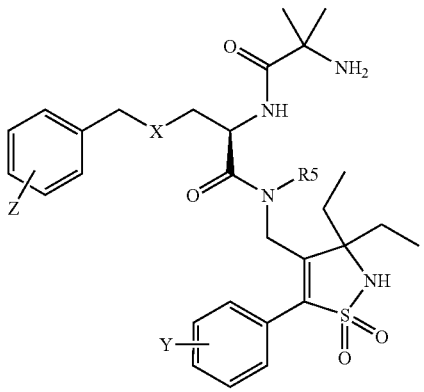

| X | Y | Z | R5 |
|---|---|---|---|
| bond | 4-Cl | 2,3,5-F₃ | Me |
| CH₂ | 4-Cl | 2,3,5-F₃ | Et |
| O | 4-Cl | 2,3,5-F₃ | Et |
| bond | 4-Cl | 2,3,5-F₃ | Et |
| CH₂ | 4-Cl | 2-Cl | Me |
| O | 4-Cl | 2-Cl | Me |
| bond | 4-Cl | 2-Cl | Me |
| CH₂ | 4-Cl | 2-Cl | Et |
| O | 4-Cl | 2-Cl | Et |
| bond | 4-Cl | 2-Cl | Et |
| CH₂ | 4-Cl | 3-Cl | Me |
| O | 4-Cl | 3-Cl | Me |
| bond | 4-Cl | 3-Cl | Me |
| CH₂ | 4-Cl | 3-Cl | Et |
| O | 4-Cl | 3-Cl | Et |
| bond | 4-Cl | 3-Cl | Et |
| CH₂ | 4-Cl | 4-Cl | Me |
| O | 4-Cl | 4-Cl | Me |
| bond | 4-Cl | 4-Cl | Me |
| CH₂ | 4-Cl | 4-Cl | Et |
| O | 4-Cl | 4-Cl | Et |
| bond | 4-Cl | 4-Cl | Et |
| CH₂ | 4-Cl | 2,6-Cl₂ | Me |
| O | 4-Cl | 2,6-Cl₂ | Me |
| bond | 4-Cl | 2,6-Cl₂ | Me |
| CH₂ | 4-Cl | 2,6-Cl₂ | Et |
| O | 4-Cl | 2,6-Cl₂ | Et |
| bond | 4-Cl | 2,6-Cl₂ | Et |
| CH₂ | 4-Cl | 2-F-6-Cl | Me |
| O | 4-Cl | 2-F-6-Cl | Me |
| bond | 4-Cl | 2-F-6-Cl | Me |
| CH₂ | 4-Cl | 2-F-6-Cl | Et |
| O | 4-Cl | 2-F-6-Cl | Et |
| bond | 4-Cl | 2-F-6-Cl | Et |
| CH₂ | 4-Cl | 2-F-3-Cl | Me |
| O | 4-Cl | 2-F-3-Cl | Me |
| bond | 4-Cl | 2-F-3-Cl | Me |
| CH₂ | 4-Cl | 2,F-3-Cl | Et |
| O | 4-Cl | 2-F-3-Cl | Et |
| bond | 4-Cl | 2-F-3-Cl | Et |
| CH₂ | 4-Cl | 2-F-4-Cl | Me |
| O | 4-Cl | 2-F-4-Cl | Me |
| bond | 4-Cl | 2-F-4-Cl | Me |
| CH₂ | 4-Cl | 2-F-4-Cl | Et |
| O | 4-Cl | 2-F-4-Cl | Et |
| bond | 4-Cl | 2-F-4-Cl | Et |
| CH₂ | 4-Cl | 3-F-4-Cl | Me |
| O | 4-Cl | 3-F-4-Cl | Me |
| bond | 4-Cl | 3-F-4-Cl | Me |
| CH₂ | 4-Cl | 3-F-4-Cl | Et |
| O | 4-Cl | 3-F-4-Cl | Et |
| bond | 4-Cl | 3-F-4-Cl | Et |
| CH₂ | 4-Cl | 2,6-F₂-3-Cl | Me |
| O | 4-Cl | 2,6-F₂-3-Cl | Me |
| bond | 4-Cl | 2,6-F₂-3-Cl | Me |
| CH₂ | 4-Cl | 2,6-F₂-3-Cl | Et |
| O | 4-Cl | 2,6-F₂-3-Cl | Et |

TABLE XIX-continued

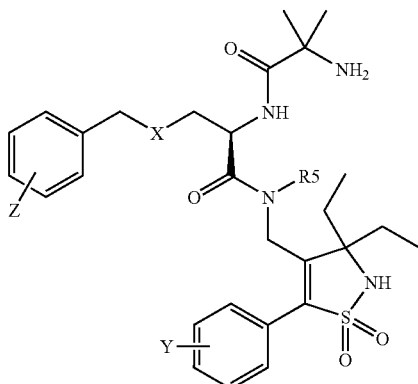

| X | Y | Z | R5 |
|---|---|---|---|
| bond | 4-Cl | 2,6-F$_2$-3-Cl | Et |
| CH$_2$ | 4-Cl | 2-Cl-3,6-F$_2$ | Me |
| O | 4-Cl | 2-Cl-3,6-F$_2$ | Me |
| bond | 4-Cl | 2-Cl-3,6-F$_2$ | Me |
| CH$_2$ | 4-Cl | 2-Cl-3,6-F$_2$ | Et |
| O | 4-Cl | 2-Cl-3,6-F$_2$ | Et |
| bond | 4-Cl | 2-Cl-3,6-F$_2$ | Et |
| CH$_2$ | 4-Cl | 2,3-Cl$_2$ | Me |
| O | 4-Cl | 2,3-Cl$_2$ | Me |
| bond | 4-Cl | 2,3-Cl$_2$ | Me |
| CH$_2$ | 4-Cl | 2,3-Cl$_2$ | Et |
| O | 4-Cl | 2,3-Cl$_2$ | Et |
| bond | 4-Cl | 2,3-Cl$_2$ | Et |
| CH$_2$ | 4-Cl | 4-F-2-Cl | Me |
| O | 4-Cl | 4-F-2-Cl | Me |
| bond | 4-Cl | 4-F-2-Cl | Me |
| CH$_2$ | 4-Cl | 4-F-2-Cl | Et |
| O | 4-Cl | 4-F-2-Cl | Et |
| bond | 4-Cl | 4-F-2-Cl | Et |
| CH$_2$ | 4-Cl | 4-CF$_3$ | Me |
| O | 4-Cl | 4-CF$_3$ | Me |
| bond | 4-Cl | 4-CF$_3$ | Me |
| CH$_2$ | 4-Cl | 4-CF$_3$ | Et |
| O | 4-Cl | 4-CF$_3$ | Et |
| bond | 4-Cl | 4-CF$_3$ | Et |
| CH$_2$ | 4-Cl | 3-CF$_3$ | Me |
| O | 4-Cl | 3-CF$_3$ | Me |
| bond | 4-Cl | 3-CF$_3$ | Me |
| CH$_2$ | 4-Cl | 3-CF$_3$ | Et |
| O | 4-Cl | 3-CF$_3$ | Et |
| bond | 4-Cl | 3-CF$_3$ | Et |
| CH$_2$ | 4-Cl | 2-CF$_3$ | Me |
| O | 4-Cl | 2-CF$_3$ | Me |
| bond | 4-Cl | 2-CF$_3$ | Me |
| CH$_2$ | 4-Cl | 2-CF$_3$ | Et |
| O | 4-Cl | 2-CF$_3$ | Et |
| bond | 4-Cl | 2-CF$_3$ | Et |
| CH$_2$ | 4-Cl | 2-F-5-CF$_3$ | Me |
| O | 4-Cl | 2-F-5-CF$_3$ | Me |
| bond | 4-Cl | 2-F-5-CF$_3$ | Me |
| CH$_2$ | 4-Cl | 2-F-5-CF$_3$ | Et |
| O | 4-Cl | 2-F-5-CF$_3$ | Et |
| bond | 4-Cl | 2-F-5-CF$_3$ | Et |
| CH$_2$ | 4-Cl | 4-OCF$_3$ | Me |
| O | 4-Cl | 4-OCF$_3$ | Me |
| bond | 4-Cl | 4-OCF$_3$ | Me |
| CH$_2$ | 4-Cl | 4-OCF$_3$ | Et |
| O | 4-Cl | 4-OCF$_3$ | Et |
| bond | 4-Cl | 4-OCF$_3$ | Et |
| CH$_2$ | 4-Cl | 3-OCF$_3$ | Me |
| O | 4-Cl | 3-OCF$_3$ | Me |
| bond | 4-Cl | 3-OCF$_3$ | Me |
| CH$_2$ | 4-Cl | 3-OCF$_3$ | Et |
| O | 4-Cl | 3-OCF$_3$ | Et |
| bond | 4-Cl | 3-OCF$_3$ | Et |
| CH$_2$ | 4-Cl | 2-OCF$_3$ | Me |
| O | 4-Cl | 2-OCF$_3$ | Me |

TABLE XIX-continued

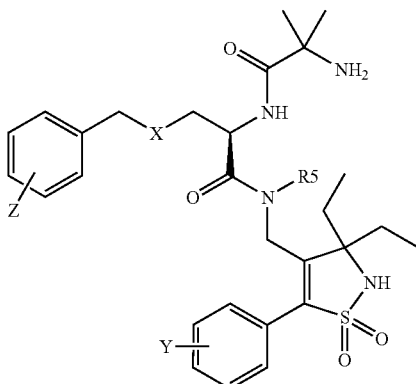

| X | Y | Z | R5 |
|---|---|---|---|
| bond | 4-Cl | 2-OCF$_3$ | Me |
| CH$_2$ | 4-Cl | 2-OCF$_3$ | Et |
| O | 4-Cl | 2-OCF$_3$ | Et |
| bond | 4-Cl | 2-OCF$_3$ | Et |
| CH$_2$ | 4-Cl | 2-CN | Me |
| O | 4-Cl | 2-CN | Me |
| bond | 4-Cl | 2-CN | Me |
| CH$_2$ | 4-Cl | 2-CN | Et |
| O | 4-Cl | 2-CN | Et |
| bond | 4-Cl | 2-CN | Et |
| CH$_2$ | 4-Cl | 3-CN | Me |
| O | 4-Cl | 3-CN | Me |
| bond | 4-Cl | 3-CN | Me |
| CH$_2$ | 4-Cl | 3-CN | Et |
| O | 4-Cl | 3-CN | Et |
| bond | 4-Cl | 3-CN | Et |
| CH$_2$ | 4-Cl | 4-CN | Me |
| O | 4-Cl | 4-CN | Me |
| bond | 4-Cl | 4-CN | Me |
| CH$_2$ | 4-Cl | 4-CN | Et |
| O | 4-Cl | 4-CN | Et |
| bond | 4-Cl | 4-CN | Et |
| CH$_2$ | 4-Cl | 4-SO$_2$CH$_3$ | Me |
| O | 4-Cl | 4-SO$_2$CH$_3$ | Me |
| bond | 4-Cl | 4-SO$_2$CH$_3$ | Me |
| CH$_2$ | 4-Cl | 4-SO$_2$CH$_3$ | Et |
| O | 4-Cl | 4-SO$_2$CH$_3$ | Et |
| bond | 4-Cl | 4-SO$_2$CH$_3$ | Et |
| CH$_2$ | 4-F | 2-F | Me |
| O | 4-F | 2-F | Me |
| bond | 4-F | 2-F | Me |
| CH$_2$ | 4-F | 2-F | Et |
| O | 4-F | 2-F | Et |
| bond | 4-F | 2-F | Et |
| CH$_2$ | 4-F | 3-F | Me |
| O | 4-F | 3-F | Me |
| bond | 4-F | 3-F | Me |
| CH$_2$ | 4-F | 3-F | Et |
| O | 4-F | 3-F | Et |
| bond | 4-F | 3-F | Et |
| CH$_2$ | 4-F | 4-F | Me |
| O | 4-F | 4-F | Me |
| bond | 4-F | 4-F | Me |
| CH$_2$ | 4-F | 4-F | Et |
| O | 4-F | 4-F | Et |
| bond | 4-F | 4-F | Et |
| CH$_2$ | 4-F | 2,3-F$_2$ | Me |
| O | 4-F | 2,3-F$_2$ | Me |
| bond | 4-F | 2,3-F$_2$ | Me |
| CH$_2$ | 4-F | 2,3-F$_2$ | Et |
| O | 4-F | 2,3-F$_2$ | Et |
| bond | 4-F | 2,3-F$_2$ | Et |
| CH$_2$ | 4-F | 2,4-F$_2$ | Me |
| O | 4-F | 2,4-F$_2$ | Me |
| bond | 4-F | 2,4-F$_2$ | Me |
| CH$_2$ | 4-F | 2,4-F$_2$ | Et |
| O | 4-F | 2,4-F$_2$ | Et |

TABLE XIX-continued

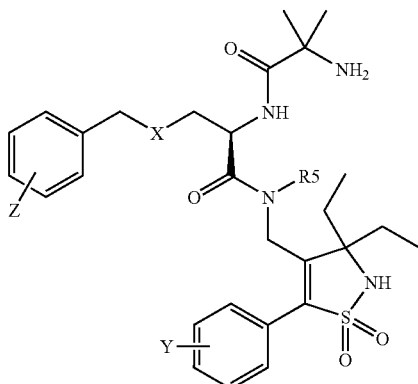

| X | Y | Z | R5 |
|---|---|---|---|
| bond | 4-F | 2,4-$F_2$ | Et |
| $CH_2$ | 4-F | 2,5-$F_2$ | Me |
| O | 4-F | 2,5-$F_2$ | Me |
| bond | 4-F | 2,5-$F_2$ | Me |
| $CH_2$ | 4-F | 2,5-$F_2$ | Et |
| O | 4-F | 2,5-$F_2$ | Et |
| bond | 4-F | 2,5-$F_2$ | Et |
| $CH_2$ | 4-F | 2,6-$F_2$ | Me |
| O | 4-F | 2,6-$F_2$ | Me |
| bond | 4-F | 2,6-$F_2$ | Me |
| $CH_2$ | 4-F | 2,6-$F_2$ | Et |
| O | 4-F | 2,6-$F_2$ | Et |
| bond | 4-F | 2,6-$F_2$ | Et |
| $CH_2$ | 4-F | 3,4-$F_2$ | Me |
| O | 4-F | 3,4-$F_2$ | Me |
| bond | 4-F | 3,4-$F_2$ | Me |
| $CH_2$ | 4-F | 3,4-$F_2$ | Et |
| O | 4-F | 3,4-$F_2$ | Et |
| bond | 4-F | 3,4-$F_2$ | Et |
| $CH_2$ | 4-F | 3,5-$F_2$ | Me |
| O | 4-F | 3,5-$F_2$ | Me |
| bond | 4-F | 3,5-$F_2$ | Me |
| $CH_2$ | 4-F | 3,5-$F_2$ | Et |
| O | 4-F | 3,5-$F_2$ | Et |
| bond | 4-F | 3,5-$F_2$ | Et |
| $CH_2$ | 4-F | 2,4,6-$F_3$ | Me |
| O | 4-F | 2,4,6-$F_3$ | Me |
| bond | 4-F | 2,4,6-$F_3$ | Me |
| $CH_2$ | 4-F | 2,4,6-$F_3$ | Et |
| O | 4-F | 2,4,6-$F_3$ | Et |
| bond | 4-F | 2,4,6-$F_3$ | Et |
| $CH_2$ | 4-F | 2,4,5-$F_3$ | Me |
| O | 4-F | 2,4,5-$F_3$ | Me |
| bond | 4-F | 2,4,5-$F_3$ | Me |
| $CH_2$ | 4-F | 2,4,5-$F_3$ | Et |
| O | 4-F | 2,4,5-$F_3$ | Et |
| bond | 4-F | 2,4,5-$F_3$ | Et |
| $CH_2$ | 4-F | 2,3,6-$F_3$ | Me |
| O | 4-F | 2,3,6-$F_3$ | Me |
| bond | 4-F | 2,3,6-$F_3$ | Me |
| $CH_2$ | 4-F | 2,3,6-$F_3$ | Et |
| O | 4-F | 2,3,6-$F_3$ | Et |
| bond | 4-F | 2,3,6-$F_3$ | Et |
| $CH_2$ | 4-F | 2,3,5-$F_3$ | Me |
| O | 4-F | 2,3,5-$F_3$ | Me |
| bond | 4-F | 2,3,5-$F_3$ | Me |
| $CH_2$ | 4-F | 2,3,5-$F_3$ | Et |
| O | 4-F | 2,3,5-$F_3$ | Et |
| bond | 4-F | 2,3,5-$F_3$ | Et |
| $CH_2$ | 4-F | 2-Cl | Me |
| O | 4-F | 2-Cl | Me |
| bond | 4-F | 2-Cl | Me |
| $CH_2$ | 4-F | 2-Cl | Et |
| O | 4-F | 2-Cl | Et |
| bond | 4-F | 2-Cl | Et |
| $CH_2$ | 4-F | 3-Cl | Me |
| O | 4-F | 3-Cl | Me |

TABLE XIX-continued

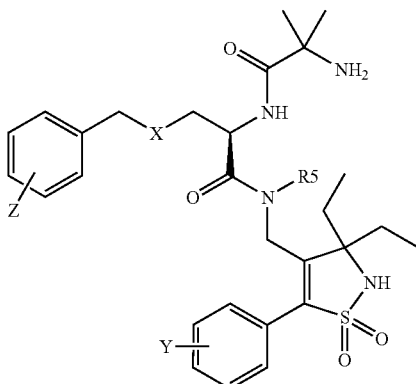

| X | Y | Z | R5 |
|---|---|---|---|
| bond | 4-F | 3-Cl | Me |
| $CH_2$ | 4-F | 3-Cl | Et |
| O | 4-F | 3-Cl | Et |
| bond | 4-F | 3-Cl | Et |
| $CH_2$ | 4-F | 4-Cl | Me |
| O | 4-F | 4-Cl | Me |
| bond | 4-F | 4-Cl | Me |
| $CH_2$ | 4-F | 4-Cl | Et |
| O | 4-F | 4-Cl | Et |
| bond | 4-F | 4-Cl | Et |
| $CH_2$ | 4-F | 2,6-$Cl_2$ | Me |
| O | 4-F | 2,6-$Cl_2$ | Me |
| bond | 4-F | 2,6-$Cl_2$ | Me |
| $CH_2$ | 4-F | 2,6-$Cl_2$ | Et |
| O | 4-F | 2,6-$Cl_2$ | Et |
| bond | 4-F | 2,6-$Cl_2$ | Et |
| $CH_2$ | 4-F | 2-F-6-Cl | Me |
| O | 4-F | 2-F-6-Cl | Me |
| bond | 4-F | 2-F-6-Cl | Me |
| $CH_2$ | 4-F | 2-F-6-Cl | Et |
| O | 4-F | 2-F-6-Cl | Et |
| bond | 4-F | 2-F-6-Cl | Et |
| $CH_2$ | 4-F | 2-F-3-Cl | Me |
| O | 4-F | 2-F-3-Cl | Me |
| bond | 4-F | 2-F-3-Cl | Me |
| $CH_2$ | 4-F | 2-F-3-Cl | Et |
| O | 4-F | 2-F-3-Cl | Et |
| bond | 4-F | 2-F-3-Cl | Et |
| $CH_2$ | 4-F | 2-F-4-Cl | Me |
| O | 4-F | 2-F-4-Cl | Me |
| bond | 4-F | 2-F-4-Cl | Me |
| $CH_2$ | 4-F | 2-F-4-Cl | Et |
| O | 4-F | 2-F-4-Cl | Et |
| bond | 4-F | 2-F-4-Cl | Et |
| $CH_2$ | 4-F | 3-F-4-Cl | Me |
| O | 4-F | 3-F-4-Cl | Me |
| bond | 4-F | 3-F-4-Cl | Me |
| $CH_2$ | 4-F | 3-F-4-Cl | Et |
| O | 4-F | 3-F-4-Cl | Et |
| bond | 4-F | 3-F-4-Cl | Et |
| $CH_2$ | 4-F | 2,6-$F_2$-3-Cl | Me |
| O | 4-F | 2,6-$F_2$-3-Cl | Me |
| bond | 4-F | 2,6-$F_2$-3-Cl | Me |
| $CH_2$ | 4-F | 2,6-$F_2$-3-Cl | Et |
| O | 4-F | 2,6-$F_2$-3-Cl | Et |
| bond | 4-F | 2,6-$F_2$-3-Cl | Et |
| $CH_2$ | 4-F | 2-Cl-3,6-$F_2$ | Me |
| O | 4-F | 2-Cl-3,6-$F_2$ | Me |
| bond | 4-F | 2-Cl-3,6-$F_2$ | Me |
| $CH_2$ | 4-F | 2-Cl-3,6-$F_2$ | Et |
| O | 4-F | 2-Cl-3,6-$F_2$ | Et |
| bond | 4-F | 2-Cl-3,6-$F_2$ | Et |
| $CH_2$ | 4-F | 2,3-$Cl_2$ | Me |
| O | 4-F | 2,3-$Cl_2$ | Me |
| bond | 4-F | 2,3-$Cl_2$ | Me |
| $CH_2$ | 4-F | 2,3-$Cl_2$ | Et |
| O | 4-F | 2,3-$Cl_2$ | Et |

TABLE XIX-continued

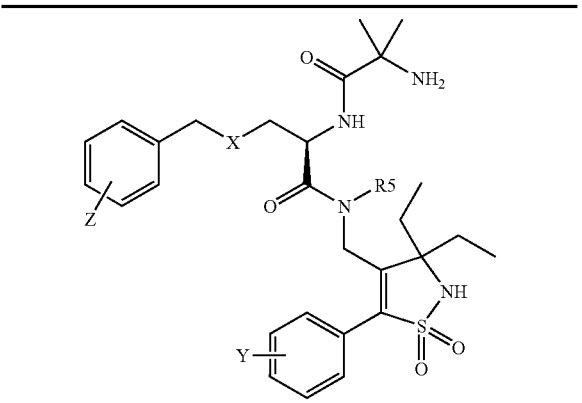

| X | Y | Z | R5 |
|---|---|---|---|
| bond | 4-F | 2,3-Cl$_2$ | Et |
| CH$_2$ | 4-F | 4-F-2-Cl | Me |
| O | 4-F | 4-F-2-Cl | Me |
| bond | 4-F | 4-F-2-Cl | Me |
| CH$_2$ | 4-F | 4-F-2-Cl | Et |
| O | 4-F | 4-F-2-Cl | Et |
| bond | 4-F | 4-F-2-Cl | Et |
| CH$_2$ | 4-F | 4-CF$_3$ | Me |
| O | 4-F | 4-CF$_3$ | Me |
| bond | 4-F | 4-CF$_3$ | Me |
| CH$_2$ | 4-F | 4-CF$_3$ | Et |
| O | 4-F | 4-CF$_3$ | Et |
| bond | 4-F | 4-CF$_3$ | Et |
| CH$_2$ | 4-F | 3-CF$_3$ | Me |
| O | 4-F | 3-CF$_3$ | Me |
| bond | 4-F | 3-CF$_3$ | Me |
| CH$_2$ | 4-F | 3-CF$_3$ | Et |
| O | 4-F | 3-CF$_3$ | Et |
| bond | 4-F | 3-CF$_3$ | Et |
| CH$_2$ | 4-F | 2-CF$_3$ | Me |
| O | 4-F | 2-CF$_3$ | Me |
| bond | 4-F | 2-CF$_3$ | Me |
| CH$_2$ | 4-F | 2-CF$_3$ | Et |
| O | 4-F | 2-CF$_3$ | Et |
| bond | 4-F | 2-CF$_3$ | Et |
| CH$_2$ | 4-F | 2-F-5-CF$_3$ | Me |
| O | 4-F | 2-F-5-CF$_3$ | Me |
| bond | 4-F | 2-F-5-CF$_3$ | Me |
| CH$_2$ | 4-F | 2-F-5-CF$_3$ | Et |
| O | 4-F | 2-F-5-CF$_3$ | Et |
| bond | 4-F | 2-F-5-CF$_3$ | Et |
| CH$_2$ | 4-F | 4-OCF$_3$ | Me |
| O | 4-F | 4-OCF$_3$ | Me |
| bond | 4-F | 4-OCF$_3$ | Me |
| CH$_2$ | 4-F | 4-OCF$_3$ | Et |
| O | 4-F | 4-OCF$_3$ | Et |
| bond | 4-F | 4-OCF$_3$ | Et |
| CH$_2$ | 4-F | 3-OCF$_3$ | Me |
| O | 4-F | 3-OCF$_3$ | Me |
| bond | 4-F | 3-OCF$_3$ | Me |
| CH$_2$ | 4-F | 3-OCF$_3$ | Et |
| O | 4-F | 3-OCF$_3$ | Et |
| bond | 4-F | 3-OCF$_3$ | Et |
| CH$_2$ | 4-F | 2-OCF$_3$ | Me |
| O | 4-F | 2-OCF$_3$ | Me |
| bond | 4-F | 2-OCF$_3$ | Me |
| CH$_2$ | 4-F | 2-OCF$_3$ | Et |
| O | 4-F | 2-OCF$_3$ | Et |
| bond | 4-F | 2-OCF$_3$ | Et |
| CH$_2$ | 4-F | 2-CN | Me |
| O | 4-F | 2-CN | Me |
| bond | 4-F | 2-CN | Me |
| CH$_2$ | 4-F | 2-CN | Et |
| O | 4-F | 2-CN | Et |
| bond | 4-F | 2-CN | Et |
| CH$_2$ | 4-F | 3-CN | Me |
| O | 4-F | 3-CN | Me |

TABLE XIX-continued

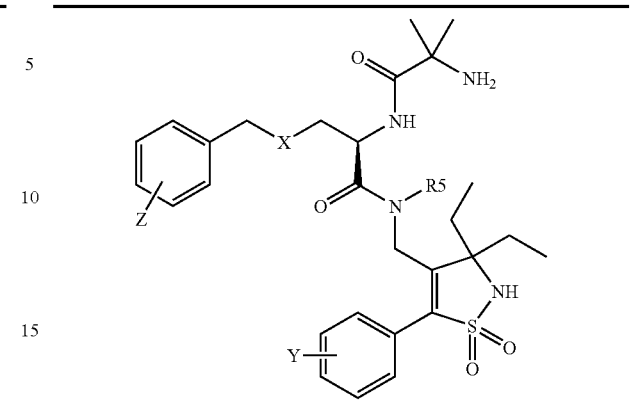

| X | Y | Z | R5 |
|---|---|---|---|
| bond | 4-F | 3-CN | Me |
| CH$_2$ | 4-F | 3-CN | Et |
| O | 4-F | 3-CN | Et |
| bond | 4-F | 3-CN | Et |
| CH$_2$ | 4-F | 4-CN | Me |
| O | 4-F | 4-CN | Me |
| bond | 4-F | 4-CN | Me |
| CH$_2$ | 4-F | 4-CN | Et |
| O | 4-F | 4-CN | Et |
| bond | 4-F | 4-CN | Et |
| CH$_2$ | 4-F | 4-SO$_2$CH$_3$ | Me |
| O | 4-F | 4-SO$_2$CH$_3$ | Me |
| bond | 4-F | 4-SO$_2$CH$_3$ | Me |
| CH$_2$ | 4-F | 4-SO$_2$CH$_3$ | Et |
| O | 4-F | 4-SO$_2$CH$_3$ | Et |
| bond | 4-F | 4-SO$_2$CH$_3$ | Et |

TABLE XX

| X | Y | Z | R5 |
|---|---|---|---|
| O | 4-Cl | 2-F | CH$_2$CH$_3$ |
| O | 4-Cl | 3-F | CH$_2$CH$_3$ |
| O | 4-Cl | 4-F | CH$_2$CH$_3$ |
| O | 4-Cl | 4-Cl | CH$_2$CH$_3$ |
| O | 4-Cl | 2,5-F$_2$ | CH$_2$CH$_3$ |
| O | 4-Cl | 2,4-F$_2$ | CH$_2$CH$_3$ |
| O | 4-Cl | 2-Cl | CH$_2$CH$_3$ |
| O | 4-Cl | 2,6-F$_2$ | CH$_2$CH$_3$ |
| O | 4-Cl | 3,5-F$_2$ | CH$_2$CH$_3$ |
| O | 4-Cl | 2,3-F$_2$ | CH$_2$CH$_3$ |
| O | 4-Cl | 3,4-F$_2$ | CH$_2$CH$_3$ |
| O | 4-Cl | 2,3,5-F$_3$ | CH$_2$CH$_3$ |
| O | 4-Cl | 2,3,6-F$_3$ | CH$_2$CH$_3$ |
| O | 4-Cl | 2,4,5-F$_3$ | CH$_2$CH$_3$ |
| O | 4-Cl | 2,6-Cl$_2$ | CH$_2$CH$_3$ |

TABLE XX-continued

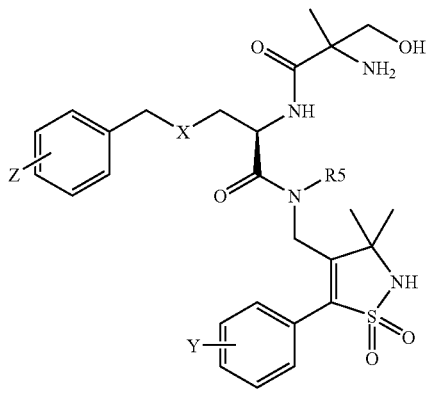

| X | Y | Z | R5 |
|---|---|---|---|
| O | 4-Cl | 2-F-3-Cl | CH₂CH₃ |
| O | 4-Cl | 2-F-6-Cl | CH₂CH₃ |
| O | 4-F | 2-F | CH₂CH₃ |
| O | 4-F | 3-F | CH₂CH₃ |
| O | 4-F | 4-F | CH₂CH₃ |
| O | 4-F | 4-Cl | CH₂CH₃ |
| O | 4-F | 2,5-F₂ | CH₂CH₃ |
| O | 4-F | 2,4-F₂ | CH₂CH₃ |
| O | 4-F | 2-Cl | CH₂CH₃ |
| O | 4-F | 2,6-F₂ | CH₂CH₃ |
| O | 4-F | 3,5-F₂ | CH₂CH₃ |
| O | 4-F | 2,3-F₂ | CH₂CH₃ |
| O | 4-F | 3,4-F₂ | CH₂CH₃ |
| O | 4-F | 2,3,5-F₃ | CH₂CH₃ |
| O | 4-F | 2,3,6-F₃ | CH₂CH₃ |
| O | 4-F | 2,4,5-F₃ | CH₂CH₃ |
| O | 4-F | 2,6-Cl₂ | CH₂CH₃ |
| O | 4-F | 2-F-3-Cl | CH₂CH₃ |
| O | 4-F | 2-F-6-Cl | CH₂CH₃ |
| CH₂ | 4-Cl | 3,5-F₂ | CH₂CH₃ |
| CH₂ | 4-Cl | 4-F | CH₂CH₃ |
| CH₂ | 4-Cl | 2,6-F₂ | CH₂CH₃ |
| CH₂ | 4-F | 3,5-F₂ | CH₂CH₃ |
| CH₂ | 4-F | 4-F | CH₂CH₃ |
| CH₂ | 4-F | 2,6-F₂ | CH₂CH₃ |
| O | 3-Cl | 3,5-F₂ | CH₂CH₃ |
| O | 3-Cl | 4-F | CH₂CH₃ |
| O | 3-Cl | 2,6-F₂ | CH₂CH₃ |
| O | 3-Cl | 2,5-F₂ | CH₂CH₃ |
| O | 3-F | 3,5-F₂ | CH₂CH₃ |
| O | 3-F | 4-F | CH₂CH₃ |
| O | 3-F | 2,6-F₂ | CH₂CH₃ |
| O | 3-F | 2,5-F₂ | CH₂CH₃ |
| O | 4-CN | 3,5-F₂ | CH₂CH₃ |
| O | 4-CN | 4-F | CH₂CH₃ |
| O | 4-CN | 2,6-F₂ | CH₂CH₃ |
| O | 4-CN | 2,5-F₂ | CH₂CH₃ |
| O | 2,5-F₂ | 3,5-F₂ | CH₂CH₃ |
| O | 2,5-F₂ | 4-F | CH₂CH₃ |
| O | 2,5-F₂ | 2,6-F₂ | CH₂CH₃ |
| O | 2,5-F₂ | 2,5-F₂ | CH₂CH₃ |
| O | 3,5-F₂ | 3,5-F₂ | CH₂CH₃ |
| O | 3,5-F₂ | 4-F | CH₂CH₃ |
| O | 3,5-F₂ | 2,6-F₂ | CH₂CH₃ |
| O | 3,5-F₂ | 2,5-F₂ | CH₂CH₃ |
| O | 3,4-F₂ | 3,5-F₂ | CH₂CH₃ |
| O | 3,4-F₂ | 4-F | CH₂CH₃ |
| O | 3,4-F₂ | 2,6-F₂ | CH₂CH₃ |
| O | 3,4-F₂ | 2,5-F₂ | CH₂CH₃ |
| O | 4-CF₃ | 3,5-F₂ | CH₂CH₃ |
| O | 4-CF₃ | 4-F | CH₂CH₃ |
| O | 4-CF₃ | 2,6-F₂ | CH₂CH₃ |
| O | 4-CF₃ | 2,5-F₂ | CH₂CH₃ |
| O | 4-Cl | 2-F | CH₃ |
| O | 4-Cl | 3-F | CH₃ |
| O | 4-Cl | 4-F | CH₃ |
| O | 4-Cl | 4-Cl | CH₃ |

TABLE XX-continued

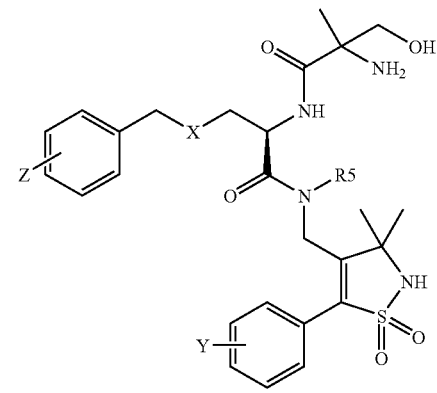

| X | Y | Z | R5 |
|---|---|---|---|
| O | 4-Cl | 2,5-F₂ | CH₃ |
| O | 4-Cl | 2,4-F₂ | CH₃ |
| O | 4-Cl | 2-Cl | CH₃ |
| O | 4-Cl | 2,6-F₂ | CH₃ |
| O | 4-Cl | 3,5-F₂ | CH₃ |
| O | 4-Cl | 2,3-F₂ | CH₃ |
| O | 4-Cl | 3,4-F₂ | CH₃ |
| O | 4-Cl | 2,3,5-F₃ | CH₃ |
| O | 4-Cl | 2,3,6-F₃ | CH₃ |
| O | 4-Cl | 2,4,5-F₃ | CH₃ |
| O | 4-Cl | 2,6-Cl₂ | CH₃ |
| O | 4-Cl | 2-F-3-Cl | CH₃ |
| O | 4-Cl | 2-F-6-Cl | CH₃ |
| O | 4-F | 2-F | CH₃ |
| O | 4-F | 3-F | CH₃ |
| O | 4-F | 4-F | CH₃ |
| O | 4-F | 4-Cl | CH₃ |
| O | 4-F | 2,5-F₂ | CH₃ |
| O | 4-F | 2,4-F₂ | CH₃ |
| O | 4-F | 2-Cl | CH₃ |
| O | 4-F | 2,6-F₂ | CH₃ |
| O | 4-F | 3,5-F₂ | CH₃ |
| O | 4-F | 2,3-F₂ | CH₃ |
| O | 4-F | 3,4-F₂ | CH₃ |
| O | 4-F | 2,3,5-F₃ | CH₃ |
| O | 4-F | 2,3,6-F₃ | CH₃ |
| O | 4-F | 2,4,5-F₃ | CH₃ |
| O | 4-F | 2,6-Cl₂ | CH₃ |
| O | 4-F | 2-F-3-Cl | CH₃ |
| O | 4-F | 2-F-6-Cl | CH₃ |
| CH₂ | 4-Cl | 3,5-F₂ | CH₃ |
| CH₂ | 4-Cl | 4-F | CH₃ |
| CH₂ | 4-Cl | 2,6-F₂ | CH₃ |
| CH₂ | 4-F | 3,5-F₂ | CH₃ |
| CH₂ | 4-F | 4-F | CH₃ |
| CH₂ | 4-F | 2,6-F₂ | CH₃ |
| O | 3-F | 3,5-F₂ | CH₃ |
| O | 3-F | 4-F | CH₃ |
| O | 3-F | 2,6-F₂ | CH₃ |
| O | 3-F | 2,5-F₂ | CH₃ |
| O | 2,5-F₂ | 3,5-F₂ | CH₃ |
| O | 2,5-F₂ | 4-F | CH₃ |
| O | 2,5-F₂ | 2,6-F₂ | CH₃ |
| O | 2,5-F₂ | 2,5-F₂ | CH₃ |
| O | 3,5-F₂ | 3,5-F₂ | CH₃ |
| O | 3,5-F₂ | 4-F | CH₃ |
| O | 3,5-F₂ | 2,6-F₂ | CH₃ |
| O | 3,5-F₂ | 2,5-F₂ | CH₃ |
| O | 3,4-F₂ | 3,5-F₂ | CH₃ |
| O | 3,4-F₂ | 4-F | CH₃ |
| O | 3,4-F₂ | 2,6-F₂ | CH₃ |
| O | 3,4-F₂ | 2,5-F₂ | CH₃ |
| O | 4-CF₃ | 3,5-F₂ | CH₃ |
| O | 4-CF₃ | 4-F | CH₃ |
| O | 4-CF₃ | 2,6-F₂ | CH₃ |
| O | 4-CF₃ | 2,5-F₂ | CH₃ |

TABLE XXI

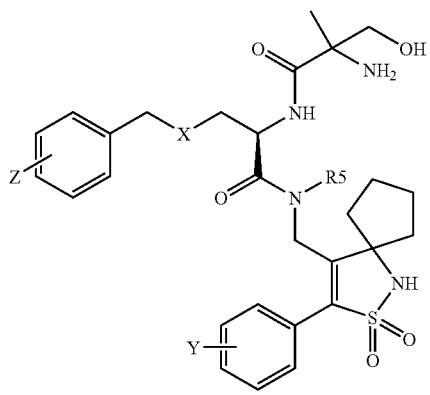

| X | Y | Z | R5 |
|---|---|---|---|
| O | 4-Cl | 2-F | CH$_2$CH$_3$ |
| O | 4-Cl | 3-F | CH$_2$CH$_3$ |
| O | 4-Cl | 4-F | CH$_2$CH$_3$ |
| O | 4-Cl | 4-Cl | CH$_2$CH$_3$ |
| O | 4-Cl | 2,5-F$_2$ | CH$_2$CH$_3$ |
| O | 4-Cl | 2,4-F$_2$ | CH$_2$CH$_3$ |
| O | 4-Cl | 2-Cl | CH$_2$CH$_3$ |
| O | 4-Cl | 2,6-F$_2$ | CH$_2$CH$_3$ |
| O | 4-Cl | 3,5-F$_2$ | CH$_2$CH$_3$ |
| O | 4-Cl | 2,3-F$_2$ | CH$_2$CH$_3$ |
| O | 4-Cl | 3,4-F$_2$ | CH$_2$CH$_3$ |
| O | 4-Cl | 2,3,5-F$_3$ | CH$_2$CH$_3$ |
| O | 4-Cl | 2,3,6-F$_3$ | CH$_2$CH$_3$ |
| O | 4-Cl | 2,4,5-F$_3$ | CH$_2$CH$_3$ |
| O | 4-Cl | 2,6-Cl$_2$ | CH$_2$CH$_3$ |
| O | 4-Cl | 2-F-3-Cl | CH$_2$CH$_3$ |
| O | 4-Cl | 2-F-6-Cl | CH$_2$CH$_3$ |
| O | 4-F | 2-F | CH$_2$CH$_3$ |
| O | 4-F | 3-F | CH$_2$CH$_3$ |
| O | 4-F | 4-F | CH$_2$CH$_3$ |
| O | 4-F | 4-Cl | CH$_2$CH$_3$ |
| O | 4-F | 2,5-F$_2$ | CH$_2$CH$_3$ |
| O | 4-F | 2,4-F$_2$ | CH$_2$CH$_3$ |
| O | 4-F | 2-Cl | CH$_2$CH$_3$ |
| O | 4-F | 2,6-F$_2$ | CH$_2$CH$_3$ |
| O | 4-F | 3,5-F$_2$ | CH$_2$CH$_3$ |
| O | 4-F | 2,3-F$_2$ | CH$_2$CH$_3$ |
| O | 4-F | 3,4-F$_2$ | CH$_2$CH$_3$ |
| O | 4-F | 2,3,5-F$_3$ | CH$_2$CH$_3$ |
| O | 4-F | 2,3,6-F$_3$ | CH$_2$CH$_3$ |
| O | 4-F | 2,4,5-F$_3$ | CH$_2$CH$_3$ |
| O | 4-F | 2,6-Cl$_2$ | CH$_2$CH$_3$ |
| O | 4-F | 2-F-3-Cl | CH$_2$CH$_3$ |
| O | 4-F | 2-F-6-Cl | CH$_2$CH$_3$ |
| CH$_2$ | 4-Cl | 3,5-F$_2$ | CH$_2$CH$_3$ |
| CH$_2$ | 4-Cl | 4-F | CH$_2$CH$_3$ |
| CH$_2$ | 4-Cl | 2,6-F$_2$ | CH$_2$CH$_3$ |
| CH$_2$ | 4-F | 3,5-F$_2$ | CH$_2$CH$_3$ |
| CH$_2$ | 4-F | 4-F | CH$_2$CH$_3$ |
| CH$_2$ | 4-F | 2,6-F$_2$ | CH$_2$CH$_3$ |
| O | 3-Cl | 3,5-F$_2$ | CH$_2$CH$_3$ |
| O | 3-Cl | 4-F | CH$_2$CH$_3$ |
| O | 3-Cl | 2,6-F$_2$ | CH$_2$CH$_3$ |
| O | 3-Cl | 2,5-F$_2$ | CH$_2$CH$_3$ |
| O | 3-F | 3,5-F$_2$ | CH$_2$CH$_3$ |
| O | 3-F | 4-F | CH$_2$CH$_3$ |
| O | 3-F | 2,6-F$_2$ | CH$_2$CH$_3$ |
| O | 3-F | 2,5-F$_2$ | CH$_2$CH$_3$ |
| O | 4-CN | 3,5-F$_2$ | CH$_2$CH$_3$ |
| O | 4-CN | 4-F | CH$_2$CH$_3$ |
| O | 4-CN | 2,6-F$_2$ | CH$_2$CH$_3$ |
| O | 4-CN | 2,5-F$_2$ | CH$_2$CH$_3$ |
| O | 2,5-F$_2$ | 3,5-F$_2$ | CH$_2$CH$_3$ |
| O | 2,5-F$_2$ | 4-F | CH$_2$CH$_3$ |
| O | 2,5-F$_2$ | 2,6-F$_2$ | CH$_2$CH$_3$ |
| O | 2,5-F$_2$ | 2,5-F$_2$ | CH$_2$CH$_3$ |
| O | 3,5-F$_2$ | 3,5-F$_2$ | CH$_2$CH$_3$ |

TABLE XXI-continued

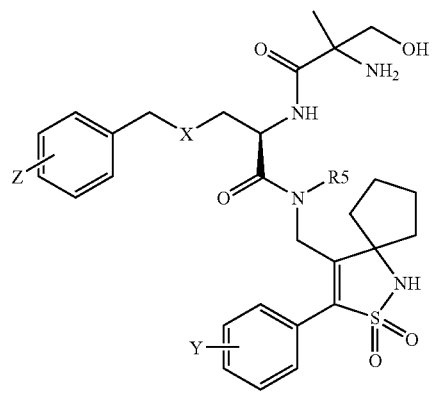

| X | Y | Z | R5 |
|---|---|---|---|
| O | 3,5-F$_2$ | 4-F | CH$_2$CH$_3$ |
| O | 3,5-F$_2$ | 2,6-F$_2$ | CH$_2$CH$_3$ |
| O | 3,5-F$_2$ | 2,5-F$_2$ | CH$_2$CH$_3$ |
| O | 3,4-F$_2$ | 3,5-F$_2$ | CH$_2$CH$_3$ |
| O | 3,4-F$_2$ | 4-F | CH$_2$CH$_3$ |
| O | 3,4-F$_2$ | 2,6-F$_2$ | CH$_2$CH$_3$ |
| O | 3,4-F$_2$ | 2,5-F$_2$ | CH$_2$CH$_3$ |
| O | 4-CF$_3$ | 3,5-F$_2$ | CH$_2$CH$_3$ |
| O | 4-CF$_3$ | 4-F | CH$_2$CH$_3$ |
| O | 4-CF$_3$ | 2,6-F$_2$ | CH$_2$CH$_3$ |
| O | 4-CF$_3$ | 2,5-F$_2$ | CH$_2$CH$_3$ |
| O | 4-Cl | 2-F | CH$_3$ |
| O | 4-Cl | 3-F | CH$_3$ |
| O | 4-Cl | 4-F | CH$_3$ |
| O | 4-Cl | 4-Cl | CH$_3$ |
| O | 4-Cl | 2,5-F$_2$ | CH$_3$ |
| O | 4-Cl | 2,4-F$_2$ | CH$_3$ |
| O | 4-Cl | 2-Cl | CH$_3$ |
| O | 4-Cl | 2,6-F$_2$ | CH$_3$ |
| O | 4-Cl | 3,5-F$_2$ | CH$_3$ |
| O | 4-Cl | 2,3-F$_2$ | CH$_3$ |
| O | 4-Cl | 3,4-F$_2$ | CH$_3$ |
| O | 4-Cl | 2,3,5-F$_3$ | CH$_3$ |
| O | 4-Cl | 2,3,6-F$_3$ | CH$_3$ |
| O | 4-Cl | 2,4,5-F$_3$ | CH$_3$ |
| O | 4-Cl | 2,6-Cl$_2$ | CH$_3$ |
| O | 4-Cl | 2-F-3-Cl | CH$_3$ |
| O | 4-Cl | 2-F-6-Cl | CH$_3$ |
| O | 4-F | 2-F | CH$_3$ |
| O | 4-F | 3-F | CH$_3$ |
| O | 4-F | 4-F | CH$_3$ |
| O | 4-F | 4-Cl | CH$_3$ |
| O | 4-F | 2,5-F$_2$ | CH$_3$ |
| O | 4-F | 2,4-F$_2$ | CH$_3$ |
| O | 4-F | 2-Cl | CH$_3$ |
| O | 4-F | 2,6-F$_2$ | CH$_3$ |
| O | 4-F | 3,5-F$_2$ | CH$_3$ |
| O | 4-F | 2,3-F$_2$ | CH$_3$ |
| O | 4-F | 3,4-F$_2$ | CH$_3$ |
| O | 4-F | 2,3,5-F$_3$ | CH$_3$ |
| O | 4-F | 2,3,6-F$_3$ | CH$_3$ |
| O | 4-F | 2,4,5-F$_3$ | CH$_3$ |
| O | 4-F | 2,6-Cl$_2$ | CH$_3$ |
| O | 4-F | 2-F-3-Cl | CH$_3$ |
| O | 4-F | 2-F-6-Cl | CH$_3$ |
| CH$_2$ | 4-Cl | 3,5-F$_2$ | CH$_3$ |
| CH$_2$ | 4-Cl | 4-F | CH$_3$ |
| CH$_2$ | 4-Cl | 2,6-F$_2$ | CH$_3$ |
| CH$_2$ | 4-F | 3,5-F$_2$ | CH$_3$ |
| CH$_2$ | 4-F | 4-F | CH$_3$ |
| CH$_2$ | 4-F | 2,6-F$_2$ | CH$_3$ |
| O | 3-F | 3,5-F$_2$ | CH$_3$ |
| O | 3-F | 4-F | CH$_3$ |
| O | 3-F | 2,6-F$_2$ | CH$_3$ |
| O | 3-F | 2,5-F$_2$ | CH$_3$ |
| O | 2,5-F$_2$ | 3,5-F$_2$ | CH$_3$ |
| O | 2,5-F$_2$ | 4-F | CH$_3$ |

TABLE XXI-continued

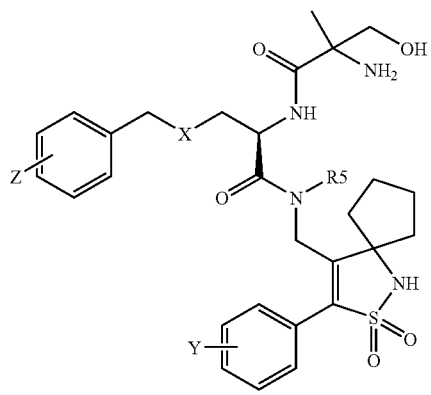

| X | Y | Z | R5 |
|---|---|---|---|
| O | 2,5-F$_2$ | 2,6-F$_2$ | CH$_3$ |
| O | 2,5-F$_2$ | 2,5-F$_2$ | CH$_3$ |
| O | 3,5-F$_2$ | 3,5-F$_2$ | CH$_3$ |
| O | 3,5-F$_2$ | 4-F | CH$_3$ |
| O | 3,5-F$_2$ | 2,6-F$_2$ | CH$_3$ |
| O | 3,5-F$_2$ | 2,5-F$_2$ | CH$_3$ |
| O | 3,4-F$_2$ | 3,5-F$_2$ | CH$_3$ |
| O | 3,4-F$_2$ | 4-F | CH$_3$ |
| O | 3,4-F$_2$ | 2,6-F$_2$ | CH$_3$ |
| O | 3,4-F$_2$ | 2,5-F$_2$ | CH$_3$ |
| O | 4-CF$_3$ | 3,5-F$_2$ | CH$_3$ |
| O | 4-CF$_3$ | 4-F | CH$_3$ |
| O | 4-CF$_3$ | 2,6-F$_2$ | CH$_3$ |
| O | 4-CF$_3$ | 2,5-F$_2$ | CH$_3$ |

TABLE XXII

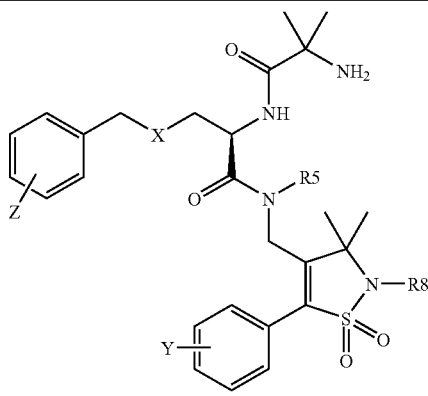

| X | Y | Z | R5 | R8 |
|---|---|---|---|---|
| O | 4-Cl | 2-F | CH$_2$CH$_3$ | CH$_3$ |
| O | 4-Cl | 3-F | CH$_2$CH$_3$ | CH$_3$ |
| O | 4-Cl | 4-F | CH$_2$CH$_3$ | CH$_3$ |
| O | 4-Cl | 4-Cl | CH$_2$CH$_3$ | CH$_3$ |
| O | 4-Cl | 2,5-F$_2$ | CH$_2$CH$_3$ | CH$_3$ |
| O | 4-Cl | 2,4-F$_2$ | CH$_2$CH$_3$ | CH$_3$ |
| O | 4-Cl | 2-Cl | CH$_2$CH$_3$ | CH$_3$ |
| O | 4-Cl | 2,6-F$_2$ | CH$_2$CH$_3$ | CH$_3$ |
| O | 4-Cl | 3,5-F$_2$ | CH$_2$CH$_3$ | CH$_3$ |
| O | 4-Cl | 2,3-F$_2$ | CH$_2$CH$_3$ | CH$_3$ |
| O | 4-Cl | 3,4-F$_2$ | CH$_2$CH$_3$ | CH$_3$ |
| O | 4-Cl | 2,3,5-F$_3$ | CH$_2$CH$_3$ | CH$_3$ |
| O | 4-Cl | 2,3,6-F$_3$ | CH$_2$CH$_3$ | CH$_3$ |
| O | 4-Cl | 2,4,5-F$_3$ | CH$_2$CH$_3$ | CH$_3$ |
| O | 4-Cl | 2,6-Cl$_2$ | CH$_2$CH$_3$ | CH$_3$ |
| O | 4-Cl | 2-F-6-Cl | CH$_2$CH$_3$ | CH$_3$ |
| O | 4-Cl | 2-F-3-Cl | CH$_2$CH$_3$ | CH$_3$ |

TABLE XXII-continued

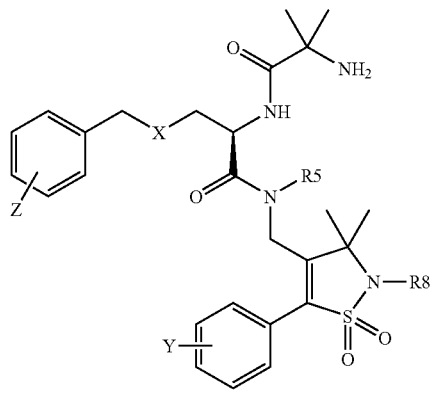

| X | Y | Z | R5 | R8 |
|---|---|---|---|---|
| O | 4-F | 2-F | CH$_2$CH$_3$ | CH$_3$ |
| O | 4-F | 3-F | CH$_2$CH$_3$ | CH$_3$ |
| O | 4-F | 4-F | CH$_2$CH$_3$ | CH$_3$ |
| O | 4-F | 4-Cl | CH$_2$CH$_3$ | CH$_3$ |
| O | 4-F | 2,5-F$_2$ | CH$_2$CH$_3$ | CH$_3$ |
| O | 4-F | 2,4-F$_2$ | CH$_2$CH$_3$ | CH$_3$ |
| O | 4-F | 2-Cl | CH$_2$CH$_3$ | CH$_3$ |
| O | 4-F | 2,6-F$_2$ | CH$_2$CH$_3$ | CH$_3$ |
| O | 4-F | 3,5-F$_2$ | CH$_2$CH$_3$ | CH$_3$ |
| O | 4-F | 2,3-F$_2$ | CH$_2$CH$_3$ | CH$_3$ |
| O | 4-F | 3,4-F$_2$ | CH$_2$CH$_3$ | CH$_3$ |
| O | 4-F | 2,3,5-F$_3$ | CH$_2$CH$_3$ | CH$_3$ |
| O | 4-F | 2,3,6-F$_3$ | CH$_2$CH$_3$ | CH$_3$ |
| O | 4-F | 2,4,5-F$_3$ | CH$_2$CH$_3$ | CH$_3$ |
| O | 4-F | 2,6-Cl$_2$ | CH$_2$CH$_3$ | CH$_3$ |
| O | 4-F | 2-F-6-Cl | CH$_2$CH$_3$ | CH$_3$ |
| O | 4-F | 2-F-3-Cl | CH$_2$CH$_3$ | CH$_3$ |
| CH$_2$ | 4-Cl | 3,5-F$_2$ | CH$_2$CH$_3$ | CH$_3$ |
| CH$_2$ | 4-Cl | 4-F | CH$_2$CH$_3$ | CH$_3$ |
| CH$_2$ | 4-Cl | 2,6-F$_2$ | CH$_2$CH$_3$ | CH$_3$ |
| CH$_2$ | 4-F | 3,5-F$_2$ | CH$_2$CH$_3$ | CH$_3$ |
| CH$_2$ | 4-F | 4-F | CH$_2$CH$_3$ | CH$_3$ |
| CH$_2$ | 4-F | 2,6-F$_2$ | CH$_2$CH$_3$ | CH$_3$ |
| O | 4-Cl | 2-F | CH$_3$ | CH$_3$ |
| O | 4-Cl | 3-F | CH$_3$ | CH$_3$ |
| O | 4-Cl | 4-F | CH$_3$ | CH$_3$ |
| O | 4-Cl | 4-Cl | CH$_3$ | CH$_3$ |
| O | 4-Cl | 2,5-F$_2$ | CH$_3$ | CH$_3$ |
| O | 4-Cl | 2,4-F$_2$ | CH$_3$ | CH$_3$ |
| O | 4-Cl | 2-Cl | CH$_3$ | CH$_3$ |
| O | 4-Cl | 2,6-F$_2$ | CH$_3$ | CH$_3$ |
| O | 4-Cl | 3,5-F$_2$ | CH$_3$ | CH$_3$ |
| O | 4-Cl | 2,3-F$_2$ | CH$_3$ | CH$_3$ |
| O | 4-Cl | 3,4-F$_2$ | CH$_3$ | CH$_3$ |
| O | 4-Cl | 2,3,5-F$_3$ | CH$_3$ | CH$_3$ |
| O | 4-Cl | 2,3,6-F$_3$ | CH$_3$ | CH$_3$ |
| O | 4-Cl | 2,4,5-F$_3$ | CH$_3$ | CH$_3$ |
| O | 4-Cl | 2,6-Cl$_2$ | CH$_3$ | CH$_3$ |
| O | 4-Cl | 2-F-6-Cl | CH$_3$ | CH$_3$ |
| O | 4-Cl | 2-F-3-Cl | CH$_3$ | CH$_3$ |
| O | 4-F | 2-F | CH$_3$ | CH$_3$ |
| O | 4-F | 3-F | CH$_3$ | CH$_3$ |
| O | 4-F | 4-F | CH$_3$ | CH$_3$ |
| O | 4-F | 4-Cl | CH$_3$ | CH$_3$ |
| O | 4-F | 2,5-F$_2$ | CH$_3$ | CH$_3$ |
| O | 4-F | 2,4-F$_2$ | CH$_3$ | CH$_3$ |
| O | 4-F | 2-Cl | CH$_3$ | CH$_3$ |
| O | 4-F | 2,6-F$_2$ | CH$_3$ | CH$_3$ |
| O | 4-F | 3,5-F$_2$ | CH$_3$ | CH$_3$ |
| O | 4-F | 2,3-F$_2$ | CH$_3$ | CH$_3$ |
| O | 4-F | 3,4-F$_2$ | CH$_3$ | CH$_3$ |
| O | 4-F | 2,3,5-F$_3$ | CH$_3$ | CH$_3$ |
| O | 4-F | 2,3,6-F$_3$ | CH$_3$ | CH$_3$ |
| O | 4-F | 2,4,5-F$_3$ | CH$_3$ | CH$_3$ |
| O | 4-F | 2,6-Cl$_2$ | CH$_3$ | CH$_3$ |
| O | 4-F | 2-F-6-Cl | CH$_3$ | CH$_3$ |
| O | 4-F | 2-F-3-Cl | CH$_3$ | CH$_3$ |

TABLE XXII-continued

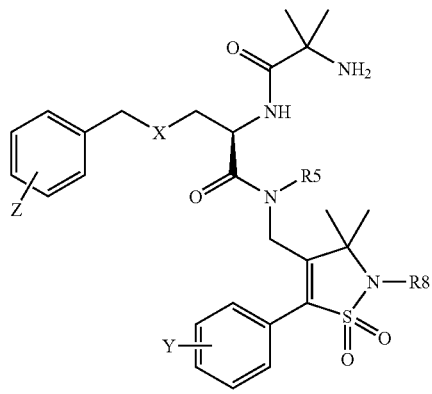

| X | Y | Z | R5 | R8 |
|---|---|---|---|---|
| CH$_2$ | 4-Cl | 3,5-F$_2$ | CH$_3$ | CH$_3$ |
| CH$_2$ | 4-Cl | 4-F | CH$_3$ | CH$_3$ |
| CH$_2$ | 4-Cl | 2,6-F$_2$ | CH$_3$ | CH$_3$ |
| CH$_2$ | 4-F | 3,5-F$_2$ | CH$_3$ | CH$_3$ |
| CH$_2$ | 4-F | 4-F | CH$_3$ | CH$_3$ |
| CH$_2$ | 4-F | 2,6-F$_2$ | CH$_3$ | CH$_3$ |
| O | 4-Cl | 2-F | CH$_2$CH$_3$ | CH$_2$CH$_3$ |
| O | 4-Cl | 3-F | CH$_2$CH$_3$ | CH$_2$CH$_3$ |
| O | 4-Cl | 4-F | CH$_2$CH$_3$ | CH$_2$CH$_3$ |
| O | 4-Cl | 4-Cl | CH$_2$CH$_3$ | CH$_2$CH$_3$ |
| O | 4-Cl | 2,5-F$_2$ | CH$_2$CH$_3$ | CH$_2$CH$_3$ |
| O | 4-Cl | 2,4-F$_2$ | CH$_2$CH$_3$ | CH$_2$CH$_3$ |
| O | 4-Cl | 2-Cl | CH$_2$CH$_3$ | CH$_2$CH$_3$ |
| O | 4-Cl | 2,6-F$_2$ | CH$_2$CH$_3$ | CH$_2$CH$_3$ |
| O | 4-Cl | 3,5-F$_2$ | CH$_2$CH$_3$ | CH$_2$CH$_3$ |
| O | 4-Cl | 2,3-F$_2$ | CH$_2$CH$_3$ | CH$_2$CH$_3$ |
| O | 4-Cl | 3,4-F$_2$ | CH$_2$CH$_3$ | CH$_2$CH$_3$ |
| O | 4-Cl | 2,3,5-F$_3$ | CH$_2$CH$_3$ | CH$_2$CH$_3$ |
| O | 4-Cl | 2,3,6-F$_3$ | CH$_2$CH$_3$ | CH$_2$CH$_3$ |
| O | 4-Cl | 2,4,5-F$_3$ | CH$_2$CH$_3$ | CH$_2$CH$_3$ |
| O | 4-Cl | 2,6-Cl$_2$ | CH$_2$CH$_3$ | CH$_2$CH$_3$ |
| O | 4-Cl | 2-F-6-Cl | CH$_2$CH$_3$ | CH$_2$CH$_3$ |
| O | 4-Cl | 2-F-3-Cl | CH$_2$CH$_3$ | CH$_2$CH$_3$ |
| CH$_2$ | 4-Cl | 3,5-F$_2$ | CH$_2$CH$_3$ | CH$_2$CH$_3$ |
| CH$_2$ | 4-Cl | 4-F | CH$_2$CH$_3$ | CH$_2$CH$_3$ |
| CH$_2$ | 4-Cl | 2,6-F$_2$ | CH$_2$CH$_3$ | CH$_2$CH$_3$ |
| O | 4-Cl | 2-F | CH$_2$CH$_3$ | CH$_2$CH$_2$CH$_3$ |
| O | 4-Cl | 3-F | CH$_2$CH$_3$ | CH$_2$CH$_2$CH$_3$ |
| O | 4-Cl | 4-F | CH$_2$CH$_3$ | CH$_2$CH$_2$CH$_3$ |
| O | 4-Cl | 4-Cl | CH$_2$CH$_3$ | CH$_2$CH$_2$CH$_3$ |
| O | 4-Cl | 2,5-F$_2$ | CH$_2$CH$_3$ | CH$_2$CH$_2$CH$_3$ |
| O | 4-Cl | 2-Cl | CH$_2$CH$_3$ | CH$_2$CH$_2$CH$_3$ |
| O | 4-Cl | 2,6-F$_2$ | CH$_2$CH$_3$ | CH$_2$CH$_2$CH$_3$ |
| O | 4-Cl | 3,5-F$_2$ | CH$_2$CH$_3$ | CH$_2$CH$_2$CH$_3$ |
| O | 4-Cl | 2,3-F$_2$ | CH$_2$CH$_3$ | CH$_2$CH$_2$CH$_3$ |
| O | 4-Cl | 3,4-F$_2$ | CH$_2$CH$_3$ | CH$_2$CH$_2$CH$_3$ |
| O | 4-Cl | 2,3,5-F$_3$ | CH$_2$CH$_3$ | CH$_2$CH$_2$CH$_3$ |
| O | 4-Cl | 2,3,6-F$_3$ | CH$_2$CH$_3$ | CH$_2$CH$_2$CH$_3$ |
| O | 4-Cl | 2,4,5-F$_3$ | CH$_2$CH$_3$ | CH$_2$CH$_2$CH$_3$ |
| O | 4-Cl | 2,6-Cl$_2$ | CH$_2$CH$_3$ | CH$_2$CH$_2$CH$_3$ |
| O | 4-Cl | 2-F-6-Cl | CH$_2$CH$_3$ | CH$_2$CH$_2$CH$_3$ |
| O | 4-Cl | 2-F-3-Cl | CH$_2$CH$_3$ | CH$_2$CH$_2$CH$_3$ |
| CH$_2$ | 4-Cl | 3,5-F$_2$ | CH$_2$CH$_3$ | CH$_2$CH$_2$CH$_3$ |
| CH$_2$ | 4-Cl | 4-F | CH$_2$CH$_3$ | CH$_2$CH$_2$CH$_3$ |
| CH$_2$ | 4-Cl | 2,6-F$_2$ | CH$_2$CH$_3$ | CH$_2$CH$_2$CH$_3$ |
| O | 4-Cl | 2-F | CH$_2$CH$_3$ | CH$_2$CH$_2$F |
| O | 4-Cl | 3-F | CH$_2$CH$_3$ | CH$_2$CH$_2$F |
| O | 4-Cl | 4-F | CH$_2$CH$_3$ | CH$_2$CH$_2$F |
| O | 4-Cl | 4-Cl | CH$_2$CH$_3$ | CH$_2$CH$_2$F |
| O | 4-Cl | 2,5-F$_2$ | CH$_2$CH$_3$ | CH$_2$CH$_2$F |
| O | 4-Cl | 2-Cl | CH$_2$CH$_3$ | CH$_2$CH$_2$F |
| O | 4-Cl | 2,6-F$_2$ | CH$_2$CH$_3$ | CH$_2$CH$_2$F |
| O | 4-Cl | 3,5-F$_2$ | CH$_2$CH$_3$ | CH$_2$CH$_2$F |
| O | 4-Cl | 2,3-F$_2$ | CH$_2$CH$_3$ | CH$_2$CH$_2$F |
| O | 4-Cl | 3,4-F$_2$ | CH$_2$CH$_3$ | CH$_2$CH$_2$F |
| O | 4-Cl | 2,3,5-F$_3$ | CH$_2$CH$_3$ | CH$_2$CH$_2$F |
| O | 4-Cl | 2,3,6-F$_3$ | CH$_2$CH$_3$ | CH$_2$CH$_2$F |

TABLE XXII-continued

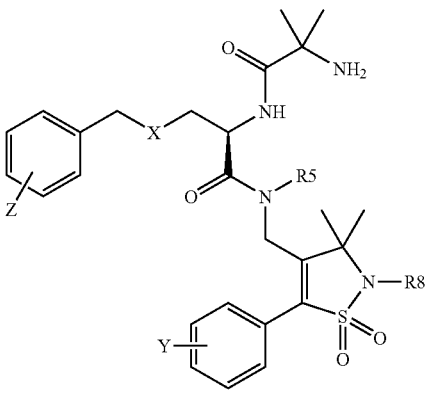

| X | Y | Z | R5 | R8 |
|---|---|---|---|---|
| O | 4-Cl | 2,4,5-F$_3$ | CH$_2$CH$_3$ | CH$_2$CH$_2$F |
| O | 4-Cl | 2,6-Cl$_2$ | CH$_2$CH$_3$ | CH$_2$CH$_2$F |
| O | 4-Cl | 2-F-6-Cl | CH$_2$CH$_3$ | CH$_2$CH$_2$F |
| O | 4-Cl | 2-F-3-Cl | CH$_2$CH$_3$ | CH$_2$CH$_2$F |
| CH$_2$ | 4-Cl | 3,5-F$_2$ | CH$_2$CH$_3$ | CH$_2$CH$_2$F |
| CH$_2$ | 4-Cl | 4-F | CH$_2$CH$_3$ | CH$_2$CH$_2$F |
| CH$_2$ | 4-Cl | 2,6-F$_2$ | CH$_2$CH$_3$ | CH$_2$CH$_2$F |
| O | 4-Cl | 2-F | CH$_2$CH$_3$ | CH$_2$CH$_2$OH |
| O | 4-Cl | 3-F | CH$_2$CH$_3$ | CH$_2$CH$_2$OH |
| O | 4-Cl | 4-F | CH$_2$CH$_3$ | CH$_2$CH$_2$OH |
| O | 4-Cl | 4-Cl | CH$_2$CH$_3$ | CH$_2$CH$_2$OH |
| O | 4-Cl | 2,5-F$_2$ | CH$_2$CH$_3$ | CH$_2$CH$_2$OH |
| O | 4-Cl | 2-Cl | CH$_2$CH$_3$ | CH$_2$CH$_2$OH |
| O | 4-Cl | 2,6-F$_2$ | CH$_2$CH$_3$ | CH$_2$CH$_2$OH |
| O | 4-Cl | 3,5-F$_2$ | CH$_2$CH$_3$ | CH$_2$CH$_2$OH |
| O | 4-Cl | 2,3-F$_2$ | CH$_2$CH$_3$ | CH$_2$CH$_2$OH |
| O | 4-Cl | 3,4-F$_2$ | CH$_2$CH$_3$ | CH$_2$CH$_2$OH |
| O | 4-Cl | 2,3,5-F$_3$ | CH$_2$CH$_3$ | CH$_2$CH$_2$OH |
| O | 4-Cl | 2,3,6-F$_3$ | CH$_2$CH$_3$ | CH$_2$CH$_2$OH |
| O | 4-Cl | 2,4,5-F$_3$ | CH$_2$CH$_3$ | CH$_2$CH$_2$OH |
| O | 4-Cl | 2,6-Cl$_2$ | CH$_2$CH$_3$ | CH$_2$CH$_2$OH |
| O | 4-Cl | 2-F-6-Cl | CH$_2$CH$_3$ | CH$_2$CH$_2$OH |
| O | 4-Cl | 2-F-3-Cl | CH$_2$CH$_3$ | CH$_2$CH$_2$OH |
| CH$_2$ | 4-Cl | 3,5-F$_2$ | CH$_2$CH$_3$ | CH$_2$CH$_2$OH |
| CH$_2$ | 4-Cl | 4-F | CH$_2$CH$_3$ | CH$_2$CH$_2$OH |
| CH$_2$ | 4-Cl | 2,6-F$_2$ | CH$_2$CH$_3$ | CH$_2$CH$_2$OH |
| O | 4-Cl | 2-F | CH$_2$CH$_3$ | benzyl |
| O | 4-Cl | 3-F | CH$_2$CH$_3$ | benzyl |
| O | 4-Cl | 4-F | CH$_2$CH$_3$ | benzyl |
| O | 4-Cl | 4-Cl | CH$_2$CH$_3$ | benzyl |
| O | 4-Cl | 2,5-F$_2$ | CH$_2$CH$_3$ | benzyl |
| O | 4-Cl | 2-Cl | CH$_2$CH$_3$ | benzyl |
| O | 4-Cl | 2,6-F$_2$ | CH$_2$CH$_3$ | benzyl |
| O | 4-Cl | 3,5-F$_2$ | CH$_2$CH$_3$ | benzyl |
| O | 4-Cl | 2,3-F$_2$ | CH$_2$CH$_3$ | benzyl |
| O | 4-Cl | 3,4-F$_2$ | CH$_2$CH$_3$ | benzyl |
| O | 4-Cl | 2,3,5-F$_3$ | CH$_2$CH$_3$ | benzyl |
| O | 4-Cl | 2,3,6-F$_3$ | CH$_2$CH$_3$ | benzyl |
| O | 4-Cl | 2,4,5-F$_3$ | CH$_2$CH$_3$ | benzyl |
| O | 4-Cl | 2,6-Cl$_2$ | CH$_2$CH$_3$ | benzyl |
| O | 4-Cl | 2-F-6-Cl | CH$_2$CH$_3$ | benzyl |
| O | 4-Cl | 2-F-3-Cl | CH$_2$CH$_3$ | benzyl |
| CH$_2$ | 4-Cl | 3,5-F$_2$ | CH$_2$CH$_3$ | benzyl |
| CH$_2$ | 4-Cl | 4-F | CH$_2$CH$_3$ | benzyl |
| CH$_2$ | 4-Cl | 2,6-F$_2$ | CH$_2$CH$_3$ | benzyl |
| O | 4-Cl | 2-F | CH$_2$CH$_3$ | cyclopropylmethyl |
| O | 4-Cl | 3-F | CH$_2$CH$_3$ | cyclopropylmethyl |
| O | 4-Cl | 4-F | CH$_2$CH$_3$ | cyclopropylmethyl |
| O | 4-Cl | 4-Cl | CH$_2$CH$_3$ | cyclopropylmethyl |
| O | 4-Cl | 2,5-F$_2$ | CH$_2$CH$_3$ | cyclopropylmethyl |
| O | 4-Cl | 2-Cl | CH$_2$CH$_3$ | cyclopropylmethyl |
| O | 4-Cl | 2,6-F$_2$ | CH$_2$CH$_3$ | cyclopropylmethyl |
| O | 4-Cl | 3,5-F$_2$ | CH$_2$CH$_3$ | cyclopropylmethyl |
| O | 4-Cl | 2,3-F$_2$ | CH$_2$CH$_3$ | cyclopropylmethyl |
| O | 4-Cl | 3,4-F$_2$ | CH$_2$CH$_3$ | cyclopropylmethyl |
| O | 4-Cl | 2,3,5-F$_3$ | CH$_2$CH$_3$ | cyclopropylmethyl |
| O | 4-Cl | 2,3,6-F$_3$ | CH$_2$CH$_3$ | cyclopropylmethyl |

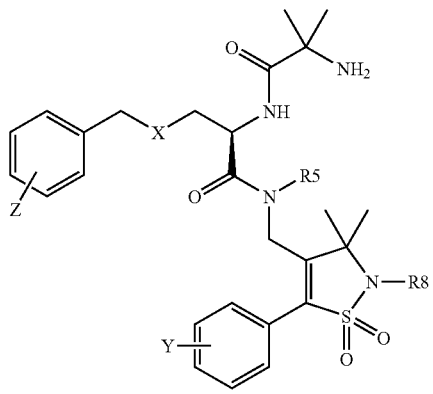
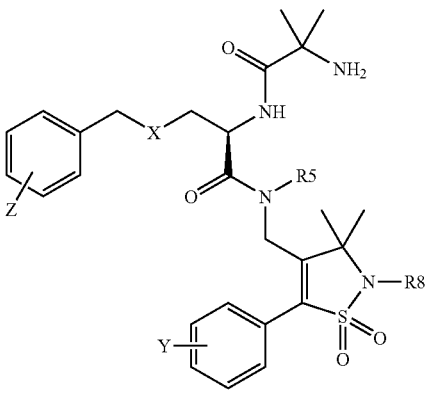

| X | Y | Z | R5 | R8 |
|---|---|---|---|---|
| O | 4-Cl | 2,4,5-F$_3$ | CH$_2$CH$_3$ | cyclopropylmethyl |
| O | 4-Cl | 2,6-Cl$_2$ | CH$_2$CH$_3$ | cyclopropylmethyl |
| O | 4-Cl | 2-F-6-Cl | CH$_2$CH$_3$ | cyclopropylmethyl |
| O | 4-Cl | 2-F-3-Cl | CH$_2$CH$_3$ | cyclopropylmethyl |
| CH$_2$ | 4-Cl | 3,5-F$_2$ | CH$_2$CH$_3$ | cyclopropylmethyl |
| CH$_2$ | 4-Cl | 4-F | CH$_2$CH$_3$ | cyclopropylmethyl |
| CH$_2$ | 4-Cl | 2,6-F$_2$ | CH$_2$CH$_3$ | cyclopropylmethyl |
| O | 4-Cl | 2-F | CH$_2$CH$_3$ | CH(CH$_3$)$_2$ |
| O | 4-Cl | 3-F | CH$_2$CH$_3$ | CH(CH$_3$)$_2$ |
| O | 4-Cl | 4-F | CH$_2$CH$_3$ | CH(CH$_3$)$_2$ |
| O | 4-Cl | 4-Cl | CH$_2$CH$_3$ | CH(CH$_3$)$_2$ |
| O | 4-Cl | 2,5-F$_2$ | CH$_2$CH$_3$ | CH(CH$_3$)$_2$ |
| O | 4-Cl | 2-Cl | CH$_2$CH$_3$ | CH(CH$_3$)$_2$ |
| O | 4-Cl | 2,6-F$_2$ | CH$_2$CH$_3$ | CH(CH$_3$)$_2$ |
| O | 4-Cl | 3,5-F$_2$ | CH$_2$CH$_3$ | CH(CH$_3$)$_2$ |
| O | 4-Cl | 2,3-F$_2$ | CH$_2$CH$_3$ | CH(CH$_3$)$_2$ |
| O | 4-Cl | 3,4-F$_2$ | CH$_2$CH$_3$ | CH(CH$_3$)$_2$ |
| O | 4-Cl | 2,3,5-F$_3$ | CH$_2$CH$_3$ | CH(CH$_3$)$_2$ |
| O | 4-Cl | 2,3,6-F$_3$ | CH$_2$CH$_3$ | CH(CH$_3$)$_2$ |
| O | 4-Cl | 2,4,5-F$_3$ | CH$_2$CH$_3$ | CH(CH$_3$)$_2$ |
| O | 4-Cl | 2,6-Cl$_2$ | CH$_2$CH$_3$ | CH(CH$_3$)$_2$ |
| O | 4-Cl | 2-F-6-Cl | CH$_2$CH$_3$ | CH(CH$_3$)$_2$ |
| O | 4-Cl | 2-F-3-Cl | CH$_2$CH$_3$ | CH(CH$_3$)$_2$ |
| CH$_2$ | 4-Cl | 3,5-F$_2$ | CH$_2$CH$_3$ | CH(CH$_3$)$_2$ |
| CH$_2$ | 4-Cl | 4-F | CH$_2$CH$_3$ | CH(CH$_3$)$_2$ |
| CH$_2$ | 4-Cl | 2,6-F$_2$ | CH$_2$CH$_3$ | CH(CH$_3$)$_2$ |
| O | 4-Cl | 2-F | CH$_2$CH$_3$ | CH$_2$CH(CH$_3$)$_2$ |
| O | 4-Cl | 3-F | CH$_2$CH$_3$ | CH$_2$CH(CH$_3$)$_2$ |
| O | 4-Cl | 4-F | CH$_2$CH$_3$ | CH$_2$CH(CH$_3$)$_2$ |
| O | 4-Cl | 4-Cl | CH$_2$CH$_3$ | CH$_2$CH(CH$_3$)$_2$ |
| O | 4-Cl | 2,5-F$_2$ | CH$_2$CH$_3$ | CH$_2$CH(CH$_3$)$_2$ |
| O | 4-Cl | 2-Cl | CH$_2$CH$_3$ | CH$_2$CH(CH$_3$)$_2$ |
| O | 4-Cl | 2,6-F$_2$ | CH$_2$CH$_3$ | CH$_2$CH(CH$_3$)$_2$ |
| O | 4-Cl | 3,5-F$_2$ | CH$_2$CH$_3$ | CH$_2$CH(CH$_3$)$_2$ |
| O | 4-Cl | 2,3-F$_2$ | CH$_2$CH$_3$ | CH$_2$CH(CH$_3$)$_2$ |
| O | 4-Cl | 3,4-F$_2$ | CH$_2$CH$_3$ | CH$_2$CH(CH$_3$)$_2$ |
| O | 4-Cl | 2,3,5-F$_3$ | CH$_2$CH$_3$ | CH$_2$CH(CH$_3$)$_2$ |
| O | 4-Cl | 2,3,6-F$_3$ | CH$_2$CH$_3$ | CH$_2$CH(CH$_3$)$_2$ |
| O | 4-Cl | 2,4,5-F$_3$ | CH$_2$CH$_3$ | CH$_2$CH(CH$_3$)$_2$ |
| O | 4-Cl | 2,6-Cl$_2$ | CH$_2$CH$_3$ | CH$_2$CH(CH$_3$)$_2$ |
| O | 4-Cl | 2-F-6-Cl | CH$_2$CH$_3$ | CH$_2$CH(CH$_3$)$_2$ |
| O | 4-Cl | 2-F-3-Cl | CH$_2$CH$_3$ | CH$_2$CH(CH$_3$)$_2$ |
| CH$_2$ | 4-Cl | 3,5-F$_2$ | CH$_2$CH$_3$ | CH$_2$CH(CH$_3$)$_2$ |
| CH$_2$ | 4-Cl | 4-F | CH$_2$CH$_3$ | CH$_2$CH(CH$_3$)$_2$ |
| CH$_2$ | 4-Cl | 2,6-F$_2$ | CH$_2$CH$_3$ | CH$_2$CH(CH$_3$)$_2$ |
| O | 4-Cl | 2-F | CH$_2$CH$_3$ | CH$_2$C(CH$_3$)$_3$ |
| O | 4-Cl | 3-F | CH$_2$CH$_3$ | CH$_2$C(CH$_3$)$_3$ |
| O | 4-Cl | 4-F | CH$_2$CH$_3$ | CH$_2$C(CH$_3$)$_3$ |
| O | 4-Cl | 4-Cl | CH$_2$CH$_3$ | CH$_2$C(CH$_3$)$_3$ |
| O | 4-Cl | 2,5-F$_2$ | CH$_2$CH$_3$ | CH$_2$C(CH$_3$)$_3$ |
| O | 4-Cl | 2-Cl | CH$_2$CH$_3$ | CH$_2$C(CH$_3$)$_3$ |
| O | 4-Cl | 2,6-F$_2$ | CH$_2$CH$_3$ | CH$_2$C(CH$_3$)$_3$ |
| O | 4-Cl | 3,5-F$_2$ | CH$_2$CH$_3$ | CH$_2$C(CH$_3$)$_3$ |
| O | 4-Cl | 2,3-F$_2$ | CH$_2$CH$_3$ | CH$_2$C(CH$_3$)$_3$ |
| O | 4-Cl | 3,4-F$_2$ | CH$_2$CH$_3$ | CH$_2$C(CH$_3$)$_3$ |
| O | 4-Cl | 2,3,5-F$_3$ | CH$_2$CH$_3$ | CH$_2$C(CH$_3$)$_3$ |
| O | 4-Cl | 2,3,6-F$_3$ | CH$_2$CH$_3$ | CH$_2$C(CH$_3$)$_3$ |
| O | 4-Cl | 2,4,5-F$_3$ | CH$_2$CH$_3$ | CH$_2$C(CH$_3$)$_3$ |
| O | 4-Cl | 2,6-Cl$_2$ | CH$_2$CH$_3$ | CH$_2$C(CH$_3$)$_3$ |
| O | 4-Cl | 2-F-6-Cl | CH$_2$CH$_3$ | CH$_2$C(CH$_3$)$_3$ |
| O | 4-Cl | 2-F-3-Cl | CH$_2$CH$_3$ | CH$_2$C(CH$_3$)$_3$ |
| CH$_2$ | 4-Cl | 3,5-F$_2$ | CH$_2$CH$_3$ | CH$_2$C(CH$_3$)$_3$ |
| CH$_2$ | 4-Cl | 4-F | CH$_2$CH$_3$ | CH$_2$C(CH$_3$)$_3$ |
| CH$_2$ | 4-Cl | 2,6-F$_2$ | CH$_2$CH$_3$ | CH$_2$C(CH$_3$)$_3$ |
| O | 4-Cl | 2-F | CH$_2$CH$_3$ | 1-phenylethyl |
| O | 4-Cl | 3-F | CH$_2$CH$_3$ | 1-phenylethyl |
| O | 4-Cl | 4-F | CH$_2$CH$_3$ | 1-phenylethyl |
| O | 4-Cl | 4-Cl | CH$_2$CH$_3$ | 1-phenylethyl |
| O | 4-Cl | 2,5-F$_2$ | CH$_2$CH$_3$ | 1-phenylethyl |
| O | 4-Cl | 2-Cl | CH$_2$CH$_3$ | 1-phenylethyl |
| O | 4-Cl | 2,6-F$_2$ | CH$_2$CH$_3$ | 1-phenylethyl |
| O | 4-Cl | 3,5-F$_2$ | CH$_2$CH$_3$ | 1-phenylethyl |
| O | 4-Cl | 2,3-F$_2$ | CH$_2$CH$_3$ | 1-phenylethyl |
| O | 4-Cl | 3,4-F$_2$ | CH$_2$CH$_3$ | 1-phenylethyl |
| O | 4-Cl | 2,3,5-F$_3$ | CH$_2$CH$_3$ | 1-phenylethyl |
| O | 4-Cl | 2,3,6-F$_3$ | CH$_2$CH$_3$ | 1-phenylethyl |
| O | 4-Cl | 2,4,5-F$_3$ | CH$_2$CH$_3$ | 1-phenylethyl |
| O | 4-Cl | 2,6-Cl$_2$ | CH$_2$CH$_3$ | 1-phenylethyl |
| O | 4-Cl | 2-F-6-Cl | CH$_2$CH$_3$ | 1-phenylethyl |
| O | 4-Cl | 2-F-3-Cl | CH$_2$CH$_3$ | 1-phenylethyl |
| CH$_2$ | 4-Cl | 3,5-F$_2$ | CH$_2$CH$_3$ | 1-phenylethyl |
| CH$_2$ | 4-Cl | 4-F | CH$_2$CH$_3$ | 1-phenylethyl |
| CH$_2$ | 4-Cl | 2,6-F$_2$ | CH$_2$CH$_3$ | 1-phenylethyl |
| O | 4-Cl | 2-F | CH$_2$CH$_3$ | CH$_2$CONH$_2$ |
| O | 4-Cl | 3-F | CH$_2$CH$_3$ | CH$_2$CONH$_2$ |
| O | 4-Cl | 4-F | CH$_2$CH$_3$ | CH$_2$CONH$_2$ |
| O | 4-Cl | 4-Cl | CH$_2$CH$_3$ | CH$_2$CONH$_2$ |
| O | 4-Cl | 2,5-F$_2$ | CH$_2$CH$_3$ | CH$_2$CONH$_2$ |
| O | 4-Cl | 2-Cl | CH$_2$CH$_3$ | CH$_2$CONH$_2$ |
| O | 4-Cl | 2,6-F$_2$ | CH$_2$CH$_3$ | CH$_2$CONH$_2$ |
| O | 4-Cl | 3,5-F$_2$ | CH$_2$CH$_3$ | CH$_2$CONH$_2$ |
| O | 4-Cl | 2,3-F$_2$ | CH$_2$CH$_3$ | CH$_2$CONH$_2$ |
| O | 4-Cl | 3,4-F$_2$ | CH$_2$CH$_3$ | CH$_2$CONH$_2$ |
| O | 4-Cl | 2,3,5-F$_3$ | CH$_2$CH$_3$ | CH$_2$CONH$_2$ |
| O | 4-Cl | 2,3,6-F$_3$ | CH$_2$CH$_3$ | CH$_2$CONH$_2$ |
| O | 4-Cl | 2,4,5-F$_3$ | CH$_2$CH$_3$ | CH$_2$CONH$_2$ |
| O | 4-Cl | 2,6-Cl$_2$ | CH$_2$CH$_3$ | CH$_2$CONH$_2$ |
| O | 4-Cl | 2-F-6-Cl | CH$_2$CH$_3$ | CH$_2$CONH$_2$ |
| O | 4-Cl | 2-F-3-Cl | CH$_2$CH$_3$ | CH$_2$CONH$_2$ |
| CH$_2$ | 4-Cl | 3,5-F$_2$ | CH$_2$CH$_3$ | CH$_2$CONH$_2$ |
| CH$_2$ | 4-Cl | 4-F | CH$_2$CH$_3$ | CH$_2$CONH$_2$ |
| CH$_2$ | 4-Cl | 2,6-F$_2$ | CH$_2$CH$_3$ | CH$_2$CONH$_2$ |
| O | 4-Cl | 2-F | CH$_2$CH$_3$ | CH$_2$CON(CH$_3$)$_2$ |
| O | 4-Cl | 3-F | CH$_2$CH$_3$ | CH$_2$CON(CH$_3$)$_2$ |
| O | 4-Cl | 4-F | CH$_2$CH$_3$ | CH$_2$CON(CH$_3$)$_2$ |
| O | 4-Cl | 4-Cl | CH$_2$CH$_3$ | CH$_2$CON(CH$_3$)$_2$ |
| O | 4-Cl | 2,5-F$_2$ | CH$_2$CH$_3$ | CH$_2$CON(CH$_3$)$_2$ |
| O | 4-Cl | 2-Cl | CH$_2$CH$_3$ | CH$_2$CON(CH$_3$)$_2$ |
| O | 4-Cl | 2,6-F$_2$ | CH$_2$CH$_3$ | CH$_2$CON(CH$_3$)$_2$ |
| O | 4-Cl | 3,5-F$_2$ | CH$_2$CH$_3$ | CH$_2$CON(CH$_3$)$_2$ |
| O | 4-Cl | 2,3-F$_2$ | CH$_2$CH$_3$ | CH$_2$CON(CH$_3$)$_2$ |
| O | 4-Cl | 3,4-F$_2$ | CH$_2$CH$_3$ | CH$_2$CON(CH$_3$)$_2$ |
| O | 4-Cl | 2,3,5-F$_3$ | CH$_2$CH$_3$ | CH$_2$CON(CH$_3$)$_2$ |
| O | 4-Cl | 2,3,6-F$_3$ | CH$_2$CH$_3$ | CH$_2$CON(CH$_3$)$_2$ |

TABLE XXII-continued

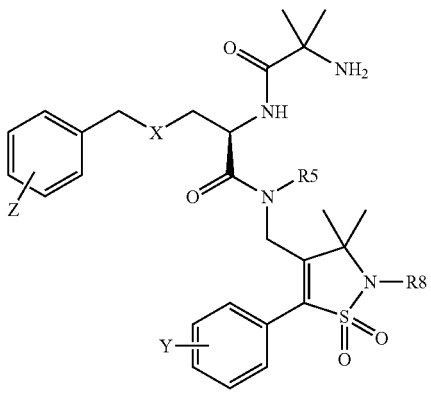

| X | Y | Z | R5 | R8 |
|---|---|---|----|----|
| O | 4-Cl | 2,4,5-$F_3$ | $CH_2CH_3$ | $CH_2CON(CH_3)_2$ |
| O | 4-Cl | 2,6-$Cl_2$ | $CH_2CH_3$ | $CH_2CON(CH_3)_2$ |
| O | 4-Cl | 2-F-6-Cl | $CH_2CH_3$ | $CH_2CON(CH_3)_2$ |
| O | 4-Cl | 2-F-3-Cl | $CH_2CH_3$ | $CH_2CON(CH_3)_2$ |
| $CH_2$ | 4-Cl | 3,5-$F_2$ | $CH_2CH_3$ | $CH_2CON(CH_3)_2$ |
| $CH_2$ | 4-Cl | 4-F | $CH_2CH_3$ | $CH_2CON(CH_3)_2$ |
| $CH_2$ | 4-Cl | 2,6-$F_2$ | $CH_2CH_3$ | $CH_2CON(CH_3)_2$ |
| O | 4-Cl | 2-F | $CH_2CH_3$ | $CH_2CH_2OCH_3$ |
| O | 4-Cl | 3-F | $CH_2CH_3$ | $CH_2CH_2OCH_3$ |
| O | 4-Cl | 4-F | $CH_2CH_3$ | $CH_2CH_2OCH_3$ |
| O | 4-Cl | 4-Cl | $CH_2CH_3$ | $CH_2CH_2OCH_3$ |
| O | 4-Cl | 2,5-$F_2$ | $CH_2CH_3$ | $CH_2CH_2OCH_3$ |
| O | 4-Cl | 2-Cl | $CH_2CH_3$ | $CH_2CH_2OCH_3$ |
| O | 4-Cl | 2,6-$F_2$ | $CH_2CH_3$ | $CH_2CH_2OCH_3$ |
| O | 4-Cl | 3,5-$F_2$ | $CH_2CH_3$ | $CH_2CH_2OCH_3$ |
| O | 4-Cl | 2,3-$F_2$ | $CH_2CH_3$ | $CH_2CH_2OCH_3$ |
| O | 4-Cl | 3,4-$F_2$ | $CH_2CH_3$ | $CH_2CH_2OCH_3$ |
| O | 4-Cl | 2,3,5-$F_3$ | $CH_2CH_3$ | $CH_2CH_2OCH_3$ |
| O | 4-Cl | 2,3,6-$F_3$ | $CH_2CH_3$ | $CH_2CH_2OCH_3$ |
| O | 4-Cl | 2,4,5-$F_3$ | $CH_2CH_3$ | $CH_2CH_2OCH_3$ |
| O | 4-Cl | 2,6-$Cl_2$ | $CH_2CH_3$ | $CH_2CH_2OCH_3$ |
| O | 4-Cl | 2-F-6-Cl | $CH_2CH_3$ | $CH_2CH_2OCH_3$ |
| O | 4-Cl | 2-F-3-Cl | $CH_2CH_3$ | $CH_2CH_2OCH_3$ |
| $CH_2$ | 4-Cl | 3,5-$F_2$ | $CH_2CH_3$ | $CH_2CH_2OCH_3$ |
| $CH_2$ | 4-Cl | 4-F | $CH_2CH_3$ | $CH_2CH_2OCH_3$ |
| $CH_2$ | 4-Cl | 2,6-$F_2$ | $CH_2CH_3$ | $CH_2CH_2OCH_3$ |
| O | 4-Cl | 2-F | $CH_2CH_3$ | $CH_2CH_2CH_2CF_3$ |
| O | 4-Cl | 3-F | $CH_2CH_3$ | $CH_2CH_2CH_2CF_3$ |
| O | 4-Cl | 4-F | $CH_2CH_3$ | $CH_2CH_2CH_2CF_3$ |
| O | 4-Cl | 4-Cl | $CH_2CH_3$ | $CH_2CH_2CH_2CF_3$ |
| O | 4-Cl | 2,5-$F_2$ | $CH_2CH_3$ | $CH_2CH_2CH_2CF_3$ |
| O | 4-Cl | 2-Cl | $CH_2CH_3$ | $CH_2CH_2CH_2CF_3$ |
| O | 4-Cl | 2,6-$F_2$ | $CH_2CH_3$ | $CH_2CH_2CH_2CF_3$ |
| O | 4-Cl | 3,5-$F_2$ | $CH_2CH_3$ | $CH_2CH_2CH_2CF_3$ |
| O | 4-Cl | 2,3-$F_2$ | $CH_2CH_3$ | $CH_2CH_2CH_2CF_3$ |
| O | 4-Cl | 3,4-$F_2$ | $CH_2CH_3$ | $CH_2CH_2CH_2CF_3$ |
| O | 4-Cl | 2,3,5-$F_3$ | $CH_2CH_3$ | $CH_2CH_2CH_2CF_3$ |
| O | 4-Cl | 2,3,6-$F_3$ | $CH_2CH_3$ | $CH_2CH_2CH_2CF_3$ |
| O | 4-Cl | 2,4,5-$F_3$ | $CH_2CH_3$ | $CH_2CH_2CH_2CF_3$ |
| O | 4-Cl | 2,6-$Cl_2$ | $CH_2CH_3$ | $CH_2CH_2CH_2CF_3$ |
| O | 4-Cl | 2-F-6-Cl | $CH_2CH_3$ | $CH_2CH_2CH_2CF_3$ |
| O | 4-Cl | 2-F-3-Cl | $CH_2CH_3$ | $CH_2CH_2CH_2CF_3$ |
| $CH_2$ | 4-Cl | 3,5-$F_2$ | $CH_2CH_3$ | $CH_2CH_2CH_2CF_3$ |
| $CH_2$ | 4-Cl | 4-F | $CH_2CH_3$ | $CH_2CH_2CH_2CF_3$ |
| $CH_2$ | 4-Cl | 2,6-$F_2$ | $CH_2CH_3$ | $CH_2CH_2CH_2CF_3$ |
| O | 4-Cl | 2-F | $CH_2CH_3$ | $CH_2CH_2CF_3$ |
| O | 4-Cl | 3-F | $CH_2CH_3$ | $CH_2CH_2CF_3$ |
| O | 4-Cl | 4-F | $CH_2CH_3$ | $CH_2CH_2CF_3$ |
| O | 4-Cl | 4-Cl | $CH_2CH_3$ | $CH_2CH_2CF_3$ |
| O | 4-Cl | 2,5-$F_2$ | $CH_2CH_3$ | $CH_2CH_2CF_3$ |
| O | 4-Cl | 2-Cl | $CH_2CH_3$ | $CH_2CH_2CF_3$ |
| O | 4-Cl | 2,6-$F_2$ | $CH_2CH_3$ | $CH_2CH_2CF_3$ |
| O | 4-Cl | 3,5-$F_2$ | $CH_2CH_3$ | $CH_2CH_2CF_3$ |
| O | 4-Cl | 2,3-$F_2$ | $CH_2CH_3$ | $CH_2CH_2CF_3$ |
| O | 4-Cl | 3,4-$F_2$ | $CH_2CH_3$ | $CH_2CH_2CF_3$ |
| O | 4-Cl | 2,3,5-$F_3$ | $CH_2CH_3$ | $CH_2CH_2CF_3$ |
| O | 4-Cl | 2,3,6-$F_3$ | $CH_2CH_3$ | $CH_2CH_2CF_3$ |

TABLE XXII-continued

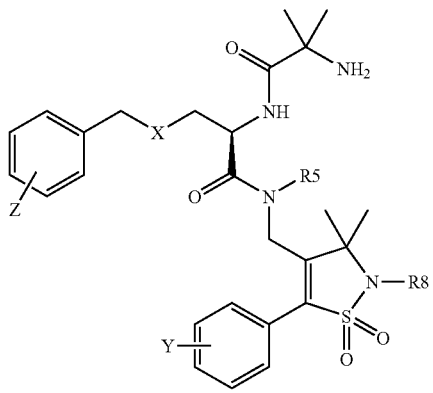

| X | Y | Z | R5 | R8 |
|---|---|---|----|----|
| O | 4-Cl | 2,4,5-$F_3$ | $CH_2CH_3$ | $CH_2CH_2CF_3$ |
| O | 4-Cl | 2,6-$Cl_2$ | $CH_2CH_3$ | $CH_2CH_2CF_3$ |
| O | 4-Cl | 2-F-6-Cl | $CH_2CH_3$ | $CH_2CH_2CF_3$ |
| O | 4-Cl | 2-F-3-Cl | $CH_2CH_3$ | $CH_2CH_2CF_3$ |
| $CH_2$ | 4-Cl | 3,5-$F_2$ | $CH_2CH_3$ | $CH_2CH_2CF_3$ |
| $CH_2$ | 4-Cl | 4-F | $CH_2CH_3$ | $CH_2CH_2CF_3$ |
| $CH_2$ | 4-Cl | 2,6-$F_2$ | $CH_2CH_3$ | $CH_2CH_2CF_3$ |

TABLE XXIII

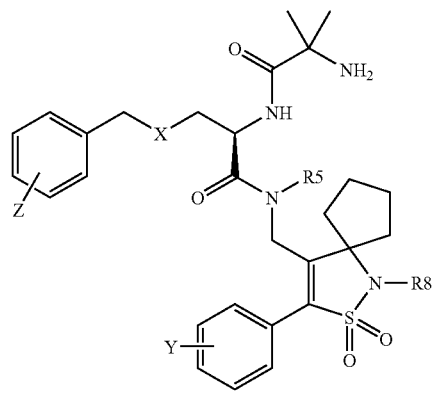

| X | Y | Z | R5 | R8 |
|---|---|---|----|----|
| O | 4-Cl | 2-F | $CH_2CH_3$ | $CH_3$ |
| O | 4-Cl | 3-F | $CH_2CH_3$ | $CH_3$ |
| O | 4-Cl | 4-F | $CH_2CH_3$ | $CH_3$ |
| O | 4-Cl | 4-Cl | $CH_2CH_3$ | $CH_3$ |
| O | 4-Cl | 2,5-$F_2$ | $CH_2CH_3$ | $CH_3$ |
| O | 4-Cl | 2,4-$F_2$ | $CH_2CH_3$ | $CH_3$ |
| O | 4-Cl | 2-Cl | $CH_2CH_3$ | $CH_3$ |
| O | 4-Cl | 2,6-$F_2$ | $CH_2CH_3$ | $CH_3$ |
| O | 4-Cl | 3,5-$F_2$ | $CH_2CH_3$ | $CH_3$ |
| O | 4-Cl | 2,3-$F_2$ | $CH_2CH_3$ | $CH_3$ |
| O | 4-Cl | 3,4-$F_2$ | $CH_2CH_3$ | $CH_3$ |
| O | 4-Cl | 2,3,5-$F_3$ | $CH_2CH_3$ | $CH_3$ |
| O | 4-Cl | 2,3,6-$F_3$ | $CH_2CH_3$ | $CH_3$ |
| O | 4-Cl | 2,4,5-$F_3$ | $CH_2CH_3$ | $CH_3$ |
| O | 4-Cl | 2,6-$Cl_2$ | $CH_2CH_3$ | $CH_3$ |
| O | 4-Cl | 2-F-6-Cl | $CH_2CH_3$ | $CH_3$ |
| O | 4-Cl | 2-F-3-Cl | $CH_2CH_3$ | $CH_3$ |
| O | 4-F | 2-F | $CH_2CH_3$ | $CH_3$ |
| O | 4-F | 3-F | $CH_2CH_3$ | $CH_3$ |
| O | 4-F | 4-F | $CH_2CH_3$ | $CH_3$ |
| O | 4-F | 4-Cl | $CH_2CH_3$ | $CH_3$ |
| O | 4-F | 2,5-$F_2$ | $CH_2CH_3$ | $CH_3$ |
| O | 4-F | 2,4-$F_2$ | $CH_2CH_3$ | $CH_3$ |
| O | 4-F | 2-Cl | $CH_2CH_3$ | $CH_3$ |
| O | 4-F | 2,6-$F_2$ | $CH_2CH_3$ | $CH_3$ |

TABLE XXIII-continued

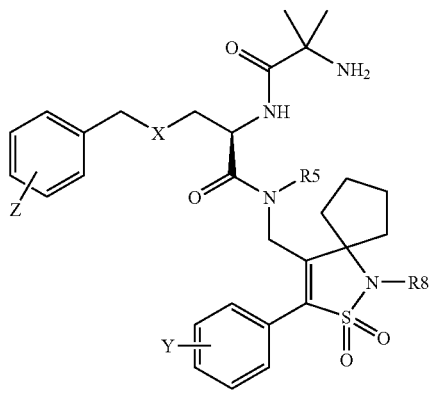

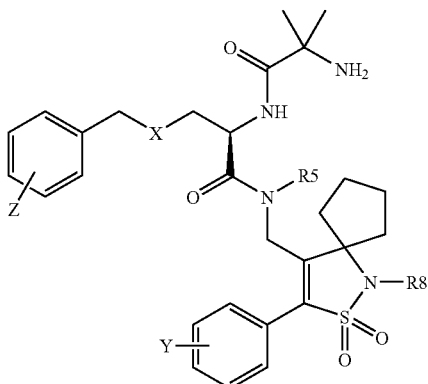

| X | Y | Z | R5 | R8 |
|---|---|---|---|---|
| O | 4-F | 3,5-F$_2$ | CH$_2$CH$_3$ | CH$_3$ |
| O | 4-F | 2,3-F$_2$ | CH$_2$CH$_3$ | CH$_3$ |
| O | 4-F | 3,4-F$_2$ | CH$_2$CH$_3$ | CH$_3$ |
| O | 4-F | 2,3,5-F$_3$ | CH$_2$CH$_3$ | CH$_3$ |
| O | 4-F | 2,3,6-F$_3$ | CH$_2$CH$_3$ | CH$_3$ |
| O | 4-F | 2,4,5-F$_3$ | CH$_2$CH$_3$ | CH$_3$ |
| O | 4-F | 2,6-Cl$_2$ | CH$_2$CH$_3$ | CH$_3$ |
| O | 4-F | 2-F-6-Cl | CH$_2$CH$_3$ | CH$_3$ |
| O | 4-F | 2-F-3-Cl | CH$_2$CH$_3$ | CH$_3$ |
| CH$_2$ | 4-Cl | 3,5-F$_2$ | CH$_2$CH$_3$ | CH$_3$ |
| CH$_2$ | 4-Cl | 4-F | CH$_2$CH$_3$ | CH$_3$ |
| CH$_2$ | 4-Cl | 2,6-F$_2$ | CH$_2$CH$_3$ | CH$_3$ |
| CH$_2$ | 4-F | 3,5-F$_2$ | CH$_2$CH$_3$ | CH$_3$ |
| CH$_2$ | 4-F | 4-F | CH$_2$CH$_3$ | CH$_3$ |
| CH$_2$ | 4-F | 2,6-F$_2$ | CH$_2$CH$_3$ | CH$_3$ |
| O | 4-Cl | 2-F | CH$_3$ | CH$_3$ |
| O | 4-Cl | 3-F | CH$_3$ | CH$_3$ |
| O | 4-Cl | 4-F | CH$_3$ | CH$_3$ |
| O | 4-Cl | 4-Cl | CH$_3$ | CH$_3$ |
| O | 4-Cl | 2,5-F$_2$ | CH$_3$ | CH$_3$ |
| O | 4-Cl | 2,4-F$_2$ | CH$_3$ | CH$_3$ |
| O | 4-Cl | 2-Cl | CH$_3$ | CH$_3$ |
| O | 4-Cl | 2,6-F$_2$ | CH$_3$ | CH$_3$ |
| O | 4-Cl | 3,5-F$_2$ | CH$_3$ | CH$_3$ |
| O | 4-Cl | 2,3-F$_2$ | CH$_3$ | CH$_3$ |
| O | 4-Cl | 3,4-F$_2$ | CH$_3$ | CH$_3$ |
| O | 4-Cl | 2,3,5-F$_3$ | CH$_3$ | CH$_3$ |
| O | 4-Cl | 2,3,6-F$_3$ | CH$_3$ | CH$_3$ |
| O | 4-Cl | 2,4,5-F$_3$ | CH$_3$ | CH$_3$ |
| O | 4-Cl | 2,6-Cl$_2$ | CH$_3$ | CH$_3$ |
| O | 4-Cl | 2-F-6-Cl | CH$_3$ | CH$_3$ |
| O | 4-Cl | 2-F-3-Cl | CH$_3$ | CH$_3$ |
| O | 4-F | 2-F | CH$_3$ | CH$_3$ |
| O | 4-F | 3-F | CH$_3$ | CH$_3$ |
| O | 4-F | 4-F | CH$_3$ | CH$_3$ |
| O | 4-F | 4-Cl | CH$_3$ | CH$_3$ |
| O | 4-F | 2,5-F$_2$ | CH$_3$ | CH$_3$ |
| O | 4-F | 2,4-F$_2$ | CH$_3$ | CH$_3$ |
| O | 4-F | 2-Cl | CH$_3$ | CH$_3$ |
| O | 4-F | 2,6-F$_2$ | CH$_3$ | CH$_3$ |
| O | 4-F | 3,5-F$_2$ | CH$_3$ | CH$_3$ |
| O | 4-F | 2,3-F$_2$ | CH$_3$ | CH$_3$ |
| O | 4-F | 3,4-F$_2$ | CH$_3$ | CH$_3$ |
| O | 4-F | 2,3,5-F$_3$ | CH$_3$ | CH$_3$ |
| O | 4-F | 2,3,6-F$_3$ | CH$_3$ | CH$_3$ |
| O | 4-F | 2,4,5-F$_3$ | CH$_3$ | CH$_3$ |
| O | 4-F | 2,6-Cl$_2$ | CH$_3$ | CH$_3$ |
| O | 4-F | 2-F-6-Cl | CH$_3$ | CH$_3$ |
| O | 4-F | 2-F-3-Cl | CH$_3$ | CH$_3$ |
| CH$_2$ | 4-Cl | 3,5-F$_2$ | CH$_3$ | CH$_3$ |
| CH$_2$ | 4-Cl | 4-F | CH$_3$ | CH$_3$ |
| CH$_2$ | 4-Cl | 2,6-F$_2$ | CH$_3$ | CH$_3$ |
| CH$_2$ | 4-F | 3,5-F$_2$ | CH$_3$ | CH$_3$ |
| CH$_2$ | 4-F | 4-F | CH$_3$ | CH$_3$ |
| CH$_2$ | 4-F | 2,6-F$_2$ | CH$_3$ | CH$_3$ |
| O | 4-Cl | 2-F | CH$_2$CH$_3$ | CH$_2$CH$_3$ |
| O | 4-Cl | 3-F | CH$_2$CH$_3$ | CH$_2$CH$_3$ |
| O | 4-Cl | 4-F | CH$_2$CH$_3$ | CH$_2$CH$_3$ |
| O | 4-Cl | 4-Cl | CH$_2$CH$_3$ | CH$_2$CH$_3$ |
| O | 4-Cl | 2,5-F$_2$ | CH$_2$CH$_3$ | CH$_2$CH$_3$ |
| O | 4-Cl | 2,4-F$_2$ | CH$_2$CH$_3$ | CH$_2$CH$_3$ |
| O | 4-Cl | 2-Cl | CH$_2$CH$_3$ | CH$_2$CH$_3$ |
| O | 4-Cl | 2,6-F$_2$ | CH$_2$CH$_3$ | CH$_2$CH$_3$ |
| O | 4-Cl | 3,5-F$_2$ | CH$_2$CH$_3$ | CH$_2$CH$_3$ |
| O | 4-Cl | 2,3-F$_2$ | CH$_2$CH$_3$ | CH$_2$CH$_3$ |
| O | 4-Cl | 3,4-F$_2$ | CH$_2$CH$_3$ | CH$_2$CH$_3$ |
| O | 4-Cl | 2,3,5-F$_3$ | CH$_2$CH$_3$ | CH$_2$CH$_3$ |
| O | 4-Cl | 2,3,6-F$_3$ | CH$_2$CH$_3$ | CH$_2$CH$_3$ |
| O | 4-Cl | 2,4,5-F$_3$ | CH$_2$CH$_3$ | CH$_2$CH$_3$ |
| O | 4-Cl | 2,6-Cl$_2$ | CH$_2$CH$_3$ | CH$_2$CH$_3$ |
| O | 4-Cl | 2-F-6-Cl | CH$_2$CH$_3$ | CH$_2$CH$_3$ |
| O | 4-Cl | 2-F-3-Cl | CH$_2$CH$_3$ | CH$_2$CH$_3$ |
| CH$_2$ | 4-Cl | 3,5-F$_2$ | CH$_2$CH$_3$ | CH$_2$CH$_3$ |
| CH$_2$ | 4-Cl | 4-F | CH$_2$CH$_3$ | CH$_2$CH$_3$ |
| CH$_2$ | 4-Cl | 2,6-F$_2$ | CH$_2$CH$_3$ | CH$_2$CH$_3$ |
| O | 4-Cl | 2-F | CH$_2$CH$_3$ | CH$_2$CH$_2$CH$_3$ |
| O | 4-Cl | 3-F | CH$_2$CH$_3$ | CH$_2$CH$_2$CH$_3$ |
| O | 4-Cl | 4-F | CH$_2$CH$_3$ | CH$_2$CH$_2$CH$_3$ |
| O | 4-Cl | 4-Cl | CH$_2$CH$_3$ | CH$_2$CH$_2$CH$_3$ |
| O | 4-Cl | 2,5-F$_2$ | CH$_2$CH$_3$ | CH$_2$CH$_2$CH$_3$ |
| O | 4-Cl | 2-Cl | CH$_2$CH$_3$ | CH$_2$CH$_2$CH$_3$ |
| O | 4-Cl | 2,6-F$_2$ | CH$_2$CH$_3$ | CH$_2$CH$_2$CH$_3$ |
| O | 4-Cl | 3,5-F$_2$ | CH$_2$CH$_3$ | CH$_2$CH$_2$CH$_3$ |
| O | 4-Cl | 2,3-F$_2$ | CH$_2$CH$_3$ | CH$_2$CH$_2$CH$_3$ |
| O | 4-Cl | 3,4-F$_2$ | CH$_2$CH$_3$ | CH$_2$CH$_2$CH$_3$ |
| O | 4-Cl | 2,3,5-F$_3$ | CH$_2$CH$_3$ | CH$_2$CH$_2$CH$_3$ |
| O | 4-Cl | 2,3,6-F$_3$ | CH$_2$CH$_3$ | CH$_2$CH$_2$CH$_3$ |
| O | 4-Cl | 2,4,5-F$_3$ | CH$_2$CH$_3$ | CH$_2$CH$_2$CH$_3$ |
| O | 4-Cl | 2,6-Cl$_2$ | CH$_2$CH$_3$ | CH$_2$CH$_2$CH$_3$ |
| O | 4-Cl | 2-F-6-Cl | CH$_2$CH$_3$ | CH$_2$CH$_2$CH$_3$ |
| O | 4-Cl | 2-F-3-Cl | CH$_2$CH$_3$ | CH$_2$CH$_2$CH$_3$ |
| CH$_2$ | 4-Cl | 3,5-F$_2$ | CH$_2$CH$_3$ | CH$_2$CH$_2$CH$_3$ |
| CH$_2$ | 4-Cl | 4-F | CH$_2$CH$_3$ | CH$_2$CH$_2$CH$_3$ |
| CH$_2$ | 4-Cl | 2,6-F$_2$ | CH$_2$CH$_3$ | CH$_2$CH$_2$CH$_3$ |
| O | 4-Cl | 2-F | CH$_2$CH$_3$ | CH$_2$CH$_2$F |
| O | 4-Cl | 3-F | CH$_2$CH$_3$ | CH$_2$CH$_2$F |
| O | 4-Cl | 4-F | CH$_2$CH$_3$ | CH$_2$CH$_2$F |
| O | 4-Cl | 4-Cl | CH$_2$CH$_3$ | CH$_2$CH$_2$F |
| O | 4-Cl | 2,5-F$_2$ | CH$_2$CH$_3$ | CH$_2$CH$_2$F |
| O | 4-Cl | 2-Cl | CH$_2$CH$_3$ | CH$_2$CH$_2$F |
| O | 4-Cl | 2,6-F$_2$ | CH$_2$CH$_3$ | CH$_2$CH$_2$F |
| O | 4-Cl | 3,5-F$_2$ | CH$_2$CH$_3$ | CH$_2$CH$_2$F |
| O | 4-Cl | 2,3-F$_2$ | CH$_2$CH$_3$ | CH$_2$CH$_2$F |
| O | 4-Cl | 3,4-F$_2$ | CH$_2$CH$_3$ | CH$_2$CH$_2$F |
| O | 4-Cl | 2,3,5-F$_3$ | CH$_2$CH$_3$ | CH$_2$CH$_2$F |
| O | 4-Cl | 2,3,6-F$_3$ | CH$_2$CH$_3$ | CH$_2$CH$_2$F |
| O | 4-Cl | 2,4,5-F$_3$ | CH$_2$CH$_3$ | CH$_2$CH$_2$F |
| O | 4-Cl | 2,6-Cl$_2$ | CH$_2$CH$_3$ | CH$_2$CH$_2$F |
| O | 4-Cl | 2-F-6-Cl | CH$_2$CH$_3$ | CH$_2$CH$_2$F |
| O | 4-Cl | 2-F-3-Cl | CH$_2$CH$_3$ | CH$_2$CH$_2$F |
| CH$_2$ | 4-Cl | 3,5-F$_2$ | CH$_2$CH$_3$ | CH$_2$CH$_2$F |
| CH$_2$ | 4-Cl | 4-F | CH$_2$CH$_3$ | CH$_2$CH$_2$F |
| CH$_2$ | 4-Cl | 2,6-F$_2$ | CH$_2$CH$_3$ | CH$_2$CH$_2$F |
| O | 4-Cl | 2-F | CH$_2$CH$_3$ | CH$_2$CH$_2$OH |

TABLE XXIII-continued

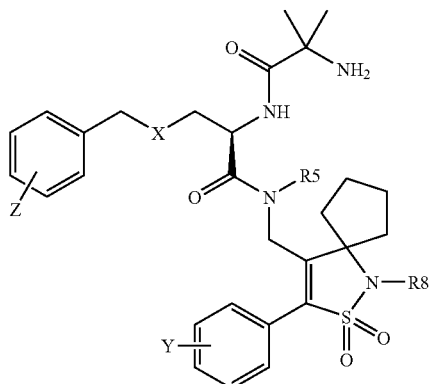

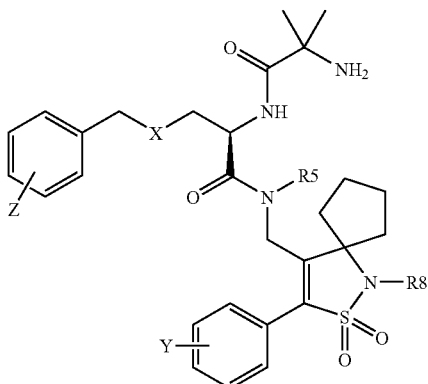

| X | Y | Z | R5 | R8 |
|---|---|---|---|---|
| O | 4-Cl | 3-F | CH₂CH₃ | CH₂CH₂OH |
| O | 4-Cl | 4-F | CH₂CH₃ | CH₂CH₂OH |
| O | 4-Cl | 4-Cl | CH₂CH₃ | CH₂CH₂OH |
| O | 4-Cl | 2,5-F₂ | CH₂CH₃ | CH₂CH₂OH |
| O | 4-Cl | 2-Cl | CH₂CH₃ | CH₂CH₂OH |
| O | 4-Cl | 2,6-F₂ | CH₂CH₃ | CH₂CH₂OH |
| O | 4-Cl | 3,5-F₂ | CH₂CH₃ | CH₂CH₂OH |
| O | 4-Cl | 2,3-F₂ | CH₂CH₃ | CH₂CH₂OH |
| O | 4-Cl | 3,4-F₂ | CH₂CH₃ | CH₂CH₂OH |
| O | 4-Cl | 2,3,5-F₃ | CH₂CH₃ | CH₂CH₂OH |
| O | 4-Cl | 2,3,6-F₃ | CH₂CH₃ | CH₂CH₂OH |
| O | 4-Cl | 2,4,5-F₃ | CH₂CH₃ | CH₂CH₂OH |
| O | 4-Cl | 2,6-Cl₂ | CH₂CH₃ | CH₂CH₂OH |
| O | 4-Cl | 2-F-6-Cl | CH₂CH₃ | CH₂CH₂OH |
| O | 4-Cl | 2-F-3-Cl | CH₂CH₃ | CH₂CH₂OH |
| CH₂ | 4-Cl | 3,5-F₂ | CH₂CH₃ | CH₂CH₂OH |
| CH₂ | 4-Cl | 4-F | CH₂CH₃ | CH₂CH₂OH |
| CH₂ | 4-Cl | 2,6-F₂ | CH₂CH₃ | CH₂CH₂OH |
| O | 4-Cl | 2-F | CH₂CH₃ | benzyl |
| O | 4-Cl | 3-F | CH₂CH₃ | benzyl |
| O | 4-Cl | 4-F | CH₂CH₃ | benzyl |
| O | 4-Cl | 4-Cl | CH₂CH₃ | benzyl |
| O | 4-Cl | 2,5-F₂ | CH₂CH₃ | benzyl |
| O | 4-Cl | 2-Cl | CH₂CH₃ | benzyl |
| O | 4-Cl | 2,6-F₂ | CH₂CH₃ | benzyl |
| O | 4-Cl | 3,5-F₂ | CH₂CH₃ | benzyl |
| O | 4-Cl | 2,3-F₂ | CH₂CH₃ | benzyl |
| O | 4-Cl | 3,4-F₂ | CH₂CH₃ | benzyl |
| O | 4-Cl | 2,3,5-F₃ | CH₂CH₃ | benzyl |
| O | 4-Cl | 2,3,6-F₃ | CH₂CH₃ | benzyl |
| O | 4-Cl | 2,4,5-F₃ | CH₂CH₃ | benzyl |
| O | 4-Cl | 2,6-Cl₂ | CH₂CH₃ | benzyl |
| O | 4-Cl | 2-F-6-Cl | CH₂CH₃ | benzyl |
| O | 4-Cl | 2-F-3-Cl | CH₂CH₃ | benzyl |
| CH₂ | 4-Cl | 3,5-F₂ | CH₂CH₃ | benzyl |
| CH₂ | 4-Cl | 4-F | CH₂CH₃ | benzyl |
| CH₂ | 4-Cl | 2,6-F₂ | CH₂CH₃ | benzyl |
| O | 4-Cl | 2-F | CH₂CH₃ | cyclopropylmethyl |
| O | 4-Cl | 3-F | CH₂CH₃ | cyclopropylmethyl |
| O | 4-Cl | 4-F | CH₂CH₃ | cyclopropylmethyl |
| O | 4-Cl | 4-Cl | CH₂CH₃ | cyclopropylmethyl |
| O | 4-Cl | 2,5-F₂ | CH₂CH₃ | cyclopropylmethyl |
| O | 4-Cl | 2-Cl | CH₂CH₃ | cyclopropylmethyl |
| O | 4-Cl | 2,6-F₂ | CH₂CH₃ | cyclopropylmethyl |
| O | 4-Cl | 3,5-F₂ | CH₂CH₃ | cyclopropylmethyl |
| O | 4-Cl | 2,3-F₂ | CH₂CH₃ | cyclopropylmethyl |
| O | 4-Cl | 3,4-F₂ | CH₂CH₃ | cyclopropylmethyl |
| O | 4-Cl | 2,3,5-F₃ | CH₂CH₃ | cyclopropylmethyl |
| O | 4-Cl | 2,3,6-F₃ | CH₂CH₃ | cyclopropylmethyl |
| O | 4-Cl | 2,4,5-F₃ | CH₂CH₃ | cyclopropylmethyl |
| O | 4-Cl | 2,6-Cl | CH₂CH₃ | cyclopropylmethyl |
| O | 4-Cl | 2-F-6-Cl | CH₂CH₃ | cyclopropylmethyl |
| O | 4-Cl | 2-F-3-Cl | CH₂CH₃ | cyclopropylmethyl |
| CH₂ | 4-Cl | 3,5-F₂ | CH₂CH₃ | cyclopropylmethyl |
| CH₂ | 4-Cl | 4-F | CH₂CH₃ | cyclopropylmethyl |
| CH₂ | 4-Cl | 2,6-F₂ | CH₂CH₃ | cyclopropylmethyl |
| O | 4-Cl | 2-F | CH₂CH₃ | CH(CH₃)₂ |
| O | 4-Cl | 3-F | CH₂CH₃ | CH(CH₃)₂ |
| O | 4-Cl | 4-F | CH₂CH₃ | CH(CH₃)₂ |
| O | 4-Cl | 4-Cl | CH₂CH₃ | CH(CH₃)₂ |
| O | 4-Cl | 2,5-F₂ | CH₂CH₃ | CH(CH₃)₂ |
| O | 4-Cl | 2-Cl | CH₂CH₃ | CH(CH₃)₂ |
| O | 4-Cl | 2,6-F₂ | CH₂CH₃ | CH(CH₃)₂ |
| O | 4-Cl | 3,5-F₂ | CH₂CH₃ | CH(CH₃)₂ |
| O | 4-Cl | 2,3-F₂ | CH₂CH₃ | CH(CH₃)₂ |
| O | 4-Cl | 3,4-F₂ | CH₂CH₃ | CH(CH₃)₂ |
| O | 4-Cl | 2,3,5-F₃ | CH₂CH₃ | CH(CH₃)₂ |
| O | 4-Cl | 2,3,6-F₃ | CH₂CH₃ | CH(CH₃)₂ |
| O | 4-Cl | 2,4,5-F₃ | CH₂CH₃ | CH(CH₃)₂ |
| O | 4-Cl | 2,6-Cl₂ | CH₂CH₃ | CH(CH₃)₂ |
| O | 4-Cl | 2-F-6-Cl | CH₂CH₃ | CH(CH₃)₂ |
| O | 4-Cl | 2-F-3-Cl | CH₂CH₃ | CH(CH₃)₂ |
| CH₂ | 4-Cl | 3,5-F₂ | CH₂CH₃ | CH(CH₃)₂ |
| CH₂ | 4-Cl | 4-F | CH₂CH₃ | CH(CH₃)₂ |
| CH₂ | 4-Cl | 2,6-F₂ | CH₂CH₃ | CH(CH₃)₂ |
| O | 4-Cl | 2-F | CH₂CH₃ | CH₂CH(CH₃)₂ |
| O | 4-Cl | 3-F | CH₂CH₃ | CH₂CH(CH₃)₂ |
| O | 4-Cl | 4-F | CH₂CH₃ | CH₂CH(CH₃)₂ |
| O | 4-Cl | 4-Cl | CH₂CH₃ | CH₂CH(CH₃)₂ |
| O | 4-Cl | 2,5-F₂ | CH₂CH₃ | CH₂CH(CH₃)₂ |
| O | 4-Cl | 2-Cl | CH₂CH₃ | CH₂CH(CH₃)₂ |
| O | 4-Cl | 2,6-F₂ | CH₂CH₃ | CH₂CH(CH₃)₂ |
| O | 4-Cl | 3,5-F₂ | CH₂CH₃ | CH₂CH(CH₃)₂ |
| O | 4-Cl | 2,3-F₂ | CH₂CH₃ | CH₂CH(CH₃)₂ |
| O | 4-Cl | 3,4-F₂ | CH₂CH₃ | CH₂CH(CH₃)₂ |
| O | 4-Cl | 2,3,5-F₃ | CH₂CH₃ | CH₂CH(CH₃)₂ |
| O | 4-Cl | 2,3,6-F₃ | CH₂CH₃ | CH₂CH(CH₃)₂ |
| O | 4-Cl | 2,4,5-F₃ | CH₂CH₃ | CH₂CH(CH₃)₂ |
| O | 4-Cl | 2,6-Cl₂ | CH₂CH₃ | CH₂CH(CH₃)₂ |
| O | 4-Cl | 2-F-6-Cl | CH₂CH₃ | CH₂CH(CH₃)₂ |
| O | 4-Cl | 2-F-3-Cl | CH₂CH₃ | CH₂CH(CH₃)₂ |
| CH₂ | 4-Cl | 3,5-F₂ | CH₂CH₃ | CH₂CH(CH₃)₂ |
| CH₂ | 4-Cl | 4-F | CH₂CH₃ | CH₂CH(CH₃)₂ |
| CH₂ | 4-Cl | 2,6-F₂ | CH₂CH₃ | CH₂CH(CH₃)₂ |
| O | 4-Cl | 2-F | CH₂CH₃ | CH₂C(CH₃)₃ |
| O | 4-Cl | 3-F | CH₂CH₃ | CH₂C(CH₃)₃ |
| O | 4-Cl | 4-F | CH₂CH₃ | CH₂C(CH₃)₃ |
| O | 4-Cl | 4-Cl | CH₂CH₃ | CH₂C(CH₃)₃ |
| O | 4-Cl | 2,5-F₂ | CH₂CH₃ | CH₂C(CH₃)₃ |
| O | 4-Cl | 2-Cl | CH₂CH₃ | CH₂C(CH₃)₃ |
| O | 4-Cl | 2,6-F₂ | CH₂CH₃ | CH₂C(CH₃)₃ |
| O | 4-Cl | 3,5-F₂ | CH₂CH₃ | CH₂C(CH₃)₃ |
| O | 4-Cl | 2,3-F₂ | CH₂CH₃ | CH₂C(CH₃)₃ |
| O | 4-Cl | 3,4-F₂ | CH₂CH₃ | CH₂C(CH₃)₃ |
| O | 4-Cl | 2,3,5-F₃ | CH₂CH₃ | CH₂C(CH₃)₃ |
| O | 4-Cl | 2,3,6-F₃ | CH₂CH₃ | CH₂C(CH₃)₃ |
| O | 4-Cl | 2,4,5-F₃ | CH₂CH₃ | CH₂C(CH₃)₃ |
| O | 4-Cl | 2,6-Cl | CH₂CH₃ | CH₂C(CH₃)₃ |
| O | 4-Cl | 2-F-6-Cl | CH₂CH₃ | CH₂C(CH₃)₃ |
| O | 4-Cl | 2-F-3-Cl | CH₂CH₃ | CH₂C(CH₃)₃ |
| CH₂ | 4-Cl | 3,5-F₂ | CH₂CH₃ | CH₂C(CH₃)₃ |
| CH₂ | 4-Cl | 4-F | CH₂CH₃ | CH₂C(CH₃)₃ |
| CH₂ | 4-Cl | 2,6-F₂ | CH₂CH₃ | CH₂C(CH₃)₃ |
| O | 4-Cl | 2-F | CH₂CH₃ | 1-phenylethyl |

TABLE XXIII-continued

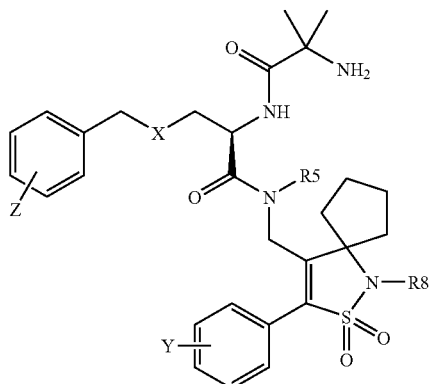

| X | Y | Z | R5 | R8 |
|---|---|---|----|----|
| O | 4-Cl | 3-F | $CH_2CH_3$ | 1-phenylethyl |
| O | 4-Cl | 4-F | $CH_2CH_3$ | 1-phenylethyl |
| O | 4-Cl | 4-Cl | $CH_2CH_3$ | 1-phenylethyl |
| O | 4-Cl | 2,5-$F_2$ | $CH_2CH_3$ | 1-phenylethyl |
| O | 4-Cl | 2-Cl | $CH_2CH_3$ | 1-phenylethyl |
| O | 4-Cl | 2,6-$F_2$ | $CH_2CH_3$ | 1-phenylethyl |
| O | 4-Cl | 3,5-$F_2$ | $CH_2CH_3$ | 1-phenylethyl |
| O | 4-Cl | 2,3-$F_2$ | $CH_2CH_3$ | 1-phenylethyl |
| O | 4-Cl | 3,4-$F_2$ | $CH_2CH_3$ | 1-phenylethyl |
| O | 4-Cl | 2,3,5-$F_3$ | $CH_2CH_3$ | 1-phenylethyl |
| O | 4-Cl | 2,3,6-$F_3$ | $CH_2CH_3$ | 1-phenylethyl |
| O | 4-Cl | 2,4,5-$F_3$ | $CH_2CH_3$ | 1-phenylethyl |
| O | 4-Cl | 2,6-$Cl_2$ | $CH_2CH_3$ | 1-phenylethyl |
| O | 4-Cl | 2-F-6-Cl | $CH_2CH_3$ | 1-phenylethyl |
| O | 4-Cl | 2-F-3-Cl | $CH_2CH_3$ | 1-phenylethyl |
| $CH_2$ | 4-Cl | 3,5-$F_2$ | $CH_2CH_3$ | 1-phenylethyl |
| $CH_2$ | 4-Cl | 4-F | $CH_2CH_3$ | 1-phenylethyl |
| $CH_2$ | 4-Cl | 2,6-$F_2$ | $CH_2CH_3$ | 1-phenylethyl |
| O | 4-Cl | 2-F | $CH_2CH_3$ | $CH_2CONH_2$ |
| O | 4-Cl | 3-F | $CH_2CH_3$ | $CH_2CONH_2$ |
| O | 4-Cl | 4-F | $CH_2CH_3$ | $CH_2CONH_2$ |
| O | 4-Cl | 4-Cl | $CH_2CH_3$ | $CH_2CONH_2$ |
| O | 4-Cl | 2,5-$F_2$ | $CH_2CH_3$ | $CH_2CONH_2$ |
| O | 4-Cl | 2-Cl | $CH_2CH_3$ | $CH_2CONH_2$ |
| O | 4-Cl | 2,6-$F_2$ | $CH_2CH_3$ | $CH_2CONH_2$ |
| O | 4-Cl | 3,5-$F_2$ | $CH_2CH_3$ | $CH_2CONH_2$ |
| O | 4-Cl | 2,3-$F_2$ | $CH_2CH_3$ | $CH_2CONH_2$ |
| O | 4-Cl | 3,4-$F_2$ | $CH_2CH_3$ | $CH_2CONH_2$ |
| O | 4-Cl | 2,3,5-$F_3$ | $CH_2CH_3$ | $CH_2CONH_2$ |
| O | 4-Cl | 2,3,6-$F_3$ | $CH_2CH_3$ | $CH_2CONH_2$ |
| O | 4-Cl | 2,4,5-$F_3$ | $CH_2CH_3$ | $CH_2CONH_2$ |
| O | 4-Cl | 2,6-$Cl_2$ | $CH_2CH_3$ | $CH_2CONH_2$ |
| O | 4-Cl | 2-F-6-Cl | $CH_2CH_3$ | $CH_2CONH_2$ |
| O | 4-Cl | 2-F-3-Cl | $CH_2CH_3$ | $CH_2CONH_2$ |
| $CH_2$ | 4-Cl | 3,5-$F_2$ | $CH_2CH_3$ | $CH_2CONH_2$ |
| $CH_2$ | 4-Cl | 4-F | $CH_2CH_3$ | $CH_2CONH_2$ |
| $CH_2$ | 4-Cl | 2,6-$F_2$ | $CH_2CH_3$ | $CH_2CONH_2$ |
| O | 4-Cl | 2-F | $CH_2CH_3$ | $CH_2CON(CH_3)_2$ |
| O | 4-Cl | 3-F | $CH_2CH_3$ | $CH_2CON(CH_3)_2$ |
| O | 4-Cl | 4-F | $CH_2CH_3$ | $CH_2CON(CH_3)_2$ |
| O | 4-Cl | 4-Cl | $CH_2CH_3$ | $CH_2CON(CH_3)_2$ |
| O | 4-Cl | 2,5-$F_2$ | $CH_2CH_3$ | $CH_2CON(CH_3)_2$ |
| O | 4-Cl | 2-Cl | $CH_2CH_3$ | $CH_2CON(CH_3)_2$ |
| O | 4-Cl | 2,6-$F_2$ | $CH_2CH_3$ | $CH_2CON(CH_3)_2$ |
| O | 4-Cl | 3,5-$F_2$ | $CH_2CH_3$ | $CH_2CON(CH_3)_2$ |
| O | 4-Cl | 2,3-$F_2$ | $CH_2CH_3$ | $CH_2CON(CH_3)_2$ |
| O | 4-Cl | 3,4-$F_2$ | $CH_2CH_3$ | $CH_2CON(CH_3)_2$ |
| O | 4-Cl | 2,3,5-$F_3$ | $CH_2CH_3$ | $CH_2CON(CH_3)_2$ |
| O | 4-Cl | 2,3,6-$F_3$ | $CH_2CH_3$ | $CH_2CON(CH_3)_2$ |
| O | 4-Cl | 2,4,5-$F_3$ | $CH_2CH_3$ | $CH_2CON(CH_3)_2$ |
| O | 4-Cl | 2,6-$Cl_2$ | $CH_2CH_3$ | $CH_2CON(CH_3)_2$ |
| O | 4-Cl | 2-F-6-Cl | $CH_2CH_3$ | $CH_2CON(CH_3)_2$ |
| O | 4-Cl | 2-F-3-Cl | $CH_2CH_3$ | $CH_2CON(CH_3)_2$ |
| $CH_2$ | 4-Cl | 3,5-$F_2$ | $CH_2CH_3$ | $CH_2CON(CH_3)_2$ |
| $CH_2$ | 4-Cl | 4-F | $CH_2CH_3$ | $CH_2CON(CH_3)_2$ |
| $CH_2$ | 4-Cl | 2,6-$F_2$ | $CH_2CH_3$ | $CH_2CON(CH_3)_2$ |
| O | 4-Cl | 2-F | $CH_2CH_3$ | $CH_2CH_2OCH_3$ |

TABLE XXIII-continued

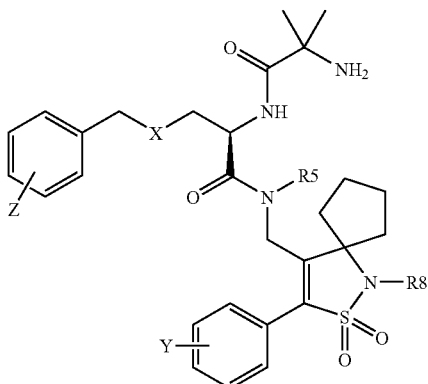

| X | Y | Z | R5 | R8 |
|---|---|---|----|----|
| O | 4-Cl | 3-F | $CH_2CH_3$ | $CH_2CH_2OCH_3$ |
| O | 4-Cl | 4-F | $CH_2CH_3$ | $CH_2CH_2OCH_3$ |
| O | 4-Cl | 4-Cl | $CH_2CH_3$ | $CH_2CH_2OCH_3$ |
| O | 4-Cl | 2,5-$F_2$ | $CH_2CH_3$ | $CH_2CH_2OCH_3$ |
| O | 4-Cl | 2-Cl | $CH_2CH_3$ | $CH_2CH_2OCH_3$ |
| O | 4-Cl | 2,6-$F_2$ | $CH_2CH_3$ | $CH_2CH_2OCH_3$ |
| O | 4-Cl | 3,5-$F_2$ | $CH_2CH_3$ | $CH_2CH_2OCH_3$ |
| O | 4-Cl | 2,3-$F_2$ | $CH_2CH_3$ | $CH_2CH_2OCH_3$ |
| O | 4-Cl | 3,4-$F_2$ | $CH_2CH_3$ | $CH_2CH_2OCH_3$ |
| O | 4-Cl | 2,3,5-$F_3$ | $CH_2CH_3$ | $CH_2CH_2OCH_3$ |
| O | 4-Cl | 2,3,6-$F_3$ | $CH_2CH_3$ | $CH_2CH_2OCH_3$ |
| O | 4-Cl | 2,4,5-$F_3$ | $CH_2CH_3$ | $CH_2CH_2OCH_3$ |
| O | 4-Cl | 2,6-$Cl_2$ | $CH_2CH_3$ | $CH_2CH_2OCH_3$ |
| O | 4-Cl | 2-F-6-Cl | $CH_2CH_3$ | $CH_2CH_2OCH_3$ |
| O | 4-Cl | 2-F-3-Cl | $CH_2CH_3$ | $CH_2CH_2OCH_3$ |
| $CH_2$ | 4-Cl | 3,5-$F_2$ | $CH_2CH_3$ | $CH_2CH_2OCH_3$ |
| $CH_2$ | 4-Cl | 4-F | $CH_2CH_3$ | $CH_2CH_2OCH_3$ |
| $CH_2$ | 4-Cl | 2,6-$F_2$ | $CH_2CH_3$ | $CH_2CH_2OCH_3$ |
| O | 4-Cl | 2-F | $CH_2CH_3$ | $CH_2CH_2CH_2CF_3$ |
| O | 4-Cl | 3-F | $CH_2CH_3$ | $CH_2CH_2CH_2CF_3$ |
| O | 4-Cl | 4-F | $CH_2CH_3$ | $CH_2CH_2CH_2CF_3$ |
| O | 4-Cl | 4-Cl | $CH_2CH_3$ | $CH_2CH_2CH_2CF_3$ |
| O | 4-Cl | 2,5-$F_2$ | $CH_2CH_3$ | $CH_2CH_2CH_2CF_3$ |
| O | 4-Cl | 2-Cl | $CH_2CH_3$ | $CH_2CH_2CH_2CF_3$ |
| O | 4-Cl | 2,6-$F_2$ | $CH_2CH_3$ | $CH_2CH_2CH_2CF_3$ |
| O | 4-Cl | 3,5-$F_2$ | $CH_2CH_3$ | $CH_2CH_2CH_2CF_3$ |
| O | 4-Cl | 2,3-$F_2$ | $CH_2CH_3$ | $CH_2CH_2CH_2CF_3$ |
| O | 4-Cl | 3,4-$F_2$ | $CH_2CH_3$ | $CH_2CH_2CH_2CF_3$ |
| O | 4-Cl | 2,3,5-$F_3$ | $CH_2CH_3$ | $CH_2CH_2CH_2CF_3$ |
| O | 4-Cl | 2,3,6-$F_3$ | $CH_2CH_3$ | $CH_2CH_2CH_2CF_3$ |
| O | 4-Cl | 2,4,5-$F_3$ | $CH_2CH_3$ | $CH_2CH_2CH_2CF_3$ |
| O | 4-Cl | 2,6-$Cl_2$ | $CH_2CH_3$ | $CH_2CH_2CH_2CF_3$ |
| O | 4-Cl | 2-F-6-Cl | $CH_2CH_3$ | $CH_2CH_2CH_2CF_3$ |
| O | 4-Cl | 2-F-3-Cl | $CH_2CH_3$ | $CH_2CH_2CH_2CF_3$ |
| $CH_2$ | 4-Cl | 3,5-$F_2$ | $CH_2CH_3$ | $CH_2CH_2CH_2CF_3$ |
| $CH_2$ | 4-Cl | 4-F | $CH_2CH_3$ | $CH_2CH_2CH_2CF_3$ |
| $CH_2$ | 4-Cl | 2,6-$F_2$ | $CH_2CH_3$ | $CH_2CH_2CH_2CF_3$ |
| O | 4-Cl | 2-F | $CH_2CH_3$ | $CH_2CH_2CF_3$ |
| O | 4-Cl | 3-F | $CH_2CH_3$ | $CH_2CH_2CF_3$ |
| O | 4-Cl | 4-F | $CH_2CH_3$ | $CH_2CH_2CF_3$ |
| O | 4-Cl | 4-Cl | $CH_2CH_3$ | $CH_2CH_2CF_3$ |
| O | 4-Cl | 2,5-$F_2$ | $CH_2CH_3$ | $CH_2CH_2CF_3$ |
| O | 4-Cl | 2-Cl | $CH_2CH_3$ | $CH_2CH_2CF_3$ |
| O | 4-Cl | 2,6-$F_2$ | $CH_2CH_3$ | $CH_2CH_2CF_3$ |
| O | 4-Cl | 3,5-$F_2$ | $CH_2CH_3$ | $CH_2CH_2CF_3$ |
| O | 4-Cl | 2,3-$F_2$ | $CH_2CH_3$ | $CH_2CH_2CF_3$ |
| O | 4-Cl | 3,4-$F_2$ | $CH_2CH_3$ | $CH_2CH_2CF_3$ |
| O | 4-Cl | 2,3,5-$F_3$ | $CH_2CH_3$ | $CH_2CH_2CF_3$ |
| O | 4-Cl | 2,3,6-$F_3$ | $CH_2CH_3$ | $CH_2CH_2CF_3$ |
| O | 4-Cl | 2,4,5-$F_3$ | $CH_2CH_3$ | $CH_2CH_2CF_3$ |
| O | 4-Cl | 2,6-$Cl_2$ | $CH_2CH_3$ | $CH_2CH_2CF_3$ |
| O | 4-Cl | 2-F-6-Cl | $CH_2CH_3$ | $CH_2CH_2CF_3$ |
| O | 4-Cl | 2-F-3-Cl | $CH_2CH_3$ | $CH_2CH_2CF_3$ |
| $CH_2$ | 4-Cl | 3,5-$F_2$ | $CH_2CH_3$ | $CH_2CH_2CF_3$ |
| $CH_2$ | 4-Cl | 4-F | $CH_2CH_3$ | $CH_2CH_2CF_3$ |
| $CH_2$ | 4-Cl | 2,6-$F_2$ | $CH_2CH_3$ | $CH_2CH_2CF_3$ |

The compounds of the present invention may be prepared by a number of routes, many of which are known to those of skill in the art. The particular order of steps to be employed in the synthesis of compounds of formula I is dependent upon the compound to be synthesized, the starting material employed, and the relative lability of the various substituted moieties.

During any of the following synthetic sequences it may be necessary or desirable to protect sensitive or reactive groups on any of the molecules concerned. This may be achieved by employing conventional protecting groups as described, supra.

The compounds used in the method of the present invention may have one or more asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in Nomenclature of Organic Compounds: Principles and Practice, (J. H. Fletcher, et al., eds., 1974) at pages 103-120.

In addition to the (R)-(S) system, the older D-L system is also used in this document to denote absolute configuration, especially with reference to amino acids. In this system, a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, a number of routes are available. As an example, a mixture of enantiomers may be prepared, and then the two enantiomers may be separated. A commonly employed method for the resolution of the racemic mixture (or mixture of enantiomers) into the individual enantiomers is to first convert the enantiomers to diastereomers by way of forming a salt with an optically active acid or base. These diastereomers may then be separated using differential solubility, fractional crystallization, chromatography, or the like. Further details regarding resolution of enantiomeric mixtures may be found in J. Jacques, et al., Enantiomers, Racemates, and Resolutions, (1991).

Representative starting material for this synthesis is a compound of formula Va, which may be reacted with an ethinylamine of formula VI, with R6 and R7 as defined in Formula I, by methods known in the art to yield a compound of formula VII. Alternatively, a compound of formula Vb may be coupled with a compound of formula VI using activating agents for N-acylation reactions known in the art, like HOBT, DCC, EDC, oxalyl chloride, TBTU or other coupling reagents known to the skilled artisan, to result in a compound of formula VII. Preferred for the practice of the present invention is TBTU. Intermediates of formula Vb and VI are commercially available or can be prepared by methods known in the art. Intermediates of formula Va may be prepared from commercial compounds by standard methods as described in Tetrahedron Lett. 25 (1984), 4553-4556.

A compound of formula VII may be hydrated by standard methods to yield a compound of formula VIII and subsequently cyclized by treatment with a deprotonating agent, such as sodium hydride, optionally in the presence of an alkylating agent to yield a compound of formula IX. Treatment of the resulting compound with a bromination reagent, such as N-bromosuccinimide, results in a compound of formula X. Reaction with an amine generates compounds of formula XI. Representative reactions are provided in Scheme A below. An example of formula IX where Q is $SO_2$, R8 is hydrogen and R9 is 4-chlorophenyl is described in Pestic. Sci. 39 (1993), 185-192.

Scheme A

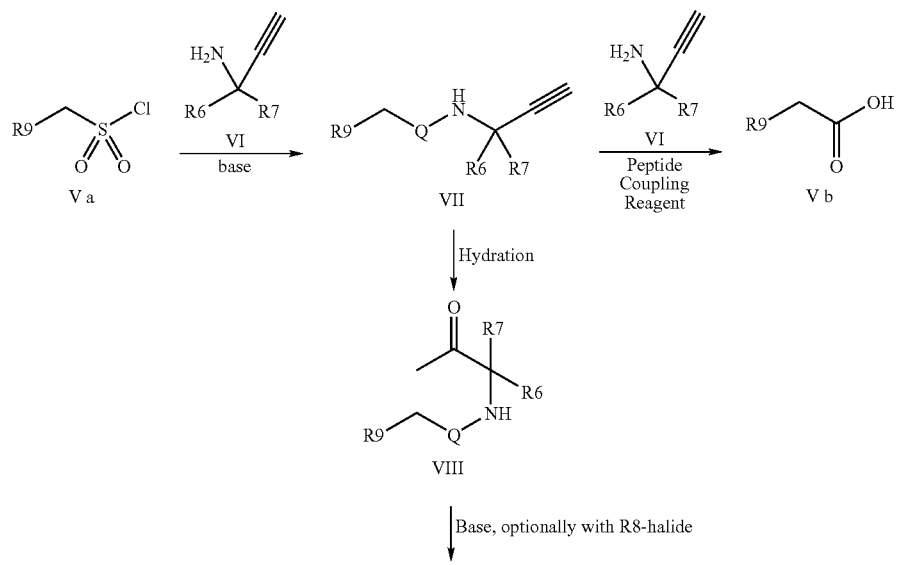

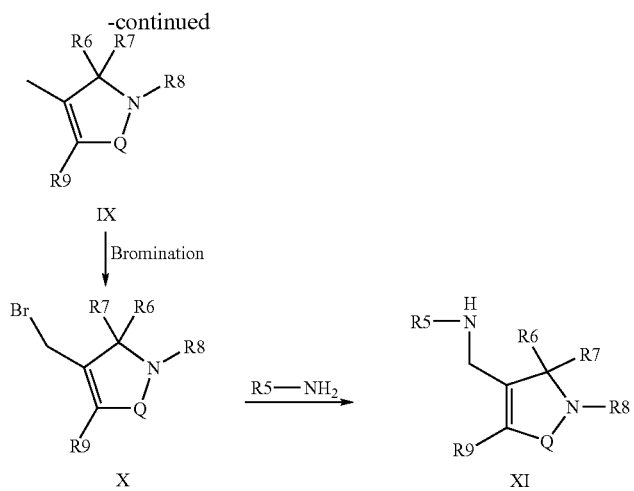

Scheme B shows an alternative synthesis for acetyl intermediates of Formula VIII:

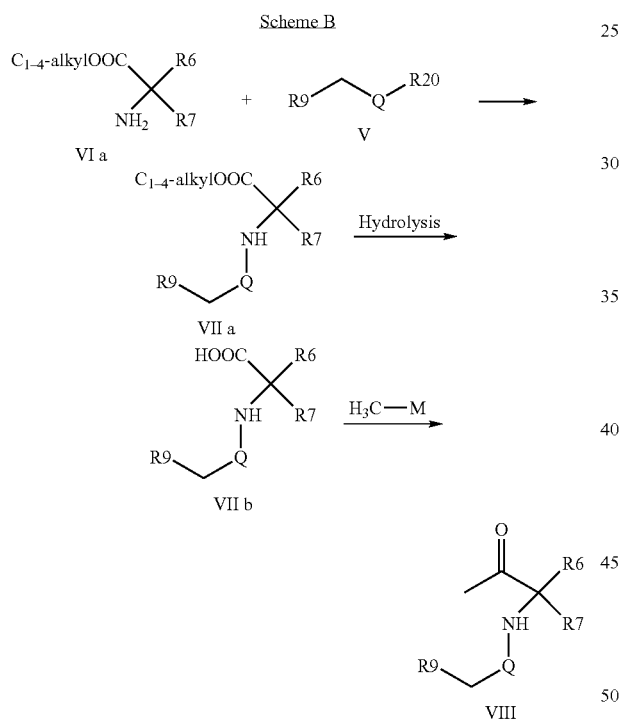

Esters of aminoacids of Formula VI a, preferably methyl or ethyl esters, are coupled with derivatives of carboxylic acids or sulfonic acids of Formula V (with R20 meaning OH or Cl, respectively) by methods described in Scheme A to give intermediates of Formula VIIa. The esters are hydrolized by standard methods to give carboxylic acids of Formula VIIb. These are treated with organometallic methyl compounds to prepare the acetyl intermediates of Formula VIII. Preferred organometallic reagents are methyl Grignard reagents (M=MgCl, MgBr, or MgI) or methyl lithium (M=Li), more preferred is methyl lithium. Examples for this reaction are known from the literature, e.g. J. Org. Chem. 58 (1993), 4758; J. Org. Chem. 62 (1997), 6862; Tetrahedron Lett. 35 (1994), 3745. In a preferred method a solution of the carboxylic acid in a solvent like THF or DME is treated with an excess of methyl lithium in diethylether at a temperature below −60° C. followed by warming to room temperature.

Compounds of Formula I in which m=2 may be prepared as shown in Scheme C below.

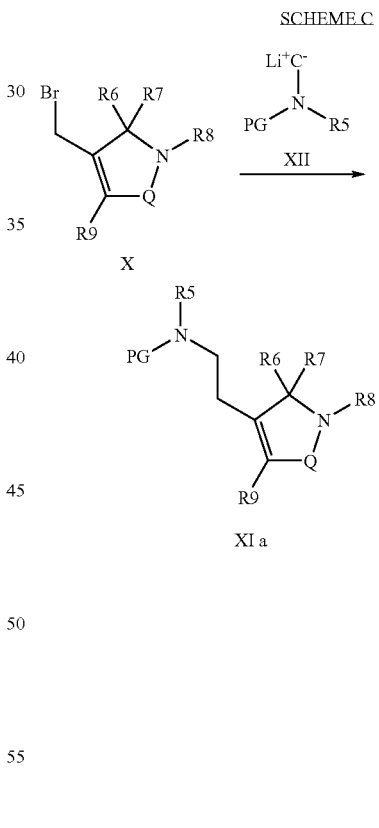

A compound of formula XII is obtained by treatment of a protected methylamine with a deprotonating agent like butyllithium as described for example in Tetrahedron Lett. 35 (24), 1994, 4067-70. The substituent "PG" means a protecting group, which is known to the artisan, and all other substituents are as defined by Formula I, herein. One preferred protecting group is the BOC group or another N-protecting group known in the art and stable under the reaction conditions. A compound of formula X is treated with a compound of formula XII to yield a compound of formula XIa.

It is to be understood that the bromine group on the compound of formula X may in fact be any suitable leaving group, as defined herein.

The term "leaving group" refers to a group of atoms that is displaced from a carbon atom by the attack of a nucleophile in a nucleophilic substitution reaction. Suitable leaving groups include bromo, chloro, and iodo, benzenesulfonyloxy, methanesulfonyloxy, and toluenesulfonyloxy. The term "leaving group" includes activating groups as defined above.

A second portion of the overall synthesis of compounds of formula I is provided in Scheme D below.

Representative starting material for this synthesis is a compound of formula XIIIa, which may be a chemically-protected derivative of the amino acid serine. By chemically-protected it is meant that both the amino- and carboxy-functional groups have been suitably protected in order to facilitate further reactions with this molecule. Such protection reactions are known to those of skill in the art, and may be applied to other suitable starting materials. Intermediates of formula XIIIa are commercially available, or may be prepared by standard syntheses of amino acids. Such syntheses are well known to persons of ordinary skill in the art and are described, for example, in Chemistry and Biochemistry of Amino Acids, (G. C. Chapman ed., 1985). The protected amino group may be specifically deprotected, e.g. if PG is a Boc group, using trifluoroacetic acid and methylene chloride, to allow for further reactions with this amino functional group. This deprotection reaction results in a compound of formula XIIIb.

A compound of formula XIIIb may then be N-acylated with an amino-protected compound of formula XIV for instance HOOC—$C_1$-$C_6$alkylNHR10 or HOOC—(substituted $C_1$-$C_6$alkyl)NHR10 or HOOC—(unsubstituted or substituted $C_3$-$C_8$ cycloalkyl)NHR10, wherein R10 is an amino protecting group (PG), to produce a compound of formula XIIIc.

Compounds of formula XIV are commercially available, or are readily prepared from suitable available starting materials. The protected carboxy group on the compound of formula XIIIc is then selectively deprotected, typically using lithium hydroxide, to generate a compound of formula XIII. A compound of formula XIII is then coupled with a compound of formula XI and subsequently deprotected to generate a compound of formula Ia.

Representative reactions are provided below in Scheme D.

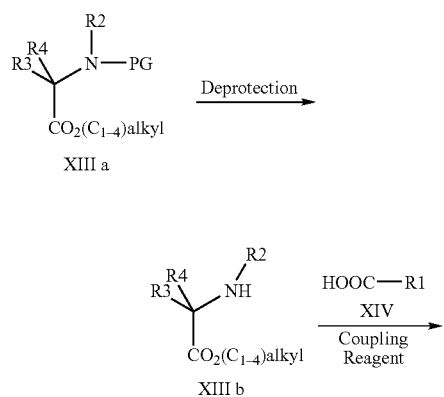

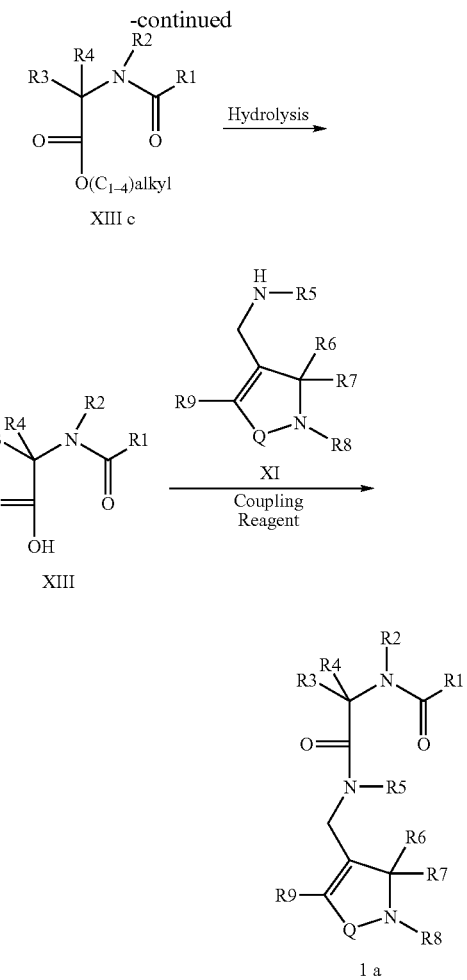

An alternative synthesis for compounds of formula Ia is shown in Scheme E below:

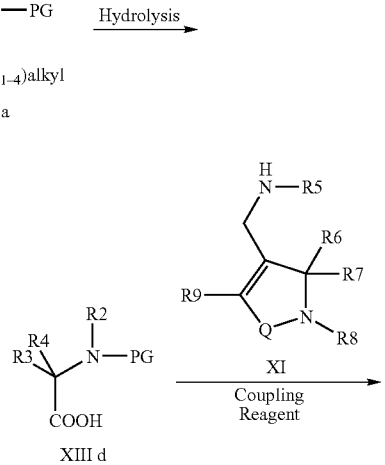

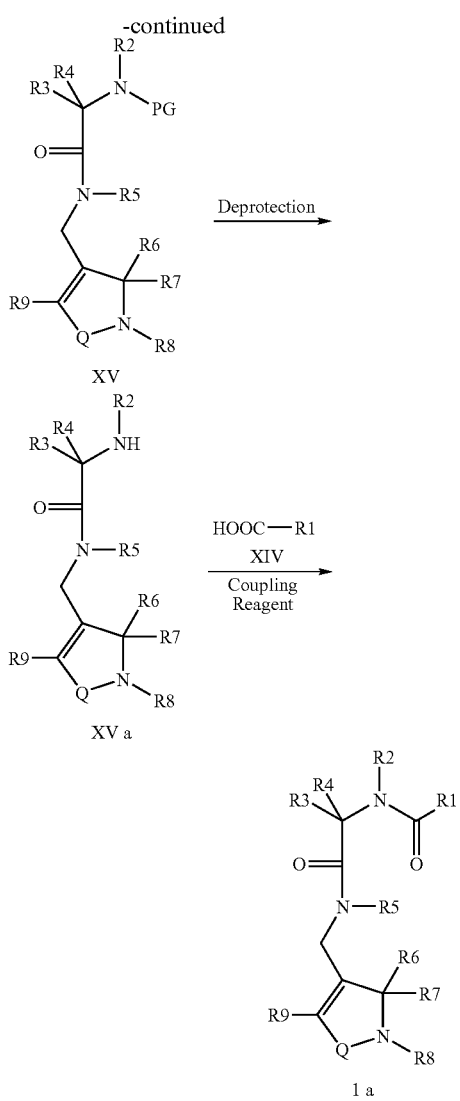

A compound of formula XIIIa, as defined for Scheme D, is selectively deprotected, typically using lithium hydroxide, to generate a compound of formula XIIId, which may then be employed to N-acylate a compound of formula XI, generating a compound of formula XV. Subsequent deprotection results in a compound of formula XVa. A compound of formula XVa is then coupled with a compound of formula XIV, as defined for Scheme D, and subsequently deprotected to generate a compound of formula I.

Suitable activating agents for the N-acylation reactions in Scheme D and Scheme E are known in the art and include DCC, HOBT, EDC, and oxalyl chloride. Preferred for the practice of the present invention are HOBT or TBTU.

Compounds of formula XIII in which the starting material XIIIa is optionally substituted 2-Nboc-amino-5-arylpentanoic acid methyl ester, optionally substituted 2-Nboc-amino-4-arylbutanoic acid methyl ester or 2-Nboc-amino-3-(3-indolyl)-propionic acid methyl ester may also be prepared by the routes described in Scheme D and Scheme E.

Compounds of formula XIb may also be employed in the reactions described in Scheme D and Scheme E.

R1, R2, R3, R4, R5, R6, R7, R8, R9 and Q in Schemes A through E are as defined for Formula I.

The preferred reaction temperature range employed in these reactions is between −40 and 150° C., and the most preferred range is between 10 and 40° C. These reactions may be conveniently carried out in situ, without isolation of the particular compound after its preparation.

The compounds of the present invention can be useful for modulating growth hormone secretion and as research tools.

Compounds of formula I possess growth hormone secretagogue activity. Growth hormone secretagogue activity can be determined using a typical assay which may employ pituitary cells established in culture, followed by a challenge with the various compounds of formula I, and the levels of growth hormone determined accordingly. Growth hormone levels may be calculated using various radioimmunoassay techniques known to those of skill in the art. One example of such an assay is detailed herein.

Thus compounds of formula I find use in the treatment of physiological conditions which are modulated or ameliorated by an increase in endogenous growth hormone. In particular the compounds of formula I are useful in the treatment of conditions or diseases which cause or are mediated by growth hormone deficiencies and maladies associated with ageing in humans. The compounds of formula I are hence useful in the treatment of osteoporosis, physiological short stature including growth hormone deficient children and short stature associated with chronic illness, growth retardation associated with the Prader-Willi syndrome, intrauterine growth retardation, pulmonary dysfunction and ventilator dependency, insulin resistance, cachexia and protein loss due to chronic illness such as cancer or AIDS, as well as congestive heart failure. The compounds of formula I also hence find use in improving muscle strength and mobility, metabolic homeostasis, renal homeostasis especially in the elderly, accelerating the recovery of patients having undergone trauma especially major surgery, improving a negative energy balance in a patient, accelerating bone fracture repair, preventing catabolic side effects associated with therapy, the attenuation of protein catabolic responses following major surgery, the acceleration of wound healing and the treatment of immunosupressed patients. In this connection, compounds of formula I also find use in the manufacture of a medicament for the treatment of the human or animal body by therapy, in particular the therapeutic treatment of conditions or diseases which cause or are mediated by growth hormone deficiencies maladies associated with ageing in humans. In particular compounds of formula I also find use in the manufacture of a medicament for any of the specific uses indicated above.

The compounds of formula I also find use in a method of increasing endogenous levels of growth hormone in mammals and in particular humans and farm or companion animals. Thus the compounds of formula I find use in a method of promoting growth, in particular, increasing lean muscle mass, in an animal, in particular an animal farmed for food including cow, sheep, pig and chicken. The compounds also find particular use in the treatment of disorders of ageing in companion animals.

The invention further encompasses methods employing the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein refers to salts of the compounds of formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, mesylate, and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

This invention further encompasses methods employing pharmaceutically acceptable solvates of the compounds of Formula I. Many of the formula I compounds can combine with solvents such as water, methanol, and ethanol to form pharmaceutically acceptable solvates such as the corresponding hydrate, methanolate, and ethanolate.

This invention also encompasses methods employing the pharmaceutically acceptable prodrugs of the compounds of formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:
1) ester or amide derivatives which may be cleaved by esterases or lipases;
2) peptides which may be recognized by specific or non-specific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, Design of Prodrugs, (1985).

As used herein, the term "effective amount" means an amount of compound of the instant invention which is capable of inhibiting, alleviating, ameliorating, treating, or preventing further symptoms in mammals, including humans, which may be due to decreased levels of endogenous growth hormone.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound required to treat, inhibit, or prevent the symptoms and/or disease of congestive heart failure in a mammal, including humans, according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy.

In addition, the growth hormone secretagogue compounds as disclosed herein may be administered to a patient in need of treatment in combination with other growth hormone secretagogues known in the art, and/or with a suitable bone anti-resorptive agent or agents for the prevention or treatment of osteoporosis and/or loss of muscle strength. Said suitable bone anti-resorptive agents include selective estrogen receptor modulators, bisphophonates, calcitonin, and hormone replacement therapeutic agents. Additionally, PTH may be administered in combination with said growth hormone secretagogues. Said combination therapy may be administered concomitantly or sequentially.

The compositions are preferably formulated in a unit dosage form, each dosage containing from about 0.01 to about 500 mg, more usually about 0.5 to about 200 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The compounds can be administered by a variety of routes including the oral, rectal, transdermal, subcutaneous, topical, intravenous, intramuscular or intranasal routes. For all indications, a typical daily dose will contain from about 0.01 mg/kg to about 20 mg/kg of the active compound of this invention. Preferred daily doses will be about 0.1 to about 10 mg/kg, ideally about 0.1 to about 5 mg/kg. However, for topical administration a typical dosage is about 1 to about 500 mg compound per $cm^2$ of an affected tissue. Preferably, the applied amount of compound will range from about 30 to about 300 mg/$cm^2$, more preferably, from about 50 to about 200 mg/$cm^2$, and, most preferably, from about 60 to about 100 mg/$cm^2$.

Suitable dosing ranges of compounds of formula I include 0.01 mg/kg/day to 60 mg/kg/day. Representative pharmaceutical formulations containing compounds of formula I-IV are provided below.

The formulations which follow are given for purposes of illustration and are not intended to be limiting in any way. The total active ingredients in such formulations comprises from 0.1% to 99.9% by weight of the formulation. The term "active ingredient" means a compound of formula I, including but not limited to compounds of formulas II, III, and IV.

Formulation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 15 mg of medicament, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation 9

An intravenous formulation may be prepared as follows:

| Ingredient | Quantity |
|---|---|
| Active Ingredient | 250.0 mg |
| Isotonic saline | 1000 mL |

Formulation 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation 11

Sublingual or buccal tablets, each containing 10 mg of active ingredient, may be prepared as follows:

| Ingredient | Quantity Per Tablet |
|---|---|
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

Another formulation employed in the methods of the present invention employs transdermal delivery devices or patches. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, the disclosure of which is herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, the disclosure of which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The following Examples and Preparations are illustrative of the processes employed in the synthesis of the compounds of the present invention. As would be understood by persons skilled in the art, other synthetic schemes may be employed to prepare the compounds of the instant invention.

Intermediate 1

N-Ethyl-N-[3-(4-methanesulfonyl-phenyl)-2,2-dioxo-2-thia-1-aza-spiro[4.5]dec-3-en-4-ylmethyl]-amine

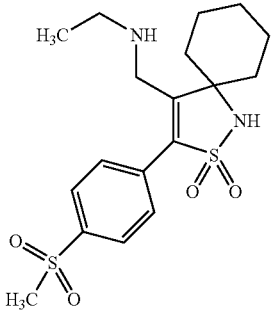

Methyl p-tolyl sulfone (24 g, 0.14 mol) in 550 ml CCl$_4$ was heated to reflux temperature, N-bromosuccinimide (17.8 g, 0.14 mol) was added in portions and the mixture was refluxed for 3 h. After cooling to room temperature, the mixture was filtered and the filtrate was concentrated to yield 4-methanesulfonylbenzyl bromide as a crystalline solid (32.9 g), $^1$H-NMR (CDCl$_3$) δ 8.05 (d, 2H), 7.70 (d, 2H), 4.45 (s, 2H), 3.09 (s, 3H). To the crude product in water (200 ml) were added sodium sulfite (33.2 g, 264 mmol) and tetrabutylammonium bromide (0.41 g, 1.64 mmol), and the mixture was refluxed for 2 h. After cooling to room temperature the solution was extracted with ethyl acetate, the aqueous phase was then concentrated to half the volume and cooled. The precipitate was filtered off and dried under vacuum at 70° C. to yield sodium 4-methanesulfonyl-benzylsulfonate (33.3 g, quant.).

POCl$_3$ (75 ml) was cooled to 5° C., 4-methanesulfonyl-benzylsulfonate (40.4 g, 162 mmol) and PCl$_5$ (47.5 g, 228 mmol) were added. The mixture was stirred overnight at room temperature and evaporated under vacuum. The residue was suspended in ethyl acetate (300 ml) and filtered. The precipitate was washed thoroughly with 2.5 l ethyl acetate. After concentration of the combined filtrates, 35.9 g (82%) of crystalline 4-methanesulfonyl-phenylmethanesulfonyl chloride, shown below, were obtained. $^1$H-NMR (CDCl$_3$) δ 7.92 (d, 2H), 7.59 (d, 2 H), 4.50 (s, 2 H), 3.05 (s, 3 H).

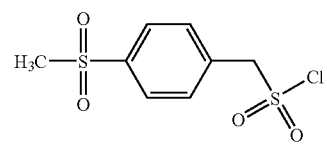

The preparation of N-(1-acetylcyclohexyl)-4-methanesulfonyl-phenylmethanesulfonamide, shown below, was performed as described in Pestic. Sci. 1993, 39, 185-192.

4-Methanesulfonyl-phenylmethanesulfonyl chloride (10.7 g, 40 mmol) in 100 ml dry tetrahydrofuran was added to a solution of ethynylcyclohexylamine (4.93 g, 40 mmol) and triethylamine (6.13 ml, 44 mmol) in dry tetrahydrofuran (100 ml) at 0-5° C. Then the mixture was stirred for 1 hour at room temperature, poured into 0.05 N hydrochloric acid and stirred again. The precipitate was filtered off, washed with water and dried to yield N-(1-ethynylcyclohexyl)-4-methanesulfonyl-phenylmethane sulfonamide (11.7 g, 82%) as a solid. $^1$H-NMR (CDCl$_3$) δ 7.93 (d, 2 H), 7.65 (d, 2 H), 4.61 (s, 2 H), 4.32 (s, 1 H), 2.75 (s, 1 H), 3.05 (s, 3 H), 2.15 (m, 2 H), 1.63 (m, 7 H), 1.27 (m, 1 H); MS (IS): 354.1 [M−H]$^−$.

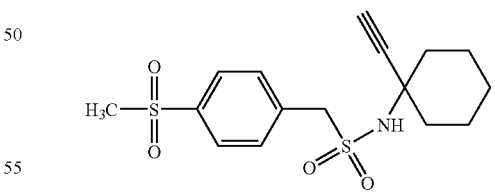

N-(1-Ethynylcyclohexyl)-4-methanesulfonyl-phenyl-methane sulfonamide (19.6 g, 55 mmol) was suspended in ethylene glycol (250 ml). 10 ml Water, 2 g HgO and 2 ml conc. sulfuric acid were added and the mixture was heated at 175° C. for 3 hours, then poured warm into 1 l crushed ice, decanted from mercury salts, stirred and the precipitate was filtered off, washed with water and dried under vacuum at 70° C. to yield N-(1-acetylcyclohexyl)-4-methanesulfonyl-phenylmethanesulfonamide, shown below, as a solid (14.4 g, 70%). $^1$H-NMR (CDCl$_3$) δ 7.95 (d, 2H), 7.68 (d, 2 H), 4.68 (s, 1 H), 4.42 (s, 2 H), 3.06 (s, 3 H), 2.29 (s, 3 H), 2.00-1.25 (m, 10 H); MS (IS): 372.1 [M–H]⁻

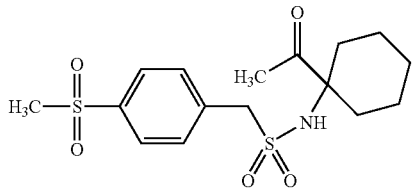

This product (14.4 g, 39 mmol) was dissolved in dry DMF (120 ml) under Ar. NaH (2.26 g, 94 mmol) was added in portions and the mixture was stirred overnight at 120° C. After dilution with water (700 ml) the solution was extracted with ethyl acetate. The organic layer was washed with NaCl solution and water, dried (Na₂SO₄) and concentrated. Recrystallisation from isopropanol yielded 11.1 g (80%) of 3-(4-methanesulfonyl-phenyl)-4-methyl-2-thia-1-azaspiro[4.5]dec-3-ene 2,2-dioxide, shown below, as a solid. Yield: 306 mg (43%); ¹H-NMR (CDCl₃) δ 8.02 (d, 2H), 7.73 (d, 2 H), 4.65 (s, 1 H), 3.09 (s, 3 H), 1.96 (s, 3H), 1.87-1.15 (m, 10 H); MS (IS): 354.1 [M–H]⁻

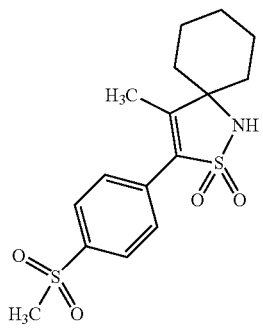

3-(4-methanesulfonyl-phenyl)-4-methyl-2-thia-1-azaspiro[4.5]dec-3-ene 2,2-dioxide (4.5 g, 12.6 mmol) and N-bromo succinimide (2.5 g, 14 mmol) were stirred in 200 ml CCl₄ with a catalytic amount of benzoyl peroxide for 4 hours at 85° C. Then the solvent was evaporated and the residue disolved in dichloromethane, washed with water and NaHCO₃ solution, dried (Na₂SO₄) and evaporated. The solid product was recrystallized from ethanol to yield 4-bromomethyl-3-(4-methanesulfonyl-phenyl)-2-thia-1-aza-spiro[4.5]dec-3-ene 2,2-dioxide (3.7 g, 68%). This product was dissolved in ethanol (20 ml), ethylamine (70% solution in water, 20 ml) was added, the mixture was left at room temperature for 3 hours and evaporated. The residue was dissolved in CH₂Cl₂, washed with water and extracted with 2 M HCl. After addition of NaOH and extraction with CH₂Cl₂ the organic layer was dried (Na₂SO₄) and evaporated. Chromatography on silica (eluent CH₂Cl₂/EtOH 95:5) yielded 1.50 g (66%) N-ethyl-N-[3-(4-methanesulfonyl-phenyl)-2,2-dioxo-2-thia-1-aza-spiro[4.5]dec-3-en-4-ylmethyl]-amine, shown below. ¹H-NMR (CDCl₃) δ 8.01 (d, 2H), 7.83 (d, 2 H), 4.81 (s, 1 H), 3.45 (s, 2 H), 3.09 (s, 3 H), 2.54 (q, 2 H), 2.02-1.15 (m, 10 H), 0.96 (t, 3 H).

Intermediate 2

N-(1-Benzyl-3-(4-fluorophenyl)-2,2-dioxo-2-thia-1-aza-spiro[4.5]dec-3-en-4-ylmethyl)-N-ethylamine

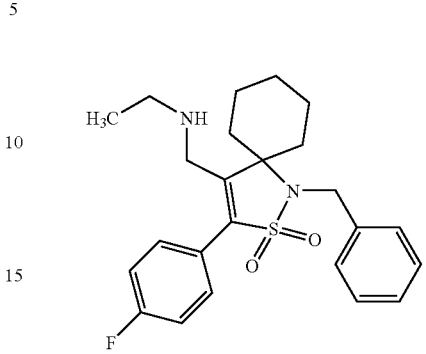

N-(3-(4-Fluorophenyl)-2,2-dioxo-2-thia-1-aza-spiro[4.5]dec-3-en-4-ylmethyl)-N-ethylamine, shown below, was prepared from 4-fluorophenylmethane sulfonyl chloride by the same procedure as described for Intermediate 1. ¹H-NMR (MeOD): δ 7.60 (m, 2 H), 7.22 (m, 2 H), 3.47 (s, 2 H), 2.45 (q, 2 H), 2.00-1.20 (m, 10 H), 0.89 (t, 3 H); MS (IS): 339.1 [M+H]⁺

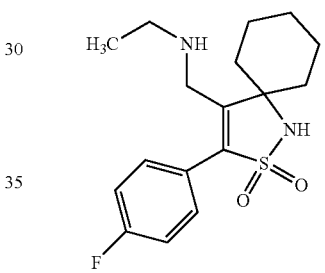

N-(3-(4-Fluorophenyl)-2,2-dioxo-2-thia-1-aza-spiro[4.5]dec-3-en-4-ylmethyl)-N-ethylamine (3.26 g, 9.6 mmol) was dissolved in 50 ml THF, cooled to 0° C. and triethylamine (2.67 ml, 18 mmol) and di-tert-butyldicarbonate (2.4 g, 11 mmol) in 10 ml THF were added. The mixture was stirred for 3 hours at 0° C. and for 3 days at room temperature. The solvent was evaporated and the residue purified by chromatography on silica (eluent: ethyl acetate/isohexane 1:1) to yield 3.61 g (86%) N-tert-butoxycarbonyl-N-(3-(4-fluorophenyl)-2,2-dioxo-2-thia-1-azaspiro[4.5]dec-3-en-4-ylmethyl)-N-ethylamine.

0.5 g (1.1 mmol) of this product was dissolved in dry DMF (5 ml), K₂CO₃ (910 mg, 6.6 mmol), a catalytic amount of potassium iodide and benzylbromide (1.31 ml, 11 mol) were added and the mixture was stirred at 60° C. for 3 days and 1 day at 80° C. The solvent was evaporated and the residue purified by chromatography on silica (eluent: CH₂Cl₂/methanol 97:3), then by HPLC (CH₃CN/H₂O) to yield 413 mg tert-butoxycarbonyl-(1-benzyl-3-(4-fluorophenyl)-2,2-dioxo-2-thia-1-azaspiro[4.5]dec-3-en-4-ylmethyl)ethylamine.

¹H-NMR (MeOD) δ 7.55-7.12 (m, 9 H), 4.69 (s, 2 H), 4.34 (s, 2 H), 2.71 (m, 2 H), 2.00-1.20 (m, 10 H), 1.35 (s, 9 H), 0.89 (t, 3 H); MS (IS): 312.2 [M+H]⁺

The product was stirred for 4 hours in a mixture of 2 ml CH₂Cl₂ and 2 ml trifluoroacetic acid, then the solvent was evaporated, the residue dissolved in methanol and poured on a strong cation exchange resin (1 g). After washing with Intermediates 3a-3al

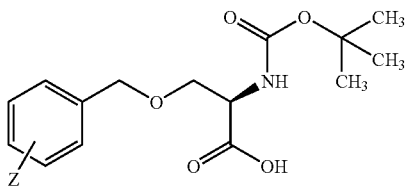

INTERMEDIATE 3a: (R)-2-tert-Butoxycarbonylamino-3-(4-fluorobenzyloxy)propionic acid (Z=4-F)

N-tert-Butoxycarbonyl-D-serine (0.5 g, 2.4 mmol) was dissolved in dry DMF (12 ml), potassium tert-butanolate (0.56 g, 5 mmol) in 4 ml dry DMF was added and the mixture was stirred for 30 min at 0° C. 4-Fluorobenzyl chloride (0.293 ml, 2.45 mmol) was added and the solution was stirred for 4 hours at room temperature. Water (50 ml) was added and the mixture was extracted with tert-butylmethylether. The aqueous layer was acidified with citric acid to pH 3 and extracted with ethylacetate. This organic layer was dried (NaSO$_4$) and evaporated and the residue purified by chromatography on silica (eluent CH$_2$Cl$_2$/EtOH 97.5:2.5) to yield the product as a colourless oil. Yield: 318 mg (42%)

$^1$H-NMR (CDCl$_3$) δ 8.85 (bs, 1 H), 7.26 (m, 2 H), 6.99 (m, 2H), 5.45 (d, 1 H), 4.49 (s, 2 H), 3.90 (d, 1 H), 3.70 (d, 1H), 1.43 (s, 9 H); MS (IS): 312.2 [M+H]$^+$

The following Intermediates were prepared by the same procedure from N-tert-butoxycarbonyl-D-serine and the corresponding benzyl halide:

INTERMEDIATE 3b: (R)-2-tert-Butoxycarbonylamino-3-(3,4-difluorobenzyloxy)propionic acid (Z=3,4-F$_2$)

Prepared from N-tert-butoxycarbonylamino-D-serine and 3,4-difluorobenzyl chloride:

Yield: 377 mg (22%); MS: 330.1 [M–H]$^-$

INTERMEDIATE 3c: (R)-2-tert-Butoxycarbonylamino-3-(2,5-difluorobenzyloxy)propionic acid (Z=2,5-F$_2$)

Prepared from N-tert-butoxycarbonylamino-D-serine and 2,5-difluorobenzyl chloride:

Yield: 294 mg (17%); MS: 330.1 [M–H]$^-$

INTERMEDIATE 3d: (R)-2-tert-Butoxycarbonylamino-3-(2,6-difluorobenzyloxy)propionic acid (Z=2,6-F$_2$)

Prepared from N-tert-butoxycarbonylamino-D-serine and 2,6-difluorobenzyl chloride:

Yield: 318 mg (18%); MS (IS): 330.1 [M–H]$^-$

INTERMEDIATE 3e: (R)-2-tert-Butoxycarbonylamino-3-(2-fluoro-5-trifluoromethylbenzyloxy)propionic acid (Z=2-F-5-CF$_3$)

MS (IS): 380.1 [M–H]$^-$

INTERMEDIATE 3f: (R)-2-tert-Butoxycarbonylamino-3-(3,5-difluorobenzyloxy)propionic acid (Z=3,5-F$_2$)

Prepared from N-tert-butoxycarbonylamino-D-serine and 3,5-difluorobenzyl chloride:

Yield: 208 mg (12%); MS: 330.1 [M–H]$^-$

INTERMEDIATE 3g: (R)-2-tert-Butoxycarbonylamino-3-(3-fluorobenzyloxy)propionic acid (Z=3-F)

MS (IS): 312.1 [M–H]$^-$

INTERMEDIATE 3h: (R)-2-tert-Butoxycarbonylamino-3-(2,3-difluorobenzyloxy)propionic acid (Z=2,3-F$_2$)

$^1$H-NMR is consistent with the structure of the desired product.

INTERMEDIATE 3i: (R)-2-tert-Butoxycarbonylamino-3-(2,4-difluorobenzyloxy)propionic acid (Z=2,4-F$_2$)

MS (IS): 332.3 [M+H]$^+$

INTERMEDIATE 3j: (R)-2-tert-Butoxycarbonylamino-3-(2-methoxybenzyloxy)propionic acid (Z=2-OCH$_3$)

MS (IS): 348.1 [M+Na]$^+$

INTERMEDIATE 3k: (R)-2-tert-Butoxycarbonylamino-3-(2,3,5-trifluorobenzyloxy)propionic acid (Z=2,3,5-F$_3$)

MS (IS): 372.1 [M+Na]$^+$; 348.1 [M–H]$^-$

INTERMEDIATE 3l: (R)-2-tert-Butoxycarbonylamino-3-(4-chlorobenzyloxy)propionic acid (Z=4-Cl)

MS (IS): 352.0 [M+Na]$^+$; 294.0 [M–C$_4$H$_9$+Na]$^+$

INTERMEDIATE 3m: (R)-2-tert-Butoxycarbonylamino-3-(2,4-dichlorobenzyloxy)propionic acid (Z=2,4-Cl$_2$)

MS (IS): 362.1 [M–H]$^-$

INTERMEDIATE 3n: (R)-2-tert-Butoxycarbonylamino-3-(2-fluorobenzyloxy)propionic acid (Z=2-F)

MS (IS): 312.1 [M–H]$^-$

INTERMEDIATE 3o: (R)-2-tert-Butoxycarbonylamino-3-(2,3,4-trifluorobenzyloxy)propionic acid (Z=2,3,4-F$_3$)

MS (IS): 221.1 [M–COOC$_4$H$_9$]$^+$; 343.1 [M+Na]$^+$

INTERMEDIATE 3p: (R)-2-tert-Butoxycarbonylamino-3-(2,3,6-trifluorobenzyloxy)propionic acid (Z=2,3,6-F$_3$)

MS (IS): 372.1 [M+Na]$^+$

INTERMEDIATE 3q: (R)-2-tert-Butoxycarbonylamino-3-(2,4,5-trifluorobenzyloxy)propionic acid (Z=2,4,5-F$_3$)

MS (IS): 348.1 [M–H]$^-$

INTERMEDIATE 3r: (R)-2-tert-Butoxycarbonylamino-3-(2-chlorobenzyloxy)propionic acid (Z=2-Cl)

MS (IS): 230.1 [M–COOC$_4$H$_9$]$^+$; 352.0 [M+Na]$^+$

INTERMEDIATE 3s: (R)-2-tert-Butoxycarbonylamino-3-(2,3-dichlorobenzyloxy)propionic acid (Z=2,3-Cl$_2$)

MS (IS pos): 264.0 [M–COOC$_4$H$_9$]$^+$; 308.0 [M–C$_4$H$_9$]$^+$; 386.0 [M+Na]$^+$ MS (IS neg): 362.1 [M–H]$^-$ INTERMEDIATE 3t: (R)-2-tert-Butoxycarbonylamino-3-(2,5-dichlorobenzyloxy)propionic acid (Z=2,5-Cl$_2$)

MS (IS): 386.0 [M+Na]$^+$

INTERMEDIATE 3u: (R)-2-tert-Butoxycarbonylamino-3-(2,6-dichlorobenzyloxy)propionic acid (Z=2,6-Cl$_2$)

MS (IS): 264.0 [M–COOC$_4$H$_9$]$^+$; 386.0 [M+Na]$^+$

INTERMEDIATE 3v: (R)-2-tert-Butoxycarbonylamino-3-(3-chloro-2-fluorobenzyloxy)propionic acid (Z=2-F-3-Cl)

MS (IS): 346.0 [M–H]$^-$

INTERMEDIATE 3w: (R)-2-tert-Butoxycarbonylamino-3-(4-chloro-2-fluorobenzyloxy)propionic acid (Z=2-F-4-Cl)

MS (IS): 346.1 [M–H]$^-$

INTERMEDIATE 3x: (R)-2-tert-Butoxycarbonylamino-3-(6-chloro-2-fluorobenzyloxy)propionic acid (Z=2-F-6-Cl)

MS (IS): 346.0 [M–H]$^-$

INTERMEDIATE 3y: (R)-2-tert-Butoxycarbonylamino-3-(2-chloro-4-fluorobenzyloxy)propionic acid (Z=4-F-2-Cl)
MS (IS pos): 248.1 [M–COOC$_4$H$_9$]$^+$; 292.0 [M–C$_4$H$_9$]$^+$; 370.0 [M+Na]$^+$
MS (IS neg): 346.1 [M–H]$^-$ INTERMEDIATE 3z: (R)-2-tert-Butoxycarbonylamino-3-(2-chloro-3,6-difluorobenzyloxy)propionic acid (Z=2-Cl-3,6-F$_2$)
MS (IS): 388.0 [M+Na]$^+$ INTERMEDIATE 3aa: (R)-2-tert-Butoxycarbonylamino-3-(2-methylbenzyloxy)propionic acid (Z=2-CH$_3$)
MS (IS): 332.1 [M+Na]$^+$ INTERMEDIATE 3ab: (R)-2-tert-Butoxycarbonylamino-3-(2,6-difluoro-3-methylbenzyloxy)propionic acid (Z=3-CH$_3$-2,6-F$_2$)
MS (IS): 246.1 [M–COOC$_4$H$_9$]$^+$; 368.1 [M+Na]$^+$ INTERMEDIATE 3ac: (R)-2-tert-Butoxycarbonylamino-3-(4-cyanobenzyloxy)propionic acid (Z=4-CN)
MS (IS pos): 221.1 [M–COOC$_4$H$_9$]$^+$; 265.0 [M–C$_4$H$_9$]$^+$; 343.1 [M+Na]$^+$
MS (IS neg): 319.1 [M–H]$^-$ INTERMEDIATE 3ad: (R)-2-tert-Butoxycarbonylamino-3-(2-cyanobenzyloxy)propionic acid (Z=2-CN)
MS (IS): 221.1 [M–COOC$_4$H$_9$]$^+$; 343.1 [M+Na]$^+$ INTERMEDIATE 3ae: (R)-2-tert-Butoxycarbonylamino-3-(4-trifluoromethylbenzyloxy)propionic acid (Z=4-CF$_3$)
MS (IS): 264.1 [M–COOC$_4$H$_9$]$^+$; 308.0 [M–C$_4$H$_9$]$^+$; 386.1 [M+Na]$^+$ INTERMEDIATE 3af: (R)-2-tert-Butoxycarbonylamino-3-(2-trifluoromethylbenzyloxy)propionic acid (Z=2-CF$_3$)
MS (IS): 264.0 [M–COOC$_4$H$_9$]$^+$; 386.0 [M+Na]$^+$ INTERMEDIATE 3ag: (R)-2-tert-Butoxycarbonylamino-3-(2-fluoro-3-trifluoromethylbenzyloxy)propionic acid (Z=2-F-3-CF$_3$)
MS (IS): 282.1 [M–COOC$_4$H$_9$]$^+$; 326.1 [M–C$_4$H$_9$]$^+$; 404.1 [M+Na]$^+$ INTERMEDIATE 3ah: (R)-2-tert-Butoxycarbonylamino-3-(2-fluoro-6-trifluoromethylbenzyloxy)propionic acid (Z=2-F-6-CF$_3$)
MS (IS): 282.1 [M–COOC$_4$H$_9$]$^+$; 326.1 [M–C$_4$H$_9$]$^+$; 404.1 [M+Na]$^+$ INTERMEDIATE 3ai: (R)-2-tert-Butoxycarbonylamino-3-(2-chloro-3-trifluoromethylbenzyloxy)propionic acid (Z=2-Cl-3-CF$_3$)
MS (IS): 298.0 [M–COOC$_4$H$_9$]$^+$; 342.0 [M–C$_4$H$_9$]$^+$; 420.0 [M+Na]$^+$ INTERMEDIATE 3aj: (R)-2-tert-Butoxycarbonylamino-3-(4-trifluoromethoxybenzyloxy)propionic acid (Z=4-OCF$_3$)
MS (IS): 280.0 [M–COOC$_4$H$_9$]$^+$; 402.0 [M+Na]$^+$ INTERMEDIATE 3ak: (R)-2-tert-Butoxycarbonylamino-3-(2-trifluoromethoxybenzyloxy)propionic acid (Z=2-OCF$_3$)
MS (IS): 378.0 [M–H]$^-$ INTERMEDIATE 3al: (R)-2-tert-Butoxycarbonylamino-3-(2-carbamoylbenzyloxy)propionic acid (Z=2-CONH$_2$)
MS (IS): 361.1 [M+H]$^+$ Intermediate 4

N-(5-(4-Chlorophenyl)-3,3-dimethyl-1,1-dioxo-2,3-dihydroisothiazol-4-yl)methyl-N-ethylamine

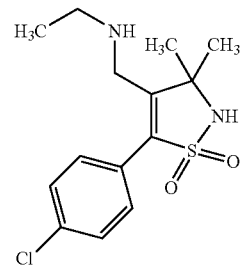

To a solution of sodium (4-chlorophenyl)methanesulfonate, 8.9 g (39.0 mmol) in 20 mL of phosphorus oxychloride at 0° C., was added 11.6 g of phosphorus pentachloride. The reaction mixture was slowly warmed to ambient temperature, stirred 48 h and concentrated to dryness.

To a solution of 1,1-dimethylpropargylamine, 3.23 g (39.0 mmol, as described in J. Am. Chem. Soc. 75 (1954), 1653) in 50 mL of dichloromethane at 0° C. was added 6.41 mL (42.9 mmol) of 1,8-diazabicyclo(5.4.0)undec-7-ene. After stirring for 10 min, 8.8 g (39.0 mmol) of the above residue in 70 mL of dichloromethane was added. The reaction mixture was stirred for 2 h at 0° C. and was concentrated to dryness and partitioned between ethyl acetate and water. The mixture was acidified to pH=2.0 with 1 N HCl and was extracted with ethyl acetate. The combined organics were washed with brine, dried over sodium sulfate, filtered and concentrated to dryness. The resulting residue was chromatographed over silica gel using 5% methanol/chloroform as eluant to yield 6.15 g (58%) of the desired product, shown below, as a white solid. $^1$H-NMR is consistent with the desired product, shown below; MS (ion spray) 270.3 (M−1); Anal. Calc'd for C$_{12}$H$_{14}$ClNO$_2$S: C, 53.04; H, 5.19; N, 5.15. Found: C, 52.54; H, 5.19; N, 4.93. C-(4-Chlorophenyl)-N-(1,1-dimethyl-prop-2-ynyl)methanesulfonamide:

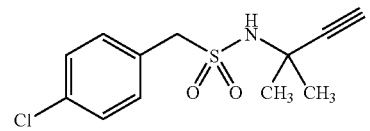

To a solution of C-(4-chloro-phenyl)-N-(1,1-dimethyl-prop-2-ynyl)methanesulfonamide, 5.88 g (22.0 mmol) in 40 mL of ethylene glycol was added 0.3 g of mercury oxide (yellow), 4 mL of water and 6 drops concentrated sulfuric acid. The mixture was heated at 170° C. for 80 min then was cooled to ambient temperature, poured into water and extracted with ethyl acetate. The combined organics were washed with brine, dried over sodium sulfate, filtered and concentrated to dryness. The resulting residue was chromatographed on silica gel using chloroform as eluant to yield 4.31 g (68%) of the desired product, shown below, as a tan solid.

¹H-NMR is consistent with structure; MS (ion spray) 288.0 (M−1); Anal. Calc'd for C₁₂H₁₆ClNO₃S: C, 49.74; H, 5.56; N, 4.83. Found: C, 49.59; H, 5.50; N, 4.73. C-(4-Chlorophenyl)-N-(1,1-dimethyl-2-oxo-propyl)-methanesulfonamide:

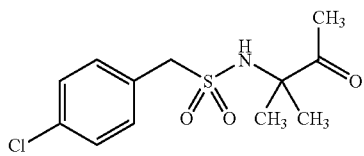

To a solution of C-(4-chloro-phenyl)-N-(1,1-dimethyl-2-oxo-propyl)-methanesulfonamide, 4.2 g (15.0 mmol) in 60 mL of dimethylformamide was added 1.3 g (31.5 mmol) of sodium hydride. The reaction mixture was heated at 90° C. for 24 h, then cooled to ambient temperature and concentrated to dryness. The residue was partitioned between ethyl acetate and water and was acidified to pH=3.0 with 1 N HCl. The mixture was extracted with ethyl acetate. The combined organics were washed with brine, dried over sodium sulfate, filtered and concentrated to dryness. The residue was chromatographed over silica using chloroform as eluant to yield 3.27 g (80%) of the desired product, shown below, as a tan solid. ¹H-NMR is consistent with structure; MS (ion spray) 270.3 (M−1); Anal. Calc'd for C₁₂H₁₄ClNO₂S: C, 53.04; H, 5.19; N, 5.15. Found: C, 52.72; H, 5.18; N, 4.98. 5-(4-Chlorophenyl)-3,3,4-trimethyl-2,3-dihydro-isothiazole-1,1-dioxide:

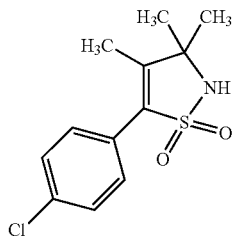

To a solution of 5-(4-chlorophenyl)-3,3,4-trimethyl-1,1-dioxo-2,3-dihydro-isothiazole, 1.5 g (5.5 mmol) in 150 mL of carbon tetrachloride was added 1.5 g (8.25 mmol) of N-bromosuccinimide and 0.13 g of 2,2'-azobis(2-methylpropionitrile). The mixture was heated to reflux for 4 h and then cooled to ambient temperature. Chloroform was added and the solution was washed with water, washed with brine, dried over sodium sulfate, filtered and concentrated to dryness. To a solution of the residue in 75 mL of absolute ethanol was added 3.6 mL (55.0 mmol) of ethylamine (70% solution in water). The reaction mixture was stirred 24 h at ambient temperature then concentrated to dryness. The residue was purified by chromatography on silica gel with methanol/chloroform as eluant to yield 0.21 g (12%) of the desired title amine as a tan oil. ¹H-NMR is consistent with structure; MS (ion spray) 313.0 (M−1); Anal. Calc'd for C₁₄H₁₉ClN₂O₂S.0.1CHCl₃: C, 51.83; H, 5.89; N, 8.57. Found: C, 51.58; H, 6.38; N, 8.04.

Intermediate 5

N-(5-(4-Chlorophenyl)-3,3-dimethyl-1,1-dioxo-2,3-dihydroisothiazol-4-yl)methyl-N-methylamine

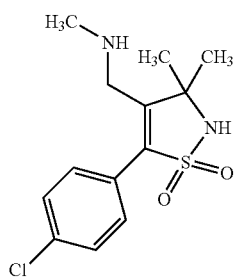

The title compound was prepared from (4-chlorophenyl)methanesulfonyl chloride and 1,1-dimethylpropargylamine according to the procedure described for Intermediate 4 replacing ethylamine by methylamine in the last step. ¹H-NMR (DMSO-d₆) δ 7.72 (bs, 1 H), 7.53 (m, 4H), 3.33 (s, 2 H), 2.16 (s, 3 H), 1.45 (s, 6 H).

Intermediate 6

N-(3-(4-Chlorophenyl)-2,2-dioxo-2-thia-1-aza-spiro[4.4]non-3-en-4-ylmethyl)-N-ethylamine

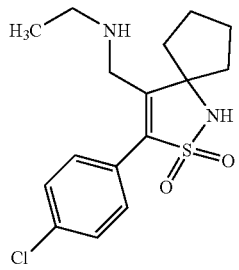

The title compound, as shown above, was prepared as follows:

1-Amino-1-cyclopentanecarboxylic acid (5.00 g, 38.8 mmol) was dissolved in methanol (100 mL) and then thionyl chloride (9.25 g, 77.7 mmol) was added dropwise with stirring. The resulting mixture was stirred overnight at room temperature and then concentrated in vacuo which left a white solid. The solid was tritruated in ethyl ether, filtered, and dried to give 6.78 g (97%) of methyl 1-amino-1-cyclopentanecarboxylate hydrochloride as a white solid. ¹H NMR was consistent with product. ESMS (M+1) 144.2

The amino-ester hydrochloride (2.50 g, 14.0 mmol) was combined with triethylamine (9.0 mL, 64.7 mmol), and 4-dimethylaminopyridine (cat. 50 mg), in dichloromethane (75 mL) at room temperature. Then (4-chlorophenyl)methanesulfonyl chloride (as described above) (3.00 g, 13.4 mmol) was added and the resulting mixture stirred overnight at room temperature. Water was then added and the pH of the aqueous phase adjusted to 2.5 with aqueous hydrochloric acid. The mixture was then extracted with dichloromethane and the combined extracts were dried over sodium sulfate and concentrated in vacuo. The resulting residue was chromatographed over silica (chloroform/methanol) to give 2.00 g (45%) of the desired sulfonamide, shown below, as a light yellow solid. $^1$H NMR was consistent with product. ESMS: (M−1)$^−$ 330.1, 331.2. Anal. Calcd. for $C_{14}H_{18}NO_4SCl$: C, 50.68; H, 5.47; N, 4.22. Found: C, 50.14; H, 5.50; N, 4.21. Methyl 1-(4-Chlorophenylmethanesulfonylamino)-1-cyclopentanecarboxylate:

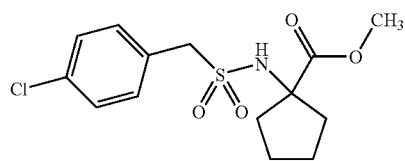

The ester from above (1.90 g, 5.74 mmol) was combined with 2 N aqueous sodium hydroxide (40 mL), tetrahydrofuran (5 mL), and ethanol (5 mL) and the mixture stirred at room temperature until hydrolysis was complete. Aqueous hydrochloric acid (5 N) was added until the aqueous mixture reached pH 2.0 and the aqueous phase was then extracted with ethyl acetate. The combined extracts were dried over sodium sulfate and the solution concentrated in vacuo. The resulting solid was triturated in diethyl ether, filtered and dried to give 1.75 g (97%) of the desired acid, shown below, as a white solid. $^1$H NMR was consistent with product. ESMS: (M+1)$^+$ 316.0, 317.1. Anal. Calcd. for $C_{13}H_{16}NO_4SCl$: C, 49.13; H, 5.08; N, 4.41. Found: C, 49.16; H, 5.01; N, 4.20. 1-(4-Chlorophenylmethanesulfonylamino)-1-cyclopentanecarboxylic acid:

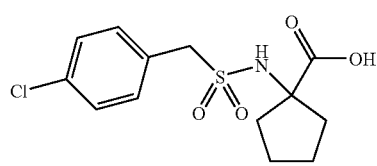

The acid from above (2.90 g, 9.2 mmol) was dissolved in anhydrous dimethoxyethane (75 mL) and the mixture cooled to −60° C. (dry ice/acetone bath) under nitrogen. Then methyl lithium (32.7 mL, 1.4 M in ethyl ether) was added via syringe and the resulting mixture stirred for 4.5 hours while slowly warming to near 0° C. The reaction was then quenched into a stirred mixture of ice/1N aqueous hydrochloric acid and the aqueous mixture extracted with ethyl acetate. The combined extracts were concentrated and the resulting residue chromatographed over silica (chloroform/methanol) which allowed for isolation of 2.30 g (79%) of the desired ketone, shown below, as a white solid. $^1$H NMR was consistent with product. ESMS: (M+1)$^+$ 316.1. Anal. Calcd. for $C_{14}H_{18}NO_3SCl$: C, 53.24; H, 5.74; N, 4.43. Found: C, 52.50; H, 5.48; N, 4.29. N-(1-Acetylcyclopentyl)-C-(4-chlorophenyl)methanesulfonamide:

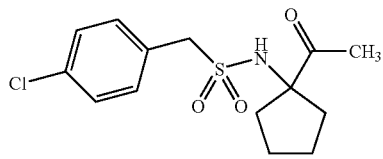

The ketone (2.50 g, 7.94 mmol) was dissolved in N,N-dimethylformamide (40 mL) and then sodium hydride (60%, 0.70 g, 17.4 mmol) was added and the resulting mixture heated at 100° C. overnight. The solvent was then removed in vacuo and the resulting residue taken up in dilute aqueous hydrochloric acid. The aqueous mixture was extracted with ethyl acetate and the combined extracts were concentrated to leave a residue. This residue was chromatographed over silica (chloroform/methanol) which allowed for isolation of the desired product, shown below, 2.00 g (84%) as a white solid. ESMS: (M+1)$^+$ 298.4. $^1$H NMR was consistent with product. Anal. Calcd. for $C_{14}H_{16}NO_2SCl$: C, 56.46; H, 5.41; N, 4.70. Found: C, 56.17; H, 5.32; N, 4.69. 3-(4-Chlorophenyl)-4-methyl-2,2-dioxo-2-thia-1-aza-spiro[4.4]non-3-ene:

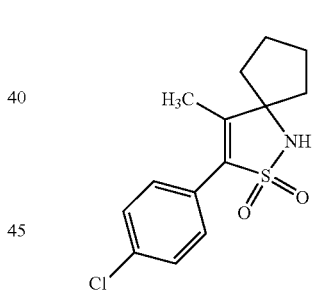

The product from above (1.80 g, 6.1 mmol) was slurried in carbon tetrachloride (50 mL) and N-bromosuccinimide (1.62 g, 9.1 mmol) and 2,2'-azobis(2-methylpropionitrile) (0.05 g, cat.) were added. This mixture was heated at reflux for 4 hours after which time the reaction was cooled to ambient temperature and diluted with dichloromethane. The organic mixture was washed with water (2×40 mL) and dried over sodium sulfate. Concentration left a residue which was taken up in ethanol (40 mL) followed by the addition of ethylamine (70%, 4.0 mL) and this mixture allowed to stir overnight at room temperature. The mixture was then concentrated and the residue chromatographed over silica (chloroform/methanol) which allowed for isolation of 0.36 g (17%) of the desired title compound. ESMS: (M+1)$^+$ 341.1, 343.0.

Intermediate 7

N-(3,3-Dimethyl-1,1-dioxo-5-(4-fluorophenyl)-2,3-dihydroisothiazol-4-yl)methyl-N-ethylamine

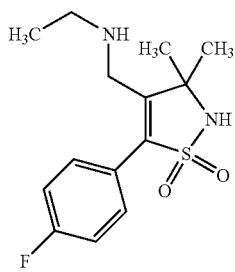

The compound was prepared essentially in the same manner as described for Intermediate 4 starting from (4-fluorophenyl)methanesulfonyl chloride.
MS (IS): 299.1 [M+H]$^+$

Intermediate 8

N-(3,3-Dimethyl-1,1-dioxo-5-(4-fluorophenyl)-2,3-dihydroisothiazol-4-yl)methyl-N-methylamine

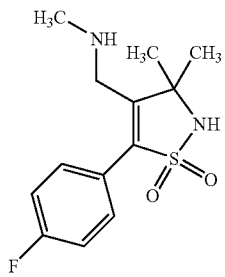

The compound was prepared essentially in the same manner as described for Intermediate 5 starting from (4-fluorophenyl)methanesulfonyl chloride.
MS (IS): 285.0 [M+H]$^+$

Intermediates 9a-9c

The intermediates 9a-9c were prepared by alkylation of diethyl acetamidomalonate with the corresponding substituted 3-phenylpropyl bromides followed by hydrolysis and Boc-protection of the resulting amino acids according to a known procedure (WO 97/36873).

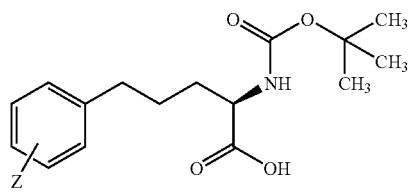

INTERMEDIATE 9a: (R)-2-tert-Butoxycarbonylamino-5-(4-fluorophenyl)pentanoic acid (Z=4-F)

INTERMEDIATE 9b: (R)-2-tert-Butoxycarbonylamino-5-(2,6-difluorophenyl)pentanoic acid (Z=2,6-F$_2$)

INTERMEDIATE 9c: (R)-2-tert-Butoxycarbonylamino-5-(3,5-difluorophenyl)pentanoic acid (Z=3,5-F$_2$)

Intermediate 10

2-tert-Butoxycarbonylamino-3-fluoro-2-fluoromethyl-propionic Acid

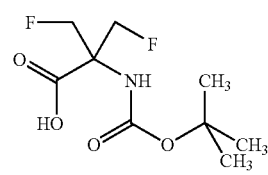

To a suspension of methyl 2-amino-3-fluoro-2-fluoromethyl-propionate hydrochloride (250 mg, 1.32 mmol; prepared as described in Synthesis, 1994, pp 701-702) in 10 mL of acetonitrile, was added Me$_4$NOH.5H$_2$O (400 mg, 2.20 mmol). The mixture was stirred at room temperature under argon for 30 min, and then di-tert-butyl dicarbonate (432 mg, 1.98 mmol) was added. The mixture was stirred for 48 h, the solvent evaporated and the residue portioned between water and ether. The aqueous layer was washed with ether, acidified with solid citric acid to pH 3-4 and extracted with ethyl acetate. The combined organic layers were washed with water, brine, dried over Na$_2$SO$_4$ and evaporated to yield 294 mg (92%) of the desired product as a white solid. $^1$H-NMR is consistent with structure; MS (ion spray) 238.1 (M−1).

Intermediate 11

N-(3-(4-Chlorophenyl)-2,2-dioxo-1-propyl-2-thia-1-aza-spiro[4.4]non-3-en-4-ylmethyl)-N-ethylamine

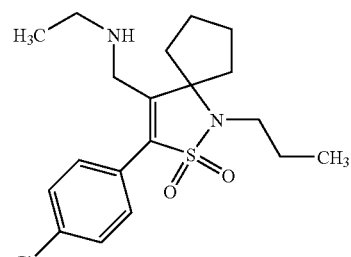

The title compound was prepared from Intermediate 6 by Boc-protection of the N-ethyl amine followed by alkylation with n-propyl bromide and deprotection in the same manner as described for Intermediate 2; MS (IS): 383.1 [M+H]$^+$

Intermediate 12

(R)-2-tert-Butoxycarbonylamino-3-(2-methylthiazol-4-ylmethoxy)propionic acid

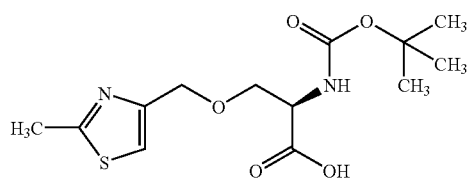

The title compound was prepared in the same manner as described for Intermediate 3a using commercial 4-chloromethyl-2-methylthiazole hydrochloride.
MS (IS): 315.1 [M–H]⁻

Intermediate 13

(R)-2-tert-Butoxycarbonylamino-3-(3,5-dimethyl-isoxazol-4-ylmethoxy)propionic acid

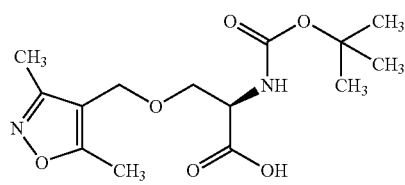

The title compound was prepared in the same manner as described for Intermediate 3a using commercial 4-chloromethyl-3,5-dimethylisoxazole.
MS (IS): 313.2 [M–H]⁻

Intermediate 14

N-(3-(4-Chlorophenyl)-2,2-dioxo-2-thia-1-aza-spiro[4.4]non-3-en-4-ylmethyl)-N-(2-fluoroethyl)amine

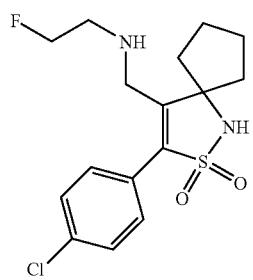

A solution of 2-fluoroethylamine hydrochloride (1.08 g, 10.9 mmol; prepared as described in J. Med. Chem. 9 (1966), 892-911) in 30 mL of absolute MeOH was treated with triethylamine (2.50 mL, 1.76 g, 17.4 mmol) at 0° C. Solid 4-bromomethyl-3-(4-chlorophenyl)-2,2-dioxo-2-thia-1-aza-spiro[4.4]non-3-ene (1.64 g, 4.35 mmol; described during the preparation of Intermediate 6) was added. The resulting mixture was stirred for 16 h at ambient temperature and concentrated to dryness under reduced pressure. The residue was purified by column chromatography on silica gel using dichloromethane/methanol as eluent to yield the title intermediate. Yield: 1.00 g (64%); MS (IS): 359.1 [M+H]⁺.

EXAMPLE 1

2-(R)-2-(2-Amino-2-methylpropionylamino)-3-(4-fluorophenyl)methoxypropionic acid N-ethyl-N-(3-(4-methanesulfonyl-phenyl)-2,2-dioxo-2-thia-1-aza-spiro[4.5]dec-3-ene-4-ylmethyl)amide Hydrochloride

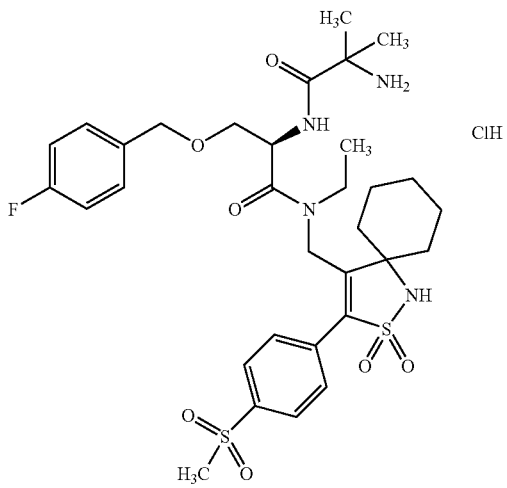

The title compound, as shown above, was prepared as follows:

N-tert-Butoxycarbonylamino-4-fluoro-benzyl-D-serine (Intermediate 3a) (188 mg, 0.6 mmol) in CH₂Cl₂ (20 ml) was stirred at room temperature for 30 min with TBTU (193 mg, 0.6 mmol) and triethylamine (0.084 ml, 0.6 mmol). N-Ethyl-N-[3-(4-methanesulfonyl-phenyl)-2,2-dioxo-2-thia-1-aza-spiro[4.5]dec-3-en-4-ylmethyl]amine (Intermediate 1) (239 mg, 0.6 mmol) in CH₂Cl₂ (10 ml) was added and the mixture was stirred overnight at room temperature. The solution was washed with 10% citric acid and saturated NaHCO₃ and the organic layer was dried (Na₂SO₄) and evaporated to yield 2-tert-butoxycarbonylamino-N-ethyl-3-(4-fluoro-benzyloxy)-N-[3-(4-methanesulfonyl-phenyl)-2,2-dioxo-2-thia-1-aza-spiro[4.5]dec-3-en-4-ylmethyl]-propionamide (328 mg, 79%). The product (0.47 mmol) was dissolved in dichloromethane (2 ml) and trifluoroacetic acid (2 ml) and stirred for 1 hour at room temperature. The mixture was evaporated, dissolved in methanol and poured on a strong cation exchange resin (1 g). After washing with methanol, the product was eluted with CH$_2$Cl$_2$/7 M NH$_3$ in methanol 8:3, and evaporated to yield 2-amino-N-ethyl-3-(4-fluoro-benzyloxy)-N-[3-(4-methanesulfonyl-phenyl)-2,2-dioxo-2-thia-1-aza-spiro[4.5]dec-3-en-4-ylmethyl]-propionamide (213 mg, 76%), shown below. MS (IS): 594.2 [M+H]$^+$

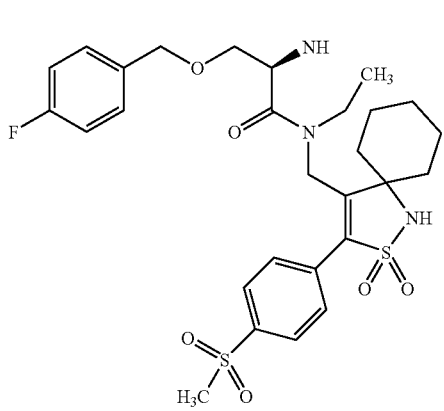

2-tert-Butoxycarbonylamino-2-methyl-propionic acid (73 mg, 0.36 mmol) in CH$_2$Cl$_2$ (10 ml) was stirred for 30 min with TBTU (116 mg, 0.36 mmol) and triethylamine (0.05 ml, 0.36 mmol), then 2-amino-N-ethyl-3-(4-fluoro-benzyloxy)-N-[3-(4-methanesulfonyl-phenyl)-2,2-dioxo-2-thia-1-aza-spiro [4.5]dec-3-en-4-ylmethyl]-propionamide (213 mg, 0.36 mmol) in CH$_2$Cl$_2$ (10 ml) was added and the mixture was stirred overnight at room temperature. The solution was washed with 10% citric acid and saturated NaHCO$_3$ and the organic layer was dried (Na$_2$SO$_4$) and evaporated to yield 309 mg 2-(R)-2-(2-(N-tert-butoxycarbonylamino)-2-methyl propionylamino)-3-(4-fluorophenyl)methoxypropionic acid N-ethyl-N-(3-(4-methanesulfonylphenyl)-2,2-dioxo-2-thia-1-azaspiro[4.5]dec-3-ene-4-ylmethyl)amide. The product was dissolved in dichloromethane (2.5 ml) and trifluoroacetic acid (2.5 ml), left at room temperature for 1 hour and was then evaporated. The residue was dissolved in methanol and poured on a strong cation exchange resin (1 g). After washing with methanol, the product was eluted with CH$_2$Cl$_2$/7 M NH$_3$ in methanol 8:3, evaporated and purified by chromatography on silica (eluent CH$_2$Cl$_2$/7 M NH$_3$ in methanol 99:1-95:5) to yield 152 mg (62%) of the tile amine. The product was dissolved in 10 ml water and 1 ml 2 M hydrochloric acid and after lyophilization the title hydrochloride was obtained as an amorphous solid. MS (IS): 679.2 [MH]$^+$

EXAMPLE 2

2-(R)-2-(2-Amino-2-methylpropionylamino)-3-(2,5-difluorophenyl)methoxypropionic acid N-ethyl-N-(3-(4-methanesulfonyl-phenyl)-2,2-dioxo-2-thia-1-aza-spiro[4.5]dec-3-ene-4-ylmethyl)amide Hydrochloride

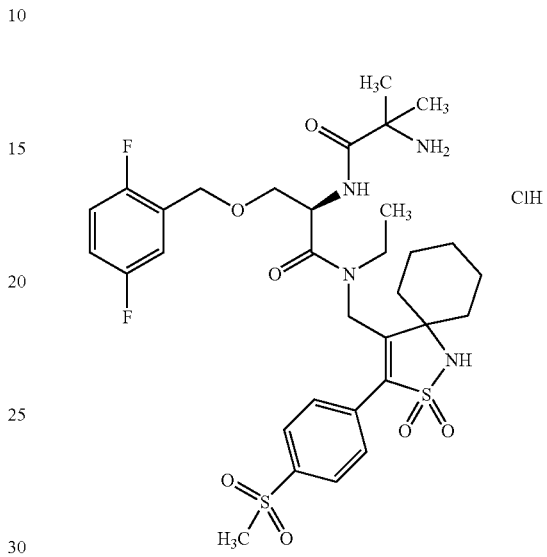

2-(R)-2-Amino-3-(2,5-difluorophenyl)-methoxypropionic acid N-ethyl-N-(3-(4-methanesulfonylphenyl)-2,2-dioxo-2-thia-1-azaspiro[4.5]dec-3-ene-4-ylmethyl)amide, shown below, was prepared from N-tert-butoxycarbonylamino-2,5-difluorobenzyl-D-serine (Intermediate 3c) and N-ethyl-N-[3-(4-methanesulfonyl-phenyl)-2,2-dioxo-2-thia-1-aza-spiro[4.5]dec-3-en-4-ylmethyl]amine (Intermediate 1) according to the methods described in Example 1. Yield: 194 mg (62%); MS: 612.2 [M+H]$^+$

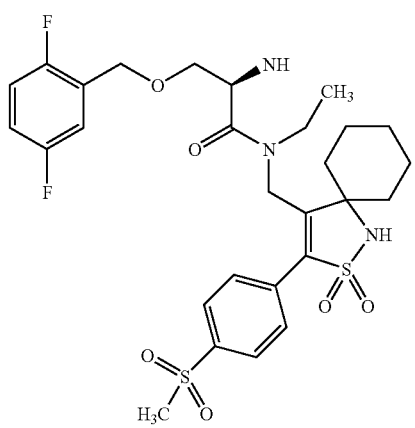

The title compound was prepared from this intermediate according to the method described in Example 1. Yield free base: 135 mg (61%); MS (IS): 697.2 [M+H]$^+$

EXAMPLE 3

2-(R)-2-(2-Amino-2-methylpropionylamino)-3-(2,6-difluorophenyl)methoxypropionic acid N-ethyl-N-(3-(4-methanesulfonyl-phenyl)-2,2-dioxo-2-thia-1-aza-spiro[4.5]dec-3-ene-4-ylmethyl)amide Hydrochloride

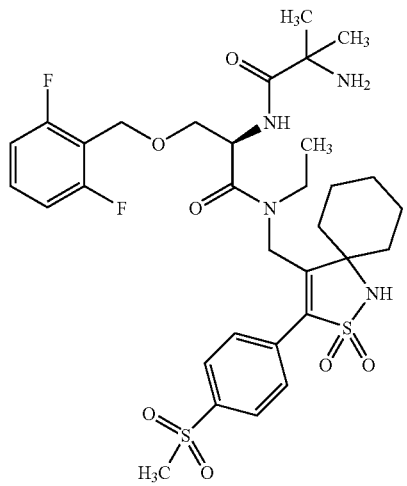

2-(R)-2-Amino-3-(2,6-difluoro-phenyl)methoxypropionic acid N-ethyl-N-(3-(4-methanesulfonyl-phenyl)-2,2-dioxo-2-thia-1-azaspiro[4.5]dec-3-ene-4-ylmethyl)amide, shown below, was prepared from N-tert-butoxycarbonylamino-2,6-difluoro-benzyl-D-serine (Intermediate 3d) and N-ethyl-N-[3-(4-methanesulfonyl-phenyl)-2,2-dioxo-2-thia-1-aza-spiro[4.5]dec-3-en-4-ylmethyl]amine (Intermediate 1) according to the methods described in Example 1. Yield: 219 mg (69%); MS: 612.2 [M+H]$^+$

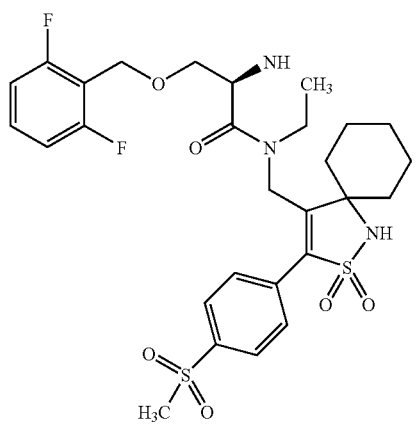

The title compound was prepared from this intermediate according to the method described in Example 1. Yield free base: 130 mg (37%); MS (IS): 697.2 [M+H]$^+$

EXAMPLE 4

2-(R)-2-(2-Amino-2-methylpropionylamino)-3-(3,4-difluorophenyl)methoxypropionic acid N-ethyl-N-(3-(4-methanesulfonyl-phenyl)-2,2-dioxo-2-thia-1-aza-spiro[4.5]dec-3-ene-4-ylmethyl)amide Hydrochloride

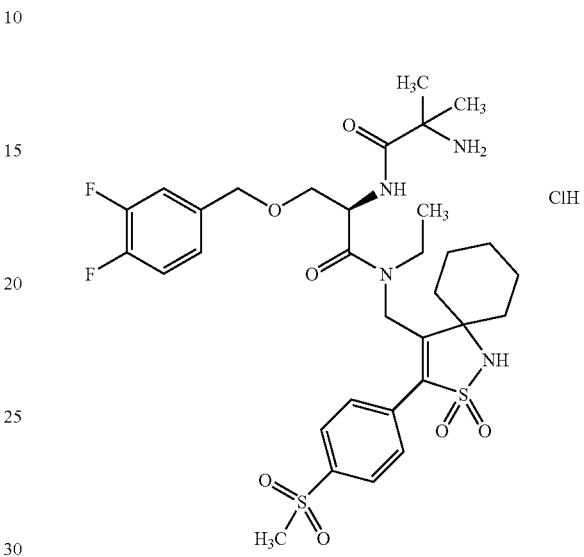

2-(R)-2-Amino-3-(3,4-difluorophenyl)methoxypropionic acid N-ethyl-N-(3-(4-methanesulfonylphenyl)-2,2-dioxo-2-thia-1-azaspiro[4.5]dec-3-ene-4-ylmethyl)amide, shown below, was prepared from N-tert-butoxycarbonylamino-3,4-difluoro-benzyl-D-serine (Intermediate 3b) and N-ethyl-N-[3-(4-methanesulfonyl-phenyl)-2,2-dioxo-2-thia-1-azaspiro[4.5]dec-3-en-4-ylmethyl]amine (Intermediate 1) according to the methods described in Example 1. Yield: 263 mg (70%); MS (IS): 612.2 [M+H]$^+$

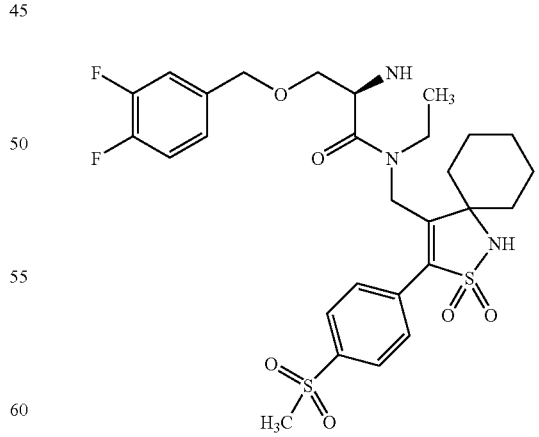

The title compound was prepared from this intermediate according to the method described in Example 1. Yield free base: 142 mg (47%); MS (IS): 697.2 [M+H]$^+$

EXAMPLE 5

2-(R)-2-(2-Amino-2-methylpropionylamino)-3-(3,5-difluorophenyl)methoxypropionic acid N-ethyl-N-(3-(4-methanesulfonyl-phenyl)-2,2-dioxo-2-thia-1-aza-spiro[4.5]dec-3-ene-4-ylmethyl)amide Hydrochloride

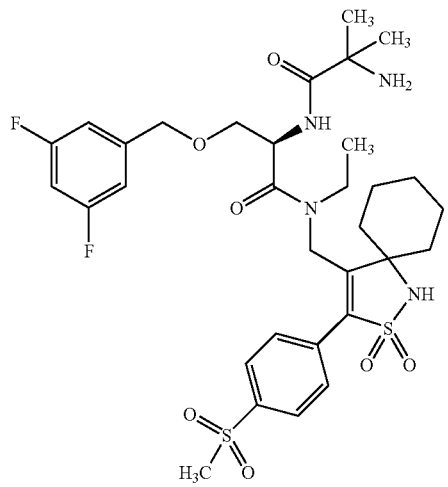

2-(R)-2-Amino-3-(3,5-difluorophenyl)methoxypropionic acid N-ethyl-N-(3-(4-methanesulfonylphenyl)-2,2-dioxo-2-thia-1-azaspiro[4.5]dec-3-ene-4-ylmethyl)amide, shown below, was prepared from N-tert-butoxycarbonylamino-3,5-difluoro-benzyl-D-serine (Intermediate 3f) and N-ethyl-N-[3-(4-methanesulfonyl-phenyl)-2,2-dioxo-2-thia-1-azaspiro[4.5]dec-3-en-4-ylmethyl]amine (Intermediate 1) according to the methods described in Example 1. Yield: 234 mg (61%); MS (IS): 612.2 [M+H]$^+$

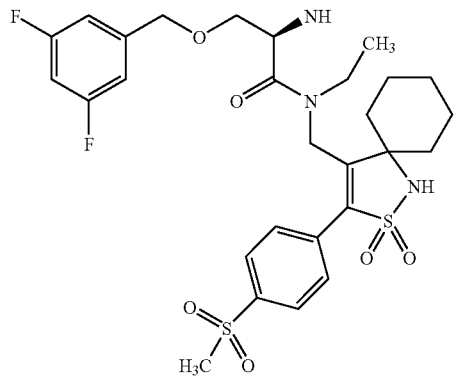

The title compound was prepared from this intermediate according to the method described in Example 1. Yield free base: 132 mg (50%); MS (IS): 697.2 [M+H]$^+$

EXAMPLE 6

2-(R)-2-(2-Amino-2-methylpropionylamino)-3-(3,4-difluorophenyl)methoxypropionic acid N-ethyl-N-(1-benzyl-3-(4-fluorophenyl)-2,2-dioxo-2-thia-1-aza-spiro[4.5]dec-3-ene-4-ylmethyl)amide Hydrochloride

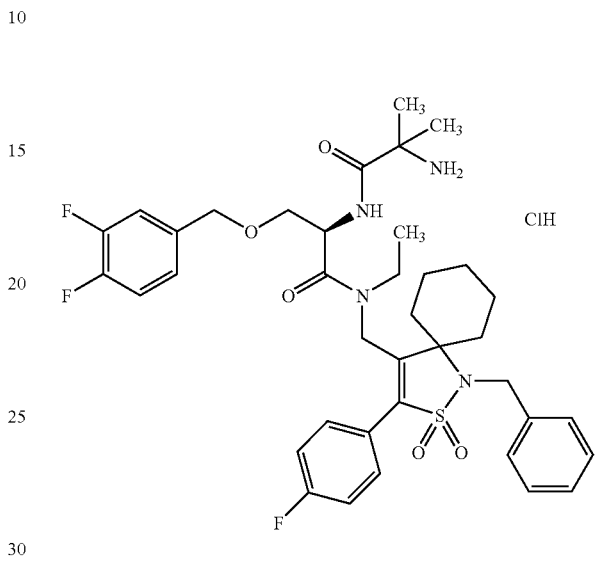

2-(R)-2-Amino-3-(3,4-difluorophenyl)methoxypropionic acid N-(1-benzyl-3-(4-fluorophenyl)-2,2-dioxo-2-thia-1-azaspiro[4.5]dec-3-ene-4-ylmethyl)-N-ethyl amide, shown below, was prepared from N-tert-butoxycarbonylamino-3,4-difluoro-benzyl-D-serine (Intermediate 3b) and N-(1-benzyl-3-(4-fluorophenyl)-2,2-dioxo-2-thia-1-aza-spiro[4.5]dec-3-en-4-ylmethyl)ethylamine (Intermediate 2) according to the methods described in Example 1. Yield: 168 mg (90%); MS (IS): 642.3 [M+H]$^+$

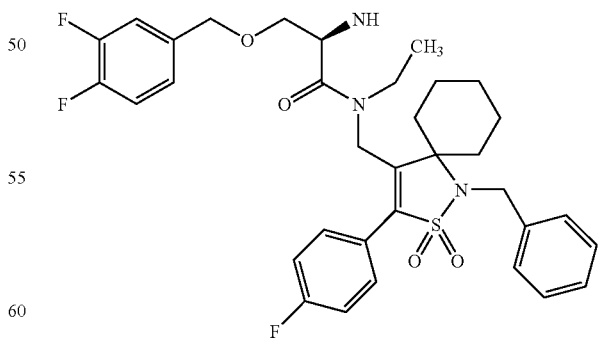

The title compound was prepared from this intermediate according to the method described in Example 1. Yield: 8 mg (4%); MS (IS): 727.3 [M+H]$^+$

EXAMPLE 7

2-(R)-2-(2-Amino-2-methylpropionylamino)-3-(4-fluorophenyl)methoxy propionic acid N-[5-(4-chlorophenyl)-3,3-dimethyl-1,1-dioxo-2,3-dihydroisothiazol-4-ylmethyl]-N-methylamide Hydrochloride

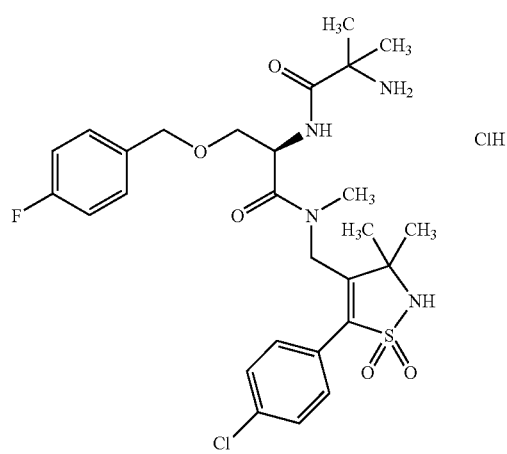

2-(R)-2-Amino-3-(4-fluorophenyl)methoxypropionic acid N-[5-(4-chlorophenyl)-3,3-dimethyl-1,1-dioxo-2,3-dihydroisothiazol-4-ylmethyl]-N-methylamide, shown below, was prepared from N-tert-butoxycarbonylamino-4-fluorobenzyl-D-serine (Intermediate 3a) and N-(5-(4-chlorophenyl)-3,3-dimethyl-1,1-dioxo-2,3-dihydroisothiazol-4-ylmethyl)-N-methylamine (Intermediate 5) according to the methods described in Example 1. Yield: 1.24 g (78%); MS (IS): 496.0 [M+H]$^+$

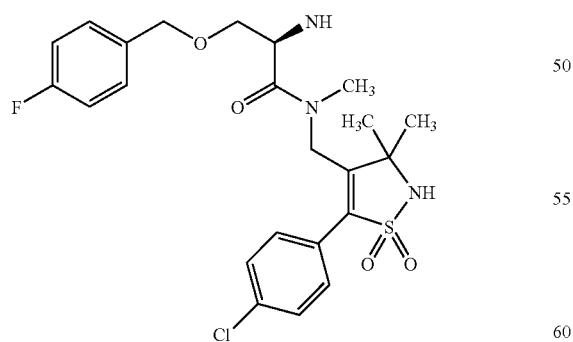

The title compound was prepared from this intermediate according to the method described in Example 1. Yield: 650 mg (45%); MS (IS): 581.0 [M+H]$^+$

EXAMPLE 8

2-(R)-2-(2-Amino-2-methylpropionylamino)-3-(2,4-difluorophenyl)methoxy propionic acid N-[5-(4-chlorophenyl)-3,3-dimethyl-1,1-dioxo-2,3-dihydroisothiazol-4-ylmethyl]-N-methylamide Hydrochloride

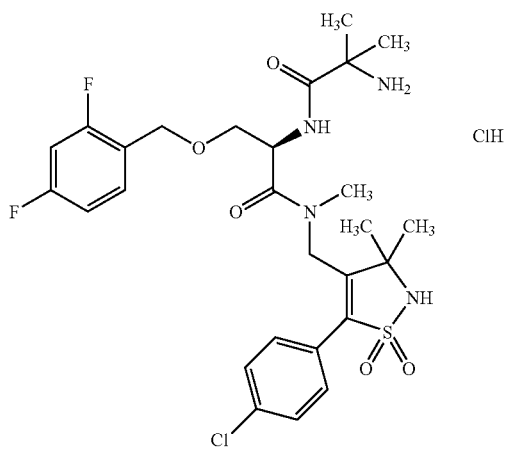

The title compound was prepared according to the methods described in Example 7 using Intermediate 3i. Yield: 1.44 g (98%); MS (IS): 599.2 [M+H]$^+$

EXAMPLE 9

2-(R)-2-(2-Amino-2-methylpropionylamino)-3-(2,5-difluorophenyl)methoxy propionic acid N-[5-(4-chlorophenyl)-3,3-dimethyl-1,1-dioxo-2,3-dihydroisothiazol-4-ylmethyl]-N-methylamide Hydrochloride

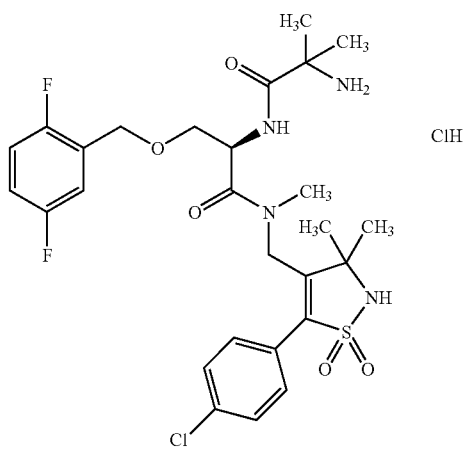

The title compound was prepared according to the methods described in Example 7 using Intermediate 3c.
MS (ESI pos): 599.2 [M+H]$^+$; 621.1 [M+Na]$^+$
MS (ESI neg): 597.2 [M–H]$^-$; 633.0 [M+Cl]$^-$

EXAMPLE 10

2-(R)-2-(2-Amino-2-methylpropionylamino)-3-(2,6-difluorophenyl)methoxy propionic acid N-[5-(4-chlorophenyl)-3,3-dimethyl-1,1-dioxo-2,3-dihydroisothiazol-4-ylmethyl]-N-methylamide Hydrochloride

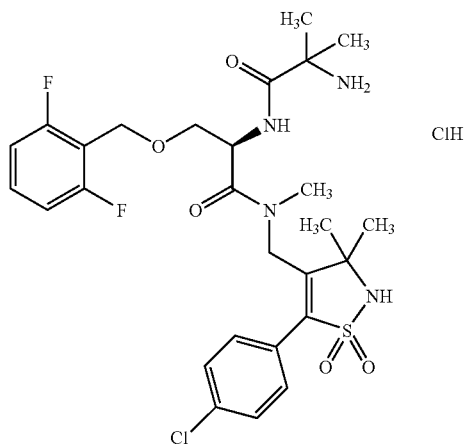

The title compound was prepared according to the methods described in Example 7 using Intermediate 3d.
MS (ESI pos): 599.2 [M+H]+; 621.1 [M+Na]+
MS (ESI neg): 597.2 [M−H]−; 633.2 [M+Cl]−

The following Examples 11-48 were prepared in essentially the same manner as described for Example 7 from Intermediate 4 and the corresponding benzyl-D-serine Intermediates 3:

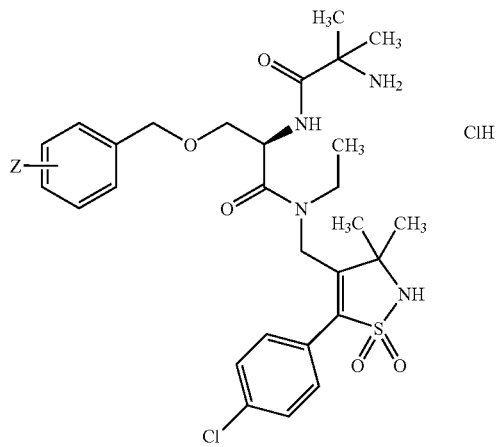

EXAMPLE 11

2-(R)-2-(2-Amino-2-methylpropionylamino)-3-(4-fluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=4-F)

Prepared from Intermediate 3a. Yield: 928 mg (61%); MS (IS): 595.1 [M+H]+

EXAMPLE 12

2-(R)-2-(2-Amino-2-methylpropionylamino)-3-(2,4-difluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,4-F$_2$)

Prepared from Intermediate 3i. Yield: 1.274 g (64%); MS (IS): 613.2 [M+H]+

EXAMPLE 13

2-(R)-2-(2-Amino-2-methylpropionylamino)-3-(4-chlorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=4-Cl)

Prepared from Intermediate 3l. Yield: 190 mg (64%); MS (IS): 613.2 [MH]+, 635.2 [M+Na]+

EXAMPLE 14

2-(R)-2-(2-Amino-2-methylpropionylamino)-3-(2,3-difluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,3-F$_2$)

Prepared from Intermediate 3h. Yield: 180 mg (64%); MS (IS): 613.2 [M+H]+

EXAMPLE 15

2-(R)-2-(2-Amino-2-methylpropionylamino)-3-(2,5-difluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,5-F$_2$)

Prepared from Intermediate 3c. Yield: 181 mg (60%); MS (IS): 613.2 [M+H]+

EXAMPLE 16

2-(R)-2-(2-Amino-2-methylpropionylamino)-3-(2,6-difluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,6-F$_2$)

Prepared from Intermediate 3d. Yield: 165 mg (58%); MS (IS): 613.2 [M+H]+

EXAMPLE 17

2-(R)-2-(2-Amino-2-methylpropionylamino)-3-(3,4-difluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=3,4-F$_2$)

Prepared from Intermediate 3b. Yield: 185 mg (62%); MS (IS): 613.2 [M+H]+

EXAMPLE 18

2-(R)-2-(2-Amino-2-methylpropionylamino)-3-(3,5-difluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=3,5-$F_2$)

Prepared from Intermediate 3f. Yield: 183 mg (71%); MS (IS): 613.2 $[M+H]^+$

EXAMPLE 19

2-(R)-2-(2-Amino-2-methylpropionylamino)-3-(2-fluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-F)

Prepared from Intermediate 3n. MS (IS): 595.1 $[M+H]^+$; 617.1 $[M+Na]^+$

EXAMPLE 20

2-(R)-2-(2-Amino-2-methylpropionylamino)-3-(4-trifluoromethoxyphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=4-$OCF_3$)

Prepared from Intermediate 3aj. MS (IS): 661.1 $[M+H]^+$; 683.0 $[M+Na]^+$

EXAMPLE 21

2-(R)-2-(2-Amino-2-methylpropionylamino)-3-(4-trifluoromethylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=4-$CF_3$)

Prepared from Intermediate 3ae. MS (IS): 645.1 $[M+H]^+$; 667.0 $[M+Na]^+$

EXAMPLE 22

2-(R)-2-(2-Amino-2-methylpropionylamino)-3-(2,3,5-trifluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,3,5-$F_3$)

Prepared from Intermediate 3k. MS (IS): 631.1 $[M+H]^+$; 653.1 $[M+Na]^+$

EXAMPLE 23

2-(R)-2-(2-Amino-2-methylpropionylamino)-3-(2,3,6-trifluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,3,6-$F_3$)

Prepared from Intermediate 3p. MS (IS): 631.2 $[M+H]^+$; 653.2 $[M+Na]^+$

EXAMPLE 24

2-(R)-2-(2-Amino-2-methylpropionylamino)-3-(2-fluoro-5-trifloromethylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-F-5-$CF_3$)

Prepared from Intermediate 3e. MS (IS): 663.2 $[M+H]^+$; 685.1 $[M+Na]^+$

EXAMPLE 25

2-(R)-2-(2-Amino-2-methylpropionylamino)-3-(2,4,5-trifluorophenyl)methoxy propionic acid N-[5-(4chlorophenyl)-3,3-dimethyl-1,1-dioxo-2,3-dihydroisothiazol-4-ylmethyl]-N-ethylamide Hydrochloride (Z=2,4,5-$F_3$)

Prepared from Intermediate 3q. MS (IS): 631.1 $[M+H]^+$; 653.2 $[M+Na]^+$

EXAMPLE 26

2-(R)-2-(2-Amino-2-methylpropionylamino)-3-(2-chlorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-Cl)

Prepared from Intermediate 3r. MS (IS): 611.2 $[M+H]^+$

EXAMPLE 27

2-(R)-2-(2-Amino-2-methylpropionylamino)-3-(4-cyanophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=4-CN)

Prepared from Intermediate 3ac. MS (IS): 602.2 $[M+H]^+$; 624.2 $[M+Na]^+$

EXAMPLE 28

2-(R)-2-(2-Amino-2-methylpropionylamino)-3-(2-trifluoromethoxyphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-$OCF_3$)

Prepared from Intermediate 3ak. MS (IS): 661.2 $[M+H]^+$

EXAMPLE 29

2-(R)-2-(2-Amino-2-methylpropionylamino)-3-(2-trifluoromethylphenyl)methoxy propionic acid N-[5-(4chlorophenyl)-3,3-dimethyl-1,1-dioxo-2,3-dihydroisothiazol-4-ylmethyl]-N-ethylamide Hydrochloride (Z=2-$CF_3$)

Prepared from Intermediate 3af. MS (IS): 645.2 $[M+H]^+$

EXAMPLE 30

2-(R)-2-(2-Amino-2-methylpropionylamino)-3-(2-cyanophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-CN)

Prepared from Intermediate 3ad. MS (IS): 602.2 [M+H]$^+$

EXAMPLE 31

2-(R)-2-(2-Amino-2-methylpropionylamino)-3-(2,6-dichlorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,6-Cl$_2$)

Prepared from Intermediate 3u. MS (IS): 647.1 [M+H]$^+$

EXAMPLE 32

2-(R)-2-(2-Amino-2-methylpropionylamino)-3-(3-fluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=3-F)

Prepared from Intermediate 3g. MS (IS): 595.2 [M+H]$^+$

EXAMPLE 33

2-(R)-2-(2-Amino-2-methylpropionylamino)-3-(6-chloro-2-fluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-F-6-Cl)

Prepared from Intermediate 3x. MS (IS): 629.2 [M+H]$^+$

EXAMPLE 34

2-(R)-2-(2-Amino-2-methylpropionylamino)-3-(3-chloro-2-fluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-F-3-Cl)

Prepared from Intermediate 3v. MS (IS): 629.2 [M+H]$^+$; 651.1 [M+Na]$^+$

EXAMPLE 35

2-(R)-2-(2-Amino-2-methylpropionylamino)-3-(2-chloro-4-fluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=4-F-2-Cl)

Prepared from Intermediate 3y. MS (IS): 629.1 [M+H]$^+$; 651.0 [M+Na]$^+$

EXAMPLE 36

2-(R)-2-(2-Amino-2-methylpropionylamino)-3-(2-chloro-3-trifluoromethylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-Cl-3-CF$_3$)

Prepared from Intermediate 3ai. MS (IS): 679.1 [M+H]$^+$; 701.2 [M+Na]$^+$

EXAMPLE 37

2-(R)-2-(2-Amino-2-methylpropionylamino)-3-(2,4-dichlorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,4-Cl$_2$)

Prepared from Intermediate 3m. MS (IS): 647.1 [M+H]$^+$

EXAMPLE 38

2-(R)-2-(2-Amino-2-methylpropionylamino)-3-(2-methylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-CH$_3$)

Prepared from Intermediate 3aa. MS (IS): 591.2 [M+H]$^+$

EXAMPLE 39

2-(R)-2-(2-Amino-2-methylpropionylamino)-3-(2-chloro-3,6-difluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-Cl-3,6-F$_2$)

Prepared from Intermediate 3z. MS (IS): 647.0 [M+H]$^+$

EXAMPLE 40

2-(R)-2-(2-Amino-2-methylpropionylamino)-3-(2,3-dichlorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,3-Cl$_2$)

Prepared from Intermediate 3s. MS (IS): 646.0 [M+H]$^+$

EXAMPLE 41

2-(R)-2-(2-Amino-2-methylpropionylamino)-3-(2,3,4-trifluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,3,4-F$_3$)

Prepared from Intermediate 3o. MS (IS): 631.1 [M+H]$^+$; 653.0 [M+Na]$^+$

EXAMPLE 42

2-(R)-2-(2-Amino-2-methylpropionylamino)-3-(2-fluoro-6-trifluoromethylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-F-6-CF$_3$)

Prepared from Intermediate 3ah. MS (IS): 663.2 [M+H]$^+$

EXAMPLE 43

2-(R)-2-(2-Amino-2-methylpropionylamino)-3-(2-fluoro-3-trifluoromethylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-F-3-CF$_3$)

Prepared from Intermediate 3ag. MS (IS): 663.2 [M+H]$^+$

EXAMPLE 44

2-(R)-2-(2-Amino-2-methylpropionylamino)-3-(2,5-dichlorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,5-Cl$_2$)

Prepared from Intermediate 3t. MS (IS): 647.1 [M+H]$^+$

EXAMPLE 45

2-(R)-2-(2-Amino-2-methylpropionylamino)-3-(2,6-difluoro-3-methylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2,6-F$_2$-3-CH$_3$)

Prepared from Intermediate 3ab. MS (IS): 627.1 [M+H]$^+$

EXAMPLE 46

2-(R)-2-(2-Amino-2-methylpropionylamino)-3-(2-methoxyphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-OCH$_3$)

Prepared from Intermediate 3j. MS (IS): 607.2 [M+H]$^+$

EXAMPLE 47

2-(R)-2-(2-Amino-2-methylpropionylamino)-3-(2-carbamoylphenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-CONH$_2$)

Prepared from Intermediate 3al. MS (IS): 620.2 [M+H]$^+$; 642.1 [M+Na]$^+$

EXAMPLE 48

2-(R)-2-(2-Amino-2-methylpropionylamino)-3-(4-chloro-2-fluorophenyl)methoxy propionic acid N-[5-(4-chlorophenyl)-3,3-dimethyl-1,1-dioxo-2,3-dihydroisothiazol-4-ylmethyl]-N-ethylamide Hydrochloride (Z=2-F-4-Cl)

Prepared from Intermediate 3w. MS (IS): 629.1 [M+H]$^+$

EXAMPLE 49

2-(R)-2-(2-Amino-2-methylpropionylamino)-3-(2-methylthiazol-4-yl)methoxy propionic acid N-[5-(4-chlorophenyl)-3,3-dimethyl-1,1-dioxo-2,3-dihydroisothiazol-4-ylmethyl]-N-ethylamide Hydrochloride

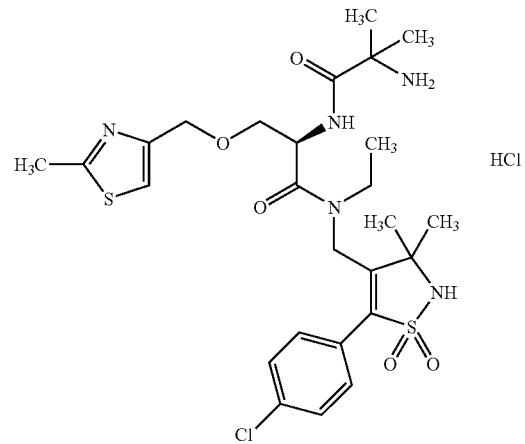

The title compound was prepared from Intermediate 4 and Intermediate 12 as described above for Example 7. MS (IS): 598.1 [M+H]$^+$; 620.1 [M+Na]$^+$

EXAMPLE 50

2-(R)-2-(2-Amino-2-methylpropionylamino)-3-(3,5-dimethylisoxazol-4-yl)methoxy propionic acid N-[5-(4-chlorophenyl)-3,3-dimethyl-1,1-dioxo-2,3-dihydroisothiazol-4-ylmethyl]-N-ethylamide Hydrochloride

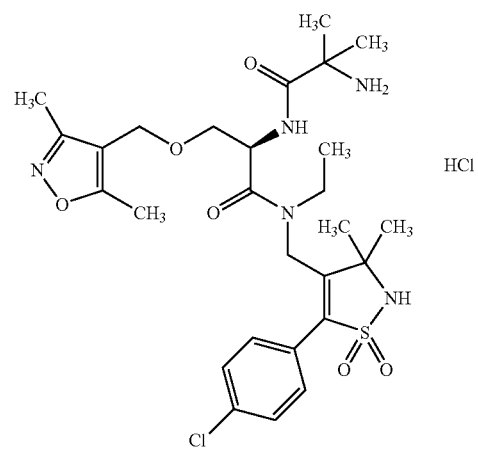

The title compound was prepared from Intermediate 4 and Intermediate 13 as described above for Example 7. MS (IS): 596.2 [M+H]$^+$

EXAMPLE 51

2-(R)-2-(2-Amino-2-methylpropionylamino)-3-(2,6-difluorophenyl)methoxy propionic acid N-[5-(4-fluorophenyl)-3,3-dimethyl-1,1-dioxo-2,3-dihydroisothiazol-4-ylmethyl]-N-methylamide Hydrochloride

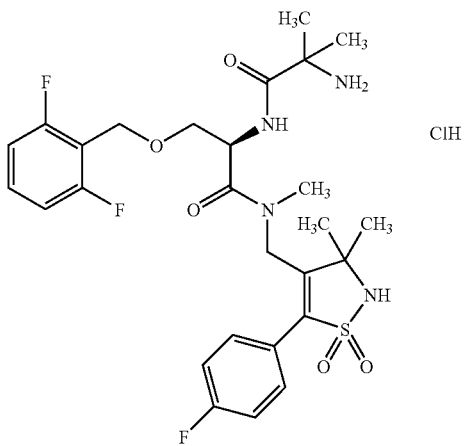

The title compound was prepared from Intermediate 8 and Intermediate 3d as described above for Example 7. MS (IS): 583.2 [M+H]$^+$; 605.2 [M+Na]$^+$ The following Examples 52-71 were prepared in essentially the same manner as described for Example 7 from Intermediate 7 and the corresponding benzyl-D-serine Intermediates 3:

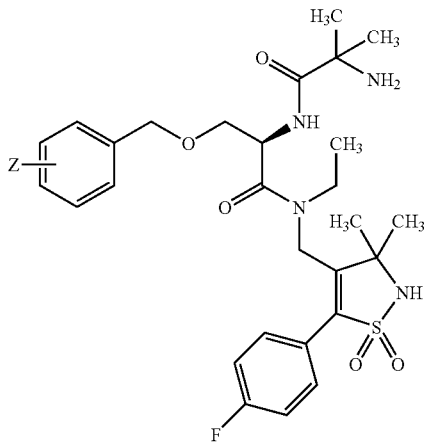

EXAMPLE 52

2-(R)-2-(2-Amino-2-methylpropionylamino)-3-(4-fluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=4-F)

Prepared from Intermediate 3a. MS (IS): 579.2 [M+H]$^+$

EXAMPLE 53

2-(R)-2-(2-Amino-2-methylpropionylamino)-3-(3-fluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=3-F)

Prepared from Intermediate 3g. MS (IS): 579.2 [M+H]$^+$

EXAMPLE 54

2-(R)-2-(2-Amino-2-methylpropionylamino)-3-(2,5-difluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2,5-F$_2$)

Prepared from Intermediate 3c. MS (IS): 597.2 [M+H]$^+$; 619.2 [M+Na]$^+$

EXAMPLE 55

2-(R)-2-(2-Amino-2-methylpropionylamino)-3-(6-chloro-2-fluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-F-6-Cl)

Prepared from Intermediate 3×. MS (IS): 613.2 [M+H]$^+$

EXAMPLE 56

2-(R)-2-(2-Amino-2-methylpropionylamino)-3-(3-chloro-2-fluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-F-3-Cl)

Prepared from Intermediate 3v. MS (IS): 613.2 [M+H]$^+$; 635.1 [M+Na]$^+$

EXAMPLE 57

2-(R)-2-(2-Amino-2-methylpropionylamino)-3-(2-cyanophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-CN)

Prepared from Intermediate 3ad. MS (IS): 586.2 [M+H]$^+$

EXAMPLE 58

2-(R)-2-(2-Amino-2-methylpropionylamino)-3-(2,6-dichlorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2,6-Cl$_2$)

Prepared from Intermediate 3u. MS (IS): 629.1 [M+H]$^+$

EXAMPLE 59

2-(R)-2-(2-Amino-2-methylpropionylamino)-3-(4-chloro-2-fluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-F-4-Cl)

Prepared from Intermediate 3w. MS (IS): 613.2 [M+H]$^-$

EXAMPLE 60

2-(R)-2-(2-Amino-2-methylpropionylamino)-3-(2,4,5-trifluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2,4,5-F$_3$)

Prepared from Intermediate 3q. MS (IS): 615.2 [M+H]$^+$

EXAMPLE 61

2-(R)-2-(2-Amino-2-methylpropionylamino)-3-(2,3,6-trifluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2,3,6-F$_3$)

Prepared from Intermediate 3p. MS (IS): 615.2 [M+H]$^+$

EXAMPLE 62

2-(R)-2-(2-Amino-2-methylpropionylamino)-3-(2,3,5-trifluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2,3,5-F$_3$)

Prepared from Intermediate 3k. MS (IS): 615.2 [M+H]$^+$; 637.1 [M+Na]$^+$

EXAMPLE 63

2-(R)-2-(2-Amino-2-methylpropionylamino)-3-(2-fluoro-5-trifluoromethylphenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-F-5-CF$_3$)

Prepared from Intermediate 3e. MS (IS): 647.2 [M+H]$^+$

EXAMPLE 64

2-(R)-2-(2-Amino-2-methylpropionylamino)-3-(2,4-difluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2,4-F$_2$)

Prepared from Intermediate 3i. MS (IS): 597.2 [M+H]$^+$; 619.2 [M+Na]$^+$

EXAMPLE 65

2-(R)-2-(2-Amino-2-methylpropionylamino)-3-(2-fluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-F)

Prepared from Intermediate 3n. MS (IS): 579.2 [M+H]$^+$; 601.2 [M+Na]$^+$

EXAMPLE 66

2-(R)-2-(2-Amino-2-methylpropionylamino)-3-(2,6-difluorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2,6-F$_2$)

Prepared from Intermediate 3d. MS (IS): 597.2 [M+H]$^+$; 619.2 [M+Na]$^+$

EXAMPLE 67

2-(R)-2-(2-Amino-2-methylpropionylamino)-3-(2-chlorophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-Cl)

Prepared from Intermediate 3r. MS (IS): 595.2 [M+H]$^+$

EXAMPLE 68

2-(R)-2-(2-Amino-2-methylpropionylamino)-3-(4-cyanophenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=4-CN)

Prepared from Intermediate 3ac. MS (IS): 586.3 [M+H]$^+$

EXAMPLE 69

2-(R)-2-(2-Amino-2-methylpropionylamino)-3-(2-trifluoromethoxyphenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=2-OCF$_3$)

Prepared from Intermediate 3ak.

EXAMPLE 70

2-(R)-2-(2-Amino-2-methylpropionylamino)-3-(4-trifluoromethylphenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=4-CF$_3$)

Prepared from Intermediate 3ae. MS (IS): 629.1 [M+H]$^+$; 651.2 [M+Na]$^+$

EXAMPLE 71

2-(R)-2-(2-Amino-2-methylpropionylamino)-3-(4-trifluoromethoxyphenyl)methoxy propionic acid N-[5-(4-fluorophenyl)-3,3-dimethyl-1,1-dioxo-2,3-dihydroisothiazol-4-ylmethyl]-N-ethylamide Hydrochloride (Z=4-OCF$_3$)

Prepared from Intermediate 3aj. MS (IS): 645.1 [M+H]$^+$

The following Examples 72-81 were prepared in essentially the same manner as described for Example 7 from Intermediate 6 and the corresponding benzyl-D-serine Intermediates 3:

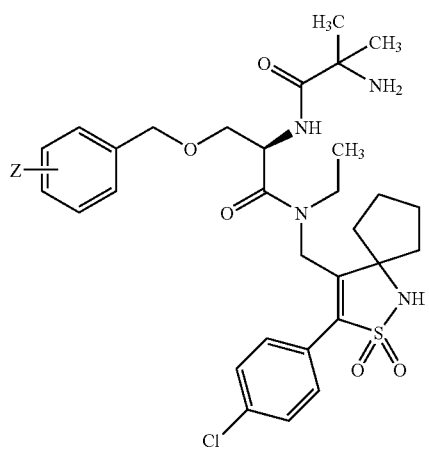

EXAMPLE 72

2-(R)-2-(2-Amino-2-methylpropionylamino)-3-(4-fluorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=4-F)

Prepared from Intermediate 3a. MS (IS): 621.1 [M+H]$^+$

EXAMPLE 73

2-(R)-2-(2-Amino-2-methylpropionylamino)-3-(3-fluorophenyl)methoxypropionic acid N-(3-(4-chlorophenyl)-2,2-dioxo-2-thia-1-azaspiro[4.4]non-3-ene-4-ylmethyl)-N-ethylamide Hydrochlorid e (Z=3-F)

Prepared from Intermediate 3g. MS (IS): 621.1 [M+H]$^+$

EXAMPLE 74

2-(R)-2-(2-Amino-2-methylpropionylamino)-3-(2,3-difluorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=2,3-F$_2$)

Prepared from Intermediate 3h. MS (IS): 639.2 [M+H]$^+$

EXAMPLE 75

2-(R)-2-(2-Amino-2-methylpropionylamino)-3-(2,4-difluorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=2,4-F$_2$)

Prepared from Intermediate 3i. MS (IS): 639.0 [M+H]$^+$

EXAMPLE 76

2-(R)-2-(2-Amino-2-methylpropionylamino)-3-(2,5-difluorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=2,5-F$_2$)

Prepared from Intermediate 3c. MS (IS): 639.1 [M+H]$^+$

EXAMPLE 77

2-(R)-2-(2-Amino-2-methylpropionylamino)-3-(2,6-difluorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=2,6-F$_2$)

Prepared from Intermediate 3d. MS (IS): 639.1 [M+H]$^+$

EXAMPLE 78

2-(R)-2-(2-Amino-2-methylpropionylamino)-3-(2,4-dichlorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=2,4-Cl$_2$)

Prepared from Intermediate 3m. MS (IS): 673.0 [M+H]$^+$

EXAMPLE 79

2-(R)-2-(2-Amino-2-methylpropionylamino)-3-(4-chlorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=4-Cl)

Prepared from Intermediate 3l. MS (IS): 637.0 [M+H]$^+$

EXAMPLE 80

2-(R)-2-(2-Amino-2-methylpropionylamino)-3-(3,5-difluorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=3,5-F$_2$)

Prepared from Intermediate 3f. MS (IS): 639.2 [M+H]$^+$

EXAMPLE 81

2-(R)-2-(2-Amino-2-methylpropionylamino)-3-(2,3,5-trifluorophenyl)methoxypropionic acid N-(3-(4-chlorophenyl)-2,2-dioxo-2-thia-1-azaspiro[4.4]non-3-ene-4-ylmethyl)-N-ethylamide Hydrochloride (Z=2,3,5-F$_3$)

Prepared from Intermediate 3k. MS (IS): 657.0 [M+H]$^+$

The following Examples 82-84 were prepared in essentially the same manner as described for Example 7 from Intermediate 4 and the corresponding pentanoic acid Intermediates 9:

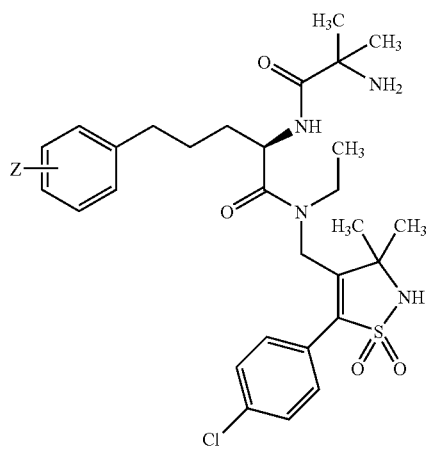

EXAMPLE 82

2-(R)-2-(2-Amino-2-methylpropionylamino)-5-(4-fluorophenyl)pentanoic acid N-[5-(4-chlorophenyl)-3,3-dimethyl-1,1-dioxo-2,3-dihydroisothiazol-4-ylmethyl]-N-ethylamide Hydrochloride (Z=4-F)

Prepared from Intermediate 9a. MS (IS): 593.2 [M+H]$^+$

EXAMPLE 83

2-(R)-2-(2-Amino-2-methylpropionylamino)-5-(2,6-difluorophenyl)pentanoic acid N-[5-(4-chlorophenyl)-3,3-dimethyl-1,1-dioxo-2,3-dihydroisothiazol-4-ylmethyl]-N-ethylamide Hydrochloride (Z=2,6-F$_2$)

Prepared from Intermediate 9b. MS (IS): 611.2 [M+H]$^+$

EXAMPLE 84

2-(R)-2-(2-Amino-2-methylpropionylamino)-5-(3,5-difluorophenyl)pentanoic acid N-[5-(4-chlorophenyl)-3,3-dimethyl-1,1-dioxo-2,3-dihydroisothiazol-4-ylmethyl]-N-ethylamide Hydrochloride (Z=3,5-F$_2$)

Prepared from Intermediate 9c. MS (IS): 611.1 [M+H]$^+$

The following Examples 85-87 were prepared in essentially the same manner as described for Example 7 from Intermediate 7 and the corresponding pentanoic acid Intermediates 9:

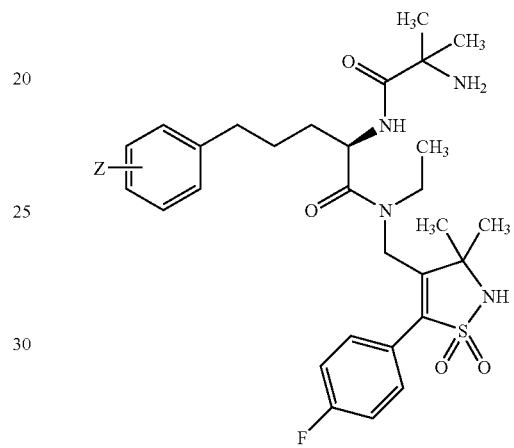

EXAMPLE 85

2-(R)-2-(2-Amino-2-methylpropionylamino)-5-(4-fluorophenyl)pentanoic acid N-[3,3-dimethyl-1,1-dioxo-5-(4-fluorophenyl)-2,3-dihydroisothiazol-4-ylmethyl]-N-ethylamide Hydrochloride (Z=4-F)

Prepared from Intermediate 9a. MS (IS): 577.2 [M+H]$^+$

EXAMPLE 86

2-(R)-2-(2-Amino-2-methylpropionylamino)-5-(2,6-difluorophenyl)pentanoic acid N-[3,3-dimethyl-1,1-dioxo-5-(4-fluorophenyl)-2,3-dihydroisothiazol-4-ylmethyl]-N-ethylamide Hydrochloride (Z=2,6-F$_2$)

Prepared from Intermediate 9b. MS (IS): 595.2 [M+H]$^+$

EXAMPLE 87

2-(R)-2-(2-Amino-2-methylpropionylamino)-5-(3,5-difluorophenyl)pentanoic acid N-[3,3-dimethyl-1,1-dioxo-5-(4-fluorophenyl)-2,3-dihydroisothiazol-4-ylmethyl]-N-ethylamide Hydrochloride (Z=3,5-F$_2$)

Prepared from Intermediate 9c. MS (IS): 595.2 [M+H]$^+$

EXAMPLE 88

2-(R)-2-(2-Amino-2-methylpropionylamino)-3-(3,5-difluorophenyl)methoxypropionic acid N-(3-(4-chlorophenyl)-2,2-dioxo-1-propyl-2-thia-1-azaspiro[4.4]non-3-ene-4-ylmethyl)-N-ethylamide Hydrochloride

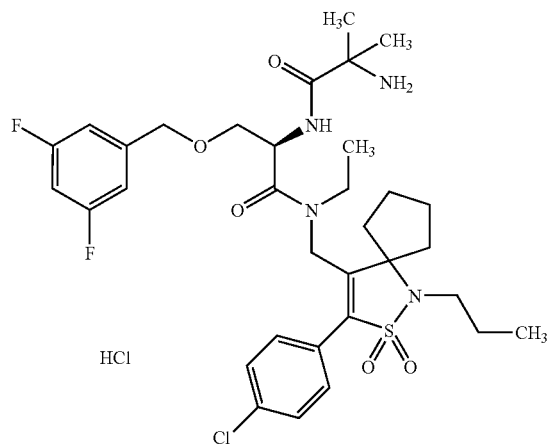

The title compound was prepared from Intermediate 3f and Intermediate 11 in the same manner as described for Example 7. MS (IS): 681.2 [M+H]$^+$

EXAMPLE 89

2-(R)-2-(2-Amino-3-fluoro-2-fluoromethyl-propionylamino)-3-(2,6-difluorophenylmethoxy)-propionic acid N-[5-(4-chlorophenyl)-3,3-dimethyl-1,1-dioxo-2,3-dihydroisothiazol-4-ylmethyl]-N-ethylamide Hydrochloride

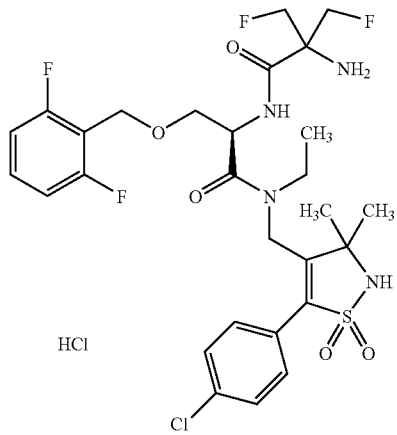

The title compound was prepared by coupling between Intermediates 3d and 4 followed by the second coupling step with Intermediate 10 in the same manner as described for Example 7 (MS, ion spray, 649.2 (M+1); overall yield for the last coupling and deprotection sequence 25%.

EXAMPLE 90

2-(R)-2-((1-Amino-cyclopropancarbonyl)amino)-3-(4-fluorophenylmethoxy)-propionic acid N-[5-(4-chlorophenyl)-3,3-dimethyl-1,1-dioxo-2,3-dihydroisothiazol-4-ylmethyl]-N-ethylamide Hydrochloride

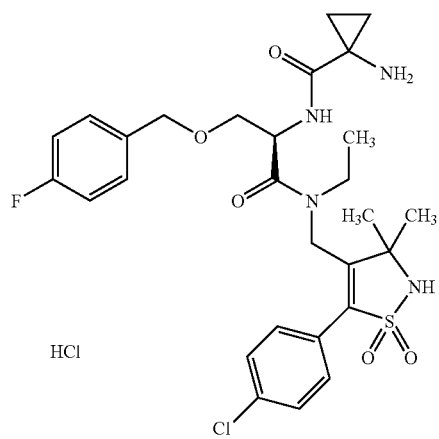

The title compound was prepared according to the methods described in Example 7 from Intermediates 3a and 4 followed by coupling with commercial 1-(tert-butoxycarbonylamino)cyclopropanecarboxylic acid. Yield: 20 mg (35%); MS (IS): 593.0 [M+H]$^+$

EXAMPLE 91

2-(R)-2-((1-Amino-cyclopropancarbonyl)amino)-3-(2,4-difluorophenylmethoxy)-propionic acid N-[5-(4-chlorophenyl)-3,3-dimethyl-1,1-dioxo-2,3-dihydroisothiazol-4-ylmethyl]-N-methylamide Hydrochloride

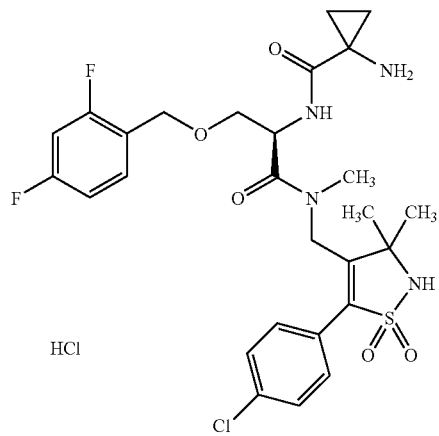

The title compound was prepared in the same manner as described for Example 90 starting from Intermediate 3i.
Yield: 19 mg (73%); MS (IS): 598.0 [M+H]$^+$.

EXAMPLE 92

2-(R)-2-(2-Amino-2-methylpropionylamino)-3-(3,5-difluorophenyl)methoxypropionic acid N-(3-(4-chlorophenyl)-2,2-dioxo-2-thia-1-azaspiro[4.4]non-3-ene-4-ylmethyl)-N-(2-fluoroethyl)amide Hydrochloride

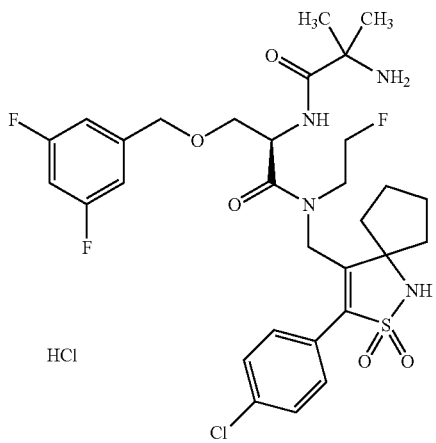

The title compound was prepared from the Intermediates 3f and 14 as described for Example 7. MS (IS): 657.1 [M+H]$^+$.

Pituitary Cell Culture Assay for Growth Hormone (GH) Secretion

Fifteen 250 g male Sprague-Dawley rats are used for each assay. The animals are killed by decapitation and anterior pituitaries are removed and placed into ice cold culture medium. The pituitaries are sectioned in small pieces and enzymatically digested using trypsin (Difco) to weaken connective tissue. Pituitary cells are dispersed by mechanical agitation, collected, pooled and then seeded into 96-well plates (50,000 cells/well). After 5 days of culture, the cells formed as monolayer (70-80% confluent). Cells are then washed with medium (without phenol red) and incubated for 90 min at 37° C. Afterwards the cells are challenged to secrete GH by the addition of GH secretagogues to the medium. After 45 min at room temperature, the medium is removed, filtered and stored frozen until radioimmunoassays for rat GH were performed. Doses of secretagogue are added in triplicates. Compounds disclosed herein are active in the assay as described. The compounds cause a stimulation of GH secretion resulting in at least 20% increase of the basal level of GH with and EC50<500 nM. Preferred compounds caused a 50% increase with an EC50<50 nM, and more preferred compounds a 50% increase with an EC50<10 nM. Both EC50 and efficacy values were calculated by the 4-parameter logistic equation. Such values were pooled and represented as mean+/−standard error, when appropriate.

| | EC50 (nM) |
|---|---|
| Example 2 | 0.23 |
| Example 4 | 0.9 |
| Example 5 | 0.6 |
| Example 7 | 1.7 |
| Example 12 | 8.0 |
| Example 15 | 2.1 |
| Example 16 | 1.1 |

The invention claimed is:

1. A compound of the Formula I

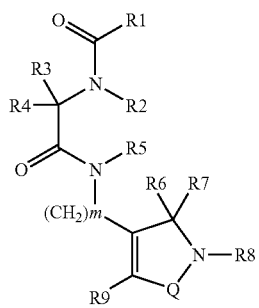

Formula I wherein:
R1 is NHR10, (substituted or unsubstituted $C_1$-$C_6$alkyl) NHR10 or (unsubstituted or substituted $C_3$-$C_8$ cycloalkyl)NHR10;
R10 is hydrogen, $C_1$-$C_6$alkyl, $C_1$-$C_6$alkyl(OH), $C_1$-$C_6$alkylidenyl(OH)R11, or an amino protecting group;
R11 is $C_1$-$C_6$alkyl, $C_2$-$C_6$alkenyl, $C_1$-$C_6$alkyl(O)$C_1$-$C_6$alkyl, C(O)O—$C_1$-$C_6$alkyl, aryl, or $C_1$-$C_6$alkylaryl;
R2 is hydrogen, $C_1$-$C_6$alkyl, aryl, or $C_1$-$C_6$alkylaryl;
R4 is hydrogen, $C_1$-$C_6$alkyl, aryl, $C_1$-$C_6$alkylaryl, or $C_2$-$C_6$alkenyl;
R5 is hydrogen, aryl, $C_1$-$C_6$alkylaryl, hydroxy, $C_1$-$C_6$alkoxy or, unsubstituted or substituted $C_1$-$C_6$alkyl;
R6 and R7 are independently hydrogen, unsubstituted or substituted $C_1$-$C_6$alkyl, unsubstituted or substituted $C_2$-$C_6$alkenyl, or R6 and R7 together with the carbon atom to which they are attached form a carbocyclic ring of up to 8 atoms which is optionally partly unsaturated or a substituted $C_3$-$C_8$ cycloalkyl group which is optionally partly unsaturated;
R8 is hydrogen, unsubstituted or substituted $C_1$-$C_6$alkyl, unsubstituted or substituted aryl, unsubstituted or substituted ($C_1$-$C_6$alkyl)$C_3$-$C_8$cycloalkyl, or unsubstituted or substituted $C_1$-$C_6$alkylaryl;
Q is —S(O)$_2$— or —C(O)—;
m is a number selected from 1 or 2;
R3 is substituted $C_1$-$C_6$alkylaryl, substituted $C_1$-$C_6$alkyl (O)—$C_1$-$C_6$alkylaryl, substituted $C_3$-$C_8$ cycloalkyl, substituted ($C_1$-$C_6$ alkyl)$C_3$-$C_8$ cycloalkyl, or aryl substituted by at least one —SO$_2$CF$_3$ group; and R9 is hydrogen, $C_1$-$C_6$alkyl, $C_2$-$C_6$alkenyl, $C_2$-$C_6$alkynyl, $C_3$-$C_8$cycloalkyl, $C_3$-$C_8$cycloalkenyl, cyano, optionally substituted aryl, optionally substituted —O-aryl, optionally substituted —N-aryl, optionally substituted —S-aryl, -aryl-aryl(K1)(K2), —O-aryl-aryl(K1)(K2), —N-aryl-aryl(K1)(K2), —S-aryl-aryl(K1)(K2), —O—$C_1$-$C_6$alkyl, or $C_1$-$C_6$alkylaryl, wherein K1 is halo or —CF₃, and K2 is hydrogen, halo or —CF₃ or K1 and K2 together form a methylenedioxy group; or R3 is optionally substituted aryl, $C_1$-$C_6$alkylaryl, $C_1$-$C_6$alkyl(O)—$C_1$-$C_6$alkylaryl, $C_3$-$C_8$ cycloalkyl, or ($C_1$-$C_6$ alkyl)$C_3$-$C_8$ cycloalkyl; and R9 is aryl substituted by at least one —SO₂CF₃ group, —O-aryl substituted by at least one —SO₂CF₃ group, —N-aryl substituted by at least one —SO₂CF₃ group, or —S-aryl substituted by at least one —SO₂CF₃ group;

or a pharmaceutically acceptable salt thereof.

2. A compound according to claim 1 having Formula II

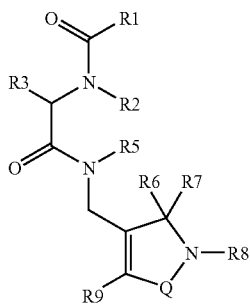

Formula II wherein
R1, R2, R3, R5, R6, R7, R8, R9 and Q are as defined in claim 1 or a pharmaceutically acceptable salt thereof.

3. A compound according to claim 2 wherein R3 is selected from substituted $C_1$-$C_6$alkylaryl, substituted $C_1$-$C_6$alkyl(O)—$C_1$-$C_6$alkylaryl, or substituted ($C_1$-$C_6$ alkyl)$C_3$-$C_8$ cycloalkyl; or a pharmaceutically acceptable salt thereof.

4. A compound according to claim 3 wherein the substituted $C_1$-$C_6$alkylaryl or substituted $C_1$-$C_6$alkyl(O)—$C_1$-$C_6$alkylaryl group contains an aryl moiety selected from phenyl, thiazolyl, pyridyl, naphthyl, thienyl, oxazolyl, isoxazolyl and indolyl which is substituted by from one to three groups independently selected from $C_1$-$C_6$ alkyl, —O$C_1$-$C_6$ alkyl, —OCF₃, amide, aryl, aryloxy, SO₂($C_{1-6}$ alkyl), SO₂CF₃, NHamide, carboxamide, sulfonamide, NHsulfonamide, imide, hydroxy, carboxy, nitro, halo, tri(chloro or fluoro)methyl, and cyano; or a pharmaceutically acceptable salt thereof.

5. A compound according to claim 2 wherein R3 is a substituted $C_1$-$C_6$ alkylaryl group or a substituted $C_1$-$C_6$alkyl(O)—$C_1$-$C_6$alkyl aryl group wherein:
the $C_1$-$C_6$alkyl moiety within the substituted $C_1$-$C_6$ alkylaryl group is methyl, ethyl or propyl;
the $C_1$-$C_6$alkyl(O)—$C_1$-$C_6$alkyl moiety within the substituted $C_1$-$C_6$alkyl(O)—$C_1$-$C_6$alkyl aryl group is a moiety of formula —CH₂OCH₂—;
the substituted aryl moiety is 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,4,6-trifluorophenyl, 2,3,4-trifluorophenyl, 2,4,5-trifluorophenyl, 2,3,6-trifluorophenyl, 2,3,5-trifluorophenyl, 2-chlorophenyl, 3-chlorophenyl, 4-chlorophenyl, 2,6-dichlorophenyl, 2,3-dichlorophenyl, 2,4-dichlorophenyl, 2,5-dichlorophenyl, 2-chloro-4-fluorophenyl, 2-methylphenyl, 2,6-difluoro-3-methylphenyl, 3,6-difluoro-2-chlorophenyl, 2-fluoro-6-chlorophenyl, 2-fluoro-3-chlorophenyl, 2-fluoro-4-chlorophenyl, 2,6-difluoro-3-chlorophenyl, 4-trifluoromethylphenyl, 3-trifluoromethylphenyl, 2-trifluoromethylphenyl, 2-fluoro-5-trifluoromethylphenyl, 2-fluoro-3-trifluoromethylphenyl, 2-fluoro-6-trifluoromethylphenyl, 2-chloro-3-trifluoromethylphenyl, 4-trifluoromethoxyphenyl, 3-trifluoromethoxyphenyl, 2-trifluoromethoxyphenyl, 2-cyanophenyl, 3-cyanophenyl, 4-cyanophenyl, 4-methanesulphonylphenyl, or 2-methyl thiazolyl;
or a pharmaceutically acceptable salt thereof.

6. A compound according to claim 2 wherein R1 is

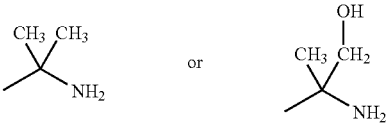

or a pharmaceutically acceptable salt thereof.

7. A compound according to claim 2 wherein R1 is selected from —C(CH₂F)₂NH₂, —C(CH₂F)(CH₂CH₂F)NH₂, —C(CF₃)(CH₃)NH₂, —C(CH₂CH₂F)₂NH₂, —C(CH₂CH₃)(CH₂CF₃)NH₂,

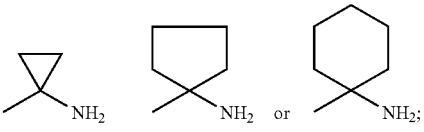

or a pharmaceutically acceptable salt thereof.

8. A compound according to claim 2 wherein R6 and R7 are each $C_1$-$C_3$ alkyl or form a five or six membered carbocyclic ring; or R6 and R7 are independently $C_1$-$C_6$alkyl or $C_2$-$C_6$alkenyl, in which one or both groups are substituted by one, two, or three halo atoms; or R6 is hydrogen and R7 is $C_1$-$C_6$alkyl, or $C_2$-$C_6$alkenyl which is substituted by one, two, or three halo atoms; or R6 and R7 together with the carbon atom to which they are attached may form a $C_3$-$C_8$cycloalkyl group which is optionally partly unsaturated and which is substituted by one, two, or three halo atoms;
or a pharmaceutically acceptable salt thereof.

9. A compound according to claim 1 wherein R4 is hydrogen or methyl, or a pharmaceutically acceptable salt thereof.

10. A compound according to claim 2 wherein R5 is hydrogen, $C_1$-$C_6$alkyl, $C_1$-$C_6$alkoxy, $C_1$-$C_6$alkyl which is substituted by hydroxy or $C_1$-$C_6$alkyl which is substituted by one, two, or three halo atoms, or a pharmaceutically acceptable salt thereof.

11. A compound according to claim 10 wherein R5 is hydrogen, methyl, ethyl, propyl or n-propyl, or a pharmaceutically acceptable salt thereof.

12. A compound according to claim 2 wherein R8 is hydrogen, $C_1$-$C_6$alkyl, ($C_1$-$C_6$alkyl)$C_3$-$C_8$cycloalkyl, benzyl, 1-phenylethyl, $C_1$-$C_6$alkyl which is substituted by hydroxy, methoxy, CONH₂, or CON(CH₃)₂, or $C_1$-$C_6$alkyl which is substituted by one, two, or three halo atoms, phenyl substituted by one, two, or three halo atoms or benzyl substituted by one, two, or three halo atoms, or a pharmaceutically acceptable salt thereof.

13. A compound according to claim 12 wherein R8 is $C_1$-$C_6$alkyl which is substituted by hydroxy or $C_1$-$C_6$alkyl which is substituted by one, two, or three halo atoms, phenyl substituted by one, two, or three halo atoms or benzyl substituted by one, two, or three halo atoms, or a pharmaceutically acceptable salt thereof.

14. A compound according to claim 2 wherein R9 is selected from the group consisting of unsubstituted or substituted thienyl, unsubstituted or substituted naphthyl, unsubstituted or substituted phenoxy and unsubstituted or substituted phenyl; wherein the substituents when present are each independently selected from the group consisting of halo, methyl, ethyl, propyl, t-butyl, trifluoromethyl, trifluoromethoxy, methoxy, ethoxy, cyano, methylsulphonyl, phenyl, phenoxy, thienyl, pyridyl, thiazolyl, oxazolyl, nitro, CONH₂, furanyl, benzothiophenyl and benzofuranyl;

or a pharmaceutically acceptable salt thereof.

15. A compound of according to claim 14 wherein R9 is selected from phenyl, 4-methylsulphonylphenyl, 3-methylsulphonylphenyl, 4-fluorophenyl, 2-fluorophenyl, 3-fluorophenyl, 3-chlorophenyl, 2-chlorophenyl, 4-chlorophenyl, 4-t-butylphenyl, 4-trifluoromethylphenyl, 3-trifluoromethylphenyl, 4-nitrophenyl, 3-nitrophenyl, 4-bromophenyl, 3-bromophenyl, 2-bromophenyl, 4-methylphenyl, 3-methylphenyl, 4-phenylphenyl, 3-phenylphenyl, 4-phenoxyphenyl, 3-phenoxyphenyl, 4-cyanophenyl, 3-cyanophenyl, 4-carbamoylphenyl, 4-methoxyphenyl, 3-methoxyphenyl, thienyl, thiazolyl, pyridyl, phenoxy, 4-chlorophenoxy, 2,3-dichlorophenyl, 3,4-dichlorophenyl, naphthyl, oxazolyl, 2,4-difluorophenyl, 3,4-difluorophenyl, 3,5-difluorophenyl, 2,3-difluorophenyl, 2,6-difluorophenyl, 2,5-difluorophenyl, 2-fluoro-3-chlorophenyl, 4-ethylphenyl, 4-ethoxyphenyl 3,4,5-trifluorophenyl, 3-fluoro-4-chlorophenyl and 4-carbamoylphenyl;

or a pharmaceutically acceptable salt thereof.

16. A pharmaceutical formulation comprising one or more compounds according to claim 1 or a pharmaceutically acceptable salt thereof, and one or more pharmaceutically acceptable diluents or carriers therefor.

17. A pharmaceutical formulation according to claim 16 wherein the formulation further comprises one or more growth hormone secretagogue compounds and/or a bone-antiresorptive agent.

18. A process for producing a compound of Formula I as defined in claim 1 comprising coupling a compound of Formula XI or XIb

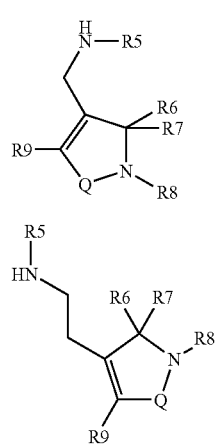

XI

XIb with a compound of formula XIII

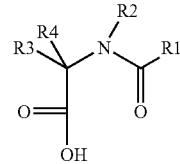

XIII wherein R1, R2, R3, R4, R5, R6, R7, R8, R9 and Q are as defined in claim 1.

19. A process for producing a compound of Formula I as defined in claim 1 comprising deprotecting a compound of Formula

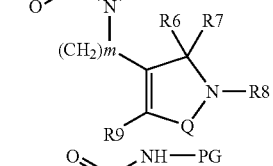

or

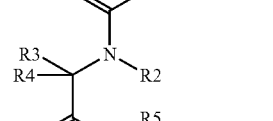

wherein R2, R3, R4, R5, R6, R7, R8, R9, m and Q are as defined in claim 1, and PG is an amino protecting group.

20. A process for producing a compound of Formula I as defined in claim 1 comprising coupling a compound of Formula

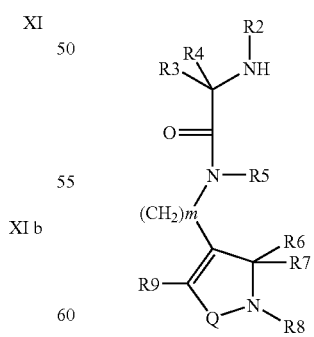

with a compound of formula XIV

HOOC—R1    XIV wherein R1, R2, R3, R4, R5, R6, R7, R8, R9 and Q are as defined in claim 1.

21. A compound having the formula

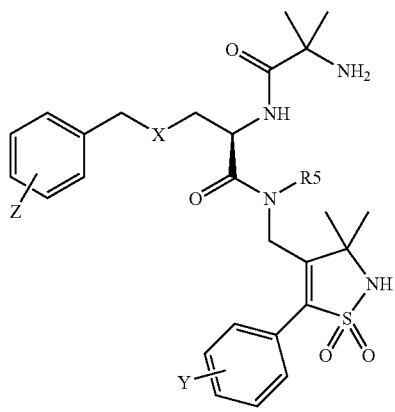

wherein:
X is O, Y is 4-Cl, Z is 2-F and R5 is Et; or
X is O, Y is 4-Cl, Z is 3-F and R5 is Et; or
X is O, Y is 4-Cl, Z is 4-F and R5 is Et; or
X is O, Y is 4-Cl, Z is 2,3-$F_2$ and R5 is Et; or
X is O, Y is 4-Cl, Z is 2,5-$F_2$ and R5 is Et; or
X is $CH_2$, Y is 4-Cl, Z is 2,6-$F_2$ and R5 is Et; or
X is O, Y is 4-Cl, Z is 2,6-$F_2$ and R5 is Et; or
X is $CH_2$, Y is 4-Cl, Z is 3,5-$F_2$ and R5 is Et; or
X is O, Y is 4-Cl, Z is 2,4,6-$F_3$ and R5 is Et; or
X is O, Y is 4-Cl, Z is 2,3,5-$F_3$ and R5 is Et; or
X is O, Y is 4-Cl, Z is 2,6-$Cl_2$ and R5 is Et; or
X is O, Y is 4-Cl, Z is 2-F-6-Cl and R5 is Et; or
X is O, Y is 4-Cl, Z is 2-Cl-3,6-$F_2$ and R5 is Et; or
X is O, Y is 4-Cl, Z is 2-CN and R5 is Et;
or a pharmaceutically acceptable salt thereof.

22. 2-(R)-2-(2-Amino-2-methylpropionylamino)-3-(2,6-difluoro-3-methylphenyl)methoxy propionic acid N-[5-(4-chlorophenyl)-3,3-dimethyl-1,1-dioxo-2,3-dihydroisothiazol-4-ylmethyl]-N-ethylamide; or a pharmaceutically acceptable salt thereof.

* * * * *